US009255141B2

(12) United States Patent
Wong et al.

(10) Patent No.: US 9,255,141 B2
(45) Date of Patent: Feb. 9, 2016

(54) MULTIMERIC IL-15 SOLUBLE FUSION MOLECULES AND METHODS OF TREATING NEOPLASIA AND HIV USING SAME

(71) Applicants: Hing C. Wong, Weston, FL (US); Peter Rhode, Miami, FL (US); Bai Liu, Cooper City, FL (US); Xiaoyun Zhu, Miami, FL (US); Kai-ping Han, Miramar, FL (US)

(72) Inventors: Hing C. Wong, Weston, FL (US); Peter Rhode, Miami, FL (US); Bai Liu, Cooper City, FL (US); Xiaoyun Zhu, Miami, FL (US); Kai-ping Han, Miramar, FL (US)

(*) Notice: Subject to any disclaimer, the term of this patent is extended or adjusted under 35 U.S.C. 154(b) by 0 days.

(21) Appl. No.: 13/769,179

(22) Filed: Feb. 15, 2013

(65) Prior Publication Data

US 2014/0242025 A1 Aug. 28, 2014

Related U.S. Application Data

(63) Continuation-in-part of application No. 13/238,925, filed on Sep. 21, 2011, now Pat. No. 8,507,222.

(60) Provisional application No. 61/384,817, filed on Sep. 21, 2010, provisional application No. 61/527,911, filed on Aug. 26, 2011.

(51) Int. Cl.

| C07K 16/18 | (2006.01) |
|---|---|
| C07K 14/54 | (2006.01) |
| C07K 14/715 | (2006.01) |
| A61K 38/20 | (2006.01) |
| C07K 16/28 | (2006.01) |
| A61K 45/06 | (2006.01) |
| A61K 38/17 | (2006.01) |

(52) U.S. Cl.
CPC .............. *C07K 16/18* (2013.01); *A61K 38/1793* (2013.01); *A61K 38/2086* (2013.01); *A61K 45/06* (2013.01); *C07K 14/5443* (2013.01); *C07K 14/7155* (2013.01); *C07K 16/2887* (2013.01); *C07K 2317/622* (2013.01); *C07K 2317/732* (2013.01); *C07K 2319/21* (2013.01); *C07K 2319/22* (2013.01); *C07K 2319/30* (2013.01)

(58) Field of Classification Search
None
See application file for complete search history.

(56) References Cited

U.S. PATENT DOCUMENTS

| 5,116,964 A | 5/1992 | Capon et al. |
| 5,541,087 A | 7/1996 | Lo et al. |
| 5,620,939 A | 4/1997 | Halasa et al. |
| 6,344,192 B1 | 2/2002 | Grooten et al. |
| 8,124,084 B2 | 2/2012 | Lefrancois et al. |
| 8,507,222 B2 | 8/2013 | Wong et al. |
| 2003/0180888 A1 | 9/2003 | Fraser |
| 2004/0156826 A1 | 8/2004 | Dangond et al. |
| 2006/0263857 A1 | 11/2006 | Lefrancois et al. |
| 2009/0117618 A1 | 5/2009 | Herrmann et al. |
| 2009/0324538 A1 | 12/2009 | Wong et al. |

FOREIGN PATENT DOCUMENTS

| EP | 0971728 A1 | 1/2000 |
| EP | 1777294 A1 | 4/2007 |
| EP | 1934353 A2 | 6/2008 |
| KR | 10-2007-0002052 A | 1/2007 |
| WO | WO-94/04689 A1 | 3/1994 |
| WO | WO-94/29350 A2 | 12/1994 |
| WO | WO-96/32478 A1 | 10/1996 |
| WO | WO-97/34631 A1 | 9/1997 |
| WO | WO-2005/046449 A2 | 5/2005 |
| WO | WO-2005085282 A1 | 9/2005 |
| WO | WO-2007001677 A2 | 1/2007 |
| WO | WO-2008/143794 A1 | 11/2008 |
| WO | WO-2009117117 A1 | 9/2009 |

OTHER PUBLICATIONS

Gomes-Giacoi et al, Plos One, 2014, vol. 9, No. 6, pp. 1-11.*
Steel et al, Cancer Research, 2010, vol. 70, No. 3, pp. 1-19.*
Matsumoto et al, (Human Gene Therapy, 2011; vol. 22, pp. 1423-1432.*
Liu et al, (Journal for Immunotherapy of Cancer 2014, 2(Suppl 3).*
Jennifer Wu, Journal of molecular and genetic medicine, 2014, vol. 7: 85, pp. 1-6.*
Belmont et al. "Potent antitumor activity of a tumor-specific soluble TCR/IL-2 fusion protein." Clin Immunol. Oct. 2006;121(1):29-39.
Benton and David, "Screening λgt Recombinant Clones by Hybridization to Single Plaques in situ", Science, vol. 196:180-182. 1977.
Bessard et al., "High antitumor activity of RLI, an interleukin-15 (IL-15)-IL-15 receptor α fusion protein, in metastatic melanoma and colorectal cancer", Mol. Cancer Ther. vol. 8:2736-2745. Sep. 2009.
Bork, 2000, Genome Research 10:398-400.
Bouchard et al., "The Exon-3-Encoded Domain of IL-15Rα Contributes to IL-15 High-Affinity Binding and Is Crucial for the IL-15 Antagonistic Effect of Soluble IL-15Rα", Journal of Molecular Biology, vol. 382:1-12. 2008.
Capon et al., "Desgining CD4 immunoadhesins for AIDS therapy", Nature, vol. 337:525-531. Feb. 1989.
Chamow and Ashenazi, "Immunoadhesins: principles and applications", Trends Biotechnology., vol. 14:52-60. Feb. 1996.

(Continued)

*Primary Examiner* — Bridget E Bunner
*Assistant Examiner* — Fozia Hamud
(74) *Attorney, Agent, or Firm* — Mintz Levin Cohn Ferris Glovsky and Popeo, P.C.; Peter F. Corless, Esq.; Daniel W. Clarke

(57) ABSTRACT

The present invention features compositions and methods featuring ALT-803, a complex of an interleukin-15 (IL-15) superagonist mutant and a dimeric IL-15 receptor α/Fc fusion protein useful for enhancing an immune response against a neoplasia (e.g., multiple myeloma, melanoma, lymphoma) or a viral infection (e.g., human immunodeficiency virus).

16 Claims, 113 Drawing Sheets

(56) References Cited

OTHER PUBLICATIONS

Cragg and Glennie, :Antibody specificity controls in vivo effector mechanisms of anti-CD20 reagents, Blood, vol. 103:2738-2743. Apr. 2004.
Davis, "Molecular Genetics of the T Cell-Receptor Beta Chain", Annual Review of Immunology, vol. 3:537-560. 1985.
Doerks et al., 1998, Trends in Genetics 14:248-250.
Dubois et al., "Preassociation of IL-15 with IL-15Rα-IgG1-Fc Enhances its Activity on Proliferation of NK and CD8+/CD44high T cells and Its Antitumor Action", Journal of Immunology, vol. 180:2099-2106. 2008.
Epardaud et al., "Interleukin-15/Interleukin-15Rα Complexes Promote Destruction of Established Tumors by Reviving Tumor-Resident CD8+ T Cells", Cancer Research, vol. 68:2972-2983. Apr. 2008.
Fleer, "Engineering yeast for high level expression" Current Opinion in Biotechnology, vol. 3:486-496. 1992.
Galfre and Milstein, "Preparation of Monoclonal Antibodies: Strategies and procedures", Methods in Enzymology, vol. 73:1-46. 1981.
Gillies et al., "An anti-CD20-IL-2 immunocytokine is highly efficacious in a CSID mouse model of establishedhuman B lymphoma", Blood, vol. 105:3972-3978. May 2005.
Graham et al., "Characteristics of a Human Cell Line Transformed by DNA from Human Adenovirus Tyoe 5", Journal of General Viology, vol. 36:59-72. 1977.
Grunstein and Hogness, "Colony hybridization: A method for the isolation of cloned DNAs that contain a specific gene", Proc. Nat. Acad. Sci. USA, vol. 72:3961-3965. Oct. 1975.
Han et al., "IL-15:IL-15 receptor alpha superagonist complex: High-level co-expression in recombinanty mammalian cells, purification and characterization", Cytokine, vol. 56:804-810. 2011.
Hessell et al., "Fc receptor but not complement binding is important in antibody protection against HIV", Nature, vol. 449:101-105. Sep. 2007.
Hezareh M et al. "Effector function activities of a panel of mutants of a broadly neutralizing antibody against human immunodeficiency virus type 1." J Virol. Dec. 2001;75(24):12161-8.
Hughes et al., "Transfer of a TCR Gene Derived from a Patient with a marked Antitumor Response Conveys Highly Active T-Cell Effector Functions", Human Gene Therapy, vol. 16:457-472. Apr. 2005.
Kimmel, "Identification and Characterization of Specific Clones: Strategy for Confirming the Validity of Presumptive Clones", Methods in Enzymology, vol. 152:507-511. 1987.
Lawrencia et al., "Transfection of urothelial cells using methyl-β-cyclodxtrin solubilized cholesterol and Dotap", Gene Therapy, vol. 8:760-768.2001.
Lazar et al. "Transforming growth factor alpha: mutation of aspartic acid 47 and leucine 48 results in different biological activities." Mol Cell Biol. Mar. 1988;8(3):1247-52.
Mortier et al., "Soluble Interleukin-15 Receptor α (IL-15Rα)-sushi as a Selective and Potent Agonist of IL-15 Action through IL-15Rβ/γ", Journal of Biological Chemistrty, vol. 281:1612-1619. Jan. 2006.
Moskaug et al., "Translocation of Diptheria Toxin A-fragment to the Cytosol", Journal of Biological Chemistry, vol. 26:15709-15713. 1989.
Mosquera et al., "In Vitro and In Vivo Characterization of a Novel Antibody-Like Single-Chain TCR Human IgG1 Fusion Protein", Journal of Immunology,vol. 174:4381-4388. 2005.
Ng et al. "Liposomal Polyene Antobiotics", Methods in Enzymology, vol. 391:304-313. 2005.
Nogawa et al., "Intravesical administration of small interfering RNA targeting PLK-1 successfully prevents the growth of bladder cancer", Journal of CLinical investigation, vol. 115:978-985. 2005.
Olsnes and Phil, "Chimeric Toxins", Pharmacology and Therapeutics, vol. 26:355-381. 1982.
Ortiz-Sánchez et al. "Antibody-cytokine fusion proteins: applications in cancer therapy." Expert Opin Biol Ther. May 2008;8(5):609-32.
Pastan et al., "Immunotoxins", Cell, vol. 47:641-648. Dec. 1986.
Pastan et al., "Recombinant Toxins as Novel Therapeutic Agents", Annual Review Biochemistry, vol. 61:331-354. 1992.

Pettit DK et al. "Structure-function studies of interleukin 15 using site-specific mutagenesis, polyethylene glycol conjugation, and homology modeling." J Biol Chem. Jan. 24, 1997;272(4):2312-8.
Rossi et al., "CD20-targeted tetrameric interferon-α, a novel and potent immunocytokine fir the therapy of B-cell lymphomas", Blood, vol. 114:3864-3870. Oct. 2009.
Rubenstein et al., "Converting IL-15 to a superagonist by binding to soluble IL-15Rα", Proc. Natl. Acad. Sci. USA, vol. 103:9166-9171. Jun. 2006.
Skolnick et al, 2000, Trends in Biotech. 18(1):34-39.
Sprent et al., "T-cell proliferation in vivo and the role of cytokines", Philos. Trans R. Soc. Lond. B. Biol. Sci., vol. 355:317-322. 2000.
Stoklasek et al., "Combined IL-15/IL-15Rα Immunotherapy Maximizes IL-15 Activity In Vivo", Journal of Immunology, vol. 177:6072-6080. 2006.
Tietze et al., "Delineation of antigen-specific and antigen-nonspecific CD8+ memory T-cell responses after cytokine-based cancer immunotherapy", Blood, vol. 119:3073-3082. Mar. 2012.
Tokuriki and Tawflik, Current Opinion in Structural Biology 2009, 19:596-604.
Tough et al., "An IFN-α-Dependent Pathway Controls Stimulation of Memory Phenotype CD8+ T Cell Turnover In vivo by IL-12, IL-18, and IFN-α", Journal of Immunology, vol. 166:6007-6011. 2001.
Trevisani et al., "Ethanol Causes Inflammation in the Airways by a Neurogenic and TRPV1-Dependent Mechanism", Journal of Pharmacology and Experimental Therapeutics, vol. 309:1167-1173. 2004.
Trevosani, "Ethanol elicits and potentiates nociceptor responses via the vanilloid receptor-1", Nature Neuroscience, vol. 5:546-551. 2001.
Tyagi et al., "Urodynamic and Immunohistochemical Evaluation of Intravesical Capsaicin Delivery Using Thermosensitive Hydrogel and Liposomes", Journal of Urology, vol. 171:483-489. Jan. 2004.
Urlaub and Chasin, "Isolation of Chinese hamster cell mutants deficient in dihydrofolate reductase activity", Proc. Natl. Acad. Sci. USA, vol. 77:4216-4220. Jul. 1980.
Villinger et al., "IL-15 is superior to IL-2 in the generation of long-lived antigen specific memory CD4 and CD8 T cells in rhesus macaques", Vaccine, vol. 22:3510-3521. 2004.
Wahl et al., "Molecular Hybridization of Immobilized Nucleic Acids: Theoretical Conepts and Practical Considerations", Methods in Enzymology, vol. 152:399-407. 1987.
Waldmann et al. IL-15 Receptors, 2000, pp. 1521-1528.
Waldmann, "The biology of interleukin-2 and interleukin-15: implications for cancer therapy and vaccine design", Nature Reviews Immunology, vol. 6:595-601. Aug. 2006.
Ward et al., "E. coli expression and purification of human and cynomolgus IL-15", Protein Expression and Purification, vol. 68:42-48. 2009.
Weidanz JA, "Display of functional alphabeta single-chain T-cell receptor molecules on the surface of bacteriophage." J Immunol Methods. Dec. 1, 1998;221(1-2):59-76.
Wells JA et al. "Additivity of mutational effects in proteins." Biochemistry. Sep. 18, 1990;29(37):8509-17.
Wen J. et al. "Targeting activity of a TCR/IL-2 fusion protein against established tumors." Cancer Immunol Immunother. Dec. 2008;57(12):1781-94.
Whitlow and Filpula, "Single-Chain Fv Proteins and Their Fusion Proteins", Methods: A Companioni to methods in Enzymology, vol. 2:97-105. Apr. 1991.
Wong et al., "Interleukin-15:Interleukin-15 receptor α scaffold for creation of multivalent targeted immune molecules", Protein Engineering, Design & Delection, vol. 24:373-383. Dec. 2010.
Xuan et al., "Targeted deliuvery of interferon-alpha via fusion to anti-CD20 results in potent antitumor activity against B-cell lymphome", Blood, vol. 115:2864-2871. Apr. 2010.
Zhang et al., "Potent and Selective Stimulation of Memory-Phenotype CD8+ T Cells In Vivo by IL-15", Immunity, vol. 8:591-599. May 1998.
Zhu X et al. "Novel human interleukin-15 agonists." J Immunol. Sep. 15, 2009;183(6):3598-607.

(56) References Cited

OTHER PUBLICATIONS

Zhu X. et al. "Visualization of p53(264-272)/HLA-A*0201 complexes naturally presented on tumor cell surface by a multimeric soluble single-chain T cell receptor." J Immunol. Mar. 1, 2006;176(5):3223-32.

Zhu, et al., "Novel Human Interleukin-15 Agonists", Journal of Immunology, vol. 183:3598-3607. 2009.

Bergamaschi et al., "Intracellular Interaction of Interleukin-15 with Its Receptor alpha during Production Leads to Mutual Stabilization and Increased Bioactivity", Journal of Biological Chermistry, vol. 283:4189-4199. Feb. 2008.

Bevan, "In thymic Selection, Peptide Diversity Gives and Takes Away", Immunity, vol. 7:175-178. Aug. 1997.

Bjorkman, "MHC Restriction in Three Dimensions: A View of T Cell Receptor/Ligand Interactions", Cell, vol. 89:167-170. Apr. 1997.

Davis and Bjorkman, "T-cell antigen receptor genes and T-cell recognition", Nature, vol. 334:395-402. Aug. 1988.

Davis, M et al., "Ligand Recognition by alpha beta T Cell Receptors", Annual Rev. Immunology. vol. 16:523-44. 1998.

Rabinowitz et al., "Kinetic discrimination in T-cell activation", Proc. Natl Acad. Sci. USA, vol. 93:1401-1405. Feb. 1996.

Tomalia, D., "Starburst/Cascade Dendrimers: Fundamental Building Blocks for a new Nanoscopic Chemistry Set", Aldrichimica Acta, vol. 26:91-101. 1993.

Tonegawa, "Somatic Generation of Immune Diversity", Bioscience Reports, vol. 8:326. Dec. 1987.

Valltuttl, et al., "Serial triggering of many T-cell receptors by a few peptide-MHC complexes", Nature, vol. 375:148-150. May 1995.

Bernard et al., "Identification of an interleukin-15alpha receptor-binding site on human interleukin-15." J Biol. Chem. 279(23):24313-24322 (2004).

Stratagene Catalog, p. 39, "Gene Characterization Kits," 2 pages (1988).

The Merck Manual, Beers and Berkow Editors, 17th Edition, pp. 986-995 (1999).

* cited by examiner

| FIG. 3A |
|---------|
| FIG. 3B |
| FIG. 3C |

FIG. 3

FIG. 3A atggacagacttacttcttcattcctgctcctgattgtccctgctacgtcttgtccca gtcagtgacgcagcccgatgctcgcgtctcgaaggagcctctctgcagctga gatgcaagtattcctactctggacaccttatctgttctggtatgtccagtacccgcgg cagggctgcagctgctcctcaagtactattcaggagaccccagtggttcaaggagtgaa tggcttcgaggctgagttcagcaagagtaactcttccttccactgcgaggaagcctctg tgcactggagcgactctgctgtgtacttctgtgttttgagcgaggatagcaactatcag ttgatctgggctctgggaccaagctaattatataaagccaggttctggcgcggtgg cagcggcggtggtggttccggtggcggcgggttcctgcggttcctcgagcaatt caaaagtcattcagactccaagatatctggtgaaagggcaaggacaaaaagcaaagatg

FIG. 3B

```
aggtgtatccctgaaaaggacatccagttgtattctggtatcaacaaataagaacaa
tgagtttaaattttgattaacttcagaatcaagaagttcttcagcaaatagacatga
ctgaaaaacgattctctgctgagtgtccttcaaactcaccttgcagcctagaaattcag
tcctctgaggcagagactcagcactgtacctctgtgccagtctgtcaggggggg
cacagaagtttctttggtaaaggaaccaggctcacagttgtagaggacctgaacaagg
tgttcccacccgaggtcgctgtgtttgagccatcagaagcagagatctccacaccaa
aaggccacactggtgtgcctggccacaggcttctccctgaccacgtggagctgagctg
gtgggtgaatgggaaggaggtgcacagtgggtcagcacggacccgcagccctcaagg
agcagccgccctcaatgactccagactactgcctgcctgagcagccgcctgaggtctcggcc
acttctctggcagaacccccaggataggccaaccactttccagtcctagttctacggctctc
ggagaatgacgagtggacccaggacgaattcatcacgtgccctccccatgtccgcagcgccg
aggctggggtagacgagccggcacggagctacagccttgtactccagcctccagatcgtcagcgccg
gcagacatctggtcaagcggcaaccccagctacagcggtacatttgaacaaggcca
tggtttcaagcgccactggacaaccccagtccccaaatgcttcaaatgcttccacc
cgaatgtcgccctggacaaccccctggcaccctcctccaagagcaccttcgcctccacc
aagggcccatcggtcttcccccctggcaccctcctccaagagcaccctctggggcacagc
ggccctgggctgcctggtcaaggactacttcccgaaccggtgacggtgtcgtggaact
```

FIG. 3C caggcgcgccctgaccagcggcgtgtgcacacttcccggctgtcctacagtcctcaggactc
tactccctcagcagcgtggtgacggtgcctcccagcagcttgggcaccagacctacat
ctgcaacgtgaatcacaagcccagcaacaccaaggtggacaagaaagttgagcccaaat
cttgtgacaaactcacacatgccaccgtgcccagcacctgaactcctgggggaccg
tcagtcttcctcttccccaaaacccaaggacacctcatgatctcccgacccctga
ggtcacatgcgtggtggtggacgtgagccacgaagaccctgaggtcaagttcaactggt
acgtggacggcgtggaggtgcataatgccaagacaaagccgcgggaggagcagtacaac
agcacgtaccgtgtgtcagcgtcctcaccgtcctgcaccaggactggctgaatggcaa
ggagtacaagtgcaaggtctccaacaaagccctcccagcccccatcgagaaaaccatct
ccaaagccaaagggcagccccgagaaccaggtcagcctgacctgcctggtcaaaggcttctatcccagcga
gagctgaccaagaaccaggtcagcctgacctgcctggtcaaaggcttctatcccagcga
catccgcgtggagtgggagagcaatgggcagccggagaacaactacaagaccacgcctc
ccgtgctggactccgacggctccttcttcctctacagcaagctcaccgtggacaagagc
aggtggcagcaggggaacgtcttctcatgctccgtgatgcatgaggctctgcacaacca
ctacacgcagaagagcctctccctgtctccgggtaaa mdrltssflllivpayvlsqsvtqpdarvtvsegaslqlrckysysgtpylfwyvqypr <—————————————><————————————————————————————————————
      Ig leader                    TCR-Vα qglqlllkyysgdpvvqgvnqfeaefsksnssfhlrkasvhwsdsavyfcvlsedsnyq
——————————————————————————————————————————————————————————
                         TCR-Vα

FIG. 4B liwgsgtkliikpdtsggggsggggsggggsggggssnskvlqtprylvkgggqkakm

TCR-Vα >< linker rcipekghpvfwyggnknnefkflinfqngevlqqidmtekrfsaecpsnspcsleiq linker >< TCR-Vβ sseagdsalylcasslsggqatevffgkgtrltvvedlnkvfppevavfepseaeishtq

TCR-Vβ >< TCR-Cβ katlvclatgffpdhvelswwvngkevhsgvstdpqplkeqpalndsryclssrlrvsa

TCR-Cβ

FIG. 4C tfwqnprnhfrcqvgfyglsendewtqdrakpvtqivsaeawgradefitcpppmsveh

TCR-Cβ  >  <  huIL-15RαSu adiwvksyslysreryicnsgfkrkagtssltecvlnkatnvahwttpslkcirefast huIL-15RαSu  >  <  huIgG1 kgpsvfplapssksstsggtaalgclvkdyfpepvtvswnsgaltsgvhtfpavlqssgl huIgG1 constant region yslssvvtvpssslgtqtyicnvnhkpsntkvdkkvepkscdkthtcppcpapellggp huIgG1 constant region

FIG. 4D svflfppkpkdtlmisrtpevtcvvvdvshedpevkfnwyvdgvevhnaktkpreeqyn
huIgG1 constant region styrvvsvltvlhqdwlngkeykckvsnkalpapiektiskakgqprepqvytlppsrd
huIgG1 constant region eltknqvsltclvkgfypsdiavewesngqpennykttppvldsdgsffflysklt vdks
huIgG1 constant region rwqqgnvfscsvmhealhnhytqkslslspgk >
huIgG1 constant region

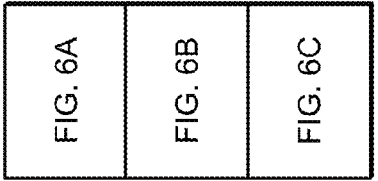

ATGGAGACAGACACACTCCTGTGTTATGGGTACTGCTGCTCTGGGTTCCAGGTTCCACCGG
TCAGTCAGTGACGCAGCCCGATGCTCGCGTCACTGTCTCTGAAGGAGCCTCTCTGCAGC
TGAGATGCAAGTATTCCTGGGACACCTTATCTGTTCTGGTATGTCCAGTACCCG
CGGCAGGGGGCTGCAGCTGCCTCCCTCAAGTACTATTCAGGAGACCCAGTGGTTCAAGGAGT
GAATGGCTTTCGAGGCTGAGTTCAGCAAGAGTAACTCTTCCTTCCACCTGCGGAAAGCCT
CTGTGCACTGGAGCGACTCTGCTGTGTACTTCTGTGTTTGAGCGAGGATAGCAACTAT
CAGTTGATCTCTGGGGCTCTGGGACCAAGCTAATTATAAAGCCAGACACTAGTGGTGGCGG
TGGCAGCGGCGGTGGTTCCGGTGGCGGTCGGTGAAAGGGCAAGGACAAAAAGCAAAG
ATTCAAAAGTCATTCAGACTCCCTGAAAGGGACATCCAGTGTATTCTGGTATCAACAAATAAGAA
ATGAGGTGTATCCCTGAAATTTTGATTAACTTTCAGAATCAAGAAGTTCTTCAGCAAATAGACA
CAATGAGTTTAAATTTTGATTCTTCTGCTGAGTGTCCTTCAAACTCACCTTGCAGCCTAGAAATT
TGACTGAAAAACGATTCTCTGCTGAGTGTCCTTCAAACTCACCTTGCAGCCTAGAAATT

FIG. 6B

CAGTCCTCTGAGGCAGGAGACTCAGCACTGTACCTCTGTGCCAGCAGTCTGTCAGGGGG
CGGCACAGAAGTTTTCTTTGGTAAAGGAACCAGGCTCACAGTTGTAGAGGACCTGAACA
AGGTGTTCCCACCCGAGGTCGCTGTGTTTGAGCCATCAGAAGCAGAGATCTCCACACC
CAAAAGGCCACACTGGTCTGCCCACAGGCTTCTTCCCTGACCACGTGGAGCTGAG
CTGGTGGGTTAAGGGAAGGAGGTGCACAGTGGGTCAGGACCCGCAGCCCCTCA
AGGAGCAGCCCCGCCCTCAATGACTCCAGATACTGCCTGAGCGTGTCAGTCCAGTCTCG
GCCACCTTCGGCAGAATGACGAGTGGACACCACTTCGCTGTCAAGTCCAGTTCTACGGCT
CTCGGAGAATGACGAGTGGACAGCAGACATCACGTGCCCCCCATGTCCGTGAACACGCA
CCGAGGCCTGGGGTAGAGCAGCTACAGCTTGTACTCCAGGCCTGACGGAGCGGTACATTTGTAACTTCTGG
GACATCTGGGGTCAAGACCGGCCAACCCCAGTCTCAAATGTATTAGAGCTAGCACCAAGGCCACGA
TTTCAAGCGTAAAGCCGGCACCTGGGGCACTCTGGGGCACAGGGCCCTGGG
ATGTCGCCACTGGACAACCCCAGTCTCAAATGTATTAGAGCTAGCACCAAGGCCCA
TCGGTCTTCCCCCTGGCACCTTCCCCGAACCGGTGACGGTGTCGTGAACTCAGGCGCC
CTGCCTGGTCAAGCGGGTGCACACCTTCCCGGCTGTCCTACAGTCCTCAGGACTCTACTCCCTC
TGACCAGCGGGTGGTGACCGTGCCCTCCAGCAGCTTGGGCACCCAGACCTACATCTGCAACGT
AGCAGCGTGACAAGCCCAAGTTGAGCAAGAAAGTTGAGCCCAAAATCTTGTGACA
GAATCACAA

FIG. 6C

AAACTCACACATGCCCAGCACCTGAACTCCTGGGGGGACCGTCAGTCTTC
CTCTTCCCCCAAAACCCAAGGACACCCTCATGATCTCCCGGACCCCTGAGGTCACATG
CGTGGTGGTGGACGTGAGCCACGAAGACCCTGAGGTCAAGTTCAACTGGTACGTGGACG
GCGTGGAGGTGCATAATGCCAAGACAAAGCCGCGGGAGGAGCAGTACAACAGCACGTAC
CGTGTGGTGTCAGCGTCCTGCACCGTCCTGCACCAGGACTGGCTGAATGGCAAGGAGTACAA
GTGCAAGGTCTCCAACAAAGCCCTCCCAGCCCCCATCGAGAAAACCATCTCCAAAGCCA
AAGGGCAGCCCCGAGAACCACAGGTGTACACCCTGCCCCCATCCCGGGATGAGCTGACC
AAGAACCAGGTCAGCCTGACCTGCCTGGTCAAAGGCTTCTATCCCAGCGACATCGCCGT
GGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACACGCA
GAAGAGCCCTCTCCCTGTCTCCGGGTAAATAA

FIG. 7

| FIG. 7A |
| FIG. 7B |
| FIG. 7C |
| FIG. 7D |

FIG. 7A metdtlllwvllllwvpgstggsvtqpdarvtvsegaslqlrckysysgqtpvlfwyvqyp
       v
       Ig leader              TCR-Vα rqglqlllkyysgdpvvqgvngfeaefsksnssfhlrkasvhwsdsavyfcvlsedsny
       TCR-Vα

FIG. 7B  qliwqsqtkliiikpdtsggggsggggsggggsggggssnskvigtpryvlkqqqkak

TCR-Vα          linker              TCR-Vβ mrcipekghpvvfwyqqnkmnefkflinfqngevlqqidmtekrfsaecpsnspcslei

TCR-Vβ qsseaqdsalylcasslsqqgtevffgkatrltvvedlnkvfppevavfepseaeisht

TCR-Vβ                                              TCR-Cβ qkatlvclatgffpdhvelswwvngkevhsgvstdpqplkeqpalndsryclssrlrvs

TCR-Cβ

FIG. 7C atfwqnprnhfrcgvqfygglsendewtqdrakpvtqivsaeawgradictcppmsveha
            TCR-Cβ                                    huIL-15RαSu

>< diwvksyslysreryicnsgfkrkagtssltecvlnkatnvahwttpslkcirastkgp
            huIL-15RαSu                                    huIgG1

>< svfplapsskstsggtaalgclvkdyfpepvtvswnsgaltsqvhtfpavlqssglysl
            huIgG1 constant region ssvvtvpssslgtqtyicnvnhkpsntkvdkkvepkscdkthtcppcpapellggpsvf
            huIgG1 constant region

FIG. 7D ifppkpkdtlmisrtpevtcvvvdvshedpevkfnwyvdgvevhnaktkpreeqynsty huIgG1 constant region rvvsvltvlhqdwlngkeykckvsnkalpapiektiskakgqprepqvytlppsrdelt huIgG1 constant region knqvsltclvkgfypsdiavewesngqpennykttppvldsdgsffflysklltvdksrwq huIgG1 constant region ggnvfscsvmhealhnhytqkslslspgk huIgG1 constant region

FIG. 9A

| FIG. 9A |
|---------|
| FIG. 9B |

FIG. 9

ATGGACAGAGACTTACTTCTTCTTCATTCCCTGCTCCCTGATTGTCCCTGCTACGTCTTGCCCA
GAAGGTAACACAGACTCAGACTTCAATTTCTGTGATGGAGAAGACAACGGTGACAATGG
ACTGTGTGTATGAAACCCGGGACAGTTCTTACTTCTCTTATTCTGGTACAAGCAAACAGCA
AGTGGGGAAATAGTTTTCCTTATTCGTCAGGACTCTTACAAAAAGGAAAATGCAACAGA
AGGTCATTATTCTCTGAACTTTCAGAAGCCCAAAAAGTTCCATCGGACTCATCATCACTG
CCACACAGATTGAGGACTCAGCAGTATATTTCTGTGCTATGAGAGACACAAATGCTTAC
AAAGTCATCTTTGGAAAAGGGACACATCTTCATGTTCTGCCTACTAGTGGTGGCGGTGG
CAGCGGCGGCGGTGGTTCCCCTGGGGCGGGGTTCTGGCGGTGGCGGTTCCTCCGAGCG
AGGCTGCCAGTCACCCAAAGTCCAAGAAGCAAGGTGGCAGTAACAGGAGGAAAGGTGACA
TTGAGCTGTGTCACCAGAGACTAATAACCATGACTATATGTACTGGTATCGGCAGGACACGGG
GCATGGGCTGAGGCTGATCCATTACTCATTATGTCGCTGACAGCACGGAGAAAGGAGATA
TCCCTGATGGGTACAAGGCCCTCCAGACCAAGCCAAGAGAATTTCTCTCATTCTGGAG

FIG. 9B

TTGGCTTCCCTTTCTCAGACAGCTGTATATTTCTGTGTGCCAGCAGCCCCCACTCCTATGA
ACAGTACTTCGGTCCCGGCACCAGGCTCACGGTTTTAGAGGACCTGAACAAGGTGTTCC
CACCCGAGGTCGCTGTGTTTGAGCCATCAGAGAAGCAGAGATCTCCCACACCAAAAGGCC
ACACTGGTCGTGCCTGGCCACAGGCTTCTCCCTGACCACGTGGAGCTGAGCTGGTGGGT
TAACGGGAAGGAGGTGCACAGTGGGGTCAGCACGGACCCGCAGCCCCTGAGGAGCAGC
CCGCCCTCAATGACTCCAGATACTGCCTGAGCAGCCGCCTCCAGTTCTACGGCTCTCGGAGAA
TGGCAGAACCCCCGCAACCACTTCCGCTGTCAAGTCCAGTTCACCCAGATCGTCAGCGCCGAGGCCT
TGACGAGTGGACCCAGGATAGGGCCAAACCTGTCACCCAGATCGTCAGCGCCGAGGCCT
GGGGTAGAGCAGACAACTGGGTGAATGTAATAAGTGATTTGAAAAAAATTGAAGATCTT
ATTCAATCTATGCATATTGATGCTACTTTATATACGGAAAGTGATGTTCACCCCAGTTG
CAAAGTAACAGCAAGTGCTTTCTCTTGGAGTTACAAGTTATTTCACTTGAGTCCG
GAGATGCAAGTATTCATGATACAGTAGAAAATCTGATCATCCTAGCAAACGACAGTTTG
TCTTCTAATGGGAATGTAACAGAATCTGGATGCAAAGAATGTGAGGAACTGGAGGAAAA
AAATATTAAAGAATTTTTGCAGAGTTTTGTACATATTGTCCAAATGTTCATCAACACTT
CTTAA

FIG. 10

| FIG. 10A |
|----------|
| FIG. 10B |
| FIG. 10C |

FIG. 10A mdrltssflllivpayvlagkvtgtqtsisvmekttvtmdcvyetrdssyflfwykqta

Ig leader        TCR-Vα sgeivflirqdsykkenateqhysinfgkpkssigliiitatqiedsavyfcamrdtnay

TCR-Vα

FIG. 10B kvifgkgthlhvlptsggggsggggspggggsggggssseaavtgspriskvavtggkvt

TCR-Vα           linker           TCR-Vβ lschqtnnhdymywyrqdtqhglrlihysyvadstekgdipdgykasrpsgqenfsille

TCR-Vβ laslsqtavyfcasssphsyeqvfgpgtrltvledlnkvfppevavfepseaeishtqka

TCR-Vβ           TCR-Cβ tlvclatgffpdhvelswwvngkevhsgvstdpqplkeqpalndsryclssrlrvsatf

TCR-Cβ

FIG. 10C wqnprnhfrcqvqfyglsendewtqdrakpvtgivsaeawgradnwvnvisdlkkiedl
    TCR-Cβ                                                    >< huIL-15N72D igsmhidatlytesdvhpsckvtamkcfllelqvislesgdasihdtvenliilandsl
    huIL-15N72D ssngnvtesgckeceeleekniikefIgsfvhivgmfints
    huIL-15N72D                            >

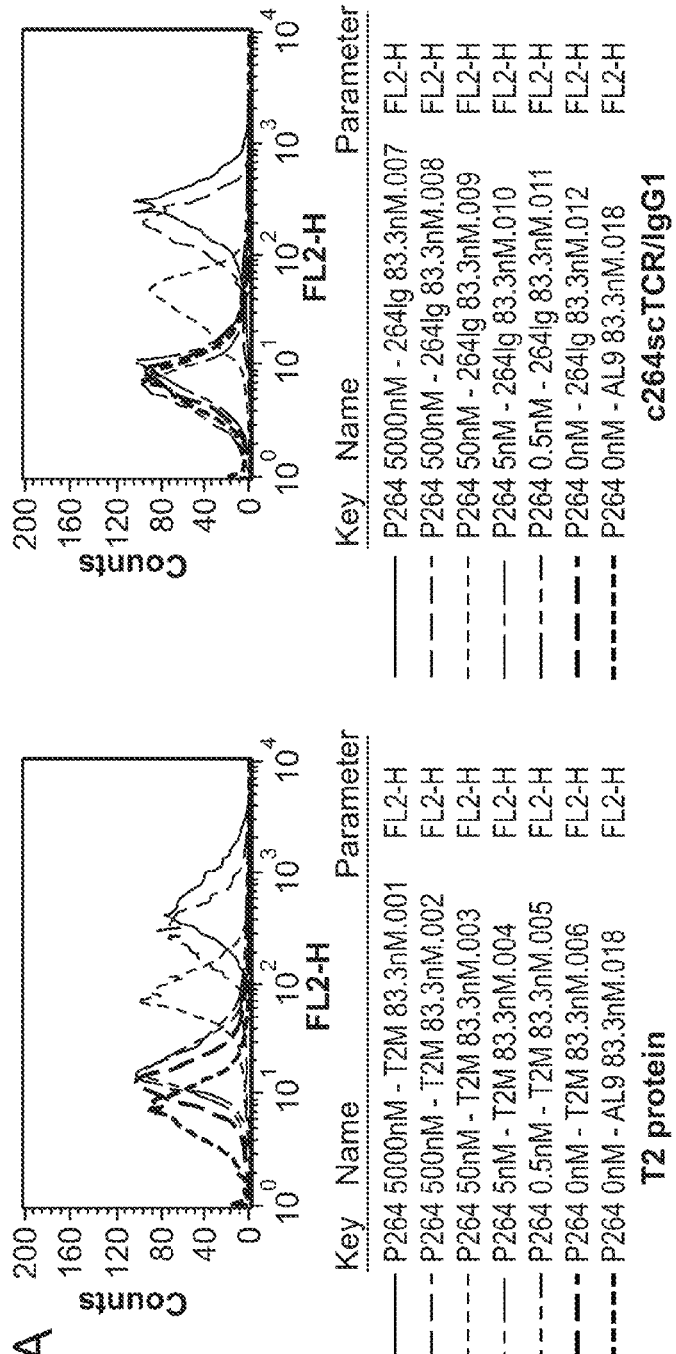
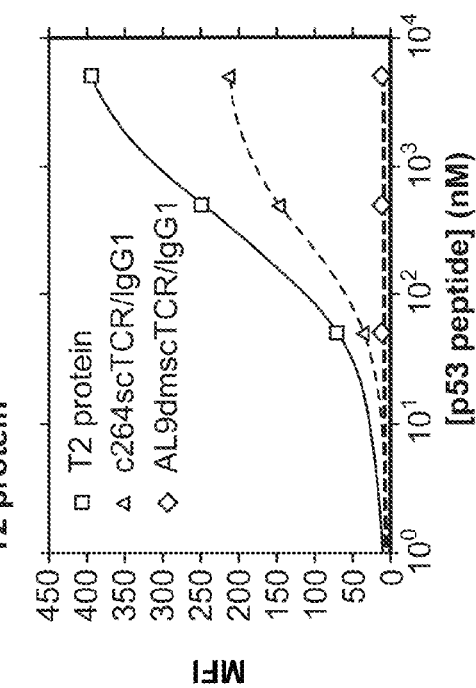
FIG. 21A
FIG. 21B

Mouse study

Monkey study

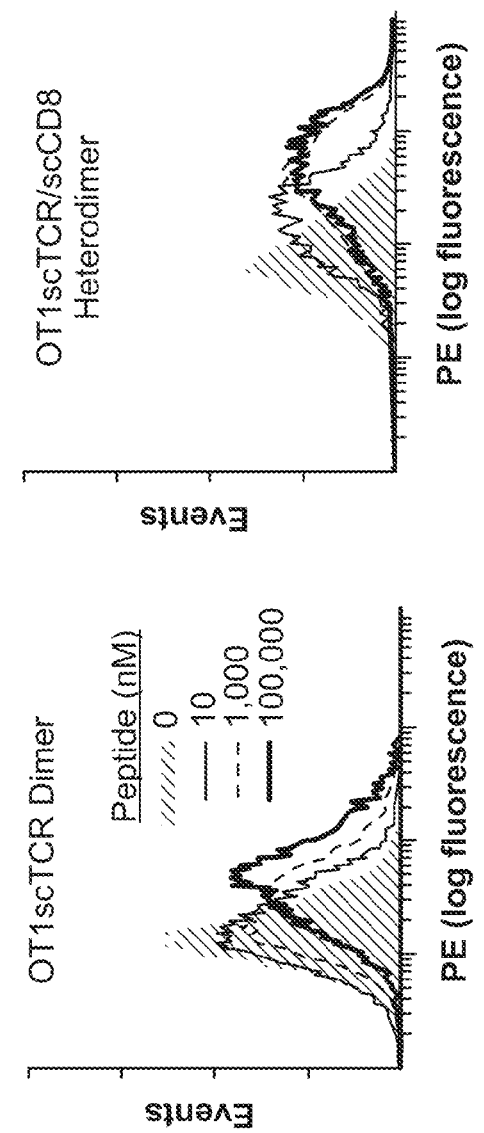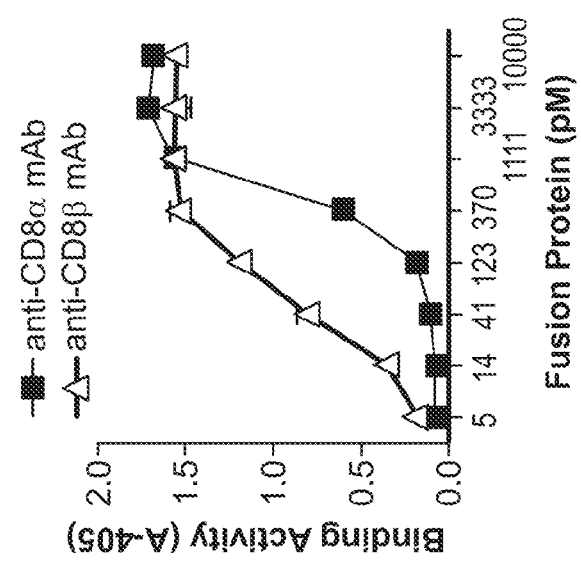
FIG. 39B
FIG. 39A

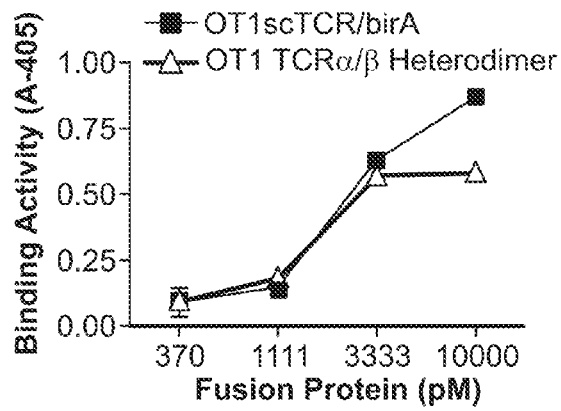
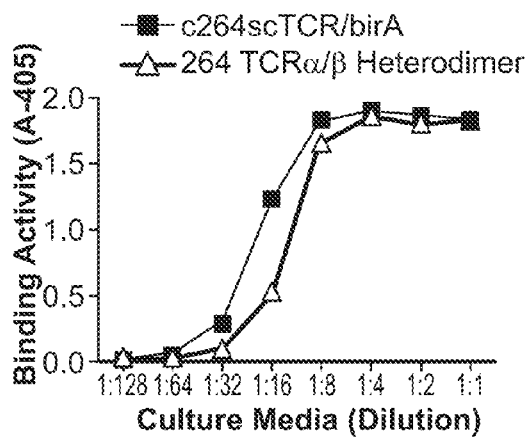
FIG. 40A
FIG. 40B
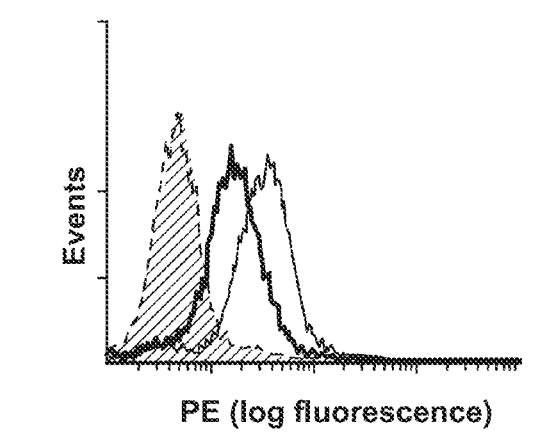
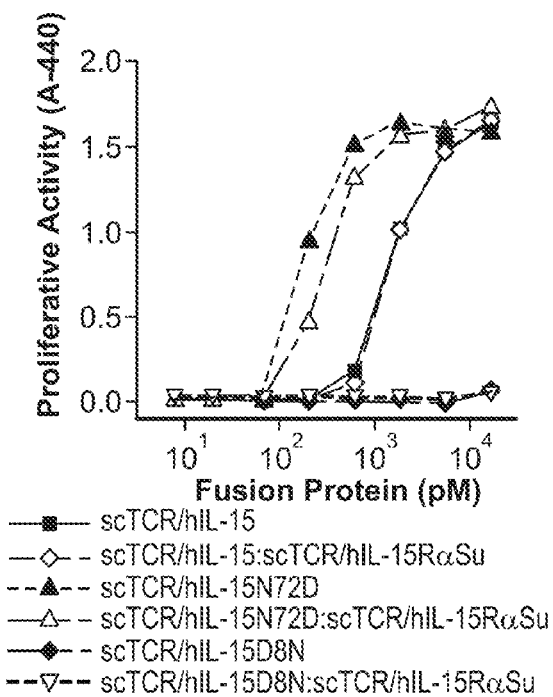
FIG. 41A
FIG. 41B epkscdkthtcppcpapelliggpsvflfppkpkdtlmisrtpevtcvvvdvshedpevk
fnwyvdgvevhnaktkpreeqynstyrvvsvltvlhqdwlngkeykckvsnkalpapie
ktiskakgqprepqvytlppsrdeltknqvsltclvkgfypsdiavewesngqpennyk
ttppvldsdgsfflysklltvdksrwqqgnvfscsvmhealhnhytqkslslspgk

| FIG. 51A |
| FIG. 51B |
| FIG. 51C |
| FIG. 51D |

FIG. 51A

ATGGAGACAGACACACTCCTGTTATGGGTACTGCTGCTCTGGGTTCCAGG
< leader seq
TTCCACCGGTCAGTCAGTGACGCAGCCCCGATGCTCCGCGTCACTGTCTCTG
>< c264scTCR
AAGGAGCCCTCTCTGCAGCTGAGATGCAAGTATTCCTACTCTGGGACACCT
TATCTGTTCTGGTATGTCCAGTACCCCGGCGGGTCAGGGGTGCAGCTGCTCCT
CAAGTACTATTCAGGAGACCCAGTGGTTCAAGGAGTGAATGGCTTCGAGG
CTGAGTTCAGCAAGAGTAACTCTTCCTTCCACCTGCGGAAAGCCTCTGTG
CACTGGAGCGACTCTGCTGTGTACTTCTGTGTTTTGAGCGAGGATAGCAA
CTATCAGTTGATCTGGGGCTCTGGGACCAAGCTAATTATAAAGCCAGACA
CTAGTGGTGGCGGTGGCAGCGGCGGTGGTTCCGGTGGCGGCGGTTCT FIG. 51B GGCGGTGGCGGTTCCTCGAGCAATTCAAAAGTCATTCAGACTCCAAGATA
TCTGGTGAAAGGGCAAGGACAAAAGCAAAGATGAGGTGTATCCCTGAAA
AGGGACATCCAGTTGTATTCTGGTATCAACAAATAAGAACAATGAGTTT
AAATTTTTGATTAACTTTCAGAATCAAGAAGTTCTTCAGCAAATAGACAT
GACTGAAAAACGATTCTCTGCTGAGTGTCCTTCAAACTCACCTTGCAGCC
TAGAAATTCAGTCCCTCTGAGGCAGGAGACTCAGCACTGTACCTCTGTGCC
AGCAGTCTGTCAGGGGGCGGCACAGAAGTCTTCTTTGGTAAAGGAACCAG
GCTCACAGTTGTAGAGGACCTGAACAAGGTGTTCCCACCCGAGGTCGCTG
TGTTTGAGCCATCAGAAGCAGAGATCTCCCACCCAAAAGGCCACACTG
GTGTGCCTGGCCACAGGCTTCTTCCCTGACCACGTGGAGCTGAGCTGGTG
GGTTAACGGGAAGGAGGTGCACAGTGGGGTCAGCACGGACCCGCAGCCCC
TCAAGGAGCAGCCCGCCCACCTTCTGGCAGAACCCCGCAACCACTTCCGCTG
CTGAGGGTCTCGGCCTCTACGGGCTCTCGGAGAATGACGAGTGGACCCAGGATA
TCAAGTCCAGTTCTACGGGCTCTCGGAGAATGACGAGTGGACCCAGGATA
GGGCCAAACCCGTCACCCAGATCGTCAGCGCCCGAGGCCCTGGGGTAGAGCA

FIG. 51C

```
GACATCACGTGCCCTCCCCCCATGTCCGTGGAACACGCAGACATCTGGGT
><    Human IL-15R α sushi domain
CAAGAGCTACAGCTTGTACTCCAGGGAGCGGGTACATTTGTAACTCTGGTT
TCAAGGGTAAAGCCGGCACGTCCAGCCCTGACGGAGTGCGTGTTGAACAAG
GCCACGGAATGTCGCCCCACTGGACAACCCCCAGTCTCAAATGCATTAGAGA
                                              ><
GCCGAAATCTTGTGACAAAACTCACACATGCCCACCGTGCCCAGCACCTG
   Human IgG1 CH2-CH3 (Fc) domain
AACTCCTGGGGGGACCGTCAGTCTCTTCCTCTTCCCCCCAAAACCCAAGGAC
ACCCTCATGATCTCCCGGACCCCTGAGGTCACATGCGTGGTGGTGGACGT
GAGCCACGAAGACCCTGAGGTCAAGTTCAACTGGTACGTGGACGGCGTGG
AGGTGCATAATGCCAAGACAAAAGCCGCGGGAGGAGCAGTACAACAGCACG
TACCGTGTGGTCAGCGTCCTCACCGTCCTGCACCAGGACTGGCTGAATGG
```

FIG. 51D

CAAGGAGTACAAGTGCAAGGTCTCCAACAAAGCCCTCCCAGCCCCCATCG

AGAAAACCATCTCCAAAGCCAAAGGGCAGCCCCGAGAACCACAGGTGTAC

ACCCTGCCCCCATCCCGGGATGAGCTGACCAAGAACCAGGTCAGCCTGAC

CTGCCTGGTCAAAGGCTTCTATCCCAGCGACATCGCCGTGGAGTGGGAGA

GCAATGGGCAGCCGGAGAACAACTACAAGACCACGCCTCCCGTGCTGGAC

TCCGACGGCTCCTTCTTCCTCTACAGCAAGCTCTTCTCATGCTCCGTGATGCATGAGGCTCTGC

GTGGCAGCAGGGGAACGTCTTCTCATGCTCCGTGATGCATGAGGCTCTGC

ACAACCACTACACGCAGAAGAGCCTCTCCCTGTCTCCCTGGTAAATAA ∧

FIG. 52 qsvtqpdarvtvsegaslglrckysysgtpylfwyvqypraglqllkysgdpvvggvn
< c264scTCR gfeaefsksnssfhlrkasvhwsdsavyfcvlsedsnyqliwgsgtkliikpdtsgggggs ggggsggggsggggssnskviqtprylvkgggkakmrcipekghpvvfwyqqnknnef kflingqevlgqidmtekrfsaecpsnspcsleiqsseagdsalylcasslsgggtev ffgkgtrltvvedlnkvfppevavfepseaeishtqkatlvclatgffpdhvelswwvng kevhsgvstdpqplkeqpalndsryclssrlrvsatfwqnprnhfrcqvqfyglsendew tqdrakpvtqivsaeawgraditcpppmsvehadiwvksyslysreryicnsgfkrkagt
>< Human IL-15R α sushi domain ssltecvlnkatnvahwttpslkcirepkscdkthtcppcpapellggpsvflfppkpkd
>< Human IgG1 CH2-CH3 (Fc) domain tlmisrtpevtcvvvdvshedpevkfnwyvdgvevhnaktkpreeqynstyrvvsvltvl hqdwlngkeykckvsnkalpapiektiskakgqprepqvytlppsrdeltknqvsltclv kgfypsdiavewesnggpennykttppvldsdgsfflyskltvdksrwqqgnvfscsvmh ealhnhytqkslslspgk
>

FIG. 53

| FIG. 53A |
|----------|
| FIG. 53B |

FIG. 53A

ATGGATTTTCAGGTGCAGATTATCAGCTTCCTGCTAATCAGTGCTTCAGT
< leader seq

CATAAATGTCCAGAGGACAAAATTGTTCTCTCCCAGTCTCCAGCAATCCCTGT

CTGCATCTCCAGGGGAGAAGGTCACAAATGACTTGCAGGGCCAGCTCAAGT
< anti-CD20 light chain V domain

GTAAGTTACATGCCACATCCAACATCCAAGAAGCCAGGATCCCTTCCCCCAAACC

CTGGATTTATGCCACATCCAACCTGGCTTCTGGAGTCCCTGTTCGCTTCA

GTGGCAGTGGGTCTGGGACTTCTTACTCTCTCACAATCAGCAGAGTGGAG

GCTGAAGATGCTGCCACTTATTACTGCCAGCAGTGGACTAGTAACCCACC

CACGTTCGGAGGGGGGACCAAGCTGGAAATCAAAAGTGGAGGTGGCGGAT
          linker
          ><

CAGGAGCCCGAGGTTCTGGCGGAGGTGGAGTCAGGTACAACTGCAGCAG

CCTGGGGCTGAGCTGGTGAAGCCTGGGGCCTCAGTGAAGATGTCCTGCAA
< anti-CD20 heavy chain V domain

GGCTTCTGGCTACACATTTACCAGTTACAATATGCACTGGGTAAAACAGA

FIG. 53B

```
CACCTGGTCGGGGCCTGGAATGGATTGGAGCTATTTATCCCGGAAATGGT
GATACTTCCTACAATCAGAAGTTCAAAGGCAAGGCCACATTGACTGCAGA
CAAATCCTCCAGCACAGCCTACATGCAGCTCAGCAGCCTGACATCTGAGG
ACTCTGCGGTCTATTACTGTGCAAGATGACTTACTACGGGGGTGACTGG
TACTTCAATGTGTCTGGGGGCGCAGGGACCACCGGTCACCGTCTCTGCAAACTG
                                                 ><

Human IL-15N72D
GGTGAATGTAATAAGTGATTTGAAAAAAATTGAAGATCTTATTCAATCTA
TGCATATATTGATGCTACTTTATATACGGAAAGTGATGTTCACCCCAGTTGC
AAAGTAACACAGCAATGAAGTGCTTTCTCTTGGAGTTACAAGTTATTTCACT
TGAGTCCGGAGATGCAAGTATTCATGATACAGTAGAAAATCTGATCATCC
TAGCAAACGACAGTTTGTCTTCTTCTAATGGAATGTAACAGAATCTGGATGC
AAAGAATGTGAGGAACTGGAGGAAAAAATATTAAAGAATTTTTGCAGAG
TTTTGTACATATTGTGTCCAAATGTTCATCAACACTTCTTAA
                                         >
```

FIG. 54 qivlsqspailsaspgekvtmtcrasssvsyihwfqqkpgsspkpwiyatsnlasgvpvr
< anti-CD20 light chain V domain fsgsgsgtsyslstisrveaedaatyyccqgwtsnppfggtkleiksggggsggggsgggg
                                         >< linker gsqvqlqqpgaelvkpgasvkmsckasgytftsynmhwvkqtpgrglewigaiypgngdt
>< anti-CD20 heavy chain V domain synqkfkgkatltadksssstaymqisslitsedsavyycarstyyggdwyfdvwgagttvt vsanwvnvisdlkkiedligsmhidatlytesdvhpscktamkcfllelqvislesgda
>< Human IL-15N72D sihdtvenliilandslssngnvtesgckeceelee

| FIG. 55A |
|----------|
| FIG. 55B |
| FIG. 55C |

ATGGATTTTCAGGTGCAGATTATCAGCTTCCTGCTAATCAGTGCTTCAGT
<       leader seq

CATAAATGTCCAGAGGACAAATTGTTCTCTCCCAGTCTCCAGCAATCCTGT
>       <

CTGCATCTCCAGGGGAGAAGGTCACAATGACTTGCAGGGCCAGCTCAAGT
anti-CD20 light chain V domain

GTAAGTTACATGCCAGCAGAAGCCAGGATCCTCCCCAAACC

CTGGATTTATGCCACATCCAACCTGGCTTCTGGAGTCCCTGTTCGCTTCA

GTGGCAGTGGGTCTGGGACTTCTTACTCTCTCACAATCAGCAGAGTGGAG

GCTGAAGATGCTGCCACTTATTACTGCCAGCAGTGGACTAGTAACCCACC

CACGTTCGGAGGGGGGACCAAGCTGGAAATCAAAAGTGGAGGTGGCGGAT
>       linker       ><

CCGGAGGTGGAGGTTCTGGTGGAGGTGGGAGTCAGGTACAACTGCAGCAG

CCTGGGGCTGAGCTGGTGAAGCCTGGGGCCTCAGTGAAGATGTCCTGCAA
anti-CD20 heavy chain V domain

FIG. 55B

```
GGCTTCTGGCTACACATTTACCAGTTACAATATGCACTGGGTAAAACAGA
CACCTGGTCGGGGCCTGGAATGGATTGGAGCTATTTATCCCGGAAATGGT
GATACTTCCTACAATCAGAAGTTCAAAGGCAAGGCCACATTGACTGCAGA
CAAATCCTCCAGCACAGCCTACATGCAGCTCAGCAGCCTGACATCTGAGG
ACTCTGCGGTCTATTACTGTGCAAGATCGACTTACTACGGCGGTGACTGG
TACTTCRATGTCTCTGGGGGCGCAGGGACCACGGTCACMGTCTCTGCAATCAC
                                              >V

GTGCCCTCCCCCCATGTCCGTGGAACACGCAGACATCTGGGTCAAGAGCT
        Human IL-15R α sushi domain ACAGCTTGTACTCCAGGGAGCGGGTACATTGTAACTCTGGTTTCAAGCGT
AAAGCCGGTCCAGCCTGACGGAGTGCGTGTTGAACAAGGCCACGAA
TGTCGCCCACTGGACAACCCCAGTCTCAAATGCATTAGAGAGCCGAAAT
                                              >V
CTTGTGACAAAACTCACACATGCCCAGCACCTGAACTCCTG
```

FIG. 55C

Human IgG1 CH2-CH3 (Fc) domain

```
GGGGGACCGTCAGTCTTCCTCTTCCCCCCAAAACCCAAGGACACCCTCAT
GATCTCCCGGACCCCTGAGGTCACATGCGTGGTGGACGTGAGCCACG
AAGACCCTGAGGTCAAGTTCAACTGGTACGTGGACGGCGTGGAGGTGCAT
AATGCCAAGACAAAGCCGCGGGAGGAGCAGTACAACAGCACGTACCGTGT
GGTCAGCGTCCTCACCGTCCTGCACCAGGACTGGCTGAATGGCAAGGAGT
ACAAGTGCAAGGTCTCCAACAAAGCCCTCCCAGCCCCCATCGAGAAAACC
ATCTCCAAAGCCAAAGGGCAGCCCCGAGAACCACAGGTGTACACCCTGCC
CCCATCCCGGGATGAGCTGACCAAGAACCAGGTCAGCCTGACCTGCCTGG
TCAAAGGCTTCTATCCCAGCGACATCGCCGTGGAGTGGGAGAGCAATGGG
CAGCCCGGAGAACAACTACAAGACCACGCCTCCCGTGCTGGACTCCGACGG
CTCCTTCTTCCTCTACAGCAAGCTCACCGTGGACAAGAGCAGGTGGCAGC
AGGGGAACGTCTTCTCATGCTCCGTGATGCATGAGGCTCTGCACAACCAC
TACACGCAGAAGAGCCTCTCCCTGTCTCCGGGTAAATAA>
```

FIG. 56 qivlsqspailsaspgekvtmtcrassvsvsyihwfgqkpgsspkpwiyatsnlasgvpvr
< anti-CD20 light chain V domain fsgsgsgtsysltisrveaedaatyycqqwtsnpptfgggtkleiksggggggggggggg
>< linker gsqvqlqqpgaelvkpgasvkmsckasgytftsynmhwvkqtpgrglewigaiypgngdt
>< anti-CD20 heavy chain V domain synqkfkgkatltadksssstaymqlssltsedsavyycarstyyggdwyfnvwgagttvt vsaitcpppmsvehadiwvksysysysreryicnsgfkrkagtssltecvlnkatnvahwt
>< Human IL-15R α sushi domain tpslkcirepkscdkthtcppcpapellggpsvflfppkpkdtlmisrtpevtcvvvdvs
>< Human IgG1 CH2-CH3 (Fc) domain hedpevkfnwyvdgvevhnaktkpreeqynstyrvvsvltvlhqdwlngkeykckvsnka lpapiektiskakgqprepqvytlppsrdeltknqvsltclvkgfypsdiavewesngqp ennykttppvldsdgsfflysklvdksrwqqgnvfscsvmhealhnhytqksllspgk
>

FIG. 60

| FIG. 60A |
| FIG. 60B |

FIG. 60A

ATGGATTTTCAGGTGCAGATTATCAGCTTCCTGCTAATCAGTGCTTCAGT
< leader seq

CATAAATGTCCAGAGGACAAAATTGTTCTCTCCCAGTCTCCAGCAATCCCTGT
><

CTGCATCTCCAGGGGAGAAGGTCACAATGACTTGCAGGGCCAGCTCAAGT
anti-CD20 light chain V / human kappa C domains

GTAAGTTACATCCACTGGTTCCAGCAGAAGCCAGGATCCTCCCCCAAACC

CTGGATTTATGCCACATCCAACCTGGCTTCTTACTCTCTCACAATCAGCAGTGGAG

GTGGCAGTGGGTCTGGGACTTCTTATTACTGCCAGCAGTGGACTAGTAACCCACC

GCTGAAGATGCTGCCACTTATTACTGCCAGCAGTGGACTAGTAACCCACC

CACGTTCGGAGGGGGACCAAGCTGGAAATCAAACGTACGGTTGCTGCAC

CATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGT

FIG. 60B

```
ACAGTGGAAGGTGGATAACGCCCTCCAATCGGGTAACTCCCAGGAGAGTG
TCACAGAGCAGGAAGACAAGCAAGGACACCTACAGCCCTCAGCAGCACCCTG
ACGCTGAGCAAAGCAGAGACTACGAGAAACACAAAGTCTACGCCCTGCGAAGT
CACCCCATCAGGGGCCTCGCGCCCGTCACAAAGAGCTTCAACAGGGGAG
AGTGTAACTGGGGTGAATGTAATAAGTGATTTGAAAAAAATTGAAGATCTT
        > Human IL-15N72D <
ATTCAATCTATGCATATTGATGCTACTTTATATACGGAAAGTGATGTTCA
CCCCAGTTGCAAAGTAACAGCAATGAAGTGCTTTCTCTTGGAGTTACAAG
TTATTTCACTTTGATGTCCGGAGATGCAAGTATTCATGATACAGTAGAAAAT
CTGATCATCCTAGCAAACGACAGTTTGTCTCTTCTAATGGAATGTAACAGA
ATCTGGATGCAAAGAATGTGAGGAACTGGAGGAAAAATATTAAAGAAT
TTTTGCAGAGTTTTGTACATATTGTCCAAATGTTCATCAACACTTCTTAA
                                                  >
```

FIG. 61 qivlsqspailsaspgekvtmtcrassvsvsyihwfgqkpgsspkpwiyatsnlasgvpvr

< anti-CD20 light chain V domain fsgsgsgtsyslitisrveaedaatyycqqwtsnpptfgggtkleikrtvaapsvfifpps

> < deqlksgtasvvcllnnfypreakvqwkvdnalqsgnsqesvteqdskdstyslsstltl human kappa C domain skadyekhkvyacevthqglsspvtksfnrgecnwvnvisdlkkiedliqsmhidatlyt > < Human IL-15N72D esdvhpsckvtamkcflleleqvislesgdasihdtvenliilandslssngnvtesgcke cee

| FIG. 62A |
| FIG. 62B |
| FIG. 62C |

ATGGGTTGGAGTCTTCATCTTGCTCTTCCTTGTCGCTGTTGCTACACGTGT
  <    leader seq
CCTGTCCCAGGTACAACTGCAGCAGCCTGGGGCTGAGCTGGTGAAGCCTG
  >  <
GGGCCTCAGTGAAGATGTCCTGCAAGGCTTCTGGCTACACATTTACCAGT
  anti-CD20 heavy chain V / human HC CH1 domains
TACAATATGCACTGGGTAAAACAGACACCTGGTCGGGGCCTGGAATGGAT
TGGAGCTATTTATCCCGGAAATGGTGATACTTCCTACAATCAGAAGTTCA
AAGGCAAGGCCACATTGACTGCAGACAAATCCTCCAGCACAGCCTACATG
CAGCTCAGCAGCCTGACATCTGAGGACTCTGCGGTCTATTACTGTGCAAG
ATCGACTTACTACGGGGTCTCTGCAGTAGCACCTCTGGGGGCACAGGGA
CCACGGTCACCGTCTCCTCAGCCTCCACCAAGGGCCCATCGGTCTTCCCC
CTGGCACCCTCCTCCAAGAGCACCTCTGGGGGCACAGCGGCCCTGGGCTG
CCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCA

FIG. 62B

GGACTCTACTCCCTCAGCAGCAGCGTGGTGACCGTGCCCTCCAGCAGCTTGGG

CACCCAGACCTACATCTGCAACGTGAATCACAAGCCCAGCAACACCAAGG

TGGACAAGAAAGTTATCACGTGCCCCCCATGTCCGTGGAACACGCA

>< Human IL-15R α sushi domain

GACATCTGGGTCAAGAGCTACAGCTTGTACTCCAGGGAGCGGTACATTTG

TAACTCTGGTTTCAAGCGTAAAGCCGGCACGTCCAGCCTGACGGAGTGCG

TGTTTGAACAAGGCCCACGAATGTCGCCCACTGGACAACCCCAGTCTCAAA

TGCATTAGAGAGCCCAAATCTTGTGACAAAACTCACACATGCCCACCGTG

>< Human IgG1 CH2-CH3 (Fc) domain

CCCAGCACCTGAACTCCTGGGGGGACCGTCAGTCTTCCTCTTCCCCCCAA

AACCCAAGGACACCCTCATGATCTCCCGGACCCCTGAGGTCACATGCCGTG

GTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGT

FIG. 62C

ACAACAGCACGTACCGTGTGGTCAGGTCCTCACCGTCCTGCACCAGGAC
TGGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAAC
CACAGGTGTACACCCTGCCCCCATCCCGGGATGAGCTGACCAAGAACCAG
GTCAGCCTGACCTGCCTGGTCAAAGGCTTCTATCCCAGCGACATCGCCGT
GGAGTGGGAGAGCAATGGGCAGCCGGAGAACAACTACAAGACCACGCCTC
CCGTGCTGGACTCCGACGGCTCCTTCTTCCTCTACAGCAAGCTCACCGTG
GACAAGAGCAGGTGGCAGCAGGGGAACGTCTTCTCATGCTCCGTGATGCA
TGAGGCTCTGCACAACCACTACACGCAGAAGAGCCTCTCCCTGTCTCCTG
GTAAATAA
^

FIG. 63

```
qvqlqqpgaelvkpgasvkmsckasgytftsynmhwvkqtpgrglewigaiypgngdtsy
<             anti-CD20 heavy chain V domain nqkfkgkatltadkssstaymqlssltsedsavyycarstyyggdwyfdvwgagttvtvs aastkgpsvfplapsskstsggtaalgclvkdyfpepvtvswnsgaltsgvhtfpavlqs
><               Human IgG1 HC CH1 domains sglyslssvvtvpssslgtqtyicnvnhkpsntkvdkkvitcpppmsvehadiwvksysl
                                      >< ysreryicnsgfkrkagtssltecvlnkatnvahwttpslkcirepkscdkthtcppcpa
          Human IL-15R α sushi domain      >< pellggpsvflfppkpkdtlmisrtpevtcvvvdvshedpevkfnwyvdgvevhnaktkp
             Human IgG1 CH2-CH3 (Fc) domain reeqynstyrvvsvltvlhqdwlngkeykckvsnkalpapiektiskakgqprepqvytl ppsrdeltknqvsltclvkgfypsdiavewesngqpennykttppvldsdgsfflysklt vdksrwqqgnvfscsvmhealhnhytqkslslspgk
                                   >
```

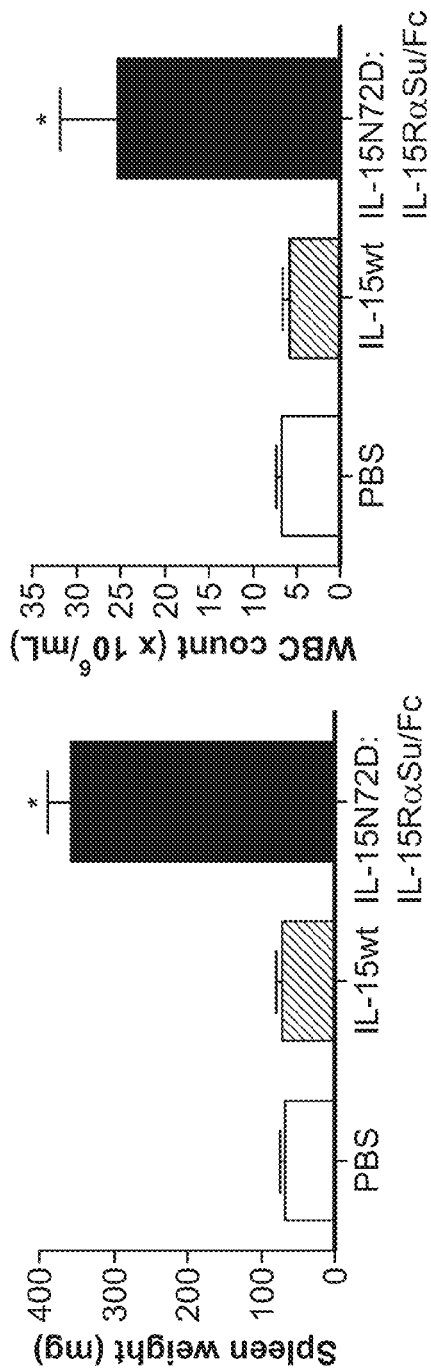
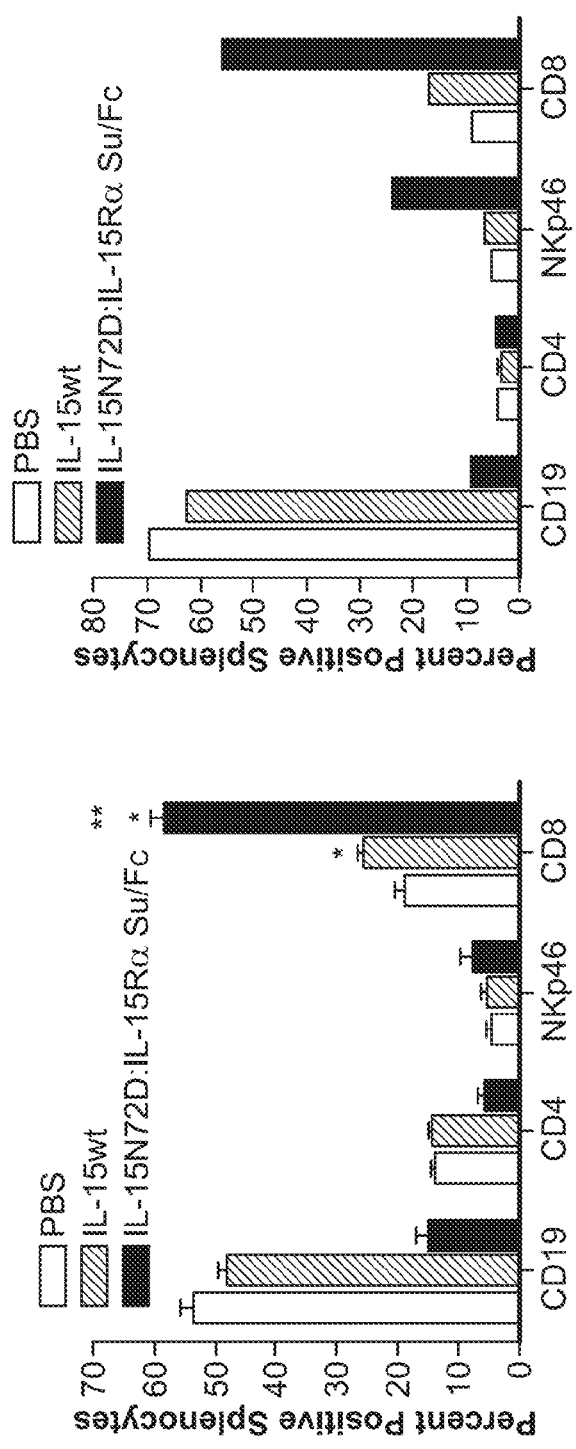
FIG. 69
FIG. 70

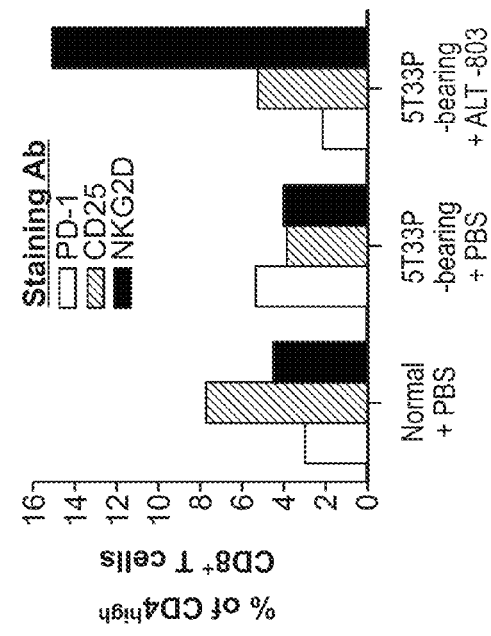
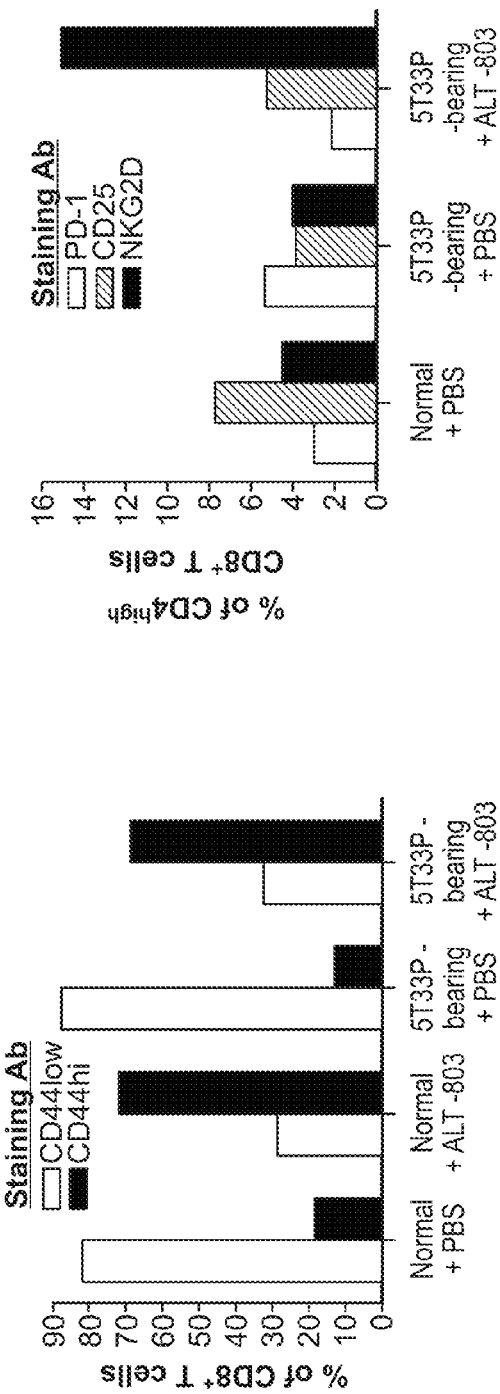
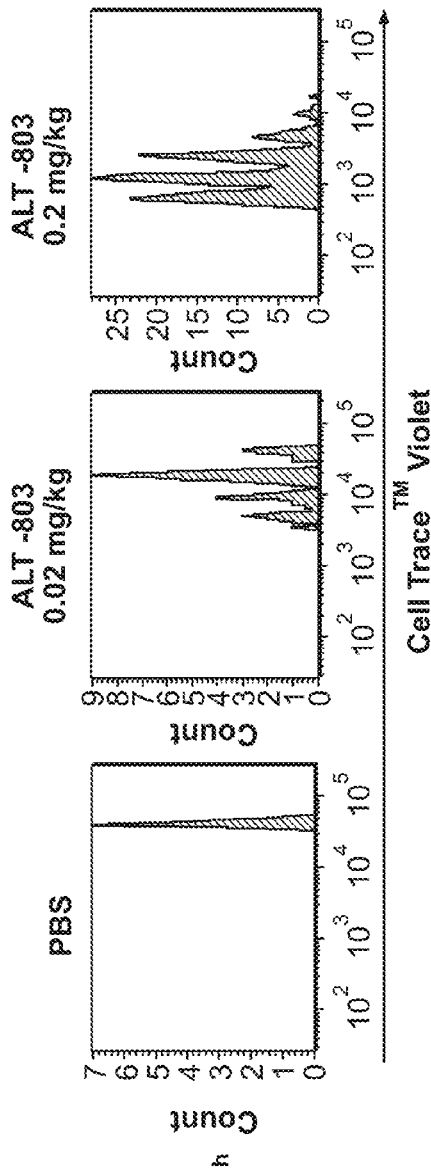
FIG. 76A
FIG. 76B
FIG. 76C

FIG. 77B-2
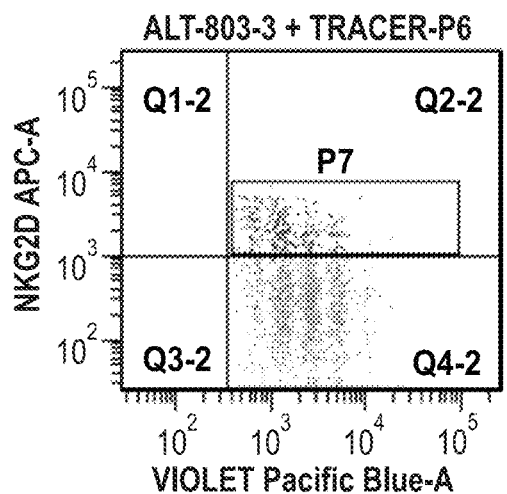
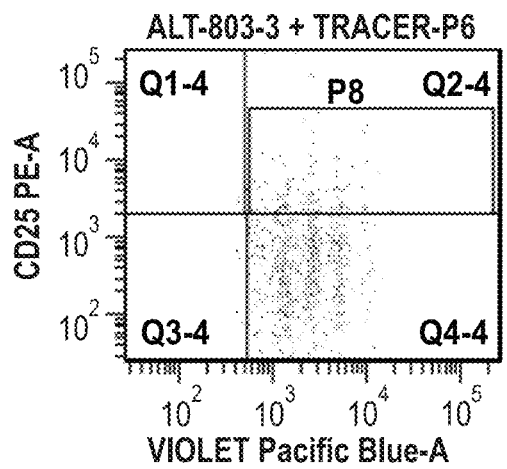
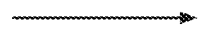
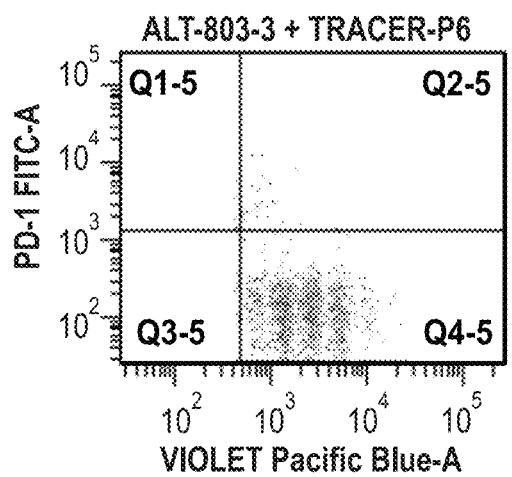

FIG. 83
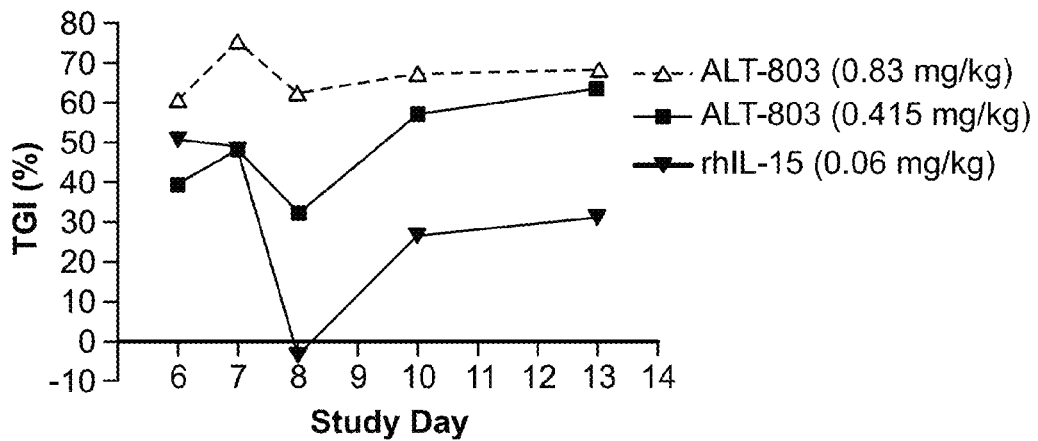
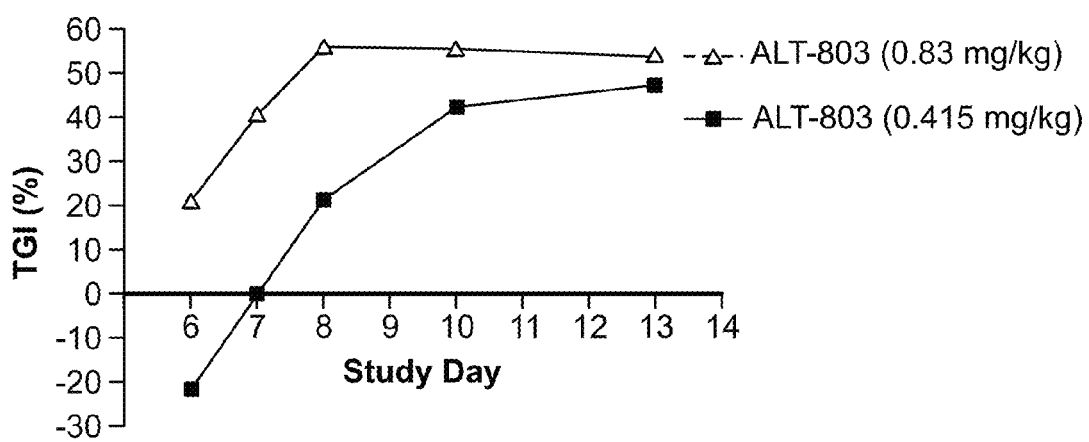

| FIG. 86A |
| --- |
| FIG. 86B |
| FIG. 86C |

IL-15N72D gene sequence atggagacagacacactcctgtgtatgggtactgctgtctctggggttccaggttccaccgg
t-
[Leader peptide]

aactgggtgaatgtaataagtgatttgaaaaaattgaagatcttattcaatctatgca
tattgatgctacttatatacggaaagtgatgttcacccagttgcaaagtaacagcaa
tgaagtgctttctcttggagttacaagttattcacttgagtccggagatgcaagtatt
catgatacagtagaaatctgatcatcctagcaaacgacagtttgtcttctaatgggaa
tgtaacagaatctggatgcaaagaatgtgaggaactggttcaaatgttcaacacttct FIG. 86B  IL-15N72D protein sequence (with leader peptide)

metdtlllwvlllwvpgstg-
[Leader peptide]

nwvnvisdlkkiedlligsmhidatlytesdvhpsckvtamkcfllelqvrislesgdasi
hdtvenliilandslssngnvtesgckeceeleeknikefIgsfvhivqmfints
[IL-15N72D]

IL-15Rα/Fc gene sequence atggacagacttacttcttcattcctgctccctgattgtccctgctacgtctgtcc-
[Leader peptide]

atcacgtgccctcccccatgtccgtggaacacgcagagacatctggtcaagagctacag
cttgtactccaggagcggtacattgtaactctggtttcaagcgtaaagccgcacgt
ccagcctgacggagtgcgtgttgaacaaggccacgaatgtgccactggacaacccc
agtctcaaatgtattaga-
[IL-15RαSu]

gagcccaaatcttgtgacaaaactcacacatgcccacc

FIG. 86C tgaatggcaaggagtacaagtgcaaggtctccaacaagccctccagcccatcgag
aaaccatctccaaggcagccaagggcagccagaaccacaggtgtacaccctgccc
atcccgggatgagctgaccagccgtgaccagcctgacctgcctggtcaaggcttct
atcccagcgacatcgccgtgctggactccgatggggagagcaatgggcagccgagaacaacaag
accacgcctcccgtgctggactccgatggggagagcggcttcttcctctacagcaagctcaccgt
ggacaagagcaggtggcagcaggggaacgtcttcatgcgtgtccgtgatgcatgaggctc
[IgG1 CH2-CH3 (Fc domain)]

taa
[Stop codon]

IL-15RαSu/Fc protein sequence (with leader peptide)

mdrltssflllivpayvls-
[Leader peptide]

itcppppmsvehadiwvksyslysreryicnsgfkrkagtssltecvlnkatnvahwttp
sikcir-
[IL-15RαSu]

epkscdkthtcppcpapellggpsvflfppkpkdtlmisrtpevtcvvvdvshedpevk
fnwyvdgvevhnaktkpreeqynstyrvvsvltvlhqdwlngkeykckvsnkalpapie
ktiskakgqprepqvytlppsrdeltknqvsltclvkgfypsdiavewesngqpennyk
ttppvldsdgsfflyskltvdksrwqqgnvfscsvmhealhnhytqkslslspgk
[IgG1 CH2-CH3 (Fc domain)]

MULTIMERIC IL-15 SOLUBLE FUSION MOLECULES AND METHODS OF TREATING NEOPLASIA AND HIV USING SAME

RELATED APPLICATIONS

This application is a continuation-in-part of U.S. patent application Ser. No. 13/238,925, filed Sep. 21, 2011 (now U.S. Pat. No. 8,507,222), which claims the benefit of U.S. Provisional Patent Application Ser. No. 61/384,817, filed Sep. 21, 2010 and U.S. Provisional Patent Application Ser. No. 61/527,911, filed Aug. 26, 2011. This application is also a continuation-in-part of said U.S. patent application Ser. No. 13/238,925. The entire contents of each of the foregoing applications are hereby incorporated herein by reference.

STATEMENT OF RIGHTS TO INVENTIONS MADE UNDER FEDERALLY SPONSORED RESEARCH

This work was supported by the following grants from the National Institutes of Health, Grant Nos: 1R43CA139810, 1R43CA174091, 1R43CA167925 and 1R43CA156740. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jul. 3, 2013, is named 84600CIP(48340)_SL.txt and is 79,925 bytes in size.

BACKGROUND OF THE INVENTION

Multiple myeloma (MM) is a plasma cell malignancy, accounting for over 1% of neoplastic diseases and 14% of all hematological cancers. MM tumor cells are susceptible to immune cell recognition and elimination, as demonstrated by the potentially curative graft-versus-myeloma activity observed in some patients following allogeneic hematopoietic stem cell transplantation and donor lymphocyte infusion therapies. However, these approaches are limited by transplantation-related mortality ranging from 30% to 50% and disease relapse in a majority of patients. Immunomodulatory chemotherapies, such as lenalidomide, are also thought to provide therapeutic benefit via mechanisms due in part to stimulation of T-cell and/or natural killer (NK) cell activity against myeloma cells. Although survival of MM patients has improved significantly by the use of these novel agents, MM remains incurable due to the persistence of minimal residual disease. Thus, novel modalities are needed to complement or improve the current treatment options for MM.

SUMMARY OF THE INVENTION

As described below, the present invention features compositions and methods featuring ALT-803, a complex of an interleukin-15 (IL-15) superagonist mutant and a dimeric IL-15 receptor α/Fc fusion protein useful for enhancing an immune response against a neoplasia (e.g., a hematological cancer, multiple myeloma, beta-cell lymphoma, urothelial/bladder carcinoma and melanoma) or a viral infection (e.g., human immunodeficiency virus).

In one aspect, the invention features a method for treating neoplasia or virus infection in a subject (e.g., human), the method containing administering to the subject an effective amount of a pharmaceutical composition containing IL-15N72D:IL-15RαSu/Fc complex (Alt-803) containing a dimeric IL-15RαSu/Fc and two IL-15N72D molecules, thereby treating the neoplasia or virus infection. In one embodiment, the IL-15RαSu/Fc comprises the following sequences ("IL-15RαSu/Fc" disclosed as SEQ ID NO: 1):

```
[IL-15RαSu]
itcpppmsvehadiwyksyslysreryicnsgfkrkagtssltecvlnkatnvahwttpslkcir-

[IgG1 CH2—CH3 (Fc domain)]
epkscdkthtcppcpapellggpsvflfppkpkdtlmisrtpevtcvvvdvshedpevkfnwyv dgvevhnaktkpreeqynstyrvvsvltvlhqdwlngkeykckvsnkalpapiektiskakgqp repqvytlppsrdeltknqvsltclvkgfypsdiavewesngqpennykttppvldsdgsffly skltvdksrwqqgnvfscsvmhealhnhytqkslslspgk.
```

In another embodiment, the IL-15N72D molecule comprises the following sequence (SEQ ID NO: 2):

```
[IL-15N72D]
nwvnvisdlkkiedliqsmhidatlytesdvhpsckvtamkcflllelqvislesgdasihdtve nliilandslssngnytesgckeceeleeknikeflqsfvhivqmfints.
```

In another aspect, the invention features a kit for the treatment of a neoplasia, the kit containing an effective amount of an IL-15N72D:IL-15RαSu/Fc complex (Alt-803) containing a dimeric IL-15RαSu/Fc and two IL-15N72D molecules and directions for the use of the kit for the treatment of a neoplasia.

In another aspect, the invention features a kit for the treatment of a virus (e.g., HIV), the kit containing an effective amount of an IL-15N72D:IL-15RαSu/Fc complex (Alt-803) containing a dimeric IL-15RαSu/Fc and two IL-15N72D molecules and directions for the use of the kit for the treatment of a neoplasia.

In another aspect, the invention features a method of treating neoplasia in a subject, the method containing administering to said subject an effective amount of a pharmaceutical composition containing an anti-CD20 scAb T2M complex or a CD20-targeted IL-15N72D:IL-15Rα/Fc fusion protein complex (2B8T2M), thereby treating the neoplasia. In one embodiment, the anti-CD20 scAb T2M contains a soluble anti-CD20 scAb/huIL-15N72D:anti-CD20 scAb/huIL-15RαSu/huIgG1 Fc complex, wherein anti-CD20 scAb/huIL-15RαSu/huIgG1 Fc has the sequence shown in FIG. 56, and the anti-CD20 scAb/hIL-15N72D has the sequence shown in FIG. 54. In another embodiment, the neoplasia is beta-cell lymphoma or Burkitt's lymphoma. In another embodiment, the effective amount is between about 1 and 100 µg/kg. In yet another embodiment, Alt-803 is administered once, twice, or three times per week. In various embodiments of the above aspects or any other aspect of the invention delineated herein, the neoplasia is multiple myeloma, beta-cell lymphoma, urothelial/bladder carcinoma or melanoma. In other embodiments, the effective amount is between about 1 and 20 µg/kg. In other embodiments, the effective amount is about 1 µg/kg, 5 µg/kg, 10 µg/kg, 15 µg/kg, or 20 µg/kg. In still other embodiments, the effective amount is 10 µg/week. In still other embodiments, the effective amount is between about 20 µg and 100 µg/kg. In still other embodiments, the effective amount is 30 µg/kg, 50 µg/kg, 75 µg/kg, or 100 µg/kg. In still other embodiments, Alt-803 is administered once, twice, or three times per week. In yet other embodiments, the pharmaceutical composition is administered systemically, intravenously, or by instillation. In still other embodiments, Alt-803 increases serum levels of IFN-γ; increases the number of CD8$^+$CD44$^{high}$ memory T cells, causes CD8$^+$CD44$^{high}$ memory T cells to acquire an innate-type phenotype and secrete IFN-γ independent of antigen requirement; and/or induces a long lasting anti-myeloma immune memory response. In still other embodiments, the virus is human immunodeficiency virus The invention provides therapeutic compositions useful for enhancing an immune response and methods of using such compositions for the treatment of viral infections, such as HIV, and neoplasias, including but not limited to multiple myeloma, beta-cell lymphoma, urothelial/bladder carcinoma and melanoma. Compositions and articles defined by the invention were isolated or otherwise manufactured in connection with the examples provided below. Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, or small compound. An exemplary therapeutic agent is Alt-803 or 2B8T2M.

By "Alt-803" is meant a complex comprising IL-15N72D noncovalently associated with a dimeric IL-15RαSu/Fc fusion protein and having immune stimulating activity. In one embodiment, the IL-15N72D and/or IL-15RαSu/Fc fusion protein comprises one, two, three, four or more amino acid variations relative to a reference sequence. An exemplary IL-15N72D amino acid sequence is provided below.

```
IL-15N72D protein sequence (with leader peptide)
[Leader peptide]
                                          (SEQ ID NO: 3)
metdtlllwvlllwvpgstg-

[IL-15N72D]
nwvnvisdlkkiedliqsmhidatlytesdvhpsckvtamkcfllelqvislesgdasihdtve nliilandslssngnvtesgckeceeleeknikeflqsfvhivqmfints
```

In one embodiment, the leader peptide is cleaved from the mature IL-15N72D polypeptide.

An exemplary IL-15RαSu/Fc amino acid sequence is provided below:

```
IL-15RαSu/Fc protein sequence (with leader peptide)
[Leader peptide]
                                          (SEQ ID NO: 4)
mdrltssflllivpayvls-

[IL-15RαSu]
itcpppmsvehadiwyksyslysreryicnsgfkrkagtssltecvlnkatnvahwttpslkcir-

[IgG1 CH2—CH3 (Fc domain)]
epkscdkthtcppcpapellggpsvflfppkpkdtlmisrtpevtcvvvdvshedpevkfnwyv dgvevhnaktkpreeqynstyrvvsvltvlhqdwlngkeykckvsnkalpapiektiskakgqp repqvytlppsrdeltknqvsltclvkgfypsdiavewesngqpennykttppvldsdgsffly skltvdksrwqqgnvfscsvmhealhnhytqkslslspgk
```

In one embodiment, the mature IL-15RαSu/Fc protein lacks the leader sequence. Other Alt-803 polypeptide and polynucleotide sequences useful in the method of the invention are provided at FIG. 86A, FIG. 86B, and FIG. 86C.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "binding to" a molecule is meant having a physicochemical affinity for that molecule.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include neoplasias and viral infections.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). In particular embodiments, the neoplasia is multiple myeloma, beta-cell lymphoma, urothelial/bladder carcinoma or melanoma. As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 3A, FIG. 3B, and FIG. 3C shows the sequence of the c264scTCR/huIL15RαSushi/huIgG1 nucleic acid sequence (SEQ ID NO: 39).

FIG. 4A, FIG. 4B, FIG. 4C, and FIG. 4D shows the protein sequence of the c264scTCR/huIL15RαSushi/huIgG1 peptide (SEQ ID NO: 40).

FIG. 6A, FIG. 6B, and FIG. 6C shows the sequence of the c264scTCR/huIL15RαSushi/huIgG1 nucleic acid sequence (SEQ ID NO: 41).

FIG. 7A, FIG. 7B, FIG. 7C, and FIG. 7D shows the protein sequence of the c264scTCR/huIL15RαSushi/huIgG1 peptide (SEQ ID NO: 42).

FIG. 9A and FIG. 9B shows the sequence of the c149scTCR/huIL15N72D nucleic acid sequence (SEQ ID NO: 43).

FIG. 10A, FIG. 10B, and FIG. 10C shows the protein sequence of the c149scTCR/huIL15N72D peptide (SEQ ID NO: 44).

FIG. 19A illustrates flow cytometry analysis showing results from an assay in which Fc-gamma receptor bearing U937 cells were incubated with 33 nM of T2 protein (composed of c264scTCR/huIL15N72D and c264scTCR/huIL15RαSushi/huIgG1 chains), c264scTCR/huIgG1 or A2AL9scTCR/IgG1 (negative control) for 20 min. Cells were washed once and incubated with PE-conjugated p53 (aa 264-272) peptide/HLA-A2 tetramer for 20 min. The binding to Fc gamma receptors on U937 cell surface was analyzed with flow cytometry. FIG. 19B illustrates flow cytometry analysis showing results from similar U937 binding studies using a range of protein concentrations as indicated. The mean fluorescent intensity for the stained cells was plotted.

FIG. 21A and FIG. 21B show results from an assay in which HLA-A2-positive T2 cells were pulsed with various amounts of p53 aa264-272 peptide to assess the binding activity of T2 protein to peptide/MHC targets on cell surface. The peptide-loaded cells were incubated with T2 protein (composed of c264scTCR/huIL15N72D and c264scTCR/huIL15RαSushi/huIgG1 chains), c264scTCR/huIgG1 or A2AL9scTCR/IgG1 (negative control), each at 83 nM. The cells were incubated with biotinylated anti-TCR Ab (BF1) and streptavidin-PE. The cells were then analyzed for antibody staining by flow cytometry (FIG. 21A) and the mean fluorescence staining intensity of the cells loaded different concentrations of peptide are plotted (FIG. 21B).

FIG. 26A is a line graph showing the results of ELISA format assays in which goat anti-human IgG Ab was used to coat the wells, and anti-human TCR Ab (W4F-BN) was used for detection; or goat anti-human IgG Ab was used to coat the plates, and anti-human IL-15 Ab was used for detection as indicated to quantify the amount of the T2 protein in the blood at the times indicated. FIG. 26B is a line graph showing the results of assays in which anti-human TCR Ab (βF-1) was used to coat the wells, and HRP conjugated goat anti-human IgG Ab was used for detection; or anti-human IL-15 Ab was used to coat the plates, and HRP conjugated goat anti-human IgG Ab was used for detection; or anti-human IL-15 Ab was used to coat the plates and anti-human TCR Ab (W4F-BN) was used for detection.

FIG. 32A shows flow cytometry histograms and FIG. 32B shows signal to noise ratio of peptide-specific to non-specific cell staining.

FIG. 39A-FIG. 39B shows OTscTCR/scCD8 heterodimer comprising the OT1scTCR/hIL-15:scCD8/hIL-15RαSu/birA complex exhibits enhanced pMHCI binding activity. Murine CD8 expression of OT1scTCR/scCD8 heterodimer was determined by ELISA (FIG. 39A). Anti-mTCR H57-597 mAb was used as capturing antibody. The biotinylated anti-murine CD8α or CD8β mAb was used as a probe followed by SA-HRP. The data represent the means±SD of triplicate determinations. EL4 cells were loaded with OVA (aa257-264) peptide at the indicated concentration and stained with OT1scTCR dimer-SA-PE (top) and OT1scTCR/scCD8 heterodimer-SA-PE (bottom) at 200 nM (FIG. 39B).

FIG. 40A-40B show that fusion proteins containing TCR α/β heterodimers comprising the TCRα/hIL-15:TCRβ/hIL-15RαSu/birA complex retain pMHCI binding activity. Binding activity of OT1scTCR/birA and OT1 TCRα/β heterodimer to OVA (aa257-264)/H-2Kb complex was determined by ELISA (FIG. 40A). Anti-mTCR H57-597 mAb was used as capturing antibody. Kb/OVA.257-264.HRP tetramer was used as a probe. Binding activity of 264scTCR/birA and 264 TCRα/β heterodimer to p53 (aa264-272)/HLA-A*0201 complex was determined by ELISA (FIG. 40B). Anti-TCR mAb was used as capturing antibody. A2/p53.264-272.HRP tetramer was used as a probe. The data represent the means±SD of triplicate determinations.

FIG. 41A and FIG. 41B shows IL-15 binding and functional activity of fusion proteins. 32Dβ cells were incubated with 320 nM of the c264scTCR dimers comprising IL-15 wild type or IL-15N72D or IL-15D8N mutein domains. The binding of the fusion proteins was in turn detected with anti-human TCR Cβ Ab (FIG. 41A). The ability of the c264scTCR dimers comprising IL-15 wild type or mutein domains to support proliferation of 32Dβ cells was determined as described in the Examples (FIG. 41B). The data represent the means±range of duplicate determinations.

FIG. 46 shows the protein sequence of the human IgG1 CH2-CH3 domain or Fc domain covalently and/or genetically fused with other protein domains to generate the fusion protein complexes (SEQ ID NO: 45).

FIG. 51A, FIG. 51B, FIG. 51C, and FIG. 51D shows the nucleic acid sequence of c264scTCR/huIL15RαSushi/huIgG1 CH2-CH3 (Fc) construct (also referred to as T2MΔCH1 and T2M2) (SEQ ID NO: 46).

FIG. 52 shows the protein sequence of the mature c264scTCR/huIL15RαSushi/huIgG1 CH2-CH3 (Fc) fusion protein (also referred to as T2MΔCH1 and T2M2) (SEQ ID NO: 47).

FIG. 53A and FIG. 53B shows the nucleic acid sequence of anti-CD20 scAb/hIL-15N72D construct (SEQ ID NO: 48).

FIG. 54 shows the protein sequence of the mature anti-CD20 scAb/hIL-15N72D fusion protein (SEQ ID NO: 49).

FIG. 55A, FIG. 55B, and FIG. 55C shows the nucleic acid sequence of anti-CD20 scAb/huIL-15RαSu/huIgG1 Fc construct (SEQ ID NO: 50).

FIG. 56 shows the protein sequence of the mature anti-CD20 scAb/huIL-15RαSu/huIgG1 Fc fusion protein (SEQ ID NO: 51).

FIG. 60A and FIG. 60B shows the nucleic acid sequence of anti-CD20 light chain V domain/human kappa constant domain/hIL-15N72D construct (SEQ ID NO: 52).

FIG. 61 shows the protein sequence of the mature anti-CD20 light chain V domain/human kappa constant domain/hIL-15N72D fusion protein (SEQ ID NO: 53).

FIG. 62A, FIG. 62B, and FIG. 62C shows the nucleic acid sequence of anti-CD20 heavy chain V domain/human IgG1 CH1 domain/huIL-15RαSu/huIgG1 Fc construct (SEQ ID NO: 54).

FIG. 63 shows the protein sequence of the mature anti-CD20 heavy chain V domain/human IgG1 CH1 domain/huIL-15RαSu/huIgG1 Fc fusion protein (SEQ ID NO: 55).

FIG. 65A shows IEF pH 3-10 gel analysis. Lane 1, IEF Marker. Lane 2, IL-15N72D:IL-15RαSu/Fc complex (Alt-803) purified by rProtein A column. Lane 3, IL-15RαSu/Fc. Lane 4, IL-15 wt. FIG. 65B shows IEF pH3-10 gel analysis. Lane 1, IEF Marker. Lane 2, IL-15N72D:IL-15RαSu/Fc complex (Alt-803) purified by Q step 1 elution. Lane 3, Q1c by Q step 2 elution. Lane 4, Q2c by Q step 2 elution. FIG. 65C shows SDS-PAGE (reduced) analysis. Lane 1, MW maker. Lane 2, IL-15N72D:IL-15RαSu/Fc complex (Alt-803) purified by rProtein A column. Lane 3, IL-15N72D:IL-15RαSu/Fc (Alt-803) (Q2c) by Q step 2 elution. Lane 4, IL-15RαSu/Fc (from Q flow through). FIG. 65D shows SDS-PAGE (reduced) analysis showing protein deglycosylation. Lane 1, MW markers. Lanes 2 and 3 show N-Glycosidase F digested and undigested IL-15N72D:IL-15RαSu/Fc protein, respectively. Lane 4, IL-15 wt.

FIG. 69 is a set of graphs showing the effect of IL-15 wt and IL-15N72D:IL-15RαSu/Fc (Alt-803) complex on spleen weight and white blood cell levels. C57BL/6 mice (5 mice per group) were injected intravenously with a single dose of IL-15N72D:IL-15RαSu/Fc fusion complex (Alt-803) at 1 mg/kg IL-15 wt at 0.28 mg/kg (molar equivalent dose), or PBS as a negative control. Spleen weights (left panel) and white blood cell counts in blood (right panel) were determined 4 days after injection. The bars represent the mean±standard error (n=5). *P>0.05 compared to PBS and IL-15 wt. The results are representative of at least two experiments.

FIG. 70 is a set of graphs showing the effect of IL-15 wt and IL-15N72D:IL-15RαSu/Fc complex (Alt-803) on mouse lymphocytes. C57BL/6 mice (5 mice per group) were injected intravenously with a single dose of IL-15N72D:IL-15RαSu/Fc fusion complex (Alt-803) at 1 mg/kg, IL-15 wt at 0.28 mg/kg (molar equivalent dose), or PBS as a negative control. The percentage of B cells (CD19), CD4 T cells (CD4), NK cells (NKp46) and CD8 T cells (CD8) were determined in splenocytes (left panel: mean±standard error (n=5)) and PBMCs (right panel: levels in pooled blood (n=5)) 4 days after injection. *P>0.05 compared to PBS, **P>0.05 compared to IL-15 wt. The results are representative of at least two experiments.

FIG. 72A and FIG. 72B show the effect of ALT-803 or IL-15 on myeloma cells in BM of 5T33P or MOPC-315P bearing mice. Female mice (5 mice/group) were injected i.v. with 5T33P (FIG. 72A) or MOPC-315P (FIG. 72B) myeloma cells ($1 \times 10^7$/mouse) on day 0. ALT-803 (0.2 mg/kg), IL-15 (0.056 mg/kg, an IL-15 molar equivalent dose to 0.2 mg/kg ALT-803), or PBS (dose volume equivalent) was then administered as a single i.v. injection on day 15 (5T33P) or 14 (MOPC-315P). BM cells were collected 4 days after study drug treatments. The cells were then stained with PE-conjugated rat anti-mouse IgG2b or IgA Ab to evaluate the percentage of 5T33P or MOPC-315P cells in BM, respectively. The plotted values represent the mean±SE; P values are presented. FIG. 72C shows that ALT-803 treatment prolonged survival of the examined mice bearing murine myeloma cells. Female C57BL/6NHsd mice (n=5/group) were injected i.v. with murine 5T33P myeloma cells ($1 \times 10^7$ cells/mouse) on day 0. A single-dose of ALT-803 was administered i.v. at 0.2 mg/kg on day 4. Control mice were treated with PBS on day 4. Survival (or morbidity due to hind leg paralysis) was monitored as a study endpoint. FIG. 72D shows that ALT-803 treatment prolongs survival of C57BL/6NHsd mice following subsequent rechallenge with 5T33P myeloma cells. 5T33P tumor-bearing mice (n=5) were treated with ALT-803 days 1 and 7 or with PBS as in 2A. ALT-803 treated mice that survived (n=4) were rechallenged with 5T33P cells ($1 \times 10^7$) on day 93. Five treatment-naïve mice were also administered 5T33P cells ($1 \times 10^7$) on day 93 as a control for tumor development.

FIG. 73A shows effects of ALT-803 on myeloma cells in bone marrow of 5T33P-bearing C57BL/6NHsd mice. Female C57BL/6NHsd mice (n=4/group) were injected i.v. with 5T33P myeloma cells ($1 \times 10^7$) on day 0. ALT-803 (various dose levels) or PBS was then administered as a single i.v. injection on day 14. Bone marrow cells were collected 4 days after test article treatment (day 18). The cells were then stained with PE-conjugated rat anti-mouse IgG2b Ab and evaluated by flow cytometry to determine the percentage of 5T33P cells in BM. The plotted values represent the mean±SE; P values are presented. FIG. 73B shows that ALT-803 treatment prolonged survival of BALB/c mice bearing MOPC-315P myeloma cells. Female BALB/c mice (ALT-803-2 doses: n=5; ALT-803-3 doses: n=6; PBS: n=6) were injected i.v. with murine MOPC-315P myeloma cells ($1 \times 10^7$) on day 0. ALT-803 was administered i.v. at 0.2 mg/kg on days 4 and 11 (ALT-803-2ds group) or on days 4, 7 and 11 (ALT-803-3ds group). Control mice were treated with PBS on days 4, 7 and 11. Survival (or morbidity due to hind leg paralysis) was monitored as a study endpoint.

In FIG. 75A, female C57BL/6NHsd mice (n=5/group) were depleted of CD8+ T cells (dpCD8), NK1.1+ cells (dpNK), or both (dpCD8/NK) by i.p. treatment with anti-CD8 and/or anti-NK1.1 Abs on days −2 and −1. Mice were then injected with 5T33P myeloma cells ($1 \times 10^7$) on day 0 and treated with anti-CD8 and/or anti-NK1.1 Abs on days 7 and 14. The mice were treated with ALT-803 on day 14. Undepleted 5T33P-bearing mice receiving PBS served as controls. Four days after ALT-803 treatment, BM cells were isolated and stained with FITC-anti-CD8b, PE-anti-NKp46 and FITC-anti-IgG2b Abs and analyzed by flow cytometry. The percentage of CD8+ T cells, NKp46+NK cells and IgG2b+5T33P myeloma cells in BM are shown. Bars represent the mean±SE. In FIG. 75B, female C57BL/6NHsd mice (n=5/group) were depleted of CD8+ T cells (dpCD8), NK1.1+ cells (dpNK), or both (dpCD8/NK) by treatment with anti-CD8 and/or anti-NK1.1 Abs on days −2 and −1 as described in FIG. 5A. Mice were then injected with 5T33P myeloma cells ($1 \times 10^7$) on day 0 and treated with anti-CD8 and/or anti-NK1.1 Abs and then weekly for 8 weeks. ALT-803 was administered i.v. at 0.2 mg/kg on days 4 and 11. Mice receiving 5T33P myeloma cells ($1 \times 10^7$) on day 0 and PBS on days 4 and 11 were used as control. For comparison of ALT-801 vs. PBS or ALT-801+Ab depletion vs. ALT-801, *, $P \leq 0.05$; , $P \leq 0.01$; and *, $P \leq 0.001$.

FIG. 76A-FIG. 76D show that ALT-803 induces CD8+ CD44$^{high}$ memory T cell proliferation and up-regulation of NKG2D. In FIG. 76A and FIG. 76B, female C57BL/6NHsd mice (5-6 weeks-old, 3 mice/group) were untreated (normal) or injected i.v. with 5T33P myeloma cells ($1 \times 10^7$/mouse) (5T33P-bearing) on day 0. ALT-803 (0.2 mg/kg) or PBS (dose volume equivalent) was administered i.v. on day 14. Four days after treatment, mouse splenocytes were isolated and stained with Abs specific to CD44 (PE-Cy7), NKG2D (APC), PD-1 (FITC), CD25 (PE), and CD8 (PerCP-Cy5.5). Stained cells were analyzed by flow cytometry. The percentage of CD44$^{low}$ and CD44$^{high}$ in CD8$^+$ T cells (FIG. 76A) and percentage of PD-1-, CD25- and NKG2D-positive cells in CD8$^+$ CD44$^{high}$ memory T cell population (FIG. 76B) are shown. In FIG. 76C, CD3$^+$ enriched cells from spleens of donor C57BL/6NHsd mice were labeled with Celltrace™ Violet and then adoptively transferred (1.5×10$^6$ cells/mouse) into syngeneic recipients (3 mice/group) on day 0 (SD0). On SD2, mice were treated (i.v.) with 0.02 mg/kg of ALT803, 0.2 mg/kg of ALT-803 or PBS (dose volume equivalent). On SD6, spleens were harvested and analyzed individually by flow cytometry for donor cells (violet label) and positive staining with Abs specific to CD44 (PE-Cy7), NKG2D (APC), PD-1 (FITC), CD25 (PE), and CD8 (PerCP-Cy5.5). Histograms show proliferation of violet-labeled CD8$^+$CD44$^{high}$ memory T cell population. In FIG. 76D, NKG2D$^{neg}$CD25$^{neg}$CD8$^+$CD44$^{high}$ memory T cells from spleens and lymph nodes of donor C57BL/6NHsd mice were sorted with BD FACS Aria (FIG. 76D) and labeled with Celltrace™ Violet. Donor cells (1×10$^6$ cells/mouse) were then adoptively transferred into syngeneic recipients (3 mice/group) on SD0. On SD2, mice were treated (i.v.) 0.2 mg/kg ALT-803 or PBS (dose volume equivalent). On SD6, spleens were harvested and analyzed by flow cytometry as described in FIG. 76C. Histograms show proliferation of violet-labeled CD8$^+$CD44$^{high}$ memory T cell population and CD8$^+$CD44$^{high}$NKG2D$^+$ and CD8$^+$CD44$^{high}$ CD25$^+$ subpopulations. The value indicates the percentage of NKG2D$^+$ or CD25$^+$ cells in the donor CD8$^+$CD44$^{high}$ memory T cell population.

FIG. 77A-1, FIG. 77A-2, FIG. 77B-1, and FIG. 77B-2 show a FACS gating strategy and analysis of donor NKG2D$^{neg}$CD25$^{neg}$CD8$^+$CD44$^{high}$ T cells prior to adoptive transfer (FIG. 77A-1 and FIG. 77A-2) and after adoptive transfer Celltrace™ Violet labeled cells in ALT-803 treated mice (FIG. 77B-1 and FIG. 77B-2).

In FIG. 79A, unfractionated or CD8$^+$ T cell enriched splenocytes (untouched) from normal C57BL/6NHsd mice (pool of 3/group) were cultured with 200 ng/mL of ALT-803 for 72 hrs. Cells were then harvested, stained with Abs specific to CD44 (PE-Cy7), NKG2D (APC), PD-1 (FITC), CD25 (PE), and CD8 (PerCP-Cy5.5), and analyzed by flow cytometry for expansion of CD8$^+$CD44$^{high}$ memory T cell populations. In FIG. 79B and FIG. 79C, unfractionated or CD8$^+$ T cell enriched splenocytes were activated as described in FIG. 79A, then washed thoroughly and re-plated in duplicate wells (1×10$^6$ cells/well) containing 0, 20, or 200 ng/mL ALT-803. NKG2D blocking antibody (10 µg/mL) or isotype control antibody (10 µg/mL) was added to appropriate wells as indicated. PHK-67 labeled 5T33P (1×10$^5$ cells/well) (FIG. 79B) or A20 tumor cells (1×10$^5$ cells/well) (FIG. 79C) were added (E:T ratio=10:1) and incubated for 24 hrs. Target cell killing of the individual cultures was assessed by analysis of PI staining of PKH-67 labeled tumor cells on a BD FACScan. The level of PI staining in cultured PHK-67 labeled 5T33P or A20 cells alone served as a background control. In FIG. 79D, in vitro 5T33P killing assay of CD8$^+$ T cell enriched spleen cells from normal, IFN-γ KO B6, and perform KO B6 mice (pool of 3/group). As described above, enriched CD8$^+$ T cells (2×10$^7$) were incubated with ALT-803 (0.2 µg/mL) for 72 hrs and then re-plated into triplicated wells (3×10$^6$ cells/well) without or with ALT-803 (20 ng/mL). PHK-67 labeled 5T33P tumor cells (3×10$^5$ cells/well) were added as target cells (E:T ratio=10:1). After incubation for 20 hrs, target cell killing was assessed as described above. The percentage of PI-positive 5T33P cells is shown. Points or bars represent the mean±SE. For comparison of target cells+effector cells vs. target cells alone or target cells+KO effector cells vs. target cells+WT effector cells under the same culture conditions, *, P≤0.05; , P≤0.01; and *, P≤0.001.

In FIG. 80A, ALT-803 induce high level of serum IFN-γ via CD8$^+$ T cells. C57BL/6NHsd mice (n=5) received three doses of anti-CD8 Ab (dpCD8), anti-NK1.1 Ab (dpNK) or both Abs (dpCD8/NK) i.p. on days −2, −1 and 7. On day 8, a single i.v. dose of ALT-803 (0.2 mg/kg) was administrated and two days later (day 10) serum IFN-γ levels were examined. Bars represent the mean±SE. For comparison of ALT-803+Ab depletion vs. ALT-803, *, P≤0.05. In FIG. 80B, C57BL/6NHsd mice (n=3) were administrated a single i.v. dose of ALT-803 (0.2 mg/kg) on day 1 or day 2 respectively. On day 3, isolated splenocytes were stained with Abs to CD44 (PE-Cy7), and CD8 (PerCP-Cy5.5), and then intracellularly stained with FITC-anti-IFN-γ Ab. Dot plots show the percentage of IFN-γ producing CD8$^+$CD44$^{high}$ memory T cells. FIG. 80C shows that IFN-γ is required for ALT-803 anti-myeloma activity. Female IFN-γ KO B6 mice (n=3/group) were injected i.v. with 5T33P myeloma cells (1×10$^7$ cells/mouse) on day 0. ALT-803 (0.2 mg/kg) or PBS was administered i.v. on days 4 and 11. Survival (or morbidity due to hind leg paralysis) was monitored as a study endpoint.

In FIG. 81A and FIG. 81B, enriched CD8$^+$ T cells (positive selection) from splenocytes and lymph nodes of IFN-γ KO B6 mice (6 weeks old) were labeled with Celltrace™ Violet and adoptively transferred (1.5×10$^6$ cell/mouse) into IFN-γ KO B6 recipients (KO, n=5) (FIG. 81A) or wild-type C57BL/6NHsd recipients (WT, n=5) (FIG. 81B) on day 0 (SD0). On SD2, 3 KO and 3 WT mice were treated with 0.2 mg/kg ALT-803 (i.v.) and the remaining 2 KO and 2 WT mice received PBS (i.v.) as controls. On SD6, spleens were harvested and analyzed individually by flow cytometry for donor cells (violet label) and positive staining with Abs specific to CD44 (PE-Cy7), NKG2D (APC), and CD8 (PerCP-Cy5.5). Histograms show proliferation of violet-labeled CD8$^+$CD44$^{high}$ and CD8$^+$CD44$^{high}$NKG2D$^+$ memory T cell population.

FIG. 83 shows a graphical presentation of tumor growth inhibition of ALT-803 versus PBS (top panel) or versus rhIL-15 (bottom panel) treatment. ALT-803 treatment at 0.415 and 0.83 mg/kg resulted in 63.5% and 68.3% TGI over PBS, and 47.1% and 54.1% TGI over rhIL-15. treatment 13

FIG. 86A, FIG. 86B, and FIG. 86C provides the amino acid sequence of the proteins making up Alt-803, as well as the nucleic acid sequence of the polynucleotide encoding Alt-803. Alt-803 is referred to as IL-15N72D:IL-15RαSu/Fc complex, huIL15N72D:huIL15RαSushi/huIgG1 CH2-CH3, IL-15N72D:IL-15Rα-IgG CH2-CH3, T2MΔTCRΔCH1 and ALT-803 at various points in the application. FIG. 86A, FIG. 86B, and FIG. 86C provide SEQ ID NOs: 56, 3, 57 and 4, respectively.

FIG. 88A shows reduced SDS—PAGE analysis of purified rituximab (C2B8, lane 1) and anti-CD20 scAb/IL-15:anti-CD20 scAb/IL-15Rα/IgG Fc protein complex (2B8T2M, lane 2). FIG. 88B shows size exclusion chromatography (SEC) analysis of purified rituximab (C2B8, top panel) and anti-CD20 scAb/IL-15:anti-CD20 scAb/IL-15Rα/IgG Fc protein complex (2B8T2M, bottom panel).

FIG. 89A is a graph showing effects of 2B8T2M protein complexes on proliferation of IL-15 dependent 32Dβ cells compared to 264T2M and 268T2M fusion proteins. FIG. 89B shows results from flow cytometry assays to test the CD20 antigen specific binding of anti-CD20 scFv/IL-15:anti-CD20 scFv/IL-15Rα/IgG Fc protein complexes (2B8T2M) to Daudi cells. Staining of CD20+ human Daudi lymphoma cells was performed with 50 nM fusion proteins.

DETAILED DESCRIPTION OF THE INVENTION

Figure 1:
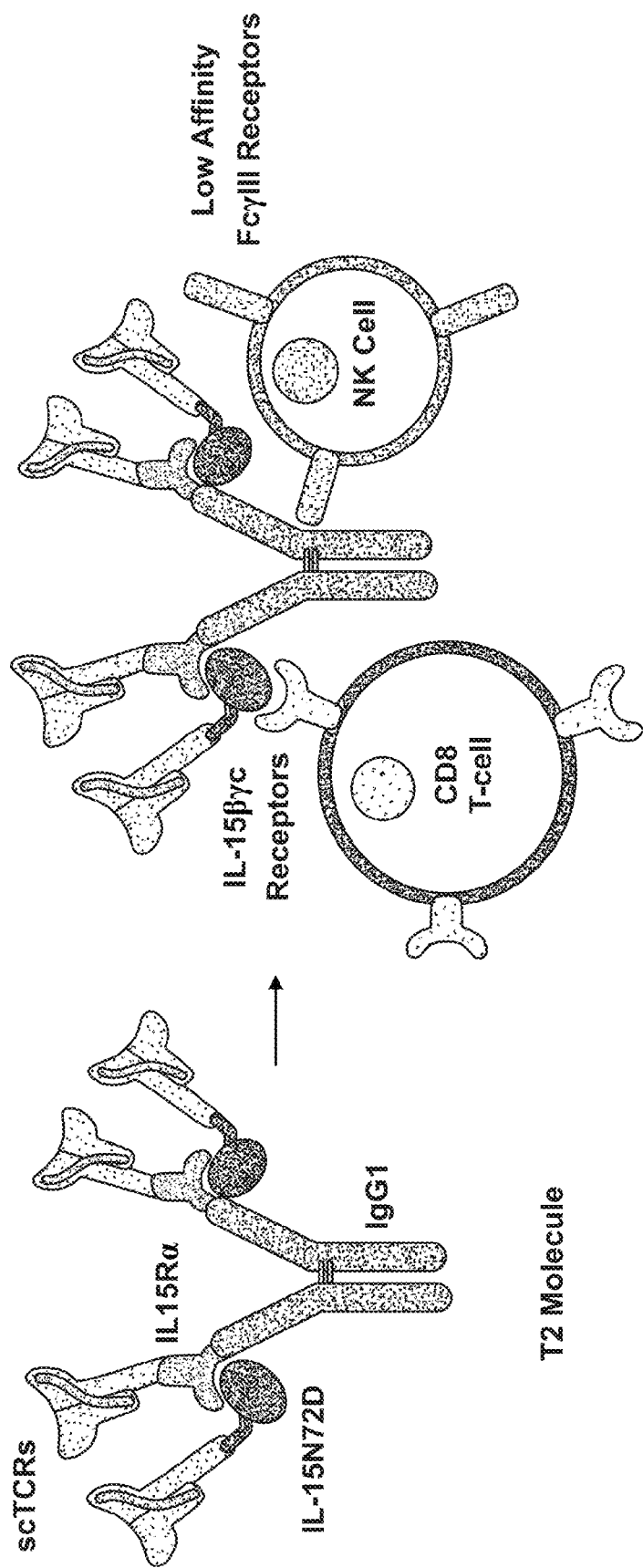
FIG. 1 shows fusion protein referred to as the T2 molecule (T2M) consists of a multichain polypeptide.

The invention provides compositions featuring ALT-803, a complex of an interleukin-15 (IL-15) superagonist mutant and a dimeric IL-15 receptor α/Fc fusion protein, and methods of using such compositions to enhance an immune response against a neoplasia (e.g., multiple myeloma, beta-cell lymphoma, urothelial/bladder carcinoma and melanoma) or a viral infection (e.g., human immunodeficiency virus).

The invention is based, at least in part, on the discovery that ALT-803 exhibited significantly stronger in vivo biological activity on NK and T cells than IL-15. As reported in more detail below, a single dose of ALT-803, but not IL-15 alone, eliminated well-established 5T33P and MOPC-315P myeloma cells in the bone marrow of tumor-bearing mice. Treatment with ALT-803 also significantly prolonged survival of myeloma-bearing mice and provided resistance to rechallenge with the same tumor cells through a CD8+ T cell-dependent mechanism. ALT-803 treatment stimulated CD8+ T cells to secrete large amounts of interferon-γ (IFN-γ) and promoted rapid expansion of CD8+CD44$^{high}$ memory T cells in vivo. These memory CD8+ T cells exhibited ALT-803-mediated up-regulation of NKG2D but not PD-1 or CD25 on their cell surfaces. ALT-803-activated CD8+ memory T cells also exhibited non-specific in-vitro cytotoxicity against myeloma and other tumor cells, whereas IFN-γ had no direct effect on myeloma cell growth. ALT-803 lost its anti-myeloma activity in tumor-bearing IFN-γ-knockout mice, but retained the ability to promote the proliferation of CD8+CD44$^{high}$ memory T cells, indicating that the stimulation of CD8+CD44$^{high}$ memory T cells by ALT-803 is IFN-γ-independent. Thus, besides well-known IL-15 biological functions in host immunity, the results reported in detail below demonstrate that IL-15-based ALT-803 could activate CD8+CD44$^{high}$ memory T cells to acquire a unique innate-like phenotype and secrete IFN-γ for non-specific tumor-cell killing. This unique immune modulatory property of ALT-803 provides for its use as a promising novel immunotherapeutic agent against cancer and viral infections.

The invention is also based, at least in part, on the discovery that Alt-803 inhibited lymphoma tumor growth in an in vivo mouse model of lymphoma.

The invention is also based, at least in part, on the discovery that Alt-803 inhibited HIV infection in an in vivo mouse model.

In other embodiments, the invention provides compositions comprising 2B8T2M for the treatment of lymphomas.

Alt-803

Alt-803 comprises a novel IL-15 mutant with increased ability to bind IL-2Rβγ and enhanced biological activity. This super agonist mutant of IL-15 was described in a publication (J Immunol 2009 183:3598) and a patent has been issued by the U.S. Patent & Trademark Office on the super agonist and several patents applications are pending (e.g., U.S. Ser. No. 12/151,980 (now U.S. Pat. No. 8,492,118) and Ser. No. 13/238,925 now U.S. Pat. No. 8,507,222). This IL-15 super agonist in combination with a soluble IL-15a receptor fusion protein (IL-15Rα-Fc) results in a protein complex with highly potent IL-15 activity in vitro and in vivo. This IL-15 super agonist complex (IL-15N72D/IL-15Rα-Fc) is referred to as ALT-803. Pharmacokinetic analysis indicated that the complex has a half-life in mice of 25 hours following i.v. administration. As reported in detail herein below, ALT-803 exhibits impressive anti-tumor activity against aggressive solid and hematological tumor models in immunocompetent mice. It can be administered as a monotherapy using a weekly i.v. dose regimen. The ALT-803 anti-tumor response is also durable. Tumor-bearing mice that were cured after ALT-803 treatment were also highly resistant to re-challenge with the same tumor cells indicating that ALT-803 induces effective immunological memory responses against the re-introduced tumor cells.

Interleukin-15

Interleukin-15 (IL-15) is an important cytokine for the development, proliferation and activation of effector NK cells and CD8$^+$ memory T cells. IL-15 binds to the IL-15 receptor α (IL-15Rα) and is presented in trans to the IL-2/IL-15 receptor β-common γ chain (IL-15 βγ$_C$) complex on effector cells. IL-15 and IL-2 share binding to the IL-15Rβγ$_c$ and signal through STAT3 and STAT5 pathways. However, unlike IL-2, IL-15 does not support maintenance of CD4$^+$CD25$^+$FoxP3$^+$ regulatory T (Treg) cells or induce cell death of activated CD8$^+$ T cells, effects that may have limited the therapeutic activity of IL-2 against multiple myeloma. Additionally, IL-15 is the only cytokine known to provide anti-apoptotic signaling to effector CD8$^+$ T cells. IL-15, either administered alone or as a complex with the IL-15Rα, exhibits potent anti-tumor activities against well-established solid tumors in experimental animal models and, thus, has been identified as one of the most promising immunotherapeutic drugs that could potentially cure cancer. However, there have been no reports showing efficacy of IL-15 against hematologic tumors.

To facilitate clinical development of an IL-15-based cancer therapeutic, a novel IL-15 mutant with increased biological activity compared to IL-15 was identified (Zhu et al., *J Immunol*, 183: 3598-3607, 2009). The pharmacokinetics and biological activity of this IL-15 super-agonist (IL-15N72D) was further improved by the creation of IL-15N72D:IL-15Rα/FC fusion complex (ALT-803), such that the super agonist complex has at least 25-times the activity of the native cytokine in vivo (Han et al., Cytokine, 56: 804-810, 2011). The results reported herein below also revealed that ALT-803 employs a novel mechanism of action against myeloma.

Fc Domain

Alt-803 comprises an IL-15N72D:IL-15Rα/FC fusion complex. Fusion proteins that combine the Fc regions of IgG with the domains of another protein, such as various cytokines and soluble receptors have been reported (see, for example, Capon et al., Nature, 337:525-531, 1989; Chamow et al., Trends Biotechnol., 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and $C_H1$ domains and light chains. The dimeric nature of fusion proteins comprising the Fc domain may be advantageous in providing higher order interactions (i.e. bivalent or bispecific binding) with other molecules. Due to the structural homology, Fc fusion proteins exhibit an in vivo pharmacokinetic profile comparable to that of human IgG with a similar isotype. Immunoglobulins of the IgG class are among the most abundant proteins in human blood, and their circulation half-lives can reach as long as 21 days. To extend the circulating half-life of IL-15 or an IL-15 fusion protein and/or to increase its biological activity, fusion protein complexes containing the IL-15 domain non-covalently bound to IL-15Rα covalently linked to the Fc portion of the human heavy chain IgG protein have been made (e.g., Alt-803).

The term "Fc" refers to a non-antigen-binding fragment of an antibody. Such an "Fc" can be in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. Fc domains containing binding sites for Protein A, Protein G, various Fc receptors and complement proteins In some embodiments, the term "Fc variant" refers to a molecule or sequence that is modified from a native Fc, but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, in certain embodiments, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means.

Fusions Protein Complexes

The invention provides Alt-803, which is a fusion protein complex, and 2B8T2M. In certain embodiments, the first fusion protein comprises a first biologically active polypeptide covalently linked to interleukin-15 (IL-15) or functional fragment thereof; and the second fusion protein comprises a second biologically active polypeptide covalently linked to soluble interleukin-15 receptor alpha (IL-15Rα) polypeptide or functional fragment thereof, where the IL-15 domain of a first fusion protein binds to the soluble IL-15Rα domain of the second fusion protein to form a soluble fusion protein complex. Fusion protein complexes of the invention also comprise immunoglobulin Fc domain or a functional fragment thereof linked to one or both of the first and second fusion proteins. Preferably the Fc domains linked to the first and second fusion proteins interact to form a fusion protein complex. Such a complex may be stabilized by disulfide bond formation between the immunoglobulin Fc domains. In certain embodiments, the soluble fusion protein complexes of the invention include an IL-15 polypeptide, IL-15 variant or a functional fragment thereof and a soluble IL-15Rα polypeptide or a functional fragment thereof, wherein one or both of the IL-15 and IL-15Rα polypeptides further include an immunoglobulin Fc domain or a functional fragment thereof.

In certain examples, one of the biologically active polypeptides comprises a first soluble TCR or fragment thereof. The other or second biologically active polypeptide comprises the first soluble TCR or functional fragment thereof and thus creates a multivalent TCR fusion protein complex with increased binding activity for cognate ligands compared to the monovalent TCR. Further, the other biologically active polypeptide comprises a second soluble TCR or functional fragment thereof, different than the first soluble TCR. In certain examples, TCRs are produced that have higher affinity, or increased binding affinity for cognate ligands as compared, for example, to the native TCR. If the soluble TCR of the invention as described herein has a higher avidity or affinity for its ligand, then it is useful as a specific probe for cell-surface bound antigen. In certain preferred examples of the invention, the TCR is specific for recognition of a particular antigen.

In exemplary embodiments, TCR is a heterodimer comprising an α chain (herein referred to as α, alpha, or α chain) and a β chain (herein referred to as β, beta, or b chain). In other exemplary embodiments, the TCR comprises a single chain TCR polypeptide. The single chain TCR may comprise a TCR V-α chain covalently linked to a TCR V-β chain by a peptide linker sequence. The single chain TCR may further comprise a soluble TCR Cβ chain fragment covalently linked to a TCR V-β chain. The single chain TCR may further comprise a soluble TCR Cα chain fragment covalently linked to a TCR V-α chain.

In a further embodiment, one or both of the first and second biologically active polypeptides comprises an antibody or functional fragment thereof.

In another embodiment, the antigen for the TCR domain comprises peptide antigen presented in an MHC or HLA molecule. In a further embodiment, the peptide antigen is derived from a tumor associated polypeptide or virus encoded polypeptide.

In another embodiment, the antigen for the antibody domain comprises a cell surface receptor or ligand.

In a further embodiment, the antigen comprises a CD antigen, cytokine or chemokine receptor or ligand, growth factor receptor or ligand, tissue factor, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

As used herein, the term "biologically active polypeptide" or "effector molecule" is meant an amino acid sequence such as a protein, polypeptide or peptide; a sugar or polysaccharide; a lipid or a glycolipid, glycoprotein, or lipoprotein that can produce the desired effects as discussed herein. Effector molecules also include chemical agents. Also contemplated are effector molecule nucleic acids encoding a biologically active or effector protein, polypeptide, or peptide. Thus, suitable molecules include regulatory factors, enzymes, antibodies, or drugs as well as DNA, RNA, and oligonucleotides. The biologically active polypeptides or effector molecule can be naturally-occurring or it can be synthesized from known components, e.g., by recombinant or chemical synthesis and can include heterologous components. A biologically active polypeptides or effector molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis. Desired effects of the invention include, but are not limited to, for example, forming a fusion protein complex of the invention with increased binding activity, killing a target cell, e.g. either to induce cell proliferation or cell death, initiate an immune response, in preventing or treating a disease, or to act as a detection molecule for diagnostic purposes. For such detection, an assay could be used, for example an assay that includes sequential steps of culturing cells to proliferate same, and contacting the cells with a TCR fusion complex of the invention and then evaluating whether the TCR fusion complex inhibits further development of the cells.

Covalently linking the effector molecule to the fusion protein complexes of the invention in accordance with the invention provides a number of significant advantages. Fusion protein complexes of the invention can be produced that contain a single effector molecule, including such a peptide of known structure. Additionally, a wide variety of effector molecules can be produced in similar DNA vectors. That is, a library of different effector molecules can be linked to the fusion protein complexes for recognition of infected or diseased cells. Further, for therapeutic applications, rather than administration of a the fusion protein complex of the invention to a subject, a DNA expression vector coding for the fusion protein complex can be administered for in vivo expression of the fusion protein complex. Such an approach avoids costly purification steps typically associated with preparation of recombinant proteins and avoids the complexities of antigen uptake and processing associated with conventional approaches.

As noted, components of the fusion proteins disclosed herein, e.g., effector molecule such as cytokines, chemokines, growth factors, protein toxins, immunoglobulin domains or other bioactive molecules and any peptide linkers, can be organized in nearly any fashion provided that the fusion protein has the function for which it was intended. In particular, each component of the fusion protein can be spaced from another component by at least one suitable peptide linker sequence if desired. Additionally, the fusion proteins may include tags, e.g., to facilitate modification, identification and/or purification of the fusion protein. More specific fusion proteins are in the Examples described below.

Pharmaceutical Therapeutics

The invention provides pharmaceutical compositions comprising Alt-803 or 2B8T2M for use as a therapeutic. For therapeutic uses, Alt-803 or 2B8T2M may be administered systemically, for example, formulated in a pharmaceutically-acceptable buffer such as physiological saline. Preferable routes of administration include, for example, instillation into the bladder, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, although in certain instances lower amounts will be needed because of the increased specificity of the compound. A compound is administered at a dosage that enhances an immune response of a subject, or that reduces the proliferation, survival, or invasiveness of a neoplastic cell as determined by a method known to one skilled in the art. In other embodiments, the compound is administered at a dosage that reduces infection by a virus of interest.

Formulation of Pharmaceutical Compositions

The administration of Alt-803 or 2B8T2M for the treatment of a neoplasia may be by any suitable means that results in a concentration of the therapeutic that, combined with other components, is effective in ameliorating, reducing, or stabilizing a neoplasia. Alt-803 or 2B8T2M may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, intravesicularly or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

In particular embodiments, Alt-803 and 2B8T2M are formulated in an excipient suitable for parenteral administration. In particular embodiments, 2B8T2M is administered at 0.5 mg/kg-about 10 mg/kg (e.g., 0.5, 1, 3, 5, 10 mg/kg).

For the treatment of bladder cancer, Alt-803 is administered by instillation into the bladder. Methods of instillation are known. See, for example, Lawrencia, et al., Gene Ther 8, 760-8 (2001); Nogawa, et al., J Clin Invest 115, 978-85 (2005); Ng, et al., Methods Enzymol 391, 304-13 2005; Tyagi, et al., J Urol 171, 483-9 (2004); Trevisani, et al., J Pharmacol Exp Ther 309, 1167-73 (2004); Trevisani, et al., Nat Neurosci 5, 546-51 (2002)); (Segal, et al., 1975). (Dyson, et al., 2005). (Batista, et al., 2005; Dyson, et al., 2005).

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition comprising Alt-803 or 2B8T2M may be administered parenterally by injection, infusion or implantation (subcutaneous, intravenous, intramuscular, intravesicularly, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions comprising Alt-803 or 2B8T2M for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions comprising Alt-803 or 2B8T2M may be in a form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

The present invention provides methods of treating neoplastic disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplastic disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplastic disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). Alt-803 or 2B8T2M may be used in the treatment of any other disorders in which an increase in an immune response is desired.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies

Optionally, an anti-neoplasia therapeutic, such as Alt-803 or 2B8T2M, may be administered in combination with any other standard anti-neoplasia therapy or conventional chemotherapeutic agent, such as an alkylating agent; such methods are known to the skilled artisan and described in Remington's Pharmaceutical Sciences by E. W. Martin. If desired, Alt-803 is administered in combination with any conventional anti-neoplastic therapy, including but not limited to, surgery, radiation therapy, or chemotherapy.

Kits or Pharmaceutical Systems

Pharmaceutical compositions comprising Alt-803 or 2B8T2M may be assembled into kits or pharmaceutical systems for use in ameliorating a neoplasia. Kits or pharmaceutical systems according to this aspect of the invention comprise a carrier means, such as a box, carton, tube or the like, having in close confinement therein one or more container means, such as vials, tubes, ampoules, bottles and the like. The kits or pharmaceutical systems of the invention may also comprise associated instructions for using Alt-803 or 2B8T2M.

Linkers

The fusion complexes of the invention preferably also include a flexible linker sequence interposed between the IL-15 or IL-15Rα domains and the biologically active polypeptide. The linker sequence should allow effective positioning of the biologically active polypeptide with respect to the IL-15 or IL-15Rα domains to allow functional activity of both domains. In embodiments where the biologically active polypeptide is a TCR, the linker sequence positions the TCR molecule binding groove so that the T cell receptor can recognize presenting MHC-peptide complexes and can deliver the effector molecule to a desired site. Successful presentation of the effector molecule can modulate the activity of a cell either to induce or to inhibit T-cell proliferation, or to initiate or inhibit an immune response to a particular site, as determined by the assays disclosed below, including the in vitro assays that includes sequential steps of culturing T cells to proliferate same, and contacting the T cells with a TCR fusion complex of the invention and then evaluating whether the TCR fusion complex inhibits further development of the cells.

In certain embodiments, the soluble fusion protein complex has a linker wherein the first biologically active polypeptide is covalently linked to IL-15 (or functional fragment thereof) by polypeptide linker sequence.

In other certain embodiments, the soluble fusion protein complex as described herein has a linker wherein the second biologically active polypeptide is covalently linked to IL-15Rα polypeptide (or functional fragment thereof) by polypeptide linker sequence.

The linker sequence is preferably encoded by a nucleotide sequence resulting in a peptide that can effectively position the binding groove of a TCR molecule for recognition of a presenting antigen or the binding domain of an antibody molecule for recognition of an antigen. As used herein, the phrase "effective positioning of the biologically active polypeptide with respect to the IL-15 or IL-15Rα domains", or other similar phrase, is intended to mean the biologically active polypeptide linked to the IL-15 or IL-15Rα domains is positioned so that the IL-15 or IL-15Rα domains are capable of interacting with each other to form a protein complex. In certain embodiments, the IL-15 or IL-15Rα domains are effectively positioned to allow interactions with immune cells to initiate or inhibit an immune reaction, or to inhibit or stimulate cell development.

The fusion complexes of the invention preferably also include a flexible linker sequence interposed between the IL-15 or IL-15Rα domains and the immunoglobulin Fc domain. The linker sequence should allow effective positioning of the Fc domain, biologically active polypeptide and IL-15 or IL-15Rα domains to allow functional activity of each domain. In certain embodiments, the Fc domains are effectively positioned to allow proper fusion protein complex formation and/or interactions with Fc receptors on immune cells or protiens of the complement system to stimulate Fc-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences can also be used to link two or more polypeptides of the biologically active polypeptide to generated a single-chain molecule with the desired functional activity.

Preferably the linker sequence comprises from about 7 to 20 amino acids, more preferably from about 8 to 16 amino acids. The linker sequence is preferably flexible so as not hold the biologically active polypeptide or effector molecule in a single undesired conformation. The linker sequence can be used, e.g., to space the recognition site from the fused molecule. Specifically, the peptide linker sequence can be positioned between the biologically active polypeptide and the effector molecule, e.g., to chemically cross-link same and to provide molecular flexibility. The linker preferably predominantly comprises amino acids with small side chains, such as glycine, alanine and serine, to provide for flexibility. Preferably about 80 or 90 percent or greater of the linker sequence comprises glycine, alanine or serine residues, particularly glycine and serine residues. For a fusion protein complex that comprise a heterodimer TCR, the linker sequence is suitably linked to the β chain of the TCR molecule, although the linker sequence also could be attached to the α chain of the TCR molecule. Alternatively, linker sequence may be linked to both α and β chains of the TCR molecule. When such a β peptide chain is expressed along with the α chain, the linked TCR polypeptide should fold resulting in a functional TCR molecule as generally depicted in FIG. 1. One suitable linker sequence is ASGGGGSGGG (i.e., Ala Ser Gly Gly Gly Gly Ser Gly Gly Gly) (SEQ ID NO: 5), preferably linked to the first amino acid of the β domain of the TCR. Different linker sequences could be used including any of a number of flexible linker designs that have been used successfully to join antibody variable regions together, see Whitlow, M. et al., (1991) *Methods: A Companion to Methods in Enzymology* 2:97-105. In some examples, for covalently linking an effector molecule to a TCR β chain molecule, the amino sequence of the linker should be capable of spanning suitable distance from the C-terminal residue of the TCR β chain to the N-terminal residue of the effector molecule. Suitable linker sequences can be readily identified empirically. Additionally, suitable size and sequences of linker sequences also can be determined by conventional computer modeling techniques based on the predicted size and shape of the TCR molecule.

T-Cell Receptors (TCR)

T-cells are a subgroup of cells which together with other immune cell types (polymorphonuclear, eosinophils, basophils, mast cells, B-cells, NK cells), constitute the cellular component of the immune system. Under physiological conditions T-cells function in immune surveillance and in the elimination of foreign antigen. However, under pathological conditions there is compelling evidence that T-cells play a major role in the causation and propagation of disease. In these disorders, breakdown of T-cell immunological tolerance, either central or peripheral is a fundamental process in the causation of autoimmune disease.

The TCR complex is composed of at least seven transmembrane proteins. The disulfide-linked (αβ or γδ) heterodimer forms the monotypic antigen recognition unit, while the invariant chains of CD3, consisting of ε, γ, δ, ζ, and η chains, are responsible for coupling the ligand binding to signaling pathways that result in T-cell activation and the elaboration of the cellular immune responses. Despite the gene diversity of the TCR chains, two structural features are common to all known subunits. First, they are transmembrane proteins with a single transmembrane spanning domain-presumably alpha-helical. Second, all TCR chains have the unusual feature of possessing a charged amino acid within the predicted transmembrane domain. The invariant chains have a single negative charge, conserved between the mouse and human, and the variant chains possess one (TCR-β) or two (TCR-α) positive charges. The transmembrane sequence of TCR-α is highly conserved in a number of species and thus phylogenetically may serve an important functional role. The octapeptide sequence containing the hydrophilic amino acids arginine and lysine is identical between the species.

A T-cell response is modulated by antigen binding to a TCR. One type of TCR is a membrane bound heterodimer consisting of an α and β chain resembling an immunoglobulin variable (V) and constant (C) region. The TCR cc chain includes a covalently linked V-α and C-α chain, whereas the β chain includes a V-β chain covalently linked to a C-β chain. The V-α and V-β chains form a pocket or cleft that can bind a superantigen or antigen in the context of a major histocompatibility complex (MHC) (known in humans as an HLA complex). See generally Davis *Ann. Rev. of Immunology* 3: 537 (1985); *Fundamental Immunology* 3rd Ed., W. Paul Ed. Rsen Press LTD. New York (1993).

The extracellular domains of the TCR chains (αβ or γδ) can also engineered as fusions to heterologous transmembrane domains for expression on the cell surface. Such TCRs may include fusions to CD3, CD28, CD8, 4-1BB and/or chimeric activation receptor (CAR) transmembrane or activation domains. TCRs can also be the soluble proteins comprising one or more of the antigen binding domains of αβ or γδ chains. Such TCRs may include the TCR variable domains or function fragments thereof with or without the TCR constant domains. Soluble TCRs may be heterodimeric or single-chain molecules.

Recombinant Protein Expression

In general, preparation of the fusion protein complexes of the invention (e.g., components of Alt-803 or 2B8T2M) can be accomplished by procedures disclosed herein and by recognized recombinant DNA techniques.

In general, recombinant polypeptides are produced by transformation of a suitable host cell with all or part of a polypeptide-encoding nucleic acid molecule or fragment thereof in a suitable expression vehicle. Those skilled in the field of molecular biology will understand that any of a wide variety of expression systems may be used to provide the recombinant protein. The precise host cell used is not critical to the invention. A recombinant polypeptide may be produced in virtually any eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transfection and the choice of expression vehicle will depend on the host system selected. Transformation methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of recombinant polypeptides. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Once the recombinant polypeptide is expressed, it is isolated, e.g., using affinity chromatography. In one example, an antibody (e.g., produced as described herein) raised against the polypeptide may be attached to a column and used to isolate the recombinant polypeptide. Lysis and fractionation of polypeptide-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980).

As used herein, biologically active polypeptides or effector molecules of the invention may include factors such as cytokines, chemokines, growth factors, protein toxins, immunoglobulin domains or other bioactive proteins such as enzymes. Also biologically active polypeptides may include conjugates to other compounds such as non-protein toxins, cytotoxic agents, chemotherapeutic agents, detectable labels, radioactive materials and such.

Cytokines of the invention are defined by any factor produced by cells that affect other cells and are responsible for any of a number of multiple effects of cellular immunity. Examples of cytokines include but are not limited to the IL-2 family, interferon (IFN), IL-10, IL-1, IL-17, TGF and TNF cytokine families, and to IL-1 through IL-35, IFN-α, IFN-β, IFNγ, TGF-β, TNF-α, and TNFβ.

In an aspect of the invention, the first fusion protein comprises a first biologically active polypeptide covalently linked to interleukin-15 (IL-15) domain or a functional fragment thereof. IL-15 is a cytokine that affects T-cell activation and proliferation. IL-15 activity in affecting immune cell activation and proliferation is similar in some respects to IL2, although fundamental differences have been well characterized (Waldmann, T A, 2006, Nature Rev. Immunol. 6:595-601).

In another aspect of the invention, the first fusion protein comprises an interleukin-15 (IL-15) domain that is an IL-15 variant (also referred to herein as IL-15 mutant). The IL-15 variant preferably comprises a different amino acid sequence that the native (or wild type) IL-15 protein. The IL-15 variant preferably binds the IL-15Rαpolypeptide and functions as an IL-15 agonist or antagonist. Preferably IL-15 variants with agonist activity have super agonist activity. In some embodiments, the IL-15 variant can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In some examples, the IL-15 variant binds with increased or decreased activity to the IL-15RβγC receptors. In some embodiments, the sequence of the IL-15 variant has at least one amino acid change, e.g. substitution or deletion, compared to the native IL-2 sequence, such changes resulting in IL-15 agonist or antagonist activity. Preferably the amino acid substitutions/deletions are in the domains of IL-15 that interact with IL-15Rβ and/or γC. More preferably, the amino acid substitutions/deletions do not affect binding to the IL-15Rαpolypeptide or the ability to produce the IL-15 variant. Suitable amino acid substitutions/deletions to generate IL-15 variants can be identified based on putative or known IL-15 structures, comparisons of IL-15 with homologous molecules such as IL-2 with known structure, through rational or random mutagenesis and functional assays, as provided herein, or other empirical methods. Additionally suitable amino acid substitutions can be conservative or non-conservative changes and insertions of additional amino acids. Preferably IL-15 variants of the invention contain one or more than one amino acid substitutions/deletions at position 6, 8, 10, 61, 65, 72, 92, 101, 104, 105, 108, 109, 111, or 112 of the mature human IL-15 sequence; particularly, D8N ("D8" refers to the amino acid and residue position in the native mature human IL-15 sequence and "N" refers to the substituted amino acid residue at that position in the IL-15 variant), I6S, D8A, D61A, N65A, N72R, V104P or Q108A substitutions result in IL-15 variants with antagonist activity and N72D substitutions result in IL-15 variants with agonist activity.

Chemokines, similar to cytokines, are defined as any chemical factor or molecule which when exposed to other cells are responsible for any of a number of multiple effects of cellular immunity. Suitable chemokines may include but are not limited to the CXC, CC, C, and $CX_3C$ chemokine families and to CCL-1 through CCL-28, CXC-1 through CXC-17, XCL-1, XCL-2, CX3CL1, MIP-1b, IL-8, MCP-1, and Rantes.

Growth factors include any molecules which when exposed to a particular cell induce proliferation and/or differentiation of the affected cell. Growth factors include proteins and chemical molecules, some of which include: GM-CSF, G-CSF, human growth factor and stem cell growth factor. Additional growth factors may also be suitable for uses described herein.

Toxins or cytotoxic agents include any substance that has a lethal effect or an inhibitory effect on growth when exposed to cells. More specifically, the effector molecule can be a cell toxin of, e.g., plant or bacterial origin such as, e.g., diphtheria toxin (DT), shiga toxin, abrin, cholera toxin, ricin, saporin, pseudomonas exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C).

Further, the effector molecule can be a chemotherapeutic drug such as, e.g., vindesine, vincristine, vinblastin, methotrexate, adriamycin, bleomycin, or cisplatin.

Additionally, the effector molecule can be a detectably-labeled molecule suitable for diagnostic or imaging studies. Such labels include biotin or streptavidin/avidin, a detectable nanoparticles or crystal, an enzyme or catalytically active fragment thereof, a fluorescent label such as green fluorescent protein, FITC, phycoerythrin, cychome, texas red or quantum dots; a radionuclide e.g., iodine-131, yttrium-90, rhenium-188 or bismuth-212; a phosphorescent or chemiluminescent molecules or a label detectable by PET, ultrasound or MRI such as Gd—or paramagnetic metal ion-based contrast agents. See e.g., Moskaug, et al. J. Biol. Chem. 264, 15709 (1989); Pastan, I. et al. Cell 47, 641, 1986; Pastan et al., Recombinant Toxins as Novel Therapeutic Agents, Ann. Rev. Biochem. 61, 331, (1992); "Chimeric Toxins" Olsnes and Phil, Pharmac. Ther., 25, 355 (1982); published PCT application no. WO 94/29350; published PCT application no. WO 94/04689; published PCT application no. WO2005046449 and U.S. Pat. No. 5,620,939 for disclosure relating to making and using proteins comprising effectors or tags.

A protein fusion or conjugate complex that includes a covalently linked IL-15 and IL-15Rα domains has several important uses. For example, the protein fusion or conjugate complex comprising a TCR can be employed to deliver the IL-15:IL-15Rα complex to certain cells capable of specifically binding the TCR. Accordingly, the protein fusion or conjugate complex provide means of selectively damaging or killing cells comprising the ligand. Examples of cells or tissue capable of being damaged or killed by the protein fusion or conjugate complexes comprising a TCR include tumors and virally or bacterially infected cells expressing one or more ligands capable of being specifically bound by the TCR. Cells or tissue susceptible to being damaged or killed can be readily assayed by the methods disclosed herein.

The IL-15 and IL-15Rα polypeptides of the invention suitably correspond in amino acid sequence to naturally occurring IL-15 and IL-15Rα molecules, e.g. IL-15 and IL-15Rα molecules of a human, mouse or other rodent, or other mammal. Sequences of these polypeptides and encoding nucleic acids are known in the literature, including human interleukin 15 (IL15) mRNA-GenBank: U14407.1, *Mus musculus* interleukin 15 (IL15) mRNA-GenBank: U14332.1, human interleukin-15 receptor alpha chain precursor (IL15RA) mRNA-GenBank: U31628.1, *Mus musculus* interleukin 15 receptor, alpha chain-GenBank: BC095982.1.

In some settings it can be useful to make the protein fusion or conjugate complexes of the present invention polyvalent, e.g., to increase the valency of the sc-TCR or sc-antibody. In particular, interactions between the IL-15 and IL-15Rα domains of the fusion protein complex provide a means of generating polyvalent complexes. In addition, the polyvalent fusion protein can made by covalently or non-covalently linking together between one and four proteins (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding tag sequences that can be modified such as the biotinylation BirA tag or amino acid residues with chemically reactive side chains such as Cys or His. Such amino acid tags or chemically reactive amino acids may be positioned in a variety of positions in the fusion protein, preferably distal to the active site of the biologically active polypeptide or effector molecule. For example, the C-terminus of a soluble fusion protein can be covalently linked to a tag or other fused protein which includes such a reactive amino acid(s). Suitable side chains can be included to chemically link two or more fusion proteins to a suitable dendrimer or other nanoparticle to give a multivalent molecule. Dendrimers are synthetic chemical polymers that can have any one of a number of different functional groups of their surface (D. Tomalia, Aldrichimica Acta, 26:91:101 (1993)). Exemplary dendrimers for use in accordance with the present invention include e.g. E9 starburst polyamine dendrimer and E9 combust polyamine dendrimer, which can link cystine residues. Exemplary nanoparticles include liposomes, core-shell particles or PLGA-based particles.

In another embodiment of the invention, one or both of the polypeptides of the fusion protein complex comprises an immunoglobulin domain. Alternatively, the protein binding domain-IL-15 fusion protein can be further linked to an immunoglobulin domain. The preferred immunoglobulin domains comprise regions that allow interaction with other immunoglobulin domains to form multichain proteins as provided above. For example, the immunoglobulin heavy chain regions, such as the IgG1 $C_H2$-$C_H3$, are capable of stably interacting to create the Fc region. Preferred immunoglobulin domains including Fc domains also comprise regions with effector functions, including Fc receptor or complement protein binding activity, and/or with glycosylation sites. In some embodiments, the immunoglobulin domains of the fusion protein complex contain mutations that reduce or augment Fc receptor or complement binding activity or glycosylation, thereby affecting the biological activity of the resulting protein. For example, immunoglobulin domains containing mutations that reduce binding to Fc receptors could be used to generate fusion protein complex of the invention with lower binding activity to Fc receptor-bearing cells, which may be advantageous for reagents designed to recognize or detect specific antigens.

Nucleic Acids and Vectors

The invention further provides nucleic acid sequences and particularly DNA sequences that encode the present fusion proteins (e.g., components of Alt-803 or 2B8T2M). Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate preparative methods described herein and to obtain significant quantities of the fusion protein. The DNA sequence can be inserted into an appropriate expression vector, i.e., a vector that contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See generally Sambrook et al., supra and Ausubel et al. supra.

Included in the invention are methods for making a soluble fusion protein complex, the method comprising introducing into a host cell a DNA vector as described herein encoding the first and second fusion proteins, culturing the host cell in media under conditions sufficient to express the fusion proteins in the cell or the media and allow association between IL-15 domain of a first fusion protein and the soluble IL-15Rα domain of a second fusion protein to form the soluble fusion protein complex, purifying the soluble fusion protein complex from the host cells or media.

In general, a preferred DNA vector according to the invention comprises a nucleotide sequence linked by phosphodiester bonds comprising, in a 5' to 3' direction a first cloning site for introduction of a first nucleotide sequence encoding a biologically active polypeptide, operatively linked to a sequence encoding an effector molecule.

The fusion protein components encoded by the DNA vector can be provided in a cassette format. By the term "cassette" is meant that each component can be readily substituted for another component by standard recombinant methods. In particular, a DNA vector configured in a cassette format is particularly desirable when the encoded fusion complex is to be used against pathogens that may have or have capacity to develop serotypes.

To make the vector coding for a fusion protein complex, the sequence coding for the biologically active polypeptide is linked to a sequence coding for the effector peptide by use of suitable ligases. DNA coding for the presenting peptide can be obtained by isolating DNA from natural sources such as from a suitable cell line or by known synthetic methods, e.g. the phosphate triester method. See, e.g., Oligonucleotide Synthesis, IRL Press (M. J. Gait, ed., 1984). Synthetic oligonucleotides also may be prepared using commercially available automated oligonucleotide synthesizers. Once isolated, the gene coding for the biologically active polypeptide can be amplified by the polymerase chain reaction (PCR) or other means known in the art. Suitable PCR primers to amplify the biologically active polypeptide gene may add restriction sites to the PCR product. The PCR product preferably includes splice sites for the effector peptide and leader sequences necessary for proper expression and secretion of the biologically active polypeptide-effector fusion complex. The PCR product also preferably includes a sequence coding for the linker sequence, or a restriction enzyme site for ligation of such a sequence.

The fusion proteins described herein are preferably produced by standard recombinant DNA techniques. For example, once a DNA molecule encoding the biologically active polypeptide is isolated, sequence can be ligated to another DNA molecule encoding the effector polypeptide. The nucleotide sequence coding for a biologically active polypeptide may be directly joined to a DNA sequence coding for the effector peptide or, more typically, a DNA sequence coding for the linker sequence as discussed herein may be interposed between the sequence coding for the biologically active polypeptide and the sequence coding for the effector peptide and joined using suitable ligases. The resultant hybrid DNA molecule can be expressed in a suitable host cell to produce the fusion protein complex. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein.

Other nucleotide sequences also can be included in the gene construct. For example, a promoter sequence, which controls expression of the sequence coding for the biologically active polypeptide fused to the effector peptide, or a leader sequence, which directs the fusion protein to the cell surface or the culture medium, can be included in the construct or present in the expression vector into which the construct is inserted. An immunoglobulin or CMV promoter is particularly preferred.

In obtaining variant biologically active polypeptide, IL-15, IL-15Rα or Fc domain coding sequences, those of ordinary skill in the art will recognize that the polypeptides may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein. In other instance, modifications to amino acid positions can be made to reduce or enhance the biological activity of the protein. Such changes can be introduced randomly or via site-specific mutations based on known or presumed structural or functional properties of targeted residue(s). Following expression of the variant protein, the changes in the biological activity due to the modification can be readily assessed using binding or functional assays.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50 C, 6×SSC (sodium chloride/sodium citrate buffer) and 0.1% SDS (sodium dodecyl sulfate) indicate about 60-70% homology, hybridization and wash conditions of 50-65 C, 1×SSC and 0.1% SDS indicate about 82-97% homology, and hybridization and wash conditions of 52 C, 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the world wide web at ncbi.nlm.nih.gov and a version of ClustalW is available at 2.ebi.ac.uk.

The components of the fusion protein can be organized in nearly any order provided each is capable of performing its intended function. For example, in one embodiment, the biologically active polypeptide is situated at the C or N terminal end of the effector molecule.

Preferred effector molecules of the invention will have sizes conducive to the function for which those domains are intended. The effector molecules of the invention can be made and fused to the biologically active polypeptide by a variety of methods including well-known chemical cross-linking methods. See e.g., Means, G. E. and Feeney, R. E. (1974) in *Chemical Modification of Proteins*, Holden-Day. See also, S. S. Wong (1991) in *Chemistry of Protein Conjugation and Cross-Linking*, CRC Press. However it is generally preferred to use recombinant manipulations to make the in-frame fusion protein.

As noted, a fusion molecule or a conjugate molecule in accord with the invention can be organized in several ways. In an exemplary configuration, the C-terminus of the biologically active polypeptide is operatively linked to the N-terminus of the effector molecule. That linkage can be achieved by recombinant methods if desired. However, in another configuration, the N-terminus of the biologically active polypeptide is linked to the C-terminus of the effector molecule.

Alternatively, or in addition, one or more additional effector molecules can be inserted into the biologically active polypeptide or conjugate complexes as needed.

Vectors and Expression

A number of strategies can be employed to express Alt-803 or 2B8T2M. For example, a construct encoding Alt-803 or 2B8T2M can be incorporated into a suitable vector using restriction enzymes to make cuts in the vector for insertion of the construct followed by ligation. The vector containing the gene construct is then introduced into a suitable host for expression of the fusion protein. See, generally, Sambrook et al., *supra*. Selection of suitable vectors can be made empirically based on factors relating to the cloning protocol. For example, the vector should be compatible with, and have the proper replicon for the host that is being employed. Further the vector must be able to accommodate the DNA sequence coding for the fusion protein complex that is to be expressed. Suitable host cells include eukaryotic and prokaryotic cells, preferably those cells that can be easily transformed and exhibit rapid growth in culture medium. Specifically preferred hosts cells include prokaryotes such as E. coli, Bacillus subtillus, etc. and eukaryotes such as animal cells and yeast strains, e.g., S. cerevisiae. Mammalian cells are generally preferred, particularly J558, NSO, SP2-O or CHO. Other suitable hosts include, e.g., insect cells such as Sf9. Conventional culturing conditions are employed. See Sambrook, supra. Stable transformed or transfected cell lines can then be selected. Cells expressing a fusion protein complex of the invention can be determined by known procedures. For example, expression of a fusion protein complex linked to an immunoglobulin can be determined by an ELISA specific for the linked immunoglobulin and/or by immunoblotting. Other methods for detecting expression of fusion proteins comprising biologically active polypeptides linked to IL-15 or IL-15Rα domains are disclosed in the Examples.

As mentioned generally above, a host cell can be used for preparative purposes to propagate nucleic acid encoding a desired fusion protein. Thus a host cell can include a prokaryotic or eukaryotic cell in which production of the fusion protein is specifically intended. Thus host cells specifically include yeast, fly, worm, plant, frog, mammalian cells and organs that are capable of propagating nucleic acid encoding the fusion. Non-limiting examples of mammalian cell lines which can be used include CHO dhfr-cells (Urlaub and Chasm, Proc. Natl. Acad. Sci. USA, 77:4216 (1980)), 293 cells (Graham et al., J Gen. Virol., 36:59 (1977)) or myeloma cells like SP2 or NSO (Galfre and Milstein, Meth. Enzymol., 73(B):3 (1981)).

Host cells capable of propagating nucleic acid encoding a desired fusion protein comples encompass non-mammalian eukaryotic cells as well, including insect (e.g., Sp. frugiperda), yeast (e.g., S. cerevisiae, S. pombe, P. pastoris., K. lactis, H. polymorpha; as generally reviewed by Fleer, R., Current Opinion in Biotechnology, 3(5):486496 (1992)), fungal and plant cells. Also contemplated are certain prokaryotes such as E. coli and Bacillus.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in E. coli. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the biologically active polypeptide coding sequence may be used. Alternatively, a signal sequence which has been selected or designed for efficient secretion and processing in the expression host may also be used. For example, suitable signal sequence/host cell pairs include the B. subtilis sacB signal sequence for secretion in B. subtilis, and the Saccharomyces cerevisiae α-mating factor or P. pastoris acid phosphatase phoI signal sequences for P. pastoris secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for E. coli host cells, nptII confers kanamycin resistance to a wide variety of prokaryotic and eukaryotic cells) or that permit the host to grow on minimal medium (e.g., HIS4 enables P. pastoris or His⁻ S. cerevisiae to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 µg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of E. coli. Numerous cloning vectors suitable for construction of the expression construct are known in the art (λZAP and pBLUESCRIPT SK-1, Stratagene, La Jolla, Calif., pET, Novagen Inc., Madison, Wis., cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into *S. cerevisiae* cells by protoplast transformation or electroporation. Electroporation of *S. cerevisiae* is readily accomplished, and yields transformation efficiencies comparable to spheroplast transformation.

The present invention further provides a production process for isolating a fusion protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium to stimulate transcription of the nucleotides sequence encoding the fusion protein of interest. Subsequently, the fusion protein of interest is isolated from harvested host cells or from the culture medium. Standard protein purification techniques can be used to isolate the protein of interest from the medium or from the harvested cells. In particular, the purification techniques can be used to express and purify a desired fusion protein on a large-scale (i.e. in at least milligram quantities) from a variety of implementations including roller bottles, spinner flasks, tissue culture plates, bioreactor, or a fermentor.

An expressed protein fusion complex can be isolated and purified by known methods. Typically the culture medium is centrifuged or filtered and then the supernatant is purified by affinity or immunoaffinity chromatography, e.g. Protein-A or Protein-G affinity chromatography or an immunoaffinity protocol comprising use of monoclonal antibodies that bind the expressed fusion complex such as a linked TCR or immunoglobulin region thereof. The fusion proteins of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatography, methods utilizing a difference in hydrophobicity such as reverse-phase high performance liquid chromatography and methods utilizing a difference in isoelectric point, such as isoelectric focusing electrophoresis, metal affinity columns such as Ni-NTA. See generally Sambrook et al. and Ausubel et al. supra for disclosure relating to these methods.

It is preferred that the fusion proteins of the present invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

In certain embodiments, soluble TCR fusion complexes of the invention contain TCR domains that is sufficiently truncated so the TCR fusion complex can be secreted into culture medium after expression. Thus, a truncated TCR fusion complex will not include regions rich in hydrophobic residues, typically the transmembrane and cytoplasmic domains of the TCR molecule. Thus, for example, for a preferred truncated TCR molecule of the invention, preferably from about the final cysteine to the C-terminal residue of the β chain and from about the final cysteine to the C-terminal residue of the α chain of the TCR molecule are not included in the truncated TCR fusion complex.

The present fusion protein complexes are suitable for in vitro or in vivo use with a variety of cells that are cancerous or are infected or that may become infected by one or more diseases.

Human interleukin-15 (hIL-15) is trans-presented to immune effector cells by the human IL-15 receptor α chain (hIL-15Rα) expressed on antigen presenting cells. IL-15Rα binds hIL-15 with high affinity (38 pM) primarily through the extracellular sushi domain (hIL-15RαSu. The hIL-15 and hIL-15RαSu domains can be used as a scaffold to construct multi-domain fusion complexes. Both bivalent and bispecific T cell receptor (TCR) fusion complexes were formed using this scaffold through the combination of various single-chain (sc) TCR domains fused to the N-termini of the hIL-15 and hIL-15RαSu chains. In these fusions, the scTCR domains retain the antigen binding activity and the hIL-15 domain exhibits receptor binding and biological activity. Bivalent scTCR fusions exhibited improved antigen binding capacity due to increased molecular binding avidity whereas fusions comprising two different scTCR domains were capable of binding two cognate peptide/MHC complexes. Bispecific molecules containing scTCR and scCD8αβ domains also exhibit significantly better binding to cognate peptide/MHC complex than either the bivalent or monovalent scTCR molecules, demonstrating that the IL-15:IL-15Rα scaffold exhibits flexibility necessary to support multi-domain interactions with given target. Surprisingly, functional TCRs could also be formed by co-expressing the TCR α and β chains separately as fusions to the hIL-15 and hIL-15RαSu domains. Finally, the fused hIL-15 domain can be manipulated through site-specific mutations to provide superagonist or antagonist cytokine activity. Together, these properties indicate that the hIL-15 and hIL-15RαSu domains can be used as versatile, functional scaffold for generating novel targeted immune molecules.

IgG domains, particularly the Fc fragment, have been used successfully as dimeric scaffolds for a number of therapeutic molecules including approved biologic drugs. For example, etanercept is a dimer of soluble human p75 tumor necrosis factor-α (TNF-α) receptor (sTNFR) linked to the Fc domain of human IgG1. This dimerization allows etanercept to be up to 1,000 times more potent at inhibiting TNF-α activity than the monomeric sTNFR and provides the fusion with a five-fold longer serum half-life than the monomeric form. As a result, etanercept is effective at neutralization of the pro-inflammatory activity of TNF-α in vivo and improving patient outcomes for a number of different autoimmune indications.

In addition to its dimerization activity, the Fc fragment also provides cytotoxic effector functions through the complement activation and interaction with Fcγ receptors displayed on natural killer (NK) cells, neutrophils, phagocytes and dendritic cells. In the context of anti-cancer therapeutic antibodies and other antibody domain-Fc fusion proteins, these activities likely play an important role in efficacy observed in animal tumor models and in cancer patients. However these cytotoxic effector responses may not be sufficient in a number of therapeutic applications. Thus, there has been considerable interest in improving and expanding on the effector activity of the Fc domain and developing other means of recruiting cytolytic immune responses, including T cell activity, to the disease site via targeted therapeutic molecules. IgG domains have been used as a scaffold to form bispecific antibodies to improve the quality and quantity of products generated by the traditional hybridoma fusion technology. Although these methods bypass the shortcomings of other scaffolds, it has been difficult to produce bispecific antibodies in mammalian cells at levels sufficient to support clinical development and use.

In an effort to develop a new, human-derived immunostimulatory multimeric scaffold, human IL-15 (hIL-15) and IL-15 receptor domains were used. hIL-15 is a member of the small four α-helix bundle family of cytokines that associates with the hIL-15 receptor α-chain (hIL-15Rα) with a high binding affinity (Equilibrium dissociation constant (KD) ~$10^{-11}$M). The resulting complex is then trans-presented to the human IL-2/15 receptor β/common γ chain (hIL-15RβγC) complexes displayed on the surface of T cells and NK cells. This cytokine/receptor interaction results in expansion and activation of effector T cells and NK cells, which play an important role in eradicating virally infected and malignant cells. Normally, hIL-15 and hIL-15Rα are co-produced in dendritic cells to form complexes intracellularly that are subsequently secreted and displayed as heterodimeric molecules on cell surfaces. Thus, the characteristics of hIL-15 and hIL-15Rα interactions suggest that these inter chain binding domains could serve as a novel, human-derived immunostimulatory scaffold to make soluble dimeric molecules capable of target-specific binding. A number of fusion proteins comprising T cell receptor (TCR) and CD8 binding domains were made to demonstrate the feasibility of using hIL-15:hIL-15Rα scaffold to create both soluble homodimers with increased functional binding affinity toward target antigens and heterodimers for multiple-site-specific protein complexes. These fusion proteins retain potent hIL-15 activity capable of stimulating immune effector cell responses.

An hIL-15:hIL-15RαSu-based scaffold was used to create novel, dimeric molecules. The dimeric fusion protein complexes retained immunostimulatory and target-specific biological activity of their hIL-15 domains and binding domains, indicating that the addition of hIL-15 and hIL-15Rα did not significantly alter the spatial arrangement of the fusion domains and provided an adequate degree of conformational flexibility without impacting cytokine activity. Thus, this scaffold could be used to form multivalent fusion complexes, such as the c264scTCR dimer, to increase the overall binding affinity of molecules, or bispecific molecules, such as the c264scTCR/c149scTCR heterodimer. In all cases, the soluble fusion proteins were produced at relatively high levels in recombinant CHO cell culture (mgs per liter in cell culture supernatant without extensive cell line screening or optimization) and could be readily purified from the cell culture supernatants. The hIL-15:hIL-15RαSu-based scaffold could be expanded to create soluble, biologically active, two-chain molecules, such as α/β TCRs, by fusing the extracellular domains of the two polypeptide chains to the N-termini of hIL-15 and hIL-15RαSu. This format resulted in a moderate decrease in hIL-15 activity, possibly due to steric hindrance between the interfolded TCR α/β chains fused to the distal N-termini of the hIL-15:hIL-15RαSu complex and the hIL-15RβγC binding site located in the middle of the complex. Other formats are possible and can be generated using routine methods.

The hIL-15:hIL-15RαSu-based scaffold was also used to generate an OT1scTCR/scCD8 heterodimer in which the CD8 α/β and TCR domains are capable of binding the same pMHCI complex but at a spatially distinct sites. Previous studies using soluble pMHCI reagents have determined that CD8 stabilizes and enhances TCR:pMHCI interactions at the cell surface through effects on both the off-rate and the on-rate. This effect is important in determining the dependency of the T cells on CD8 co-receptor activity, such that the requirement for CD8 for pMHCI-specific T cell activation is inversely correlated with TCR:pMHCI affinity. However, several binding studies using soluble purified CD8 α/β, TCR and pMHCI proteins have shown that TCR:pMHCI interactions are not affected by the presence or absence of CD8, suggesting no cooperative binding effects.

The results of cell-based and SPR binding studies with the OT1scTCR/scCD8 heterodimer are in contrast with earlier reports showing that TCR and CD8 domains displayed on the same soluble molecule exhibited much better peptide/MHC binding activity than was observed with molecules carrying monovalent or divalent TCR domains. This effect is reflected in both a slower off-rate and faster on-rate of the pMHCI:OT1scTCR/scCD8 heterodimer complex, consistent with the observations for pMHCI binding to CD8 and TCR molecules on T cells. Thus, the OT1scTCR/scCD8 heterodimer mimics binding of the OT1 TCR on T cells, which exhibits a strong dependence of CD8 coreceptor activity for pMHC interactions. These results indicate that the scTCR/scCD8 heterodimer and variants of this molecule could serve as very useful tools for further dissecting molecular interactions between the tertiary TCR:pMHCI:CD8 complex in a cell-free system. In addition, scTCR/scCD8 heterodimer-based reagents with enhanced pMHCI binding activity could have utility in detecting antigen presentation on diseased cells, without the need of mutating the TCR domain for increased binding affinity.

The results of SPR experiments on the OT1scTCR fusions differ from those reported by Alam et al. where the binding affinity of monovalent OT1 TCRα/β heterodimer to immobilized OVA peptide/H-2Kb complex was shown to be approximately 6 µM. In our studies, we were unable to detect OVA peptide/H-2Kb-binding of the OT1scTCR/birA monomer and the OT1scTCR/birA dimer exhibited an apparent KD of 30 µM. It is possible that the OT1 TCR lost binding activity when formatted as a single-chain Vα-linker-Vβ-β molecule. However, we observed equivalent activity when comparing OT1scTCR/birA and a two-chain construct. Moreover, previous studies have shown that OVA peptide/H-2Kb tetramers with Kb mutations that abrogate CD8 binding exhibit little or no specific binding activity to OT1 TCR-bearing cells even when high concentrations of tetramers were used, suggesting very low affinity interactions between OT1 TCR and its cognate pMHCI. In contrast, OVA peptide/H-2Kb tetramers without the CD8 binding mutations were able to brightly stain OT1 TCR-bearing cells, consistent with the ability of CD8 to enhance OT1 TCR binding activity observed in this study.

The hIL-15:hIL-15RαSu-based scaffold can be exploited much like the Fc domain of the IgG scaffold to generate multivalent or multispecific targeted therapeutics. With its potent activity for stimulating proliferation and activation of effector NK and CD8+ memory T cells, the hIL-15 domain expands the scope of potential immunotherapeutic mechanisms beyond antibody-dependent cellular cytotoxicity and complement activation associated with IgG-based approaches. Using approaches similar to those used to manipulate the activity of the Fc domain of IgG molecules, we demonstrate that the IL-15 domain can be mutated to increase or decrease its functional activity. We show that hIL-15:hIL-15RαSu fusion molecule containing an N72D mutation in the IL-15 domain exhibit a 3-4 fold increase in biological activity, whereas IL-15 D8N mutation exhibit little or no activity. While IL-15 superagonist-based fusion proteins could serve as targeted immunotherapeutics for cancer and infectious diseases, an IL-15 antagonist capable of inhibiting IL-15 responsive cells at the disease site may have therapeutic potential in treating allograft rejection and inflammatory autoimmune diseases, particularly if memory CD8 T cells play a role in disease pathology. A non-targeted IL-15 mutant/Fcγ2a antagonist protein has already been shown to be effective at inhibiting islet and cardiac allograft rejection and preventing development and progression of arthritis in experimental animal models. Similar approaches with IL-15 antagonist domains in the context of the hIL-15: hIL-15RαSu fusion proteins are possible. In addition, under certain circumstances, it may desirable to have a functionally inert scaffold for generation of multimeric molecules. For example, we have found that scTCR/hIL-15:scTCR/hIL-15RαSu fusions containing an IL-15 D8N mutation, which eliminates interactions with IL-15Rβγ, provide better TCR antigen-specific staining of cells displaying IL-15 receptor complex.

Although TCRs and CD8 molecules were used as targeting domains for demonstration purposes herein, it is understood that the hIL-15:hIL-15RαSu scaffold could be used to construct other novel molecules with protein domains derived from antibodies, adhesion molecules, or other receptors. It is also possible to create protein domain fusions to the C-termini of the hIL-15 and hIL-15RαSu which, based on the crystal structure, are accessible for modification. The resulting molecules can contain up to four different target-recognition capabilities. With the appropriate fusion partners, these types of molecules can promote the conjugation of immune effectors cells and target cells and achieve effective killing of target cells. In addition, the IL-15 domain of the complex can further augment these processes by providing immunostimulatory activity to support effector cell proliferation and cytotoxicity. A variety of multi-functional molecules based on this concept for use as anti-cancer and anti-viral immunotherapeutic agents.

Previously, the poor expression level in standard mammalian cell system limited the development of recombinant hIL-15 as a therapeutic. As demonstrated herein, expression of scTCR/hIL-15:scTCR/hIL-15RαSu complexes at levels capable of supporting clinical development and potentially product commercialization can be achieved. In addition, it has been shown that the IL-15Rα chain enhances the in vivo activity of hIL-15, without being bound by mechanism, possibly by improving the pharmacokinetics of the cytokine. These two characteristics of hIL-15:hIL-15RαSu complexes, in combination with its multivalent nature and/or multispecific targeting design, provides an opportunity to capture the full potential of hIL-15 as an immunotherapeutic agent against cancer and viral infections.

As provided in the Examples, hIL-15:hIL-15RαSu fusion protein complexes comprising immunoglobulin Fc domains were found to have additional advantages. Association of the Fc domains allows generation of multichain molecules capable of multivalent and multispecific interactions. In fact, the fusion protein complexes of the invention comprising the multiple domains of the same scTCR exhibited enhanced antigen binding activity than that expected based on the activity of the dimeric scTCR fusion. In some cases, the fusion complex of the invention is capable of binding and activating both IL-15RβγC-bearing immune cells and Fc receptor-bearing immune cells, allowing for potent immune stimulatory activity. The protein fusion complex of the invention comprising two IL-15 domains was found to exhibited better IL-15 activity than that expected when compared to other IL-15 fusion proteins. Additionally, the protein fusion complex of the invention was more effective at mediating antibody Fc depended cellular cytotoxicity against peptide/MHC presenting target cells than the TCR-IgG1 fusion protein. The improved activity may have been the result of enhanced binding of the protein fusion complexes to the peptide/MHC complex and/or increase reactivity to the effector cells displaying Fc receptors or IL-15 receptors. Moreover, through mutagenesis analysis it was found that of each of the TCR, IL-15 and IgG Fc domains of the fusion protein complexes could be readily and independently manipulated to alter its binding and functional activity to provide a multispecific complex with the desired biological effects.

The fusion protein complexes of the invention were demonstrated to have a significantly better pharmacokinetic profile in mammals than free IL-15. In addition, based on the similar PK profile observed with different methods of analysis, the fusion protein complexes remains intact in vivo as a multichain molecule with no evidence of polypeptide chain cleavage or dissociation. Additionally, the fusion protein complexes of the invention are shown to be capable of mediating antitumor activity against both target bearing and non-target bearing tumors in animals and exhibited more potent antitumor efficacy than rhIL-15 administered at an equivalent molar dose. Moreover, treatment with effective doses of the fusion proteins was well tolerated in these animal models.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Construction of Expression Vectors Containing c264scTCR/huIL15RαSushi-huIgG1 and c149scTCR/huIL15N72D Gene Fusions The fusion protein referred to as the T2 molecule (T2M) consists of a multichain polypeptide (FIG. 1). In one embodiment of the invention, one of these polypeptides comprises a fusion between a protein-binding domain and IL-15 (or IL-15 variants) as disclosed in WO2008143794 (incorporated herein by reference). A second polypeptide of T2 comprises a fusion between a protein binding domain, an IL-15Rα domain and an immunoglobulin domain. Alternatively, the protein binding domain-IL-15 fusion protein can be further linked to an immunoglobulin domain. The preferred immunoglobulin domains comprise regions that allow interaction with other immunoglobulin domains to form multichain proteins. For example, the immunoglobulin heavy chain regions, such as the IgG1 $C_H2$-$C_H3$, are capable of interacting to create the Fc region. Preferred immunoglobulin domains also comprise regions with effector functions, including Fc receptor or complement protein binding activity, and/or with glycosylation sites. In some embodiments, the immunoglobulin domains of the T2 molecule contain mutations that reduce or augment Fc receptor or complement binding activity or glycosylation, thereby affecting the biological activity of the resulting protein. For example, immunoglobulin domains containing mutations that reduce binding to Fc receptors could be used to generate T2 molecules with lower binding activity to Fc receptor-bearing cells, which may be advantageous for reagents designed to recognize or detect TCR-specific antigens.

Figure 2:
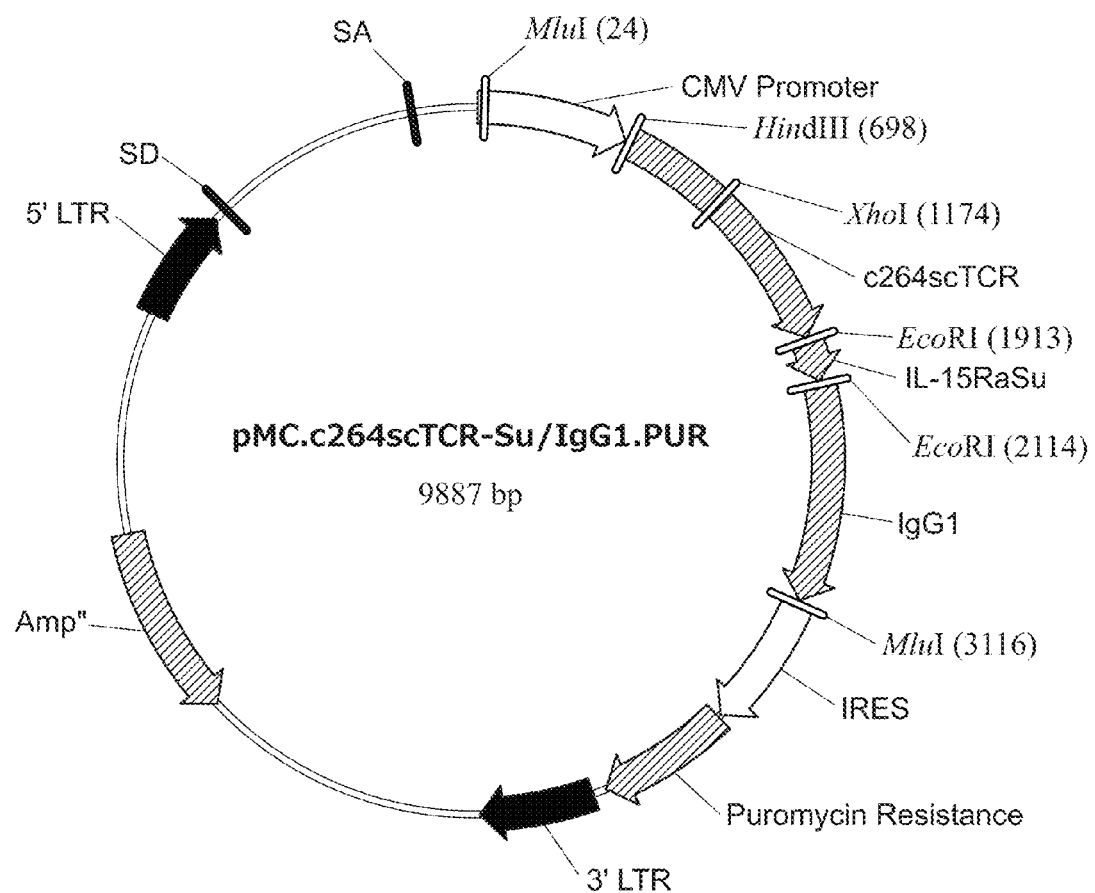
FIG. 2 shows the vector (pMC.c264scTCR-Su/IgG1.PUR) containing the human IL15RαSushi gene insert.

Construction of an expression vector containing the p53 (aa 264-272) single-chain TCR (referred to a c264scTCR) fused to human IL-15Rαsushi domain (huIL15RαSushi) and human IgG1 constant regions (huIgG1 $C_H1$-$C_H2$-$C_H3$) was carried out as follows. The c264scTCR/huIgG1 gene fragment was removed from the previous constructed the pNEF38-c264scTCR/huIgG1 vector by restricted digestion with PacI and MluI. The gene fragment was gel-purified and ligated to pMSGV vector digested with the same restriction enzymes, resulted in the construct called as pMSGV-c264scTCR/huIgG1. A DNA fragment containing the CMV promoter was purified from pcDNA3.1 following digestion with NruI and HindIII. This fragment was ligated into pMSGV-c264scTCR/huIgG1 which had been digested with PacI and filled in with DNA polymerase to create blunt ends and then digested with HindIII. The resulting construct was named as pMC-c264scTCR/huIgG1. A huIL15RαSushi gene fragment from a previous constructed, pNEF38-c264scTCR/huIL15RαSushi (see WO2008143794), was amplified with front primer:

(SEQ ID NO: 6)
5'-TGTTGGGAATTCATCACGTGCCCTC-3' and back primer:

(SEQ ID NO: 7)
5'-TGGTGTGAATTCTCTAATGCATTTGAGACTGG-3' by KOD Hot Start DNA Polymerase (EMD) under following PCR conditions: 95 C, 2 min, 1 cycle; 95 C, 20 sec, 65 C, 20 sec; 70 C, 20 sec, 35 cycles; 72 C, 10 min, 1 cycle. The PCR product of human IL15RαSushi gene was gel-purified and digested with EcoRI. The gene was ligated into pMC-c264scTCR/huIgG1 which had been digested with EcoRI. Cloning of the DNA fragment encoding the human IL15RαSushi domain into the pMC-c264scTCR/huIgG1 resulted in a c264scTCR/huIL15RαSushi-huIgG1 fusion gene comprising the following sequence: 3'-immunoglobulin heavy chain leader-264 TCR V-α-peptide linker-264 TCR V-β-human TCR C-β-human IL15RαSushi-human IgG1 heavy chain. The resulting vector (pMC.c264scTCR-Su/IgG1.PUR), shown in FIG. 2, containing the correct human IL15RαSushi gene insert was identified based on the diagnostic PCR and reconfirmed by DNA sequencing. The sequences of the c264scTCR/huIL15RαSushi/huIgG1 gene and protein are shown at FIGS. 3A-3C and FIGS. 4A-4C, respectively.

A different expression vector containing c264scTCR/huIL15RαSushi-huIgG1 gene fusion was constructed that lacked the internal EcoRI sites (and corresponding coding sequences). For this vector, a portion of the c264scTCR gene fragment was amplified from the c264scTCR/huIgG1 vector with front primer:

(SEQ ID NO: 8)
5'GTACGACTTAATTAACTCGAGCCACCATGGAGACAGACACACTCCTG

TTATGG3' and back primer:

(SEQ ID NO: 9)
5'CTTCCCGTTAACCCACCAGCTCAGCTCCACGTG3'.

The remainder of the TCR β constant region of the c264scTCR gene fragment was amplified from c264scTCR/huIgG1 vector with front primer:

(SEQ ID NO: 10)
5'CTGGTGGGTTAACGGGAAGGAGGTGCACAGTGGGGTC3' and back primer:

(SEQ ID NO: 11)
5'GAGGGCACGTGATGTCTGCTCTACCCCAGGCCTC3'

The huIL15RαSushi gene fragment was amplified from the c264scTCR/huIL15RαSushi vector with front primer:

(SEQ ID NO: 12)
5'GTAGAGCAGACATCACGTGCCCTCCCCCCATG3' and the back primer:

(SEQ ID NO: 13)
5'CCTTGGTGCTAGCTCTAATACATTTGAGACTGGGGGTTGTCC3'.

The huIgG1 heavy chain constant region gene fragment was amplified from the c264scTCR/huIgG1 vector with front primer:

(SEQ ID NO: 14)
5'CCAGTCTCAAATGTATTAGAGCTAGCACCAAGGGCCCATCGGTC3' and back primer:

(SEQ ID NO: 15)
5'GTAATATTCTAGACGCGTTCATTATTTACCAGGAGACAGGGAGAGGC

TCTTC3'.

The resulting products containing the TCR β constant region sequence and huIL15RαSushi gene were used as templates to generate a gene fragment by PCR using with front primer:

(SEQ ID NO: 10)
5'CTGGTGGGTTAACGGGAAGGAGGTGCACAGTGGGGTC3' and back primer:

(SEQ ID NO: 13)
5'CCTTGGTGCTAGCTCTAATACATTTGAGACTGGGGGTTGTCC3'

The resulting PCR product and the huIgG1 gene fragment served as templates to generate a TCRβc/huIL15RαSushi/huIgG1 fusion gene by PCR with front primer:

(SEQ ID NO: 10)
5'CTGGTGGGTTAACGGGAAGGAGGTGCACAGTGGGGTC3' and back primer:

(SEQ ID NO: 15)
5'GTAATATTCTAGACGCGTTCATTATTTACCAGGAGACAGGGAGAGGCTCTTC3'

Figure 5:
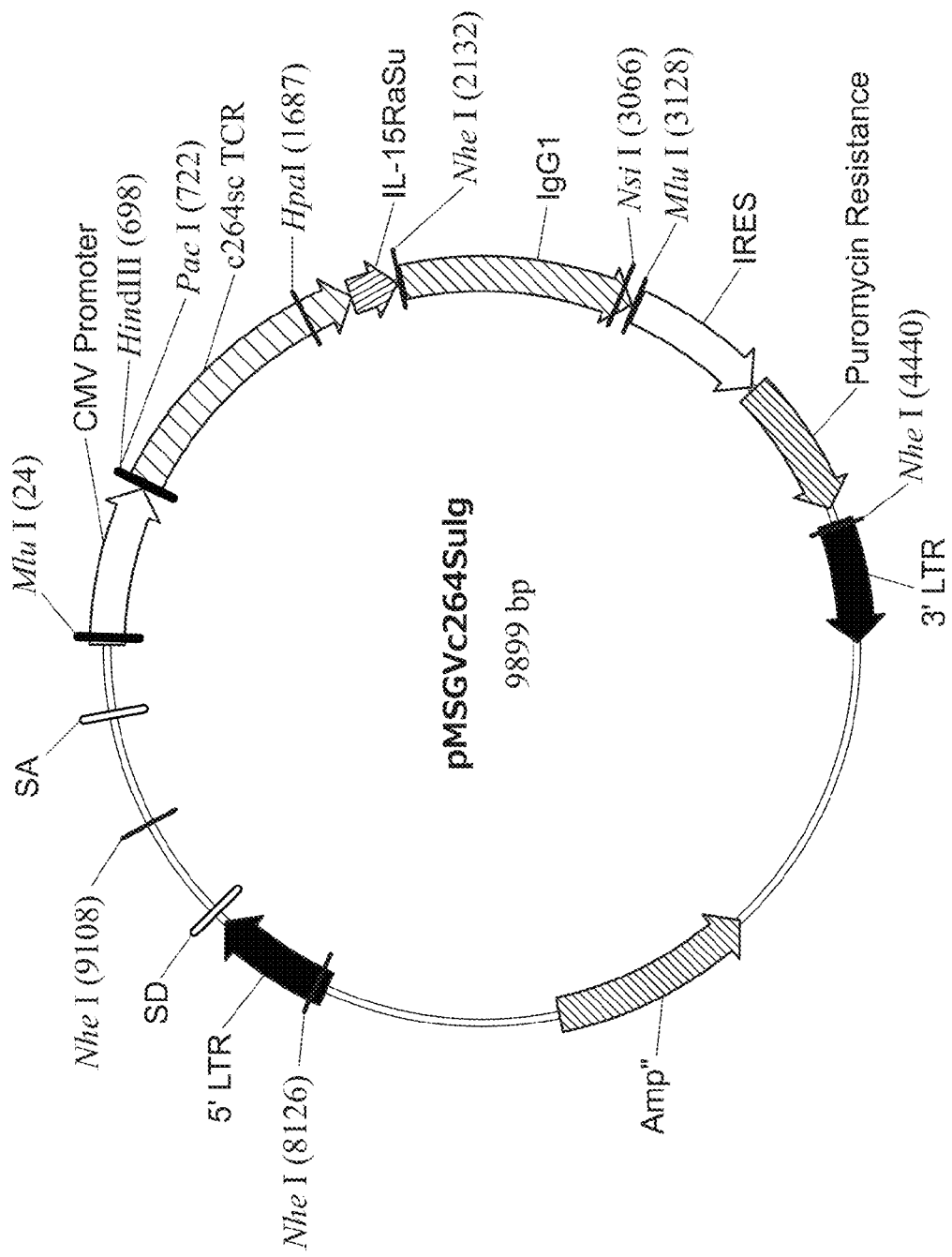
FIG. 5 shows the vector designated as c264scTCR/Sushi/hIgG1-pMSGVc or pMSGVc264SuIg.

The c264scTCR PCR product was digested with PacI and HpaI and the TCRβc/huIL15RαSushi/huIgG1 fusion gene was digested with HpaI and NsiI. The digested gene fragments were ligated into a CMV promoter-containing pMSGV retrovirus vector. The resulting vector was designated as c264scTCR/Sushi/hIgG1-pMSGVc or pMSGVc264SuIg (FIG. 5). The sequences of the c264scTCR/huIL15RαSushi/huIgG1 gene and protein are shown at FIG. 6A, FIG. 6B, FIG. 6C and FIG. 7A, FIG. 7B, FIG. 7C, and FIG. 7D, respectively.

Generation of expression vectors producing a fusion between single-chain TCR binding domain (i.e. c264scTCR) and IL-15 (or IL-15 variants) has been disclosed in WO2008143794. Particularly useful IL-15 variants are those that reduce or eliminate IL-15 biological activity or that increase IL-15 biological activity. For example, human IL-15 variants with substitutions at position 72 (i.e. N72D substitution) can increase the IL-15 biological activity 5 to 10 fold. IL-15 variants are provided in the table below:

| Mutants | Position | 8 | 61 | 65 | 72 | 108 | IL15Rβγc receptor binding | IL15Rα binding | Proliferation Activity |
|---|---|---|---|---|---|---|---|---|---|
| | WT aa | D | D | N | N | Q | + | + | + |
| 1 | 8 | N | | | | | − | + | − |
| 2 | 8 | A | | | | | − | + | − |
| 3 | 61 | | A | | | | − | + | − |
| 4 | 65 | | | D | | | − | + | − |
| 5 | 65 | | | A | | | − | + | − |
| 6 | 72 | | | | D | | 3+ | + | 3+ |
| 8 | 72 | | | | R | | − | + | − |
| 9 | 108 | | | | | A | − | + | − |
| 10 | 8 + 65 | N | | A | | | − | + | − |
| 11 | 8 + 108 | A | | | | A | − | + | − |
| 12 | 8 + 65 | S | | R | | | − | + | − |

The fusion protein complexes comprising IL-15 variants as described in the table immediately above were characterized for their ability to bind the TCR-specific antigen, p53 (aa264-272)/HLA-A2.1. To generate cells presenting p53 (aa264-272)/HLA-A2.1, HLA-A2.1-positive T2 cells (2×10⁶/mL) were loaded with 20 μM p53 (aa264-272) peptide at 37° C. in the presence of 1×PLE (Altor Bioscience) for 2-3 hrs. T2 cells that were not incubated with peptide and 32Dβ cells expressing IL-2/15Rβγ$_C$ serve as controls. The p53 peptide-loaded T2 cells, control T2 cells, or 32Dβ cells (2×10⁵/100 μL) were then incubated for 30 min at 4 C with 320 nM of following dimeric fusion protein complexes: 1) c264scTCR/huIL15+c264scTCR/huIL15Rα Sushi, 2) c264scTCR/huIL15D8A+c264scTCR/huIL15Rα Sushi, and 3) c264scTCR/huIL15D8N+c264scTCR/huIL15Rα Sushi. These complexes were generated by incubating 160 nM of purified c264scTCRhuIL15 fusion protein and 160 nM of purified c264scTCRhuIL15Rα Sushi fusion protein at 4 C for 3 hours. Following staining, cells were washed once with washing buffer (PBS containing 0.5% BSA and 0.05% sodium azide) and stained with 0.5 μg of biotinylated mouse monoclonal anti-human TCR Cβ antibody (BF1) in 100 μL of washing buffer for 30 min at 4 C. Cells were washed once and stained with 0.5 μg of R-Phycoerythrin conjugated streptavidin in 100 μL of washing buffer for 30 min at 4 C. Cells were washed and resuspended for analysis by flow cytometry.

The c264scTCR/huIL15D8A+c264scTCR/huIL15RαSushi complex and c264scTCR/huIL15D8N+c264scTCR/huIL15RαSushi complex exhibited equivalent activity as the c264scTCR/huIL15+c264scTCR/huIL15RαSushi complex for specifically staining p53 peptide-loaded T2 cells. These results indicate that the multivalent scTCR domains are fully functional in each of these fusion complexes. Fusion protein complexes comprising IL-15 variants (D8A and D8N) do not show binding activity to the IL-15Rβγ$_c$ receptors present on the 32Dβ cells. Similar studies of IL-15Rβγ$_c$ receptor binding were carried out with other fusion proteins comprising IL-15 variants and are summarized in Table 1. The results indicate that fusion proteins and fusion protein complexes of the invention comprising IL-15 variants retain activity to recognize peptide/MHC complexes and exhibit decreased or increased binding activity for IL-15Rβγ$_c$ receptors.

For certain T2 molecules, it is useful to have multiple different binding domains fused to the IL-15 and IL-15Rα components. In one example to illustrate the activity of such molecules, a single-chain TCR domain (called c149scTCR), specific to the p53 (aa 149-157) peptide presented in the context of HLA-A2, was linked to the IL-15N72D domain and the resulting fusion protein co-expressed with the c264scTCR/huIL15RαSushi/huIgG1 fusion protein to produce a multichain T2 protein with c264scTCR and c149scTCR binding domains.

To generate the c149scTCR/IL15N72D gene fusion, a c149scTCR gene fragment (TCR-α, linker, TCR-β and TCR-β constant fragment) was amplified from c149scTCR/huIgG1 expression vector with the front primer:

(SEQ ID NO: 16)
5'GACTTCAAGCTTAATTAAGCCACCATGGACAGACTTACTTCTTC3' and the back primer:

(SEQ ID NO: 9)
5'-CTTCCCGTTAACCCACCAGCTCAGCTCCACGTG-3'

The remainder of the TCR β constant region of the c149scTCR/huIgG1 vector was amplified with front primer:

(SEQ ID NO: 17)
5'CTGGTGGGTTAACGGGAAGGAGGTGCACAGTGGGGTC3' and the back primer:

(SEQ ID NO: 18)
5'CACCCAGTTGTCTGCTCTACCCCAGGCCTC3'

The huIL15N72D gene was amplified from c264scTCR/huIL15N72D expression vector with the front primer:

(SEQ ID NO: 19)
5'CTGGGGTAGAGCAGACAACTGGGTGAATGTAATAAGTGATTTG3' and the back primer:

(SEQ ID NO: 20)
5'CCTCATGCATTCGAATCCGGATCATTAAGAAGTGTTGATGAACATTTGG3'

The resulting products containing the TCR β constant region sequence and huIL15N72D gene were used as templates to generate a gene fragment by PCR using with front primer:

(SEQ ID NO: 10)
5"CTGGTGGGTTAACGGGAAGGAGGTGCACAGTGGGGTC3' and the back primer:

(SEQ ID NO: 20)
5'CCTCATGCATTCGAATCCGGATCATTAAGAAGTGTTGATGAACATTTGG3'

Figure 8:
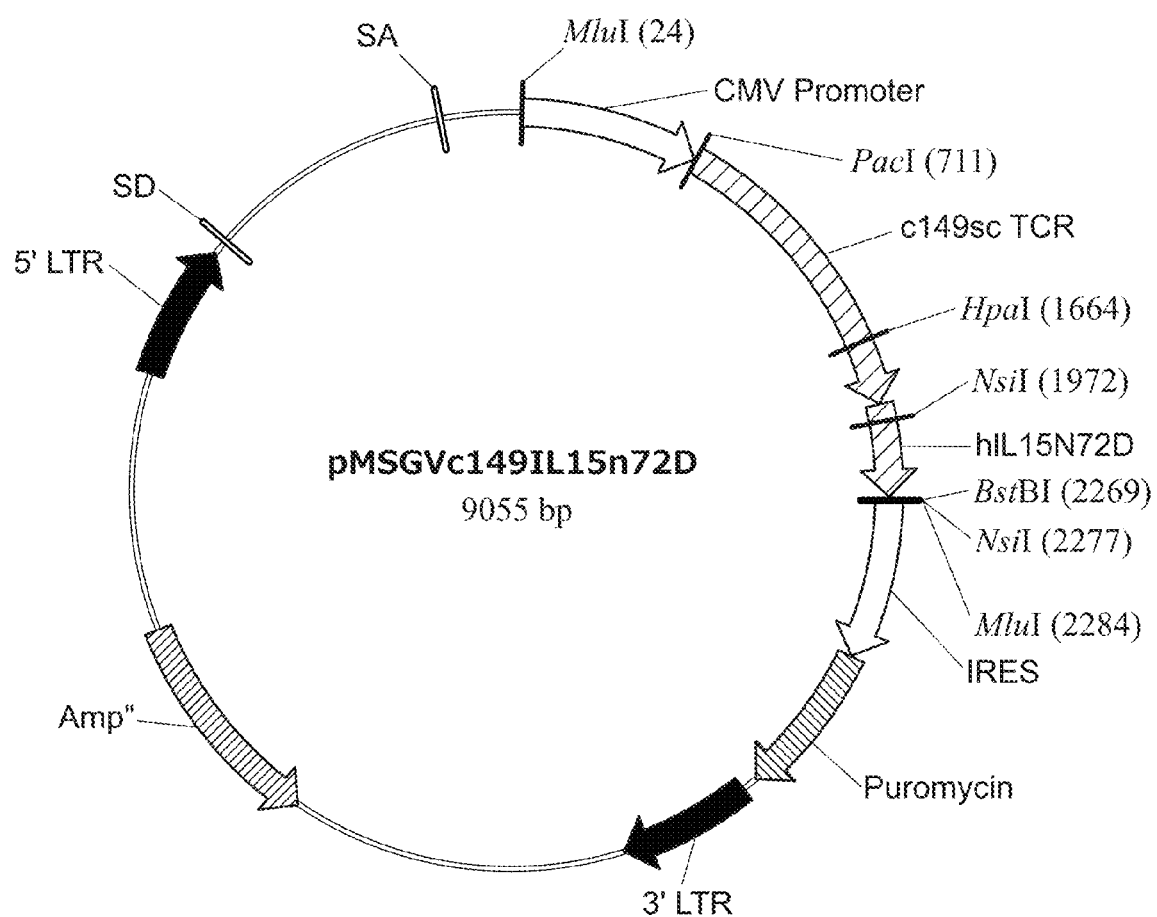
FIG. 8 shows the vector designated as c149scTCR/IL15N72D-pMSGVn or pMSGV-c149IL15N72D.

The c149scTCR PCR product was digested with Pac I and Hpa I and the TCRβc/huIL15N72D PCR product was digested with Hpa I and BstB I. The digested gene fragments were ligated into a CMV promoter-containing pMSGV retrovirus vector. The resulting vector was designated as c149scTCR/IL15N72D-pMSGVn or pMSGV-c149IL15N72D (FIG. 8). The sequences of the c149scTCR/huIL15N72D gene and protein are shown at FIG. 9A and FIG. 9B and FIG. 10A, FIG. 10B, and FIG. 10C, respectively.

Example 2

Generation of Transfected Host Cell Lines Producing Fusion Proteins

The expression vectors can be introduced into a variety of host cell lines by several different transformation, transfection or transduction methods. In one such method, CHO-K1 cells (5×10⁵) were seeded in a 6-well plate and cultured overnight in a $CO_2$ incubator. The cells were transfected with 5 µg of expression vector containing the c264scTCR/huIL15N72D fusion genes using 10 µL of Mirus TransIT-LT1 reagent (Mirus) according to the manufacturer's protocol. The cells were selected with 4 mg/mL of G418 (Invitrogen) one day after the transfection. The G418 resistant cells were expanded and TCR/IL15 fusion protein expressing cells were subcloned three times by the limiting dilution and production cell lines were screened based on the level of soluble fusion protein secreted into the culture media by TCR and huIL15-specific ELISA with a capture antibody, anti-human TCR Cβ antibody (BF1), and a detection antibody, biotinylated anti-human IL-15 antibody (BAM 247, R&D Systems) described previously (see WO2008143794). The c264scTCR/IL15N72D producing cell line was then transducted with the pseudotyped retroviral vector containing c264scTCR/huIL15RαSushi-huIgG1 fusion gene as follows.

To produce the pseudotyped retroviral vector, 2×10⁶ of the 293GP packaging cells in a poly-lysine coated 10 cm dish (BD Bioscience) were cultured for 2 days at 37° C. in a $CO_2$ incubator. The cells were then co-transfected using Lipofectamine 2000 (Invitrogen) with 9 µg of the plasmid pMC-c264scTCR/huIL15RαSushi/huIgG1 and 4 µg of the plasmid pMD-G encoding VSV-G envelope protein. The supernatant containing virus was collected 48 hrs post-transfection and cell debris was removed by passing through a 0.45 µM polyvinylidene fluoride filter. Virus was applied to the c264scTCR/IL15N72D producing cells (1×10⁵ cells/well in a 6-well plate) in the presence of 10 µg/ml of polybrene (Sigma-Aldrich). Cells were selected with 10 µg/ml of puromycin and 2 mg/ml of G418 2 days post-transduction. The puromycin and G418 resistant cells were expanded and the T2 fusion protein complex expressing cells were subcloned three times by the limiting dilution and production cell lines were screened based on the level of soluble fusion protein secreted into the culture media using a huIgG1/huIL15-specific ELISA with a capture antibody, anti-human IgG antibody (Jackson ImmunoResearch), and a detection antibody, biotinylated anti-human IL-15 antibody (BAM 247, R&D Systems).

Example 3

Generation and Purification of T2 Fusion Proteins

Cell lines expressing c264scTCR/huIL15N72D and c264scTCR/huIL15RαSushi/huIgG1 were cultured under growth conditions (i.e. 25-37° C. for 5 to 28 days in small scale culture flasks, spinner or shaker flasks or in large scale hollow-fiber, wave bag or stir tank bioreactors or equivalent culture vessels and reactors) to produce the T2 molecule as a soluble protein in the culture media. To purify the T2 molecule the culture media was pH-adjusted and loaded on to an immunoaffinity column containing an anti-TCR antibody (BF1) covalently coupled to Sepharose. The column was washed and T2 molecules eluted with 0.5 M Na-citrate pH 4.0. The eluted protein was concentrated and buffer exchanged into phosphate buffered saline (PBS) and then loaded on rProtein A-Sepharose column. Following wash steps, the protein was eluted with 0.5 M Na-citrate pH 4.0 and then buffer exchanged into PBS. The resulting protein was characterized by Coomassie-stained SDS-PAGE and size exclusion chromatography.

Figure 11:
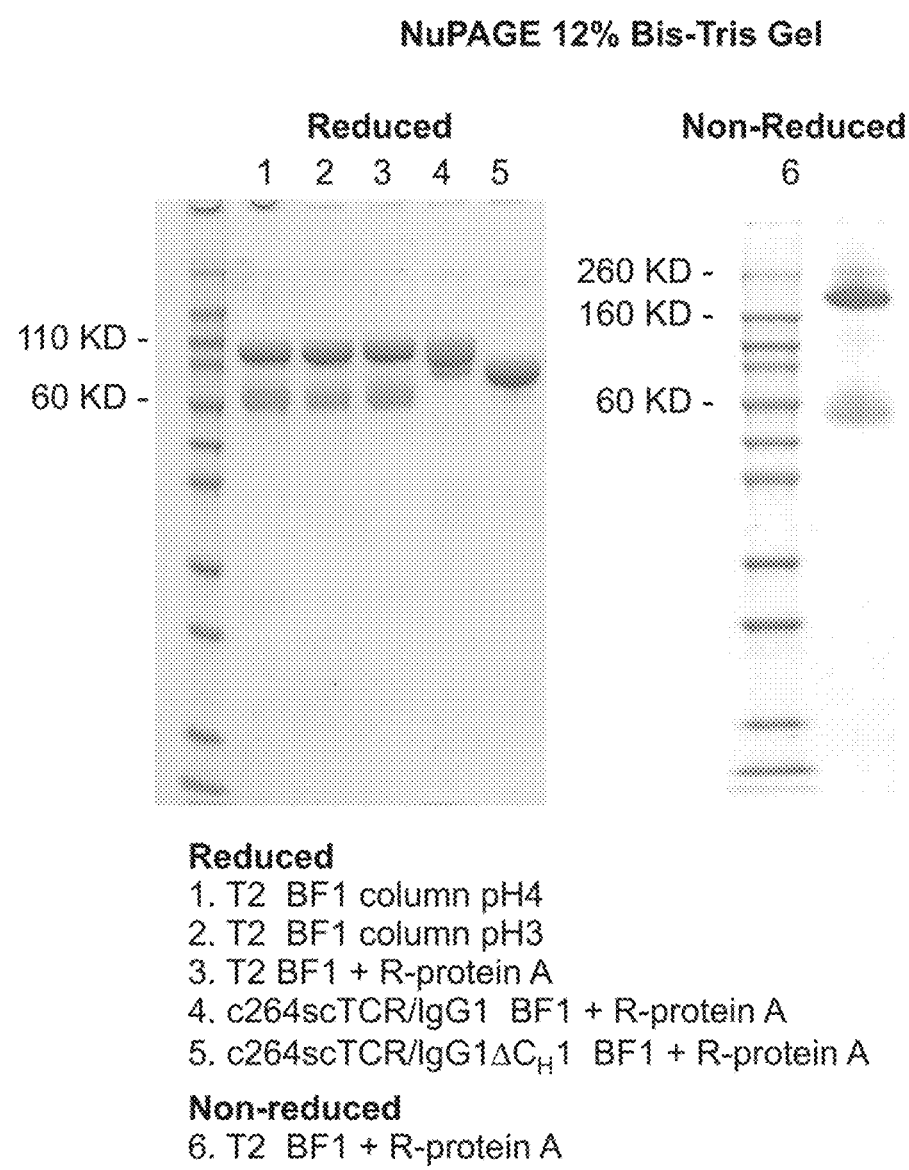
FIG. 11 shows an SDS-PAGE analysis of purification fractions of the T2, c264scTCR/huIgG1 and c264scTCR/huIgG1ΔCH1 fusion proteins under reducing and non-reducing conditions. Under reducing conditions, the T2 molecule bands migrate at molecular weights consisted with the c264scTCR/huIL15 and c264scTCR/huIL15RαSushi/huIgG1 polypeptides. Under non-reducing denaturing conditions, the c264scTCR/huIL15RαSushi/huIgG1 band migrates at a molecular weight consistent with a dimeric disulfide-linked c264scTCR/huIL15RαSushi/huIgG1 complex and a c264scTCR/huIL15N72D polypeptide.
Figure 12:
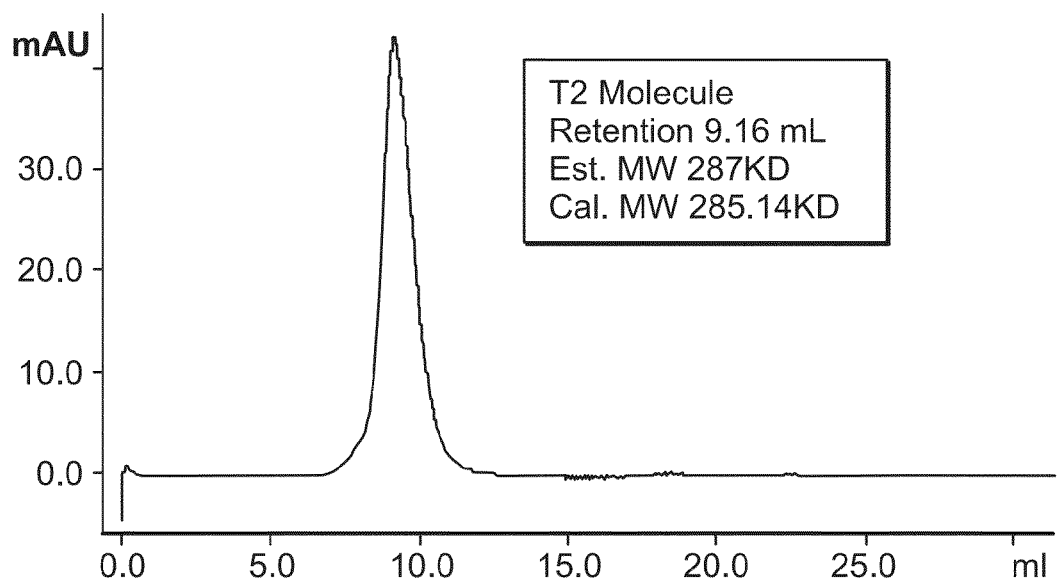
FIG. 12 shows results from size exclusion gel filtration chromatography demonstrating that the native T2 protein eluted at the expected molecular weight of a four-chain (2×c264scTCR/IL15N72D, 2×c264scTCR/huIL15RαSushi/huIgG1) molecule.

Under reducing SDS-PAGE conditions, the purified T2 protein migrated as two polypeptide bands corresponding to the molecular weights expected of the c264scTCR/huIL15N72D and c264scTCR/huIL15RαSushi/huIgG1 components compared to purified c264scTCR/huIgG1 and c264scTCR/huIgG1ΔCH1 fusion proteins which migrate single bands expected of homodimeric molecules (FIG. 11). Under non-reducing denaturing conditions, the c264scTCR/huIL15RαSushi/huIgG1 band migrates at a molecular weight consistent with a dimeric polypeptide whereas the c264scTCR/huIL15N72D band is consistent with its monomeric form (FIG. 11). By size exclusion gel filtration chromatography, the native T2 protein eluted at the expected molecular weight of a four-chain (2×c264scTCR/IL15N72D, 2×c264scTCR/huIL15RαSushi/huIgG1) molecule (FIG. 12). These results confirm that the T2 molecule exhibits a multichain conformation consistent with the interactions between the huIL15N72D and huIL15RαSushi domains and covalent interactions between the huIgG1 as shown in FIG. 1.

Similar mammalian cell expression and affinity chromatography purification methods were used to generate other T2 protein complexes described herein.

Example 4

In Vitro Characterization of the Binding Activities of the T2 Molecule

In vitro assays were carried out to characterize the binding activities of the domains of the T2 molecule and to compare these activities with those of other fusion molecules. To characterize the IgG1 domain, microtiter wells were coated with anti-human IgG1 antibody and equivalent molar amounts of purified T2 protein, composed of c264scTCR/huIL15N72D and c264scTCR/huIL15RαSushi/huIgG1 chains, or purified c264scTCR/huIgG1 fusion protein were applied to the wells. Following binding and washing steps, the bound proteins were detected with anti-human IgG1 antibody under standard ELISA conditions.

Figure 13:
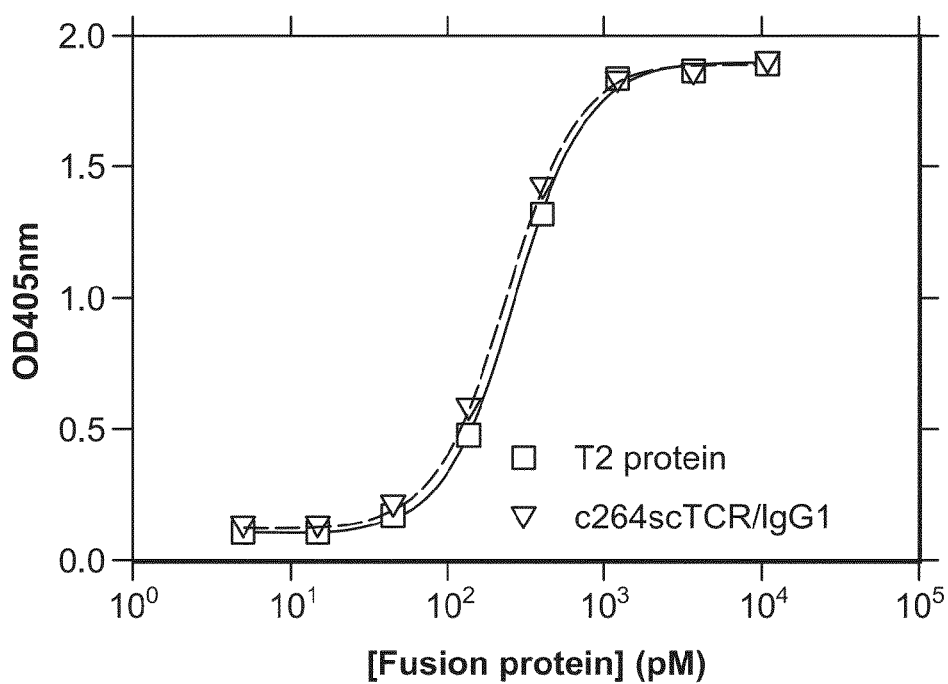
FIG. 13 shows results from an in vitro binding assay in which equimolar amounts of purified T2 protein, composed of c264scTCR/huIL15N72D and c264scTCR/huIL15RαSushi/huIgG1 chains, or purified c264scTCR/huIgG1 fusion protein were captured on wells coated with anti-human IgG1 antibody. Following binding, proteins were detected using anti-human IgG1 antibody under standard ELISA conditions.

The results of the assay shown in FIG. 13 demonstrate that the IgG1 domain of the T2 molecule shows equivalent antibody binding activity as the comparable domain of the TCR/IgG1 fusion, indicating that the T2 IgG1 domain retains a native conformation. The TCR domain of the T2 molecule was assessed in a similar assay. Equivalent molar amounts of T2 or c264scTCR/huIgG1 proteins were captured on anti-human IgG1 Ab coated wells and detected with an anti-human TCR Cβ antibody (W4F).

Figure 14:
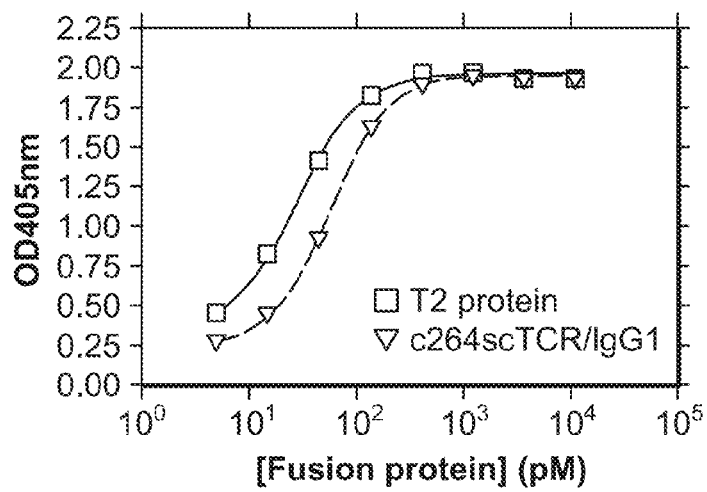
FIG. 14 shows results from an in vitro binding assay in which equimolar amounts of T2 or c264scTCR/huIgG1 proteins were captured on anti-human IgG1 Ab coated wells and detected with an anti-human TCR Cβ antibody (W4F).
Figure 15:
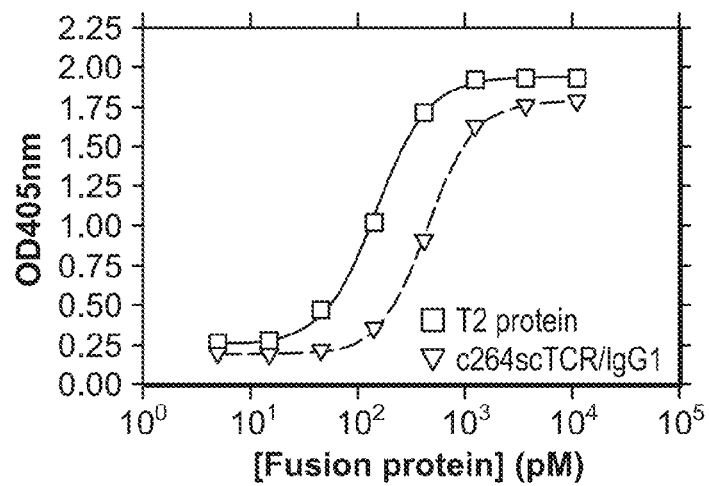
FIG. 15 shows results from an in vitro binding assay in which the peptide/MHC binding activity of the TCR domains of the T2 molecule was assessed. Equimolar amounts of T2 (composed of c264scTCR/huIL15N72D and c264scTCR/huIL15RαSushi/huIgG1 chains) or c264scTCR/huIgG1 proteins were captured on anti-human IgG1 Ab coated wells and detected with p53 (aa 264-272) peptide/HLA-A2 streptavidin-HRP tetramers.

As shown in FIG. 14, the T2 protein exhibited 2-fold higher reactivity than the c264scTCR/huIgG1 protein to the anti-TCR antibody. This is expected given the four-chain TCR fusion protein composition of the T2 molecule compared with the homodimeric composition of the c264scTCR/huIgG1 fusion. The peptide/MHC binding activity of the TCR domains of the T2 molecule was assessed. Equivalent molar amounts of T2 (composed of c264scTCR/huIL15N72D and c264scTCR/huIL15RαSushi/huIgG1 chains) or c264scTCR/huIgG1 proteins were captured on anti-human IgG1 Ab coated wells and detected with p53 (aa 264-272) peptide/HLA-A2 streptavidin-HRP tetramers. As shown in FIG. 15, the T2 protein exhibited 3-fold higher binding activity than the c264scTCR/huIgG1 protein to the peptide/MHC reagent. This was unexpected since based on its structure and anti-TCR Ab reactivity (see FIG. 14) the T2 protein was anticipated to only exhibit 2-fold higher TCR binding activity than c264scTCR/huIgG1. Thus the T2 molecular structure provides a better antigen-specific binding activity than expected based on the individual components. This enhanced binding activity may be the result of less steric interference, better avidity effects, cooperative interactions and/or a better conformational fit between the TCR domain and peptide/MHC antigen.

Example 5

Characterization of the Biological Activity of the T2 IL-15 Domain

The activity of the IL-15 domain of the T2 molecule was also assessed. Microtiter wells were coated with anti-human IL-15 antibody and equivalent molar amounts of purified T2 protein, composed of c264scTCR/huIL15N72D and c264scTCR/huIL15RαSushi/huIgG1 chains, or purified c264scTCR/huIL15N72D fusion protein were applied to the wells. Following binding and washing steps, the bound proteins were detected with anti-human IL-15 antibody under standard ELISA conditions.

Figure 16:
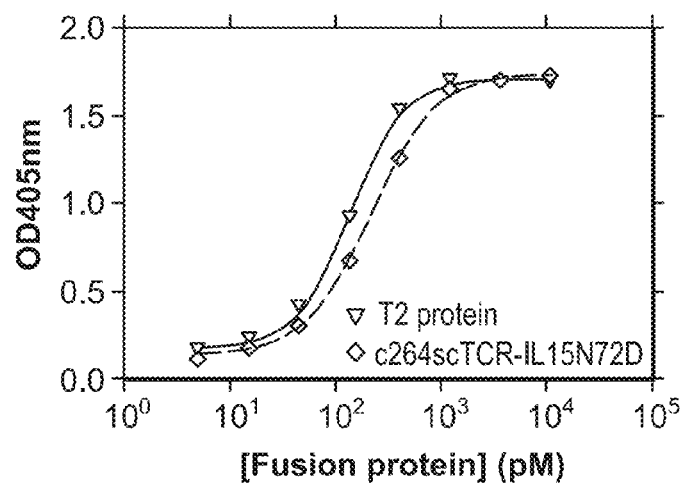
FIG. 16 shows results from an in vitro assay to demonstrate the activity of the IL-15 domain of the T2 molecule. Microtiter wells were coated with anti-human IL-15 antibody and equivalent molar amounts of purified T2 protein, composed of c264scTCR/huIL15N72D and c264scTCR/huIL15RαSushi/huIgG1 chains, or purified c264scTCR/huIL15N72D fusion protein were applied to the wells. Following binding and washing steps, the bound proteins were detected with anti-human IL-15 antibody under standard ELISA conditions.

As shown in FIG. 16, the T2 protein exhibited increased reactivity (1.6-fold higher) compared to c264scTCR/huIL15N72D fusion for the anti-IL15 Ab, as expected based on hypothesis that each T2 molecule contains two IL-15 domains. The biological activity of the IL-15 domain of the T2 molecules was further characterized in proliferation assays using the cytokine-dependent 32Dβ cell line. To measure cell proliferation, 32Dβ cells (2×10$^4$ cells/well) were incubated with increasing concentrations of T2 protein (composed of c264scTCR/huIL15N72D and c264scTCR/huIL15RαSushi/huIgG1 chains) or c264scTCR/huIL15N72D fusion protein for 48 h at 37° C. Cell proliferation reagent WST-1 (Roche Applied Science) was added during the last 4 h of cell growth according to the manufacturer's procedures. Conversion of WST-1 to the colored formazan dye by metabolically active cells was determined through absorbance measurements at 440 nm.

Figure 17:
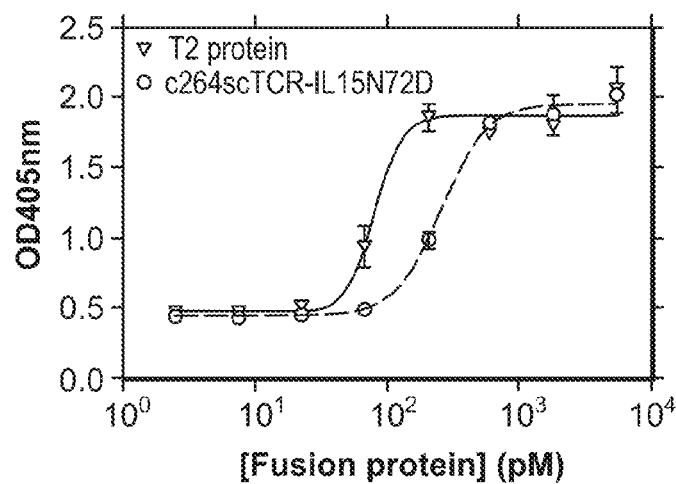
FIG. 17 shows the results from a proliferation assay to further characterize the functional activity of the IL-15 domain of the T2 molecules using the cytokine-dependent 32Dβ cell line. To measure cell proliferation, 32Dβ cells ($2 \times 10^4$ cells/well) were incubated with increasing concentrations of T2 protein (composed of c264scTCR/huIL15N72D and c264scTCR/huIL15RαSushi/huIgG1 chains) or c264scTCR/huIL15N72D fusion protein for 48 h at 37° C. Cell proliferation reagent WST-1 (Roche® Applied Science) was added during the last 4 h of cell growth according to the manufacturer's procedures. Conversion of WST-1 to the colored formazan dye by metabolically active cells was determined through absorbance measurements at 440 nm.

As shown in FIG. 17, the T2 protein exhibits 3-fold better biological activity than the c264scTCR/huIL15N72D fusion protein. This was unexpected since based on its structure and anti-IL-15 Ab reactivity (see FIG. 16), the T2 protein was anticipated to only exhibit 2-fold higher IL-15 activity than c264scTCR/huIL15N72D. Together these results illustrate a number of advantages to the T2 molecular format in providing increased TCR binding activity and IL-15 biological activity than was not observed with these components alone or in the context of other fusion protein formats.

Figure 18A:
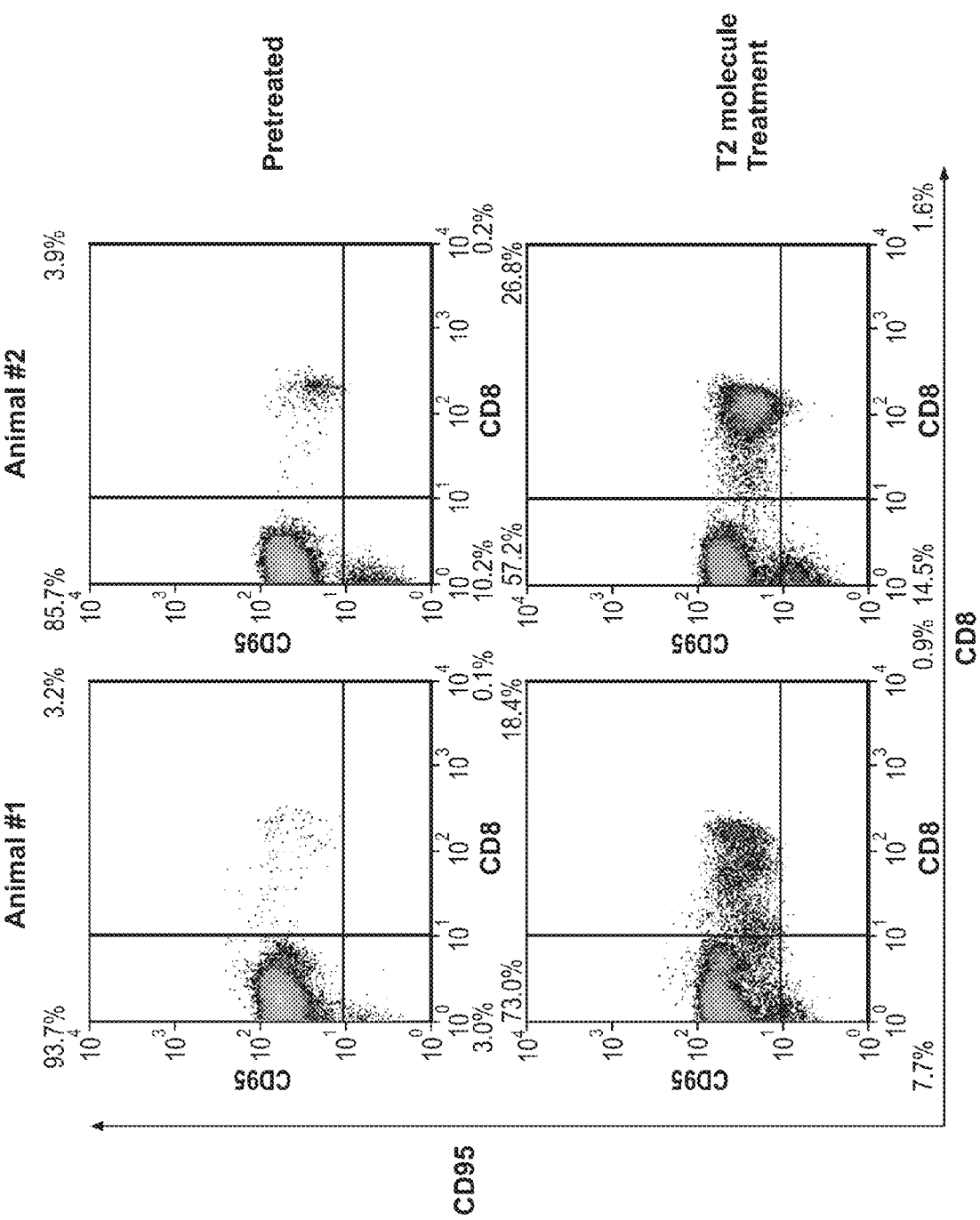
FIG. 18A and FIG. 18B show the results from an in vivo primate model to determine the ability of the T2 protein to promote proliferation of IL-15 responsive immune cells. Blood was collected five days after injection with T2 protein and was stained for CD8 memory T cells markers (CD8 and CD95) (FIG. 18A) and NK cell markers (CD56 and CD16) (FIG. 18B) and compared to blood taken prior to treatment.
Figure 18B:
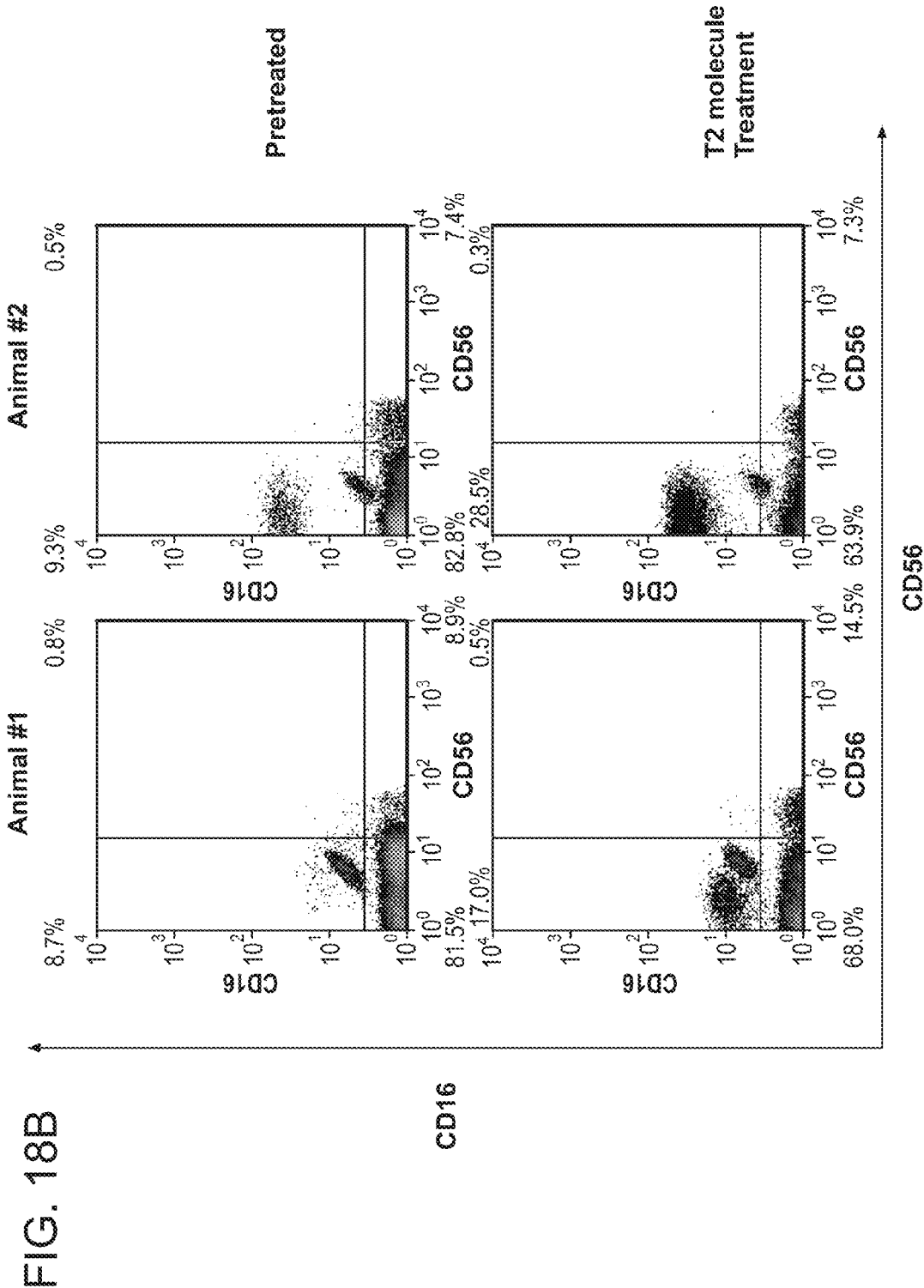

The ability of the T2 protein to promote proliferation of IL-15-responsive immune cells was examined in a primate model. Cynomolgus monkeys (n=2, 1m, 1f) were injected intravenously with purified T2 protein (composed of c264scTCR/huIL15N72D and c264scTCR/huIL15RαSushi/huIgG1 chains) at 0.5 mg/kg. Blood collected 5 days later was stained for CD8 memory T cells markers (CD8 and CD95) and NK cell markers (CD56 and CD16) and compared to blood taken prior to treatment. As shown in FIG. 18, T2 treatment resulted in an expansion of CD8$^+$CD95$^+$ memory T cells (A) and CD56$^{dim}$ CD16$^+$ effector NK cells (B). These results are consistent with the T2 molecule displaying potent IL-15 activity in vivo.

Example 6

Characterization of the Binding and Biological Activity of the T2 Fc Domain

Figure 19A:
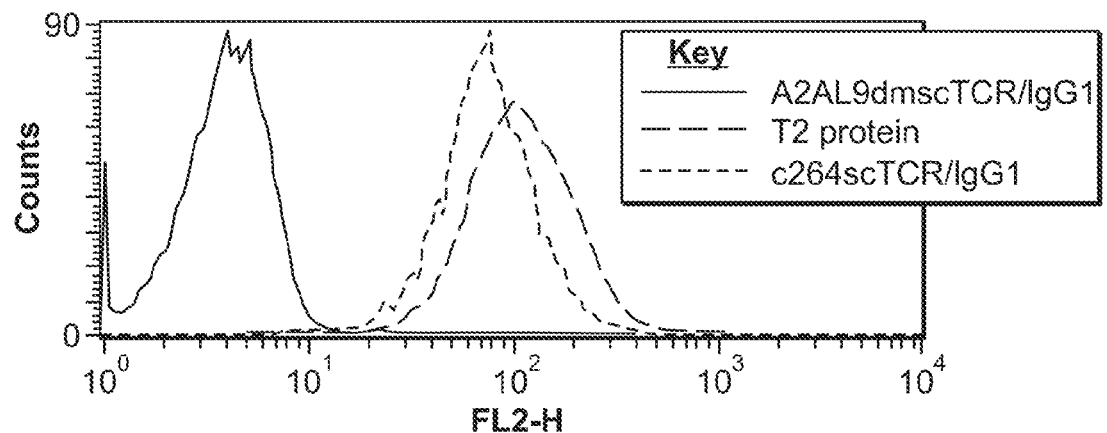
FIG. 19A and FIG. 19B show cell binding assays characterizing the binding activity of the IgG1 Fc domain of the T2 molecule.
Figure 19B:
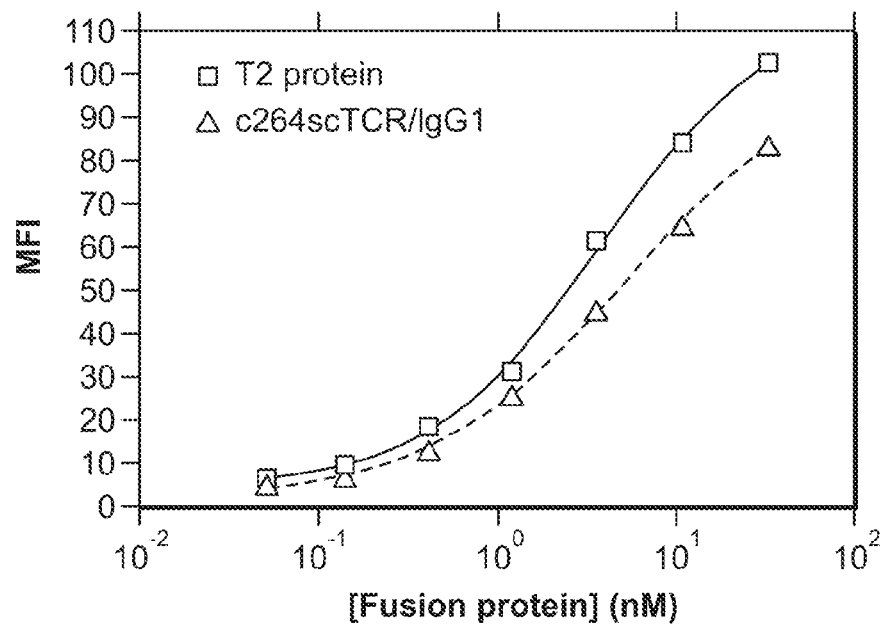

The binding activity of the IgG1 Fc domain of the T2 molecule was characterized in cell binding assays. Fc-gamma receptor bearing U937 cells were incubated with 33 nM of T2 protein (composed of c264scTCR/huIL15N72D and c264scTCR/huIL15RαSushi/huIgG1 chains), c264scTCR/huIgG1 or A2AL9scTCR/IgG1 (negative control) for 20 min. Cells were washed once and incubated with PE-conjugated p53 (aa 264-272) peptide/HLA-A2 tetramer for 20 min. The binding to Fc gamma receptors on U937 cell surface was analyzed with flow cytometry as shown in FIG. 19A. Similar U937 binding studies using a range of protein concentrations was also carried out and the mean fluorescent intensity for the stained cells was plotted in FIG. 19B.

The results of these studies indicate that the U937 cells are stained more effectively with the T2 molecules than the corresponding c264scTCR/huIgG1 fusion proteins, verifying the Fc receptor binding activity of the T2 molecules. To assess the biological activity of the Fc domains, the ability of the T2 molecule to mediate antibody dependent cellular cytotoxicity (ADCC) activity was assessed. In this study, T2 protein, c264scTCR/huIgG1 or A2AL9scTCR/IgG1 (negative control) were added to a 96-well plate at 0.137 to 100 nM. HLA-A2-positive T2 target cells were pulsed with 10 µM of p53 aa264-272 peptide and labeled with 50 ug/ml of Calcein-AM. The fusion proteins were mixed with $1\times10^4$ of the target cell per well and $1\times10^6$/well of fresh human PBMC were added. The plate was incubated at 37° C. in a $CO_2$ incubator for 2 hrs and 100 µl of the conditional medium were collected and analyzed for Calcein released from lysed cells. Calcein was quantitated with a fluorescence reader at Ex-485 nm, Em-538 nm, and Cutoff-530 nm. The specific cell lysis is calculated with the following formula: Specific Lysis=[exp−(background-auto release)]/[Complete release−(background-auto release)]×100%. Exp=fusion protein+T2 cells+PBMC; Background=medium only; Auto release=T2 cells only; Complete release=T2 cells+0.5% Triton X-100.

Figure 20:
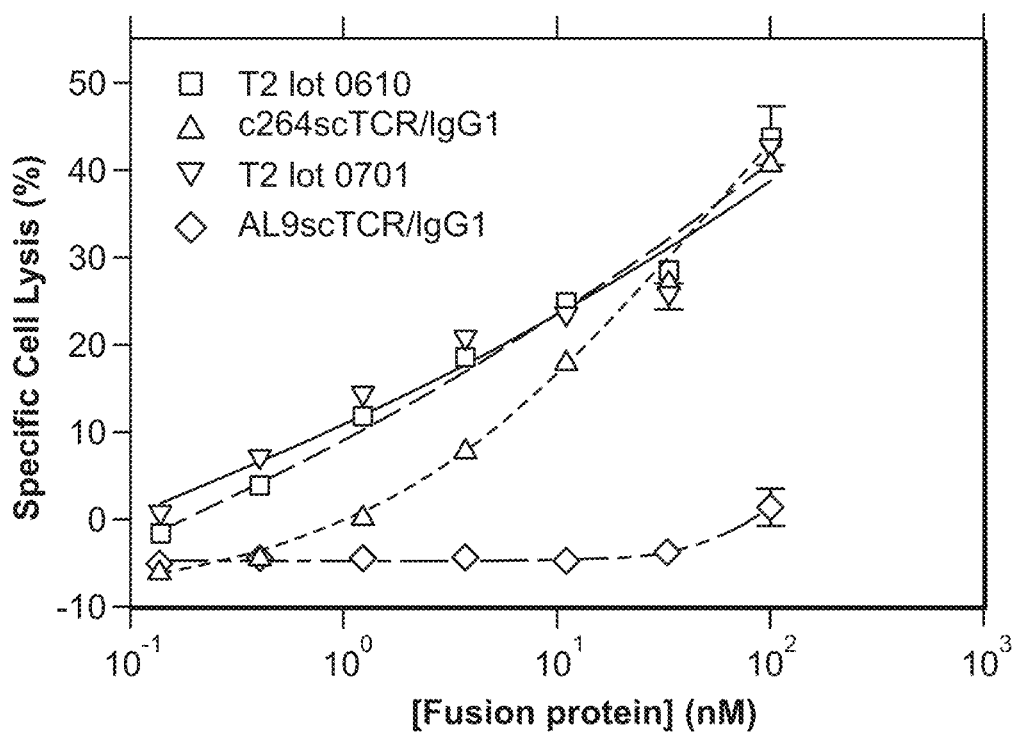
FIG. 20 shows results from an assay to assess the biological activity of the Fc domains of the T2 molecules to mediate antibody dependent cellular cytotoxicity activity. T2 protein, c264scTCR/huIgG1 or A2AL9scTCR/IgG1 (negative control) were added to a 96-well plate at a concentration of 0.137 nM to 100 nM. HLA-A2-positive T2 target cells were pulsed with 10 μM of p53 aa264-272 peptide and labeled with 50 μg/ml of Calcein-AM. The fusion proteins were mixed with 1×10$^4$ of the target cell per well and 1×10$^6$/well of fresh human PBMC were added. The plate was incubated at 37° C. in a CO$_2$ incubator for 2 hrs and 100 μl of the conditional medium were collected and analyzed quantitatively for Calcein released from lysed cells.

The results of triplicate determinations per data point are shown in FIG. 20 where two different lots of the T2 proteins were characterized. The results indicate that the T2 protein was more effective at mediating ADCC-like activity against peptide/MHC presenting target cells than the TCR-IgG1 fusion protein. The improved activity may have been the result of enhanced binding of the T2 molecules to the peptide/MHC complex and/or increase reactivity to the effector cells displaying Fc receptors or IL-15 receptors.

Example 7

Characterization of T2 Molecule Binding to Peptide/MHC Complexes Displayed on Cells To assess the binding activity of T2 protein to peptide/MHC targets on cells, HLA-A2-positive T2 cells were pulsed with various amounts of p53 aa264-272 peptide. The cells were then incubated with T2 protein (composed of c264scTCR/huIL15N72D and c264scTCR/huIL15RαSushi/huIgG1 chains), c264scTCR/huIgG1 or A2AL9scTCR/IgG1 (negative control), each at 83 nM. The cells were incubated with biotinylated anti-TCR Ab (BF1) and streptavidin-PE. The cell were then analyzed by flow cytometry as shown in FIG. 21A. The mean fluorescent intensity for the stained cells was plotted in FIG. 21B.

The results show that the T2 molecules exhibit enhanced ability to detect p53 peptide/HLA-A2 complexes on cells compared to the c264scTCR/huIgG1 fusion protein. These results indicate that the T2 protein is capable of binding more effectively than c264scTCR/huIgG1 fusions to tumor-associated peptide antigens on target cells.

Similar results are expected using T2 molecules comprising TCR domains specific to other peptide/MHC targets. For example, various peptides derived from the human tumor associated proteins; p53, gp100, MART1, MAGE-A3, PSMA, PSA, Her2/neu, hTERT, tyrosinase, survivin, WT1, PR1, NY-ESO1, EGFR, BRAF and others, are known to bind HLA molecules and be targets for human T cell responses via TCR interactions. Additionally, TCRs specific to HLA complexes displaying viral peptide antigens from HIV, HCV, HBC, CMV, HTLV, HPV, EBV and other virus have been identified. These TCR could be fused to the IL-15 or huIL15RαSushi proteins and characterized for peptide/MHC reactivity on the appropriate peptide loaded antigen presenting cells as described above.

Example 8

Characterization of T2 Molecules Bearing Two Different TCR Domains

As indicated above, it is useful to have multiple different TCR domains fused to the IL-15, IL-15Rα and IgG components of the T2 molecule. This allows more than one antigen targeting activity to be present in a single multichain protein. To demonstrate the feasibility of this approach, c264scTCR-Sushi-hIgG1-pMSGVc and c149scTCR-hIL15N72D-pMSGVn expression vectors were co-transfected into CHO cells cultured in IMDM-10 medium. The culture supernatant was harvested after 6 days culture of the transfectants at room temperature. The T2 molecules of c149scTCR/huIL15N72D and c264scTCR/huIL15RαSushi/huIgG1 were characterized with ELISAs. The purified T2-molecules of c264scTCR/huIL15RαSushi/huIgG1 and c264 scTCR/huIL15N72D were used as a control. In one assay to assess the TCR domains, wells were coated with anti-human TCR Ab (BF1), the fusion protein was added and the bound protein was detected with biotinylated anti-human TCR Ab (W4F-BN).

Figure 22:
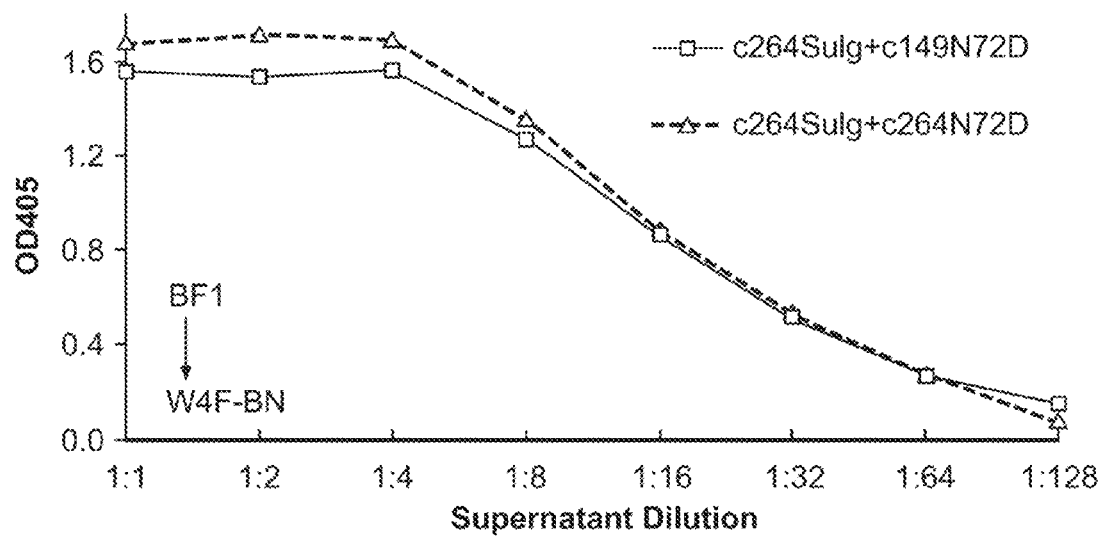
FIG. 22 shows the results from an ELISA in which T2 molecules of c149scTCR/huIL15N72D and c264scTCR/huIL15RαSushi/huIgG1 or c264scTCR/huIL15N72D and c264scTCR/huIL15RαSushi/huIgG1 (in cell culture supernatant) were captured on microtiter plates coated with the anti-human TCR antibody BF1, and the bound T2 molecules were detected using the anti-human TCR antibody W4F-BN.

The results shown in FIG. 22 indicate that the TCR domains of T2 molecules composed of c149scTCR/huIL15N72D and c264scTCR/huIL15RαSushi/huIgG1 were detectable by anti-TCR antibodies. To assess the IgG1 and IL-15 domains of the T2 proteins, an ELISA comprised of a goat anti-human IgG Ab capture and anti-human IL-15 Ab detection described above as used.

Figure 23:
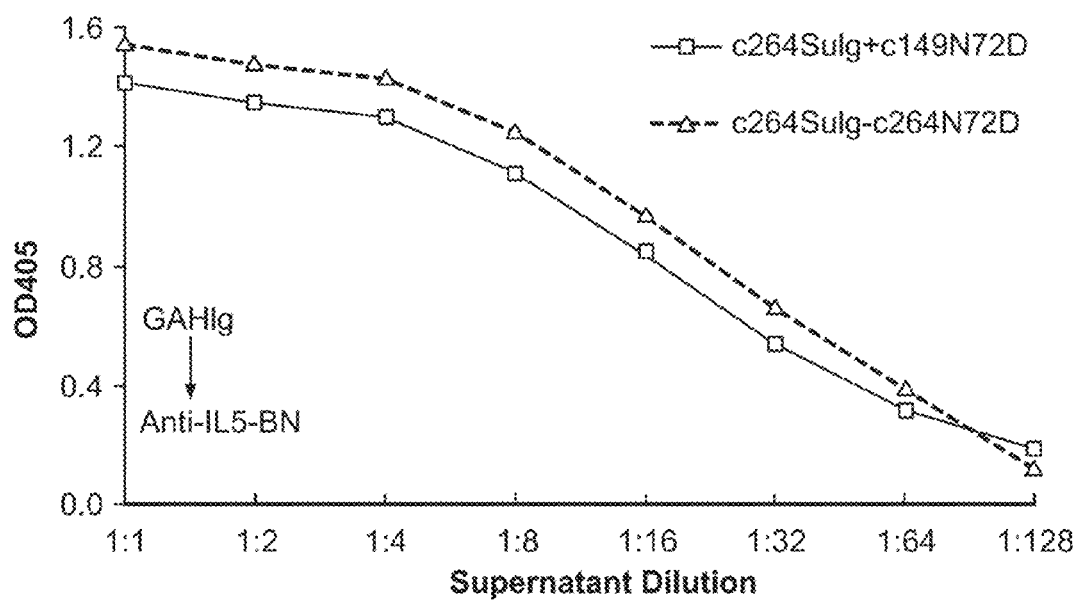
FIG. 23 shows the results from an ELISA in which T2 molecules of c149scTCR/huIL15N72D and c264scTCR/huIL15RαSushi/huIgG1 or c264scTCR/huIL15N72D and c264scTCR/huIL15RαSushi/huIgG1 (in cell culture supernatant) were captured on microtiter plates coated with the goat anti-human IgG antibody, and bound T2 molecules were detected using the anti-human IL-15 antibody.

As shown in FIG. 23, the T2 molecule composed of c149scTCR/huIL15N72D and c264scTCR/huIL15RαSushi/huIgG1 was detectable in this format indicating interaction between the protein chains containing the IgG and IL-15N72D domains. The activity of the c149scTCR domain was also examined in an ELISA using anti-human IgG Ab capture and detection with p53 (aa 149-157) peptide/HLA-A2 streptavidin-HRP tetramers.

Figure 24:
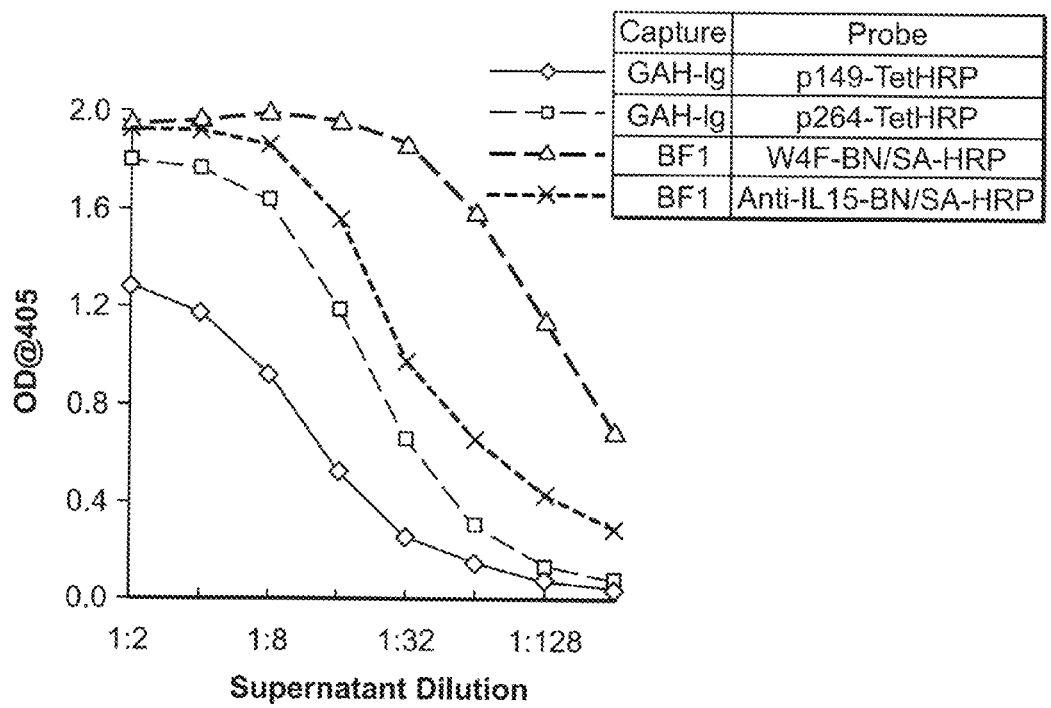
FIG. 24 shows the results from an ELISA in which T2 molecules of c149scTCR/huIL15N72D and c264scTCR/huIL15RαSushi/huIgG1 (in cell culture supernatant) were captured on microtiter plates were coated with either goat anti-human IgG antibody or anti-human TCR antibody BF1. The BF1-captured T2 molecules were detected with either anti-human TCR antibody W4F-BN or anti-human IL-15 antibody. The goat anti-human IgG Ab-captured T2 molecules were detected with either the p53 (aa 149-157) peptide/HLA-A2 streptavidin-HRP tetramers or the p53 (aa 264-272) peptide/HLA-A2 streptavidin-HRP tetramers.

Shown in FIG. 24, the T2 molecule composed of c149scTCR/huIL15N72D and c264scTCR/huIL15RαSushi/huIgG1 was detectable in this format indicating molecules with a IgG1 domain also have binding activity to the p53 (aa 149-157) peptide/HLA-A2 complex via interactions between the c149scTCR/huIL15N72D and c264scTCR/huIL15RαSushi/huIgG1 chains. Additional assays consisting of anti-human IgG Ab capture and detection with either p53 (aa 149-157) peptide/HLA-A2 or p53 (aa 264-272) peptide/HLA-A2 tetramers or anti-TCR Ab (BF1) capture and anti-TCR Ab or anti IL15 Ab detection verified that each of the domains was functionally linked in the T2 protein composed of the c264scTCR/huIL15RαSushi/huIgG1 and c149scTCR/huIL15N72D chains (FIG. 24).

T2 molecules in which these two TCR domains were expressed on the other protein chains, i.e. c264scTCR/huIL15N72D and c149scTCR/huIL15RαSushi/huIgG1 chains, were also generated. The Fc and TCR activity of these molecules were assessed following binding to U937 cells and detection with p53 (aa 264-272) peptide/HLA-A2 tetramers followed by flow cytometry.

Figure 25:
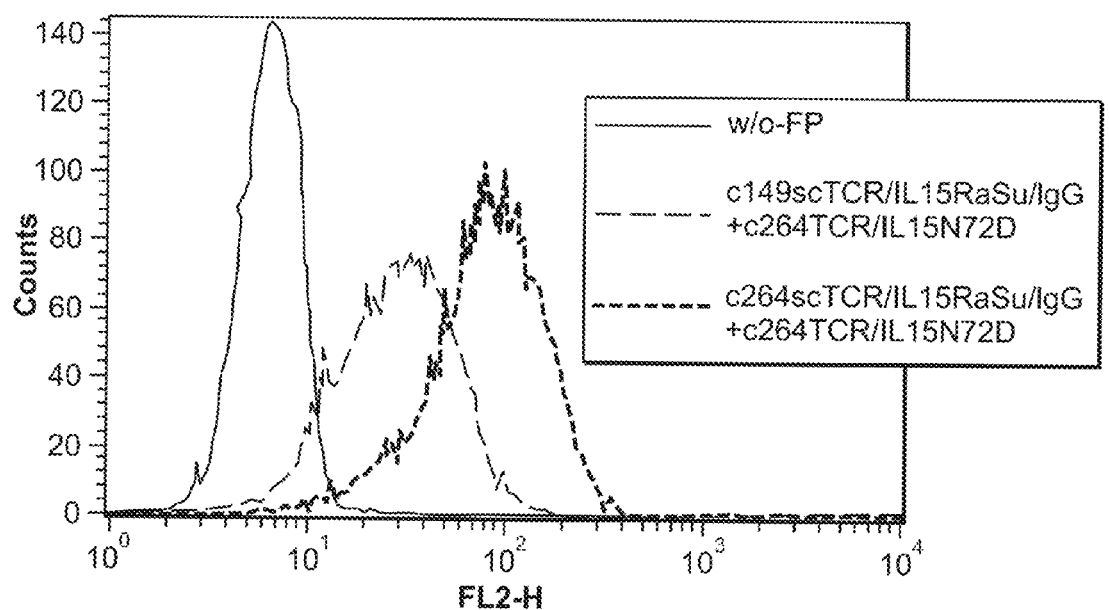
FIG. 25 shows results from a flow cytometry assay in which T2 molecules comprising two different TCR domains, i.e. c264scTCR/huIL15N72D and c149scTCR/huIL15RαSushi/huIgG1 chains, were characterized. The Fc and TCR activity of these molecules were assessed following binding to Fc-gamma receptor bearing U937 cells and detection with p53 (aa 264-272) peptide/HLA-A2 tetramers followed by flow cytometry.

As shown in FIG. 25, T2 molecules composed of c264scTCR/huIL15N72D and c149scTCR/huIL15RαSushi/huIgG1 chains were capable of binding Fc gamma receptors on U937 cells via the Fc domain and recognizing p53 (aa 264-272) peptide/HLA-A2 complex via the c264scTCR domain. These studies verify the T2 molecules with multiple functional TCR domains and IL-15 and IL15Rα and IgG1 domains are capable of forming structures as shown in FIG. 1.

Example 9

Characterization of T2 Protein Pharmacokinetics in Mice and Cynomolgus Monkeys

A major limitation with potential therapies with IL-15 is the very short biological half-life of the cytokine in vivo. To assess the biological pharmacokinetic properties of the T2 molecules in an animal model, HLA-A2/Kb-transgenic mice (5 mice/timepoint) were injected intravenously with purified T2 protein (composed of c264scTCR/huIL15N72D and c264scTCR/huIL15RαSushi/huIgG1 chains) at 135 µg/mouse. The HLA-A2/Kb-transgenic mouse model was selected since presence of HLA-A2.1 domain, for which this c264scTCR is restricted, may influence the pharmacokinetics of the protein and should give a more relevant "humanized" view of pharmacokinetics than other non-human models. In this study, blood was collected at 0, 1, 4, 8, 24, 48, and 72, 96 hours post injection and the levels of T2 protein in the serum was measured by ELISA. Two different ELISA formats were used: 1) goat anti-human IgG Ab capture and anti-human TCR Ab (W4F-BN) detection or 2) goat anti-human IgG Ab capture and anti-human IL-15 Ab detection. These assays allow assessment of the stability of the intact protein and multichain protein complex.

Figure 26A:
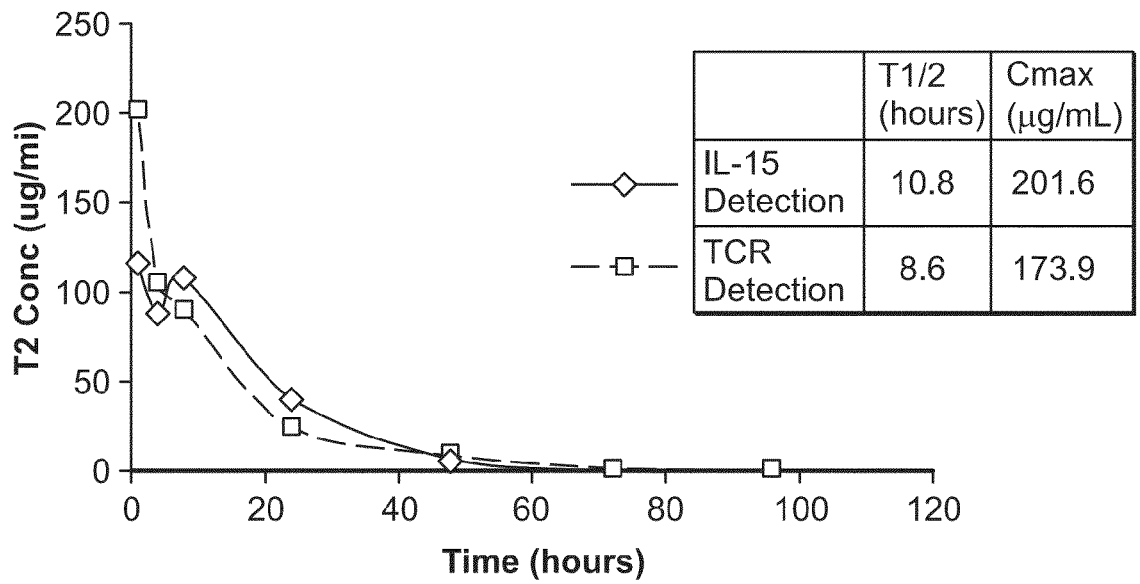
FIG. 26A and FIG. 26B show the results from a pharmacokinetic assay in which mice (FIG. 26A) or monkeys (FIG. 26B) were injected with purified T2 protein composed of c264scTCR/huIL15N72D and c264scTCR/huIL15RαSushi/huIgG1 chains. Samples were collected at the indicated times.

As shown in FIG. 26A, the T2 molecule had a biological half-life of about 9-11 hours following intravenous injection. This is considerably longer than the reported ~1 hour half-life of human IL-15 observed in mice after IP injection (Stoklasek T A et al. 2006. J. Immunol. 177: 6072). Additionally the T2 molecule reached serum concentrations consistent with the dose delivered, whereas very little of the administered dose of IL-15 was recovered in the serum in the study reported previously (Stoklasek T A et al. 2006. J. Immunol. 177: 6072). Thus, the T2 molecule has a significantly better pharmacokinetic profile than free human IL-15. In addition, based on the similar PK profile observed with the two ELISAs, the T2 protein remained intact as a multichain molecule with no evidence of cleavage.

To assess the biological pharmacokinetic properties of the T2 molecules in a primate model, cynomolgus monkeys (n=2, 1m, 1f) were injected intravenously with purified T2 protein (composed of c264scTCR/huIL15N72D and c264scTCR/huIL15RαSushi/huIgG1 chains) at 0.5 mg/kg. In this study, blood was collected at 0, 1, 4, 8, 24, 48, 72, 96 and 120 hours post injection and the levels of T2 protein in the serum was measured by ELISA. Three different ELISA formats were used: 1) anti-human TCR Ab (βF-1) capture and HRP conjugated goat anti-human IgG Ab detection or 2) anti-human IL-15 Ab capture and HRP conjugated goat anti-human IgG Ab detection or 3) anti-human IL-15 Ab capture and anti-human TCR Ab (W4F-BN) detection. These assays allow assessment of the stability of the intact protein and the multichain protein complex.

Figure 26B:
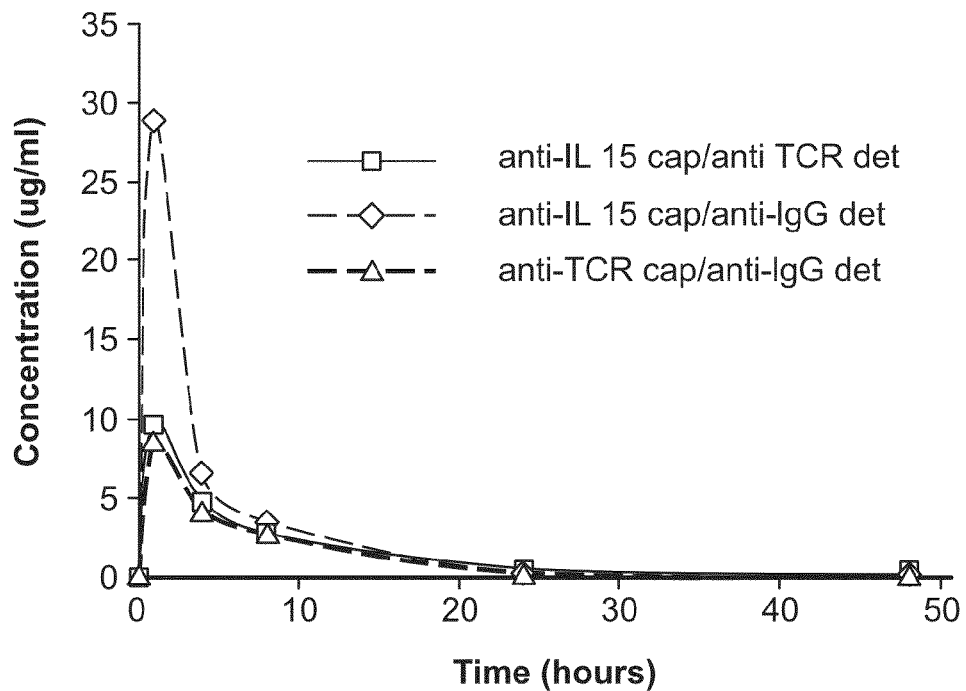

As shown in FIG. 26B, the T2 molecule had a biological half-life of about 4-6 hours following intravenous injection. This is considerably longer than the reported ~1 hour half-life of IL-15 observed in monkeys following subcutaneous injection (Villinger, F. et al. 2004. Vaccine 22: 3510). Thus, the T2 molecule appears to have a significantly better pharmacokinetic profile than free IL-15. In addition, based on the similar PK profile observed with the three ELISAs, these data supports the murine PK data that suggests the T2 protein remains intact as a multichain molecule with no evidence of cleavage.

Example 10

Figure 27:
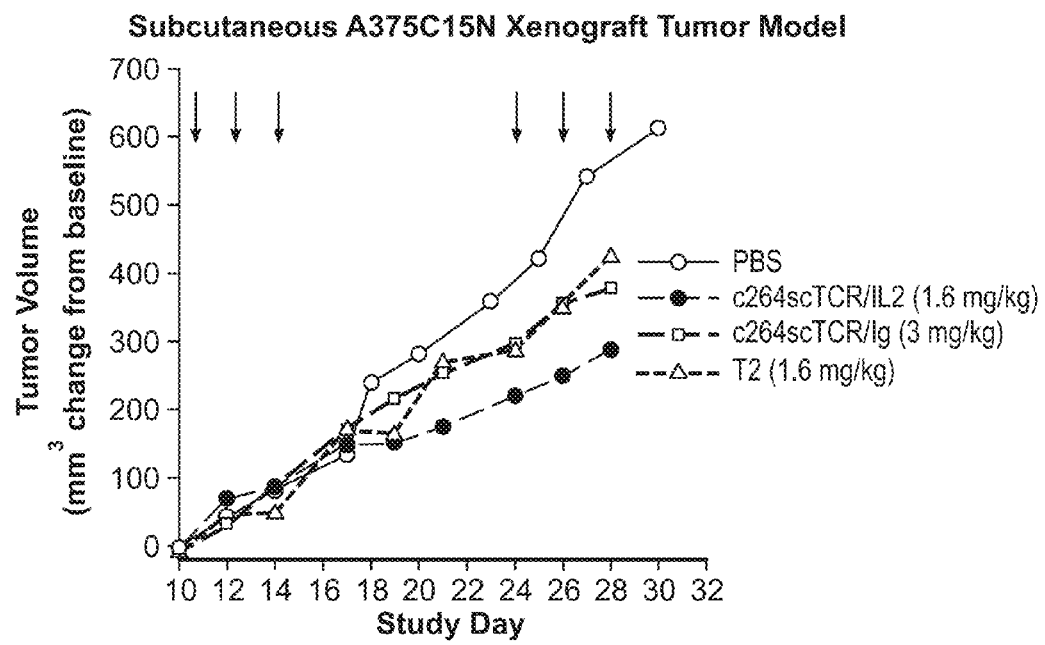
FIG. 27 shows results from a primary tumor growth model using a human p53+HLA-A2+A375 melanoma cell line in nude mice. Tumor-bearing mice were injected intravenously with 32 μg/dose (1.6 mg/kg) T2 protein composed of c264scTCR/huIL15N72D and c264scTCR/huIL15RαSushi/huIgG1 chains, 32 μg/dose (1.6 mg/kg) c264scTCR/huIL2, or 60 μg/dose (3 mg/kg) 264scTCR/huIgG1. Tumor growth was measured and data are shown in the figure.

Anti-Tumor Activity of T2 Molecules Against Solid Human Tumors in Xenograft Tumor Mouse Model To determine the therapeutic effects of the T2 protein, we examined antitumor activity in a primary tumor growth model with the human p53+HLA-A2+A375 melanoma cell line in nude mice. Tumor cells were injected subcutaneously into nude mice and tumors were allowed to grow to 100 mm$^3$ before treatment began. Tumor-bearing mice were injected intravenously with 32 µg/dose (1.6 mg/kg) T2 protein composed of c264scTCR/huIL15N72D and c264scTCR/huIL15RαSushi/huIgG1 chains, 32 µg/dose (1.6 mg/kg) c264scTCR/huIL2, or 60 µg/dose (3 mg/kg) 264scTCR/huIgG1. The mice were treated every other day for one week (3 injections) followed by a 9 day rest period and then every other day for an additional week (3 injections). During the study, tumor growth was measured and the tumor volumes were plotted (FIG. 27). The results were compared to A375 tumor growth in mice treated with only PBS.

As shown in FIG. 27, A375 tumor growth was inhibited in nude mice treated with either T2 molecule or TCR-IL2 or TCR-IgG fusion proteins. Previous studies showed that the antitumor effects of the p53 specific TCR-IL2 or TCR-IgG fusion proteins in this model were the results of targeting the effector domain activity to the tumor site via the TCR domain (Belmont et al. 2006 Clin. Immunol. 121:29, Mosquera et al. 2005 J. Immunol. 174:4781). To assess this possibility, T2 proteins with non-targeted TCR domains will be tested in the A375 tumor xenograft mouse model. A decrease in efficacy of the non-targeted T2 molecules compared with the p53-specific T2 proteins against the A375 tumor will provide evidence that tumor antigen targeting play a role in the antitumor activity of the T2 molecules.

Example 11

Characterization of T2 Molecules with Mutations in the IL-15 and Fc Domains

Figure 28:
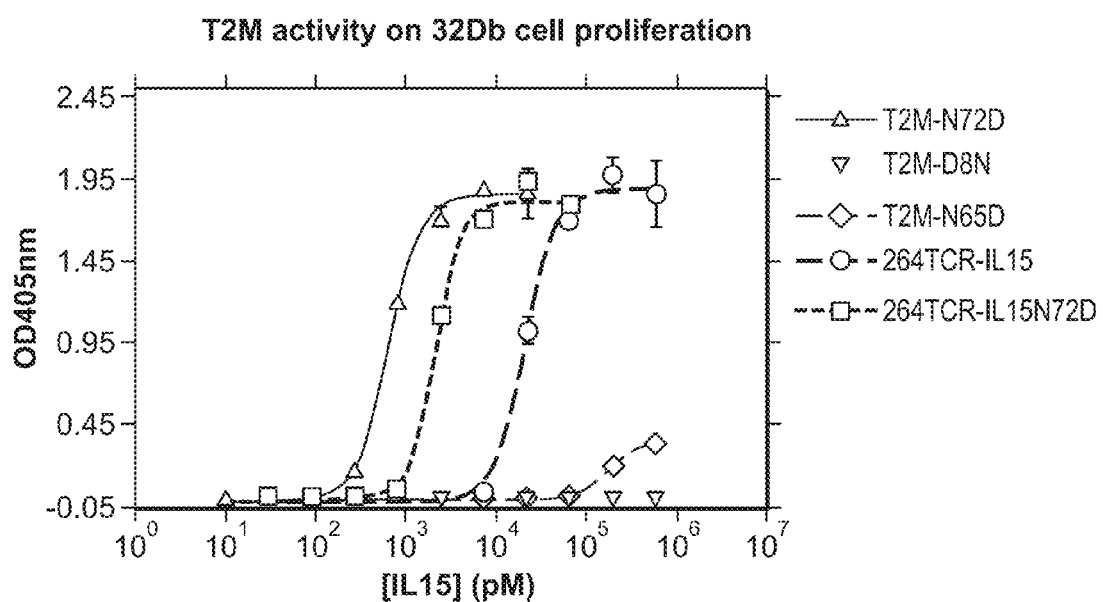
FIG. 28 shows the results from IL-15 activity assays of T2 molecules with various point mutations in the IL-15 domain as measured by proliferation of 32Dβ cells.

As disclosed in WO2008143794, mutations can be introduced into the IL-15 domain that increase or decrease its ability to interact with the IL-15Rβγ chains and affect its biological activities. For example, as indicated above, the N72D substitution can increase the IL-15 biological activity 5 to 10 fold. In other instances, it is useful to decrease IL-15 activity to provide antagonist function. To examine the effects of such mutations in the context of the T2 molecular format, c264scTCR/huIL15 constructs containing substitutions at positions 8 (i.e., D8N) and 65 (i.e., N65D) of the IL-15 domain were generated and co-expressed with the c264scTCR/huIL15RαSushi/huIgG1 protein. The resulting complexes of c264scTCR/huIL15 variant and c264scTCR/huIL15RαSushi/huIgG1 chains were tested for IL-15 biological activity using the 32Dβ cells as described in Example 5. As shown in FIG. 28, the T2 molecules comprising IL-15 D8N and N65D variants exhibited a significant decrease in their ability to support 32Dβ cell proliferation compared to the T2 molecules comprising IL-15 N72D domain or the c264scTCR/huIL15 fusions. Consistent with the results of Example 5, the T2 molecules comprising IL-15 N72D domain exhibited more IL-15 activity than either the c264scTCR/huIL15N72D or c264scTCR/huIL15 fusions.

Mutations were also introduced into the IgG1 Fc domain that were previously shown to decrease its ability to interact with Fc gamma receptor or complement (Hessell, A. J., et al. 2007. Nature 449: 101-1040, incorporated herein by reference). For example, the substitution of leucine residues at positions 234 and 235 of the IgG1 $C_H2$ (numbering based on antibody consensus sequence) (i.e. . . . P E L L G G . . . ) (SEQ ID NO: 21) with alanine residues (i.e. . . . P E A A G G . . . ) (SEQ ID NO: 22) results in a loss of Fc gamma receptor binding whereas the substitution of the lysine residue at position 322 of the IgG1 $C_H2$ (numbering based on antibody consensus sequence) (i.e. . . . K C K S L . . . ) (SEQ ID NO: 23) with an alanine residue (i.e. . . . K C A S L . . . ) (SEQ ID NO: 24) results in a loss of complement activation (Hessell, A. J., et al. 2007. Nature 449: 101-1040, incorporated herein by reference). These substitutions were introduced into the c264scTCR/huIL15RαSushi/huIgG1 construct and the resulting protein was co-expressed with c264scTCR/huIL15N72D or the other TCR-IL-15 variants described above. The ability of these complexes to mediate ADCC activity of human PBMCs against p53 aa264-272 peptide-loaded HLA-A2-positive T2 target cells was assessed as described in Example 6. Other mutations known to alter Fc function are provided, for example, in Lazar et al., PNAS, 103:4005-4010, 2006 (incorporated herein by reference).

Figure 29:
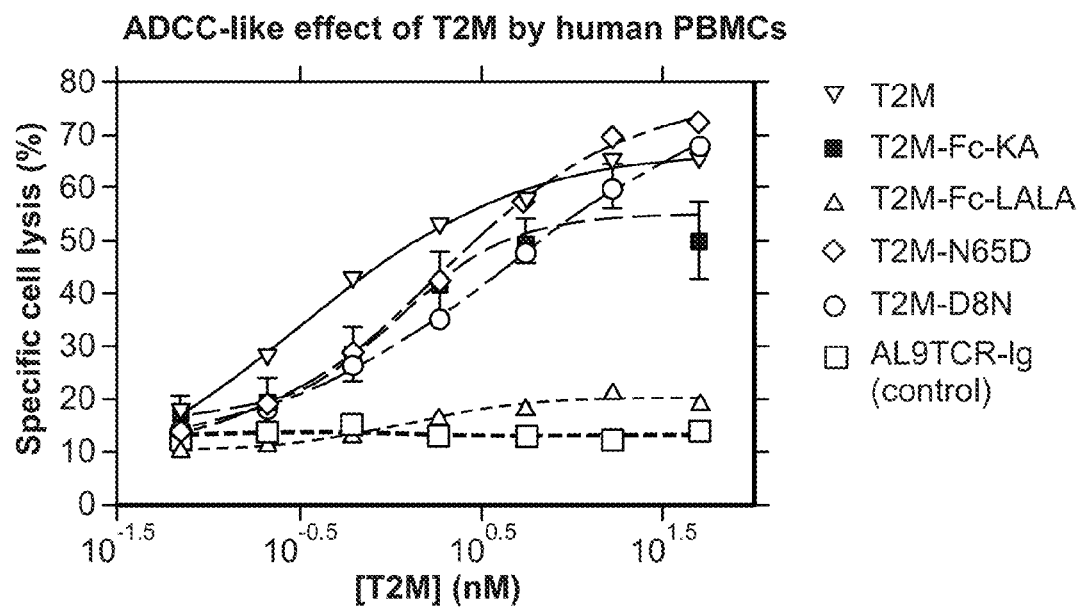
FIG. 29 shows results from an antibody dependent cellular cytotoxicity assay using T2 molecules with various point mutations in the IL-15 and IgG Fc domains as measured by PBMC-dependent lysis of peptide-loaded T2 target cells.

As show in FIG. 29, the T2 complex comprising the c264scTCR/huIL15RαSushi/huIgG1-LALA and c264scTCR/huIL15N72D chains was not capable of mediating high levels of ADCC activity consistent with the loss of Fc gamma receptor binding exhibited by the Fc-LALA variant. In contrast, complexes comprising c264scTCR/huIL15RαSushi/huIgG1-KA and c264scTCR/huIL15N72D chains or the IL-15 variants (N65D or D8N) described above exhibited the same level of ADCC activity as the c264scTCR/huIL15RαSushi/huIgG1-c264scTCR/huIL15N72D complex. Without being bound by mechanism, these data are also expected based on the likelihood that the IL-15 domain and the Fc complement-binding domain are not involved in mediating ADCC activity.

The effects of the IL-15 and Fc mutations on the ability of the T2 molecules to stimulate human NK and T cell responses were also examined. Human PBMCs at 1.8 to $5 \times 10^5$ cells/mL were incubated for 4 days at 37° C. in media containing 1 nM T2 molecules comprising the mutations described above or with 10 ng/mL recombinant human IL-2 or IL-15 as a control.

NK cell cytotoxicity was then assessed using NK-sensitive K-562 cells as target cells following labeling with 50 ug/ml of Calcein-AM. Various ratios of PBMCs and K-562 cells were mixed and incubated at 37° C. in a $CO_2$ incubator for 2 hrs and 100 µl of the conditional medium were collected and analyzed for Calcein released from lysed cells. Calcein was quantitated with a fluorescence reader at Ex-485 nm, Em-538 nm, and Cutoff-530 nm. The specific cell lysis is calculated with the following formula: Specific Lysis=[exp−(background-auto release)]/[Complete release−(background-auto release)]×100%. Exp=K-562 cells+PBMC; Background=medium only; Auto release=K-562 cells only; Complete release=K-562 cells+0.5% Triton X-100.

Figure 30:
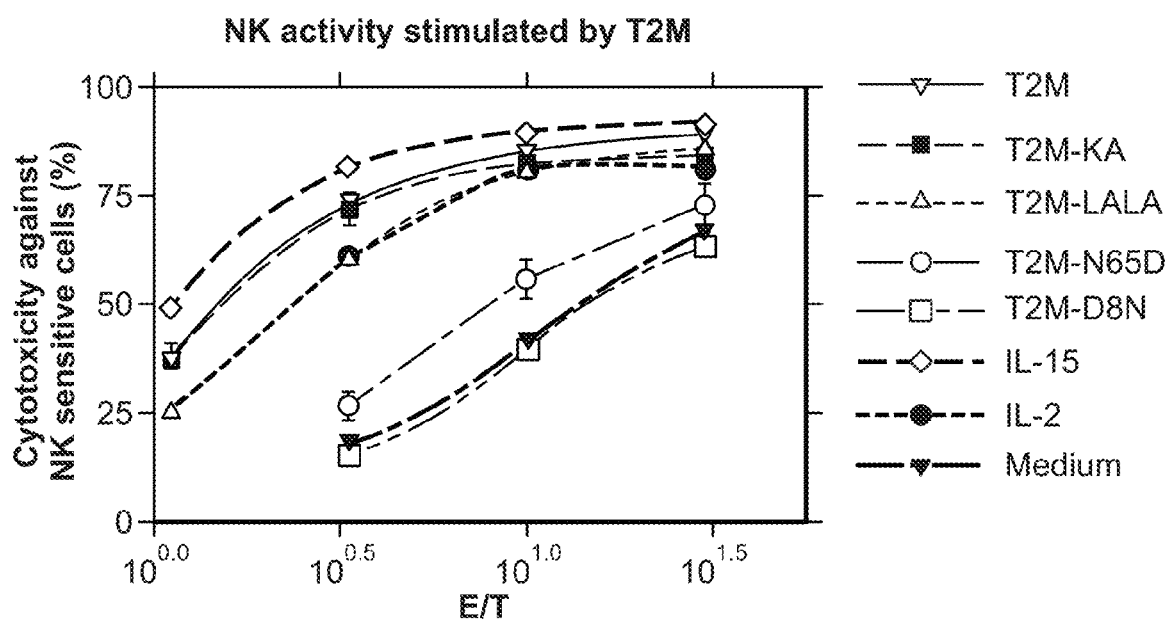
FIG. 30 shows results from an assay to detect the effects of the IL-15 and Fc mutations on the ability of the T2 molecules to stimulate human NK and T cell responses. Human PBMCs at 1.8 to 5×10$^5$ cells/mL were incubated for 4 days at 37° C. in media containing 1 nM T2 molecules comprising the mutations indicated or with 10 ng/mL recombinant human IL-2 or IL-15 as a control. NK cell cytotoxicity was then assessed using NK-sensitive K-562 cells as target cells following labeling with 50 ug/ml of Calcein-AM.
Figure 31:
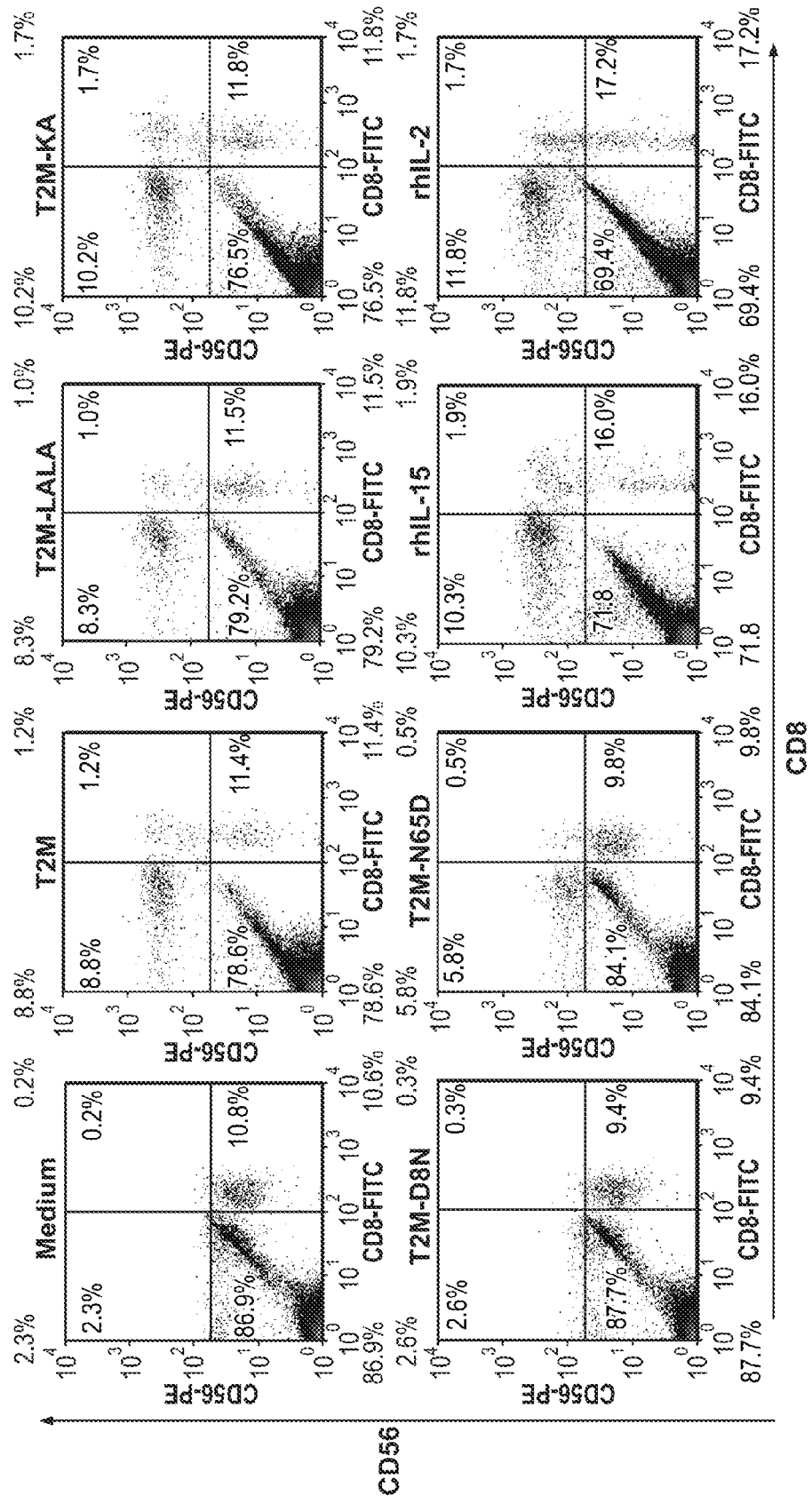
FIG. 31 shows results from NK cell proliferation assay in which human PBMCs were incubated with T2 molecules comprising various point mutations in the IL-15 and IgG Fc domains or with recombinant human IL-2 or IL-15 as a control. T2 molecules comprising the c264scTCR/huIL15RαSushi/huIgG1 and c264scTCR/huIL15N72D chains or those with the Fc domain LALA and KA variants resulted in an increase in proliferation of CD56+NK cells whereas T2 molecules comprising IL-15 N65D or D8N substitutions did not provide as much NK cell proliferative activity.

As shown in FIG. 30, incubation with the T2 molecule comprising the c264scTCR/huIL15RαSushi/huIgG1 and c264scTCR/huIL15N72D chains was capable of stimulating NK cell cytolytic activity of human PBMCs compared to that observed following incubation with media alone. In addition the T2 molecules comprising the Fc domain LALA and KA variants were also capable of stimulating NK cell activity whereas those comprising N65D or D8N substitutions in the IL-15 domain should little or no ability to stimulate NK cell cytotoxicity. Consistent with these results, incubation of human PBMCs with T2 molecules comprising the c264scTCR/huIL15RαSushi/huIgG1 and c264scTCR/huIL15N72D chains or those with the Fc domain LALA and KA variants resulted in an increase in proliferation of CD56+ NK cells whereas T2 molecules comprising IL-15 N65D or D8N substitutions did not provide as much NK cell proliferative activity (FIG. 31). These results are expected based on the functionality of each of the IL-15 domain.

Figure 32A:
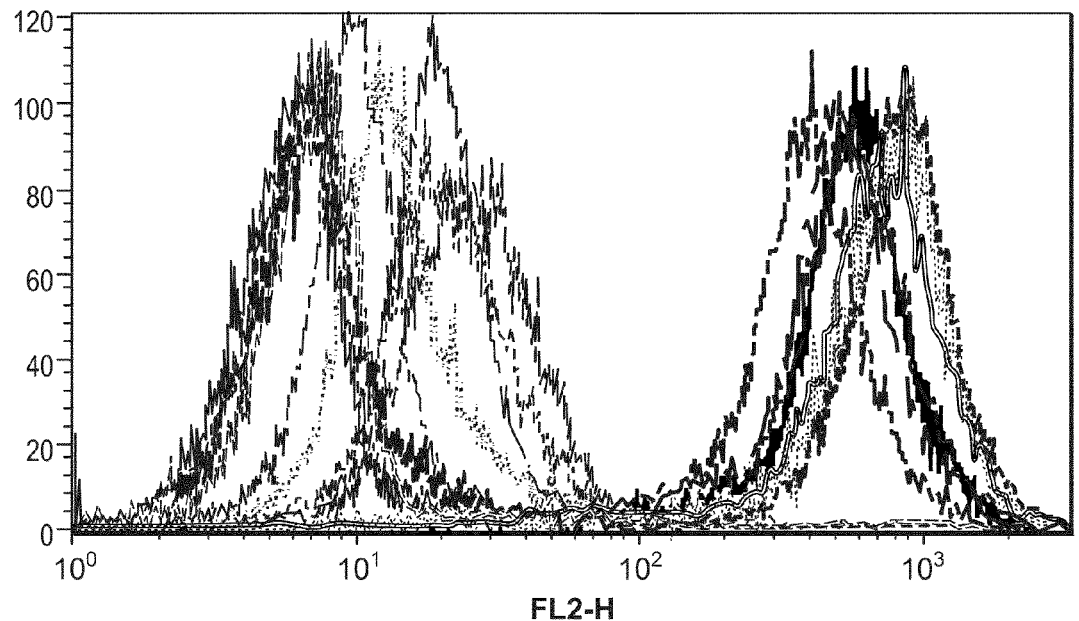
FIG. 32A and FIG. 32B show results from flow cytometry assays to test the antigen specific binding of T2 molecules including IL-15 and Fc mutations to T2 cells with (T2.265) and without loaded p53 peptide (T2).
Figure 32B:
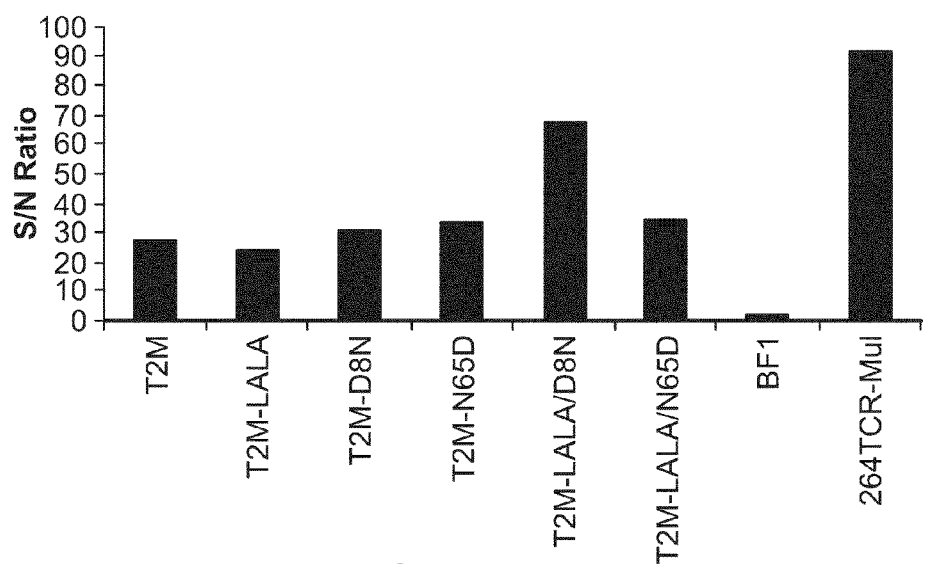

For some applications, decreased interactions between the T2 molecules and the IL-15 or Fc receptors may be desirable to reduce non-specific binding to cells bearing these receptors. To assess this, T2 molecules containing IL-15 and Fc mutations were evaluated for TCR-specific target cell recognition using T2 cells loaded with peptide. Cell staining with the T2 molecules or c264scTCR-streptavidin tetramer positive control was performed on T2 cells with (T2.265) and without loaded p53 peptide (T2) using the method described in Example 7 (FIG. 32A). Based on the staining of unloaded cells, it is clear that the T2 molecule comprising the c264scTCR/huIL15RαSushi/huIgG1 and c264scTCR/huIL15N72D chains shows significant cell binding compared to the c264scTCR-streptavidin tetramer or BF1 antibody controls. Introduction of the Fc LALA or IL-15 N65D or D8N mutations reduced this cell binding indicating that interactions with both Fc and IL-15 receptors play a role in T2 complex binding. Combination of the Fc LALA and IL-15 N65D or D8N mutations further reduced T2 complex binding such that the molecule comprising c264scTCR/huIL15RαSushi/huIgG1-LALA and c264scTCR/huIL15 D8N did not show binding to unloaded T2 cells above the BF1 antibody negative control. Staining of p53 peptide loaded cells was also effected by introduction of the Fc or IL-15 mutations. However, when the mean fluorescence intensity of T2 molecule staining for peptide loaded verses non-loaded cells was compared (specific to nonspecific ratio), it is clear that the T2 molecule comprising c264scTCR/huIL15RαSushi/huIgG1-LALA and c264scTCR/huIL15 D8N chains provided the highest staining specificity for the p53 peptide antigen (FIG. 32B). These results indicate that the binding activities of each of the TCR, IL-15 and IgG Fc domains of the T2 molecule can be readily and independently manipulated to provide a multispecific complex with the desired biological activity.

In other cases, it is useful to modify the activity of the IL-15 domain and the IgG Fc domains to optimize the therapeutic index and minimize toxicity of the T2 complex. For example, targeted complexes relying in part on ADCC activity for their therapeutic effect may require dosing at high levels (i.e. 1-20 mg/kg) that exceed the tolerable dose level of the IL-15 component. In such a case, complexes containing a mutation in the IL-15 domain that reduces its activity are expected to provide better therapeutic activity and lower toxicity. T2 molecules containing N65D or D8N substitutions in the IL-15 domain described above or other substitutions including I6S, D8A, D61A, N65A, N72R, V104P or Q108A, which has been found to reduce IL-15 activity, are of particular interest.

Example 12

Characterization of Non-Targeted T2 Molecules

Figure 33A:
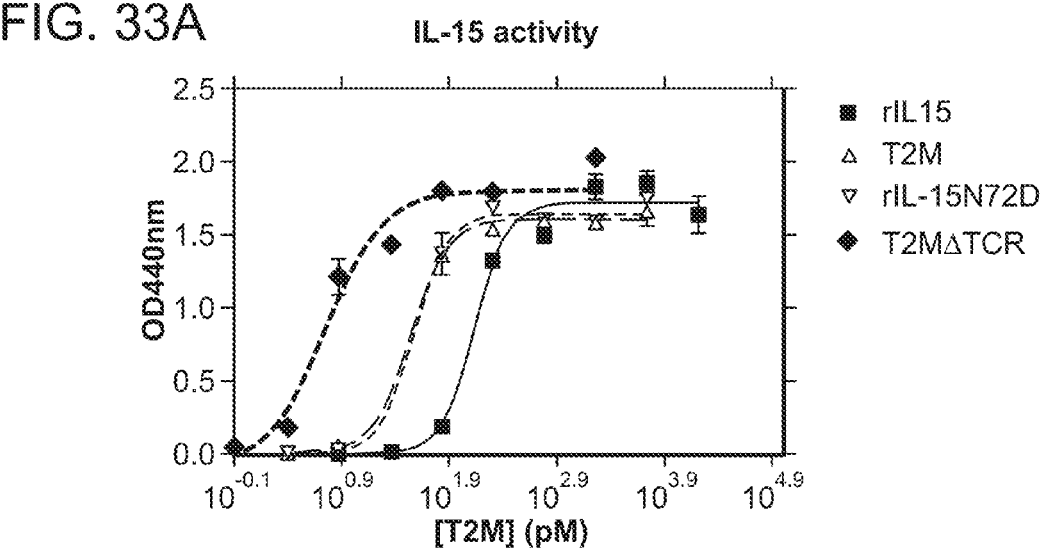
FIG. 33A, FIG. 33B, and FIG. 33C show results from assays to detect the activity of various T2 molecules and IL-15 molecules to support 32Dβ cell growth (FIG. 33A), to stimulate expansion of various T cell populations (FIG. 33B), and to stimulate NK cell activity (FIG. 33C).

In some applications, it is not necessary to target specific antigens with the T2 complex. In such molecules the antigen-specific domains such as the TCR binding domains can be inactivated by mutations or completely deleted. Using the methods described herein, the activity of such a molecule comprising huIL15RαSushi/huIgG1 and huIL15 D8N chains referred to as T2MΔTCR was compared to the T2 molecule comprising c264scTCR/huIL15RαSushi/huIgG1 and c264scTCR/huIL15N72D chains (referred to as T2M) and a T2 molecule lacking the huIgG1 chain (c264scTCR/huIL15RαSushi and c264scTCR/huIL15N72D, referred to as T2MΔIg or c264scTCR dimer). When tested for ability to support 32Dβ cell growth as described in Example 5, the T2MΔTCR exhibited very potent IL-15 activity (FIG. 33A) that was >24 fold that observed with recombinant human IL-15.

Figure 33B:
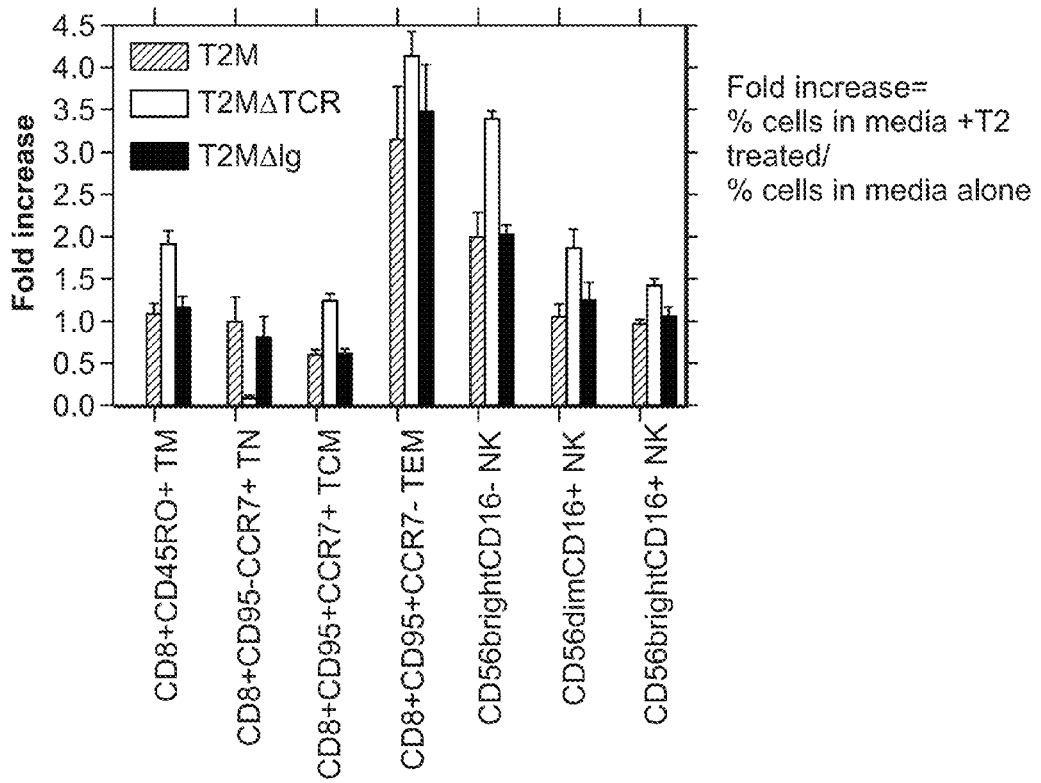
Figure 33C:
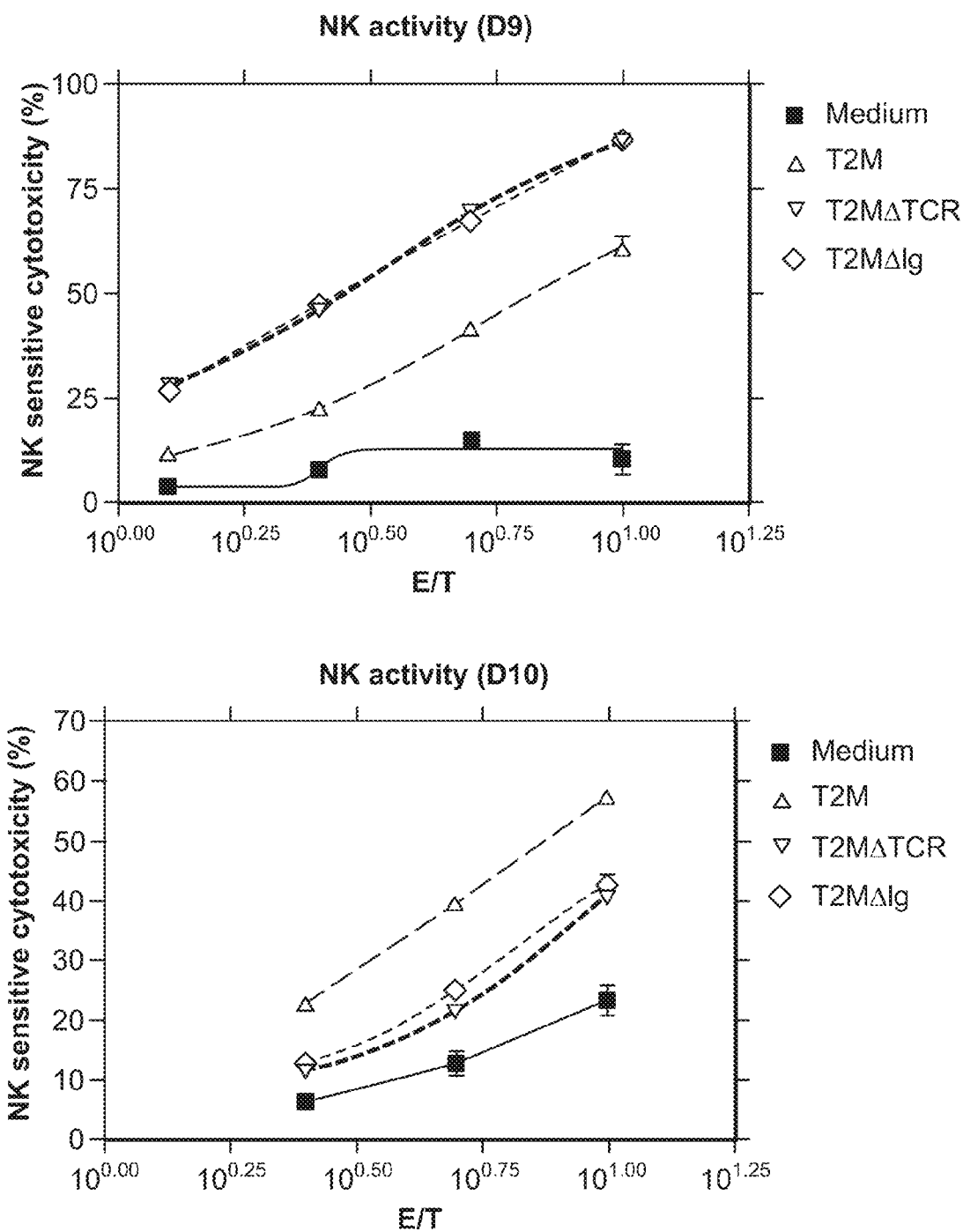

The ability of the T2MΔTCR to support human immune cell growth was also assessed. Human PBMC at $1\times10^6$ cells/ml were incubated with media in the presence or absence of T2M (0.5 nM), T2MΔTCR (0.5 nM), or T2MΔIg (1 nM) for 7 days. Cells were stained with anti-CD45R0 and anti-CD8, or anti-CD8, anti-CD95, and anti-CCR7, or anti-CD56 and anti-CD16, and analyzed with FACScan. The averaged results from 8 different donors shown in FIG. 33B indicate that the T2MΔTCR and other T2 molecules could effectively stimulate expansion of various CD8+ memory T cell and NK cell subsets including effector memory T cells. The NK cell activity of these cells was examined using the methods described in Example 11. Representative results from 2 donor PBMC preparations shown in FIG. 33C indicate that the T2MΔTCR and other T2 molecules could effectively stimulate NK cell cytolytic activity. Overall these results indicate that the T2MΔTCR protein is a potent immunostimulatory molecule.

Example 13

In Vivo Activity of T2 Molecules

To further characterize the immunostimulatory activity of the T2 molecules, T2M, T2MΔTCR, T2MΔTCR lacking the IgG1 CH1 domain (T2MΔTCRΔCH1), T2M with the Fc-LALA mutation (T2MLALA) and T2 with the IL-15 D8N mutation (T2MD8N) were tested for their ability to induce expansion of NK and CD8 T-cells in C57BL/6 mice. In addition, c264scTCR/huIL15N72D, c264scTCR/huIL15RαSushi and c264scTCR/huIL15N72D+c264scTCR/huIL15RαSushi complexes were evaluated.

Figure 34A:
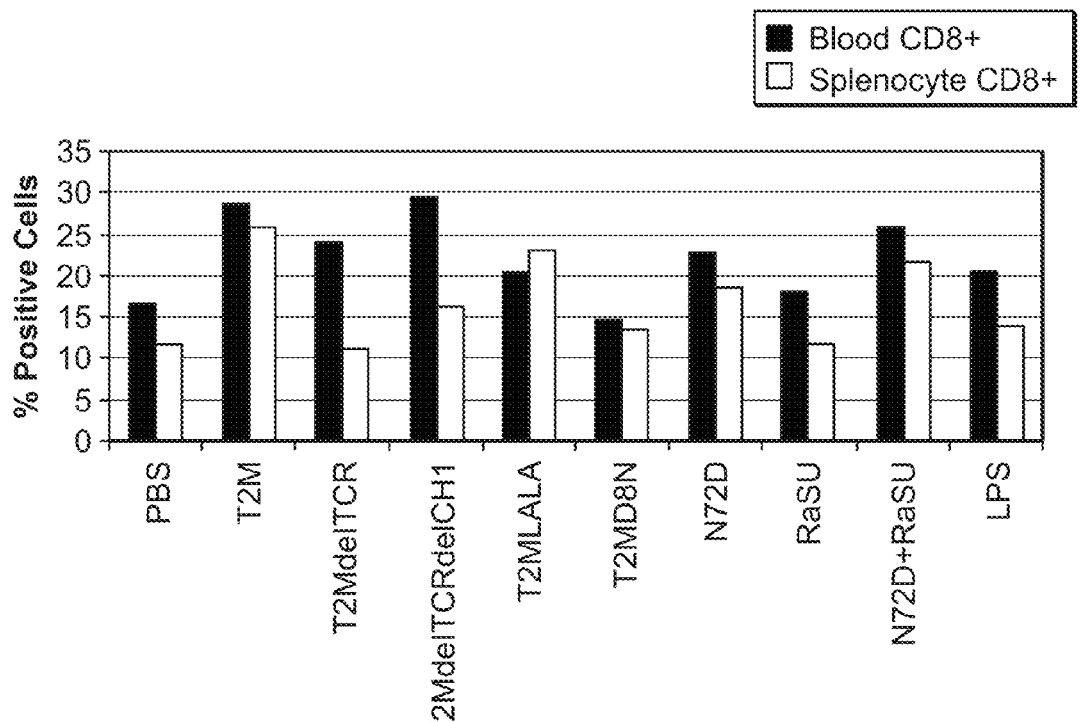
FIG. 34A and FIG. 34B show results from an in vivo assay to determine the immunostimulatory activity of various T2 molecules in mice as indicated by changes in the percentage of CD8+ T-cells (FIG. 34A) and NK cells (FIG. 34B) in blood and spleen cells as detected using flow cytometry.
Figure 34B:
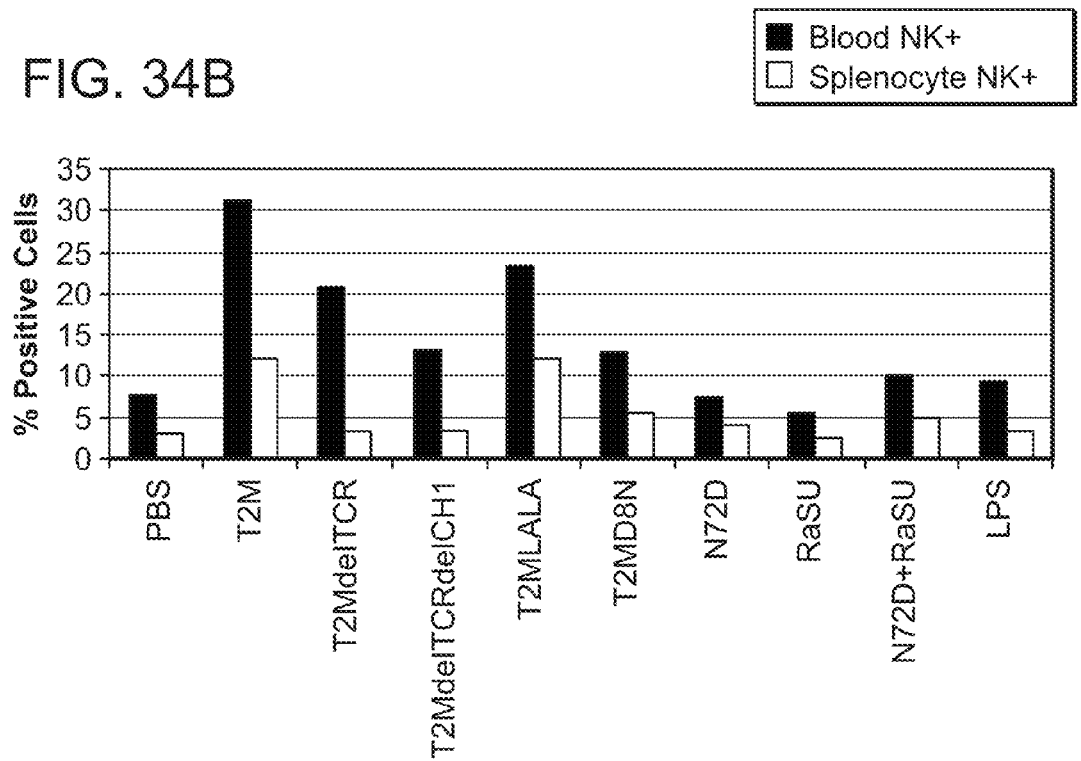

Mice were i.v. injected on day 1 and 4 with the fusion proteins at an amount equivalent to a 2.5 μg dose of IL-15. On day 8, blood cells and splenocytes were collected, stained for CD8 T-cells and NK cells, and analyzed by flow cytometry. The results shown in FIG. 34A and FIG. 34B indicate that T2 molecules are effective at expanding both blood and splenic NK cells and CD8 T cells in vivo. T2MLALA showed similar activity as T2M, suggesting FcR binding and signaling may not play a significant role in NK and CD8 T cell expansion. T2MD8N treatment resulted in decreased activity when compared with T2M, confirming the finding that D8N mutation diminished the molecule's immunostimulatory activity in vitro using human PBMC. Deletion of TCR (T2MΔTCR) and deletions of TCR and CH1 (T2MΔTCRΔCH1) showed decreased activity. These effects may have been due to the shorter half-lives of these smaller molecules. The c264scTCR/huIL15N72D, c264scTCR/huIL15RαSushi and c264scTCR/huIL15N72D+c264scTCR/huIL15RαSushi complexes also showed reduced in vivo activity relative to the T2M, verifying the in vitro results indicating that the T2 molecule is a more potent immunostimulatory compound.

Example 14

Multispecific T2 Molecules

To further characterize the ability of the IL-15 and IL-15Rα/IgG Fc fusion domains to act as a scaffold for multiple binding domains, a fusion protein complex (OT1-CD8-T2M) was created comprising a single-chain TCR domain (OT1scTCR) specific for H-2K$^b$-restricted OVA aa257-264 peptide (SIINFEKL) (SEQ ID NO: 25) linked to huIL15N72D and a single chain CD8α/β domain linked to the huIL15RαSushi/huIgG1 fusion. The single chain CD8α/β domain comprises the extracellular domain of murine CD8α linked via a (G$_4$S)$_4$ (SEQ ID NO: 26) peptide linker to the extracellular domain of murine CD8β. It is well characterized that CD8 binds to a site in the MHC molecule distal to the TCR-specific peptide/MHC interface. Thus both the OT1scTCR and scCD8α/β domains of the OT1-CD8-T2M complex are expected to interact at different sites on the OVA aa257-264/H-2K$^b$-molecule. To test this, binding activity of OT1-CD8-T2M was compared to that of the OT1scTCR/huIL15N72D fusion by ELISA. Equal molar amounts of each protein was captured on a well coated with anti-TCR Cβ mAb (H57) and probed with OVA aa257-264/H-2K$^b$ tetramers or mAbs to IL15, CD8α, CD8β or TCR Vα2. Assays were also preformed with wells coated with anti-human Ig and probed with anti-TCR Vα2.

Figure 35A:
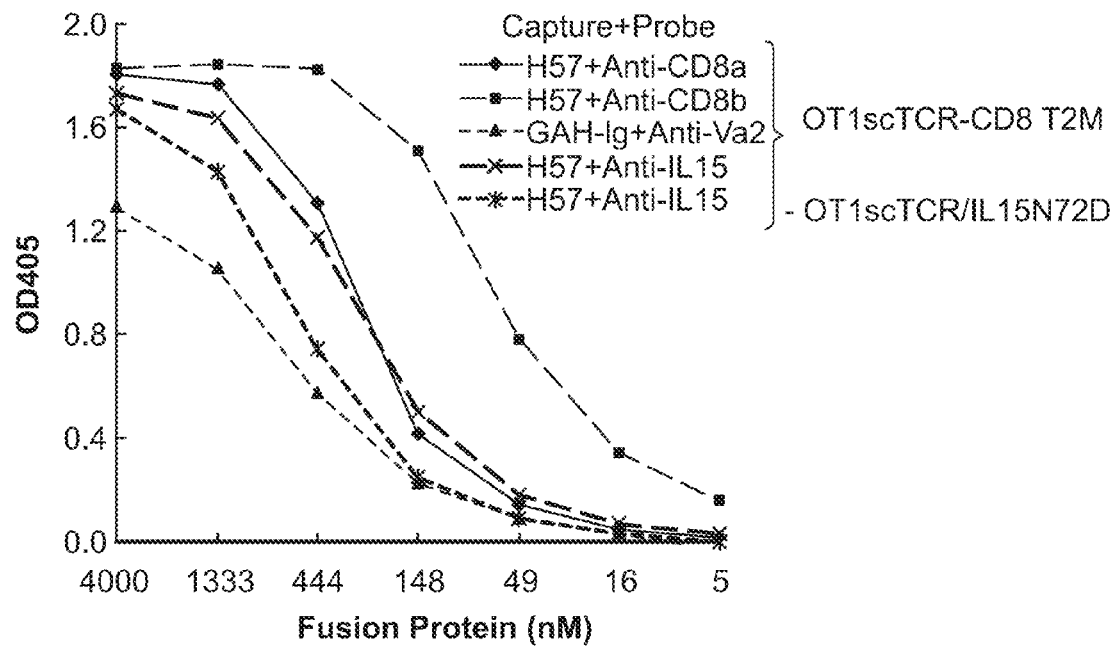
FIG. 35A and FIG. 35B show results from an ELISA using a multispecific T2 molecule comprising 1) the huIL15N72D domain fused to a scTCR specific to the peptide from amino acids 257-264 of ovalbumin and 2) a single chain CD8α/β domain linked to the huIL15RαSushi/huIgG1 fusion. Binding activity of OT1-CD8-T2M was compared to that of the OT1scTCR/huIL15N72D fusion by ELISA. Equal molar amounts of each protein was captured on a well coated with anti-TCR Cβ mAb (H57) and probed with OVA aa257-264/H-2Kb tetramers (FIG. 35B) or mAbs to IL15, CD8α, CD8β or TCR Vα2 (FIG. 35A). Assays were also performed with wells coated with anti-human Ig and probed with anti-TCR Vβ2.
Figure 35B:
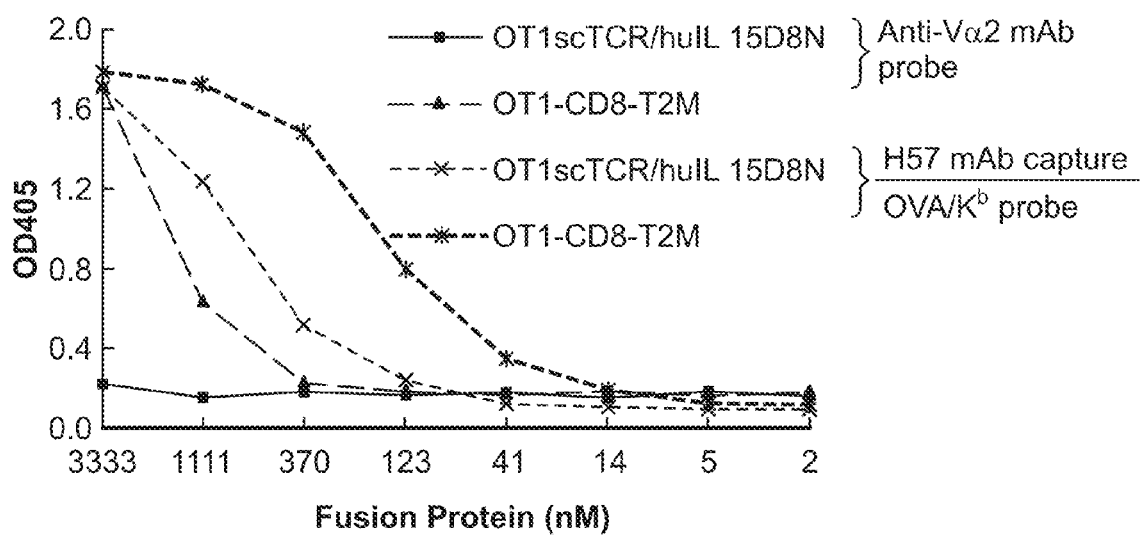

As shown in FIG. 35A, the OT1-CD8-T2M protein exhibited reactivity to anti-IL15, CD8α, CD8β, TCR Vα2 and human Ig antibodies. There was about a 3-fold higher reactivity to anti-TCR Vα2 mAb than OT1scTCR/huIL15N72D, as expected based on the multivalent format of the T2M fusion complex. However, the OT1scTCR/huIL15N72D fusion showed little or no binding to OVA aa257-264/H-2K$^b$ tetramers whereas binding was clearly apparent with the OT1-CD8-T2M protein (FIG. 35B). These results indicate that both the OTscTCR and scCD8α/β domains of the OT1-CD8-T2M complex bind to the OVA aa257-264/H-2K$^b$ molecule to provide high affinity stable interactions.

Example 15

IL-15:IL-15Rα Domains as a Functional Scaffold

Preparation of Peptide/MHC Class I (pMHCI) Tetramers—The murine H-2Kb gene was cloned from total RNA extracted from C57BL/6 mouse lymphocytes as described above. The extracellular region was ligated into the HLA-A*0201 heavy chain expression vector (31) replacing the HLA-A*0201 coding sequence (31). The β2m, HLA-A*0201 and H-2Kb expression vectors were individually transformed into E. coli and expression of the recombinant proteins were induced as described (31), and were expressed as insoluble inclusion bodies. The active and soluble proteins in complex with the peptides were obtained by the re-folding method described at microbiology.emory.edu/altman/jdaWebSite_v3/ptetPrepOverview.shtml. The p53 (aa264-

272) and (aa149-157) peptide/HLA-A*0201 reagents are referred to as A2/p53.264-272 and A2/p53.149-157, respectively, and the OVA (aa257-264) peptide/H-2Kb is referred to as Kb/OVA.257-264.

ELISA—

Immunoplates (Maxisorb, Nunc, Rochester, N.Y.) were coated with (BF1) 8A3.31 mAb for capturing c264scTCR fusion proteins or with H57-597 mAb for capturing OT1scTCR fusion proteins. After washing, the proteins were detected using various probes as detailed in the Results section. ABTS (2,2'-azinobis[3-ethylbenzothiazoline-6-sulfonic acid]-diammonium salt) substrate was then added and absorbance was measured at 405 nm using a 96-well plate reader (Versamax, Sunnyvale, Calif.).

Flow Cytometry—

For characterization of the c264scTCR fusion protein complexes, T2 cells were pulsed with p53 (aa264-272) peptide at 37° C. for 2 h in the presence of peptide loading enhancer (PLE, Altor BioScience Corp., Miramar, Fla.). For the OT1scTCR fusion protein complexes, murine lymphoma EL4 cells were pulsed with OVA peptide at 100 µg/ml and PLE at 37° C. for 6 h. The various birA fusion proteins (complexed with SA-PE) were added and incubated at 4° C. for 1 h. The samples were washed two times and analyzed on a FACScan flow cytometer using CellQuest software (BD Biosciences, San Jose, Calif.).

To assess IL-15 domain binding activity, 32Dβ cells were incubated with 320 nM of the c264scTCR fusion protein complexes for 30 min at 4° C. The binding of the proteins was in turn detected with biotinylated (BF1) 8A3.31 mAb for 15 min and SA-PE (5 µg/ml each) for 15 min. The stained cells were analyzed by flow cytometry as described above.

Cell Proliferation Assays—

Cell proliferation was measured as previously described (25). Briefly, 32Dβ cells ($1\times10^5$ cells/well) were incubated with increasing concentrations of scTCR/hIL-15 or scTCR/hIL-15 muteins in the presence or absence of an equal molar concentration of scTCR/hIL-15RαSu for 48 h at 37° C. Cell proliferation reagent WST-1 (Roche Applied Science, Indianapolis, Ind.) was added during the last 4 h of cell growth according to the manufacturer's procedures. Conversion of WST-1 to the colored formazan dye by metabolically active cells was determined through absorbance measurements at 440 nm. The $EC_{50}$ was determined with the dose-response curve generated from the experimental data by nonlinear regression variable slope curve-fitting with Prizm4 software (GraphPad Software, La Jolla, Calif.).

Surface Plasmon Resonance—

The affinity constants of the OT1scTCR fusion proteins to their cognate pMHCI were determined using surface plasmon resonance (SPR) methodology on a BIAcore 2000 instrument (GE Healthcare, Piscataway, N.J.). Biotinylated pMHCI complexes were immobilized onto the streptavidin-coated surface of a SA5 sensor chip (GE Healthcare, Piscataway, N.J.) by injecting protein at 2 µg/ml in HBS buffer (10 mM HEPES, 150 mM NaCl, 3.4 mM EDTA, 0.005% P20 surfactant, pH 7.4) at a flow rate of 10 µl/min. This resulted in 1000-1200 RU of immobilized pMHCI complexes.

The purified OT1scTCR fusion proteins were diluted to 1 µM, 0.5 µM and 0.25 µM in HBS. Each concentration was injected once (50 µl) at a flow rate of 10 µl/min over a freshly immobilized pMHCI surface as well as over a control streptavidin surface blocked with biotin (baseline) and the binding curves were registered. The dissociation constant ($K_D$) and association ($k_{on}$) and dissociation ($k_{off}$) rates were calculated from the corrected binding curves (baseline subtracted) using the BIAevaluation 4.1.1 software (GE Healthcare Sciences, Piscataway, N.J.).

Creation of scTCR Dimers Using the hIL-15:hIL-15Rα Scaffold—

Figure 36A:
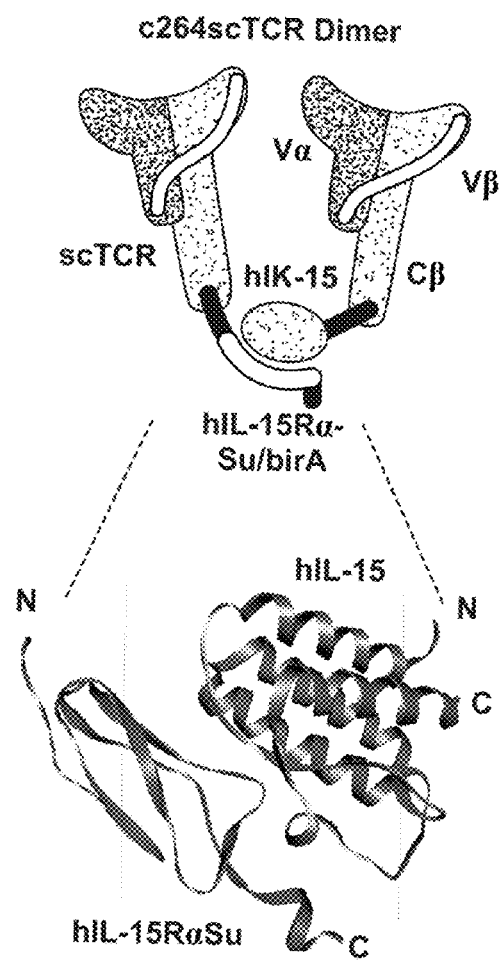
FIG. 36A shows a schematic diagram of the c264scTCR/hIL-15:c264scTCR/hIL-15RαSu/birA complex (c264scTCR dimer). The model of the dimeric hIL-15:hIL-15RαSu domains is based on the published crystal structure of the human IL-15:IL-15Rα complex (33) (PDB 2Z3Q)

We have previously shown that a biologically active, bifunctional fusion protein, designated as c264scTCR/hIL-15, could be created by fusing the N-terminus of hIL-15 to a three-domain, HLA-A*0201-restricted chimeric TCR specific for the p53 (aa264-272) peptide antigen (c264scTCR) (25) (FIG. 36A). We constructed a similar fusion protein with c264scTCR and the sushi-binding domain (aa 1-66) of human IL-15Rα(hIL-15RαSu), which has been shown to contain the structural elements responsible for hIL-15 binding. This fusion protein was genetically linked to a birA peptide tag to allow for biotinylation and subsequent multimerization in the presence of streptavidin (32). This fusion protein is designated c264scTCR/hIL-15RαSu/birA and its expression and purification from CHO cells were similar to that of c264scTCR/hIL-15 (25). These fusion proteins are readily produced at a level of mgs per liter of cell-culture supernatants (data not shown).

Based on the high specific binding activity between the hIL-15 and hIL-15RαSu domains, we anticipated that the fusion proteins could form a heterodimeric complex. In addition, examination of the crystal structure of the human IL-15:IL15Rα complex indicated that the N-termini of the two proteins are at opposite ends of the complex approximately 50 Å apart (33). Hence, fusion of the scTCR domains to these regions is not expected to block complex formation.

Initial evidence of binding between the c264scTCR/hIL-15 and c264scTCR/hIL-15RαSu/birA fusion proteins was observed in ELISAs using the plate-bound c264scTCR/hIL-15RαSu/birA to capture hIL-15 and c264scTCR/hIL-15 proteins (25). To further characterize the dimeric c264scTCR fusion protein complexes (referred to as c264scTCR dimer), equal molar amounts of purified c264scTCR/hIL-15 and c264scTCR/hIL-15RαSu/BirA fusion proteins were mixed and allowed to associate at room temperature for more than 10 min. The complexes and the individual protein fusions were evaluated by size exclusion chromatography.

Figure 36B:
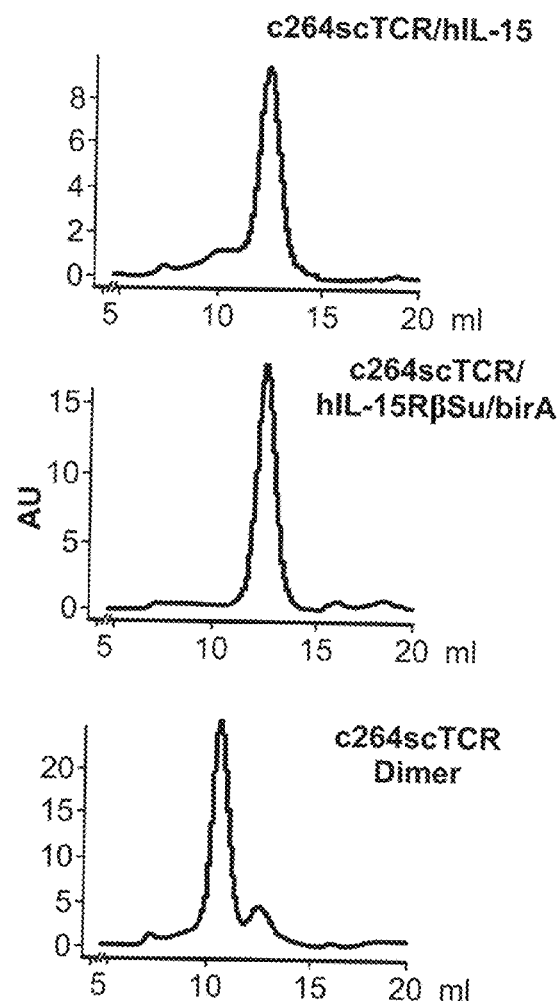
FIG. 36B shows SEC analysis of c264scTCR fusion proteins. Panels show size analysis of c264scTCR/hIL-15 (top), c264scTCR/hIL-SRαSu/birA (middle) and c264scTCR/hIL-15:c264scTCR/hIL-15RαSu/birA complex (c264scTCR dimer) (bottom) with dashed lines indicating relative protein peaks.

As shown in FIG. 36B, the major species in the purified c264scTCR/hIL-15 and c264scTCR/hIL-15RαSu/BirA fusion protein preparations displayed an SEC profile consistent with monomeric proteins (molecular weight (MW)=115 and 113 kDa, respectively) whereas the mixture of the two proteins resulted in a major peak with a molecular weight corresponding to a dimeric complex (MW>192 kDa). Thus, the appearance of the larger molecular weight species in the c264scTCR dimer preparations is evidence that the heterodimeric complex has been generated.

Figure 37B:
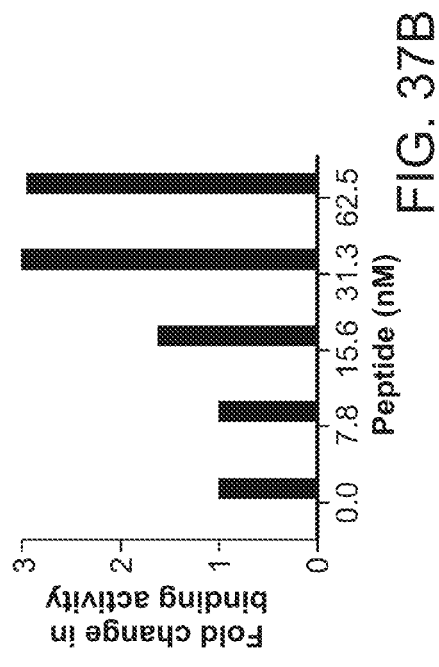
FIG. 37A-FIG. 37C show characterization of the binding activity of the c264scTCR dimer comprising the c264scTCR/hIL-15:c264scTCR/hIL-15RαSu/birA complex and c264scTCR/c149scTCR heterodimer comprising the c149scTCR/hIL-15:c264scTCR/hIL-15RαSu/birA complex. T2 cells were pulsed with 0-62.5 nM of p53 (aa264-272) peptide. The cells were stained with equivalent amounts (80 nM) of PE-conjugated multimers of the c264scTCR dimer or c264scTCR/birA (FIG. 37A). The relative increase in cell staining comparing c264scTCR dimer with c264scTCR/birA reagents was determined at different peptide concentrations (FIG. 37B). Fold increase=(Geo mean of T2 cells stained by c264scTCR dimer)/(Geo Mean of T2 cells stained by c264scTCR/birA). The p53 peptide/HLA-A*0201 binding activity of c264scTCR/c149scTCR heterodimer was determined by ELISA (FIG. 37C). Anti-hIL-15 monoclonal antibody (R&D System) was used as a capturing antibody. A2/p53.264-272.HRP or A2/p53.149-157.HRP tetramers were used as the probes. The data represent the means±SD of triplicate determinations.
Figure 37C:
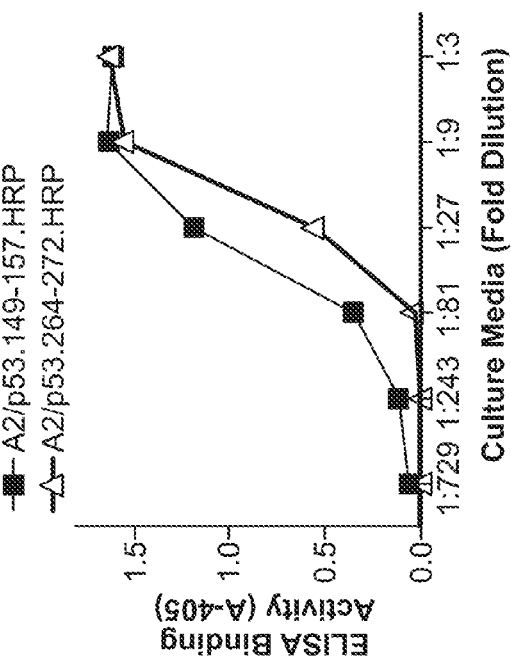
Figure 37A:
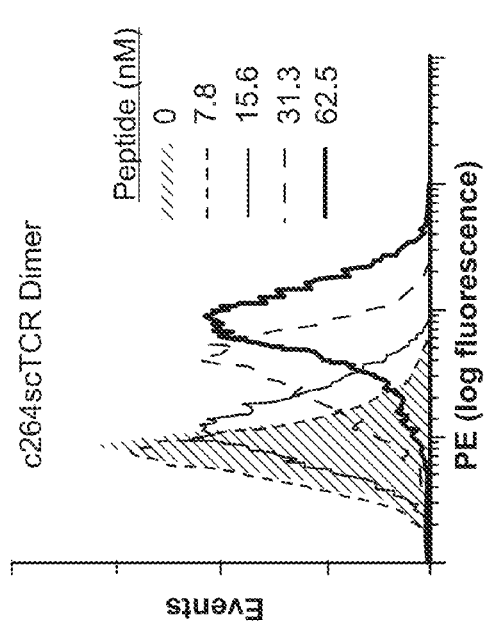

The c264scTCR dimer was compared with monomeric c264scTCR/BirA protein for their ability to bind the TCR-specific antigen, p53 (aa264-272)/HLA-A*0201. In each case, the proteins were biotinylated with biotin ligase followed by complexing with SA-PE (32) to generate multimeric flow cytometry staining reagents as previously described (32). When used to stain HLA-A*0201-positive T2 cells pulsed with varying concentrations of p53 (aa264-272) peptide, both reagents exhibited antigen-specific binding that increased in a peptide-concentration dependent manner (FIG. 37A). However, the staining reagents comprising the c264scTCR dimer stained up to three times better than the monomer-derived c264scTCR/birA counterparts (FIG. 37B). Without being bound by mechanism, these data suggest that dimerization through IL-15:IL-15Rα interaction preserves the functional activity of the scTCRs and increases the effective affinity of scTCR fusion complex to its cognate HLA/peptide through increased avidity. Similar results were observed when biotinylation via the birA tag was directed to the C-terminus of the scTCR/hIL-15 of the complex (data not shown). This demonstrates that the C termini of the complex are accessible to conjugation to molecular probes of significant size (MW of streptavidin is approximately 60 kDa) without interfering with either the dimerization or antigen binding domains of the fusion protein complex.

These studies were extended to examine the possibility of generating bispecific molecules. A second scTCR (c149scTCR) was created which recognizes an HLA-A*0201 restricted epitope of the human p53 protein spanning the amino acid residues of 149 to 157 (24). This scTCR was fused to hIL-15 and the resulting protein, designated c149scTCR/hIL-15, was co-expressed in CHO cells with the c264scTCR/hIL-15αSu/birA fusion. The fusion complex observed in the supernatant of the recombinant CHO cell culture was immobilized using an anti-IL-15 antibody and probed either by HRP-labeled p53 (aa264-272) or p53 (aa149-157) peptide/HLA-A*0201 tetramers. As shown in FIG. 37C, the anti-IL-15 antibody captured fusion protein complex was able to bind both of the peptide-loaded HLA tetramers. The result demonstrates that the individual scTCR molecules retain functional activity when fused to the hIL-15:hIL-15RαSu scaffold and the spatial arrangement of hIL-15:hIL-15RαSu complex does not significantly interfere with the packing of the scTCR domains which have an individual molecular weight of approximately 40 kDa.

Figure 42:
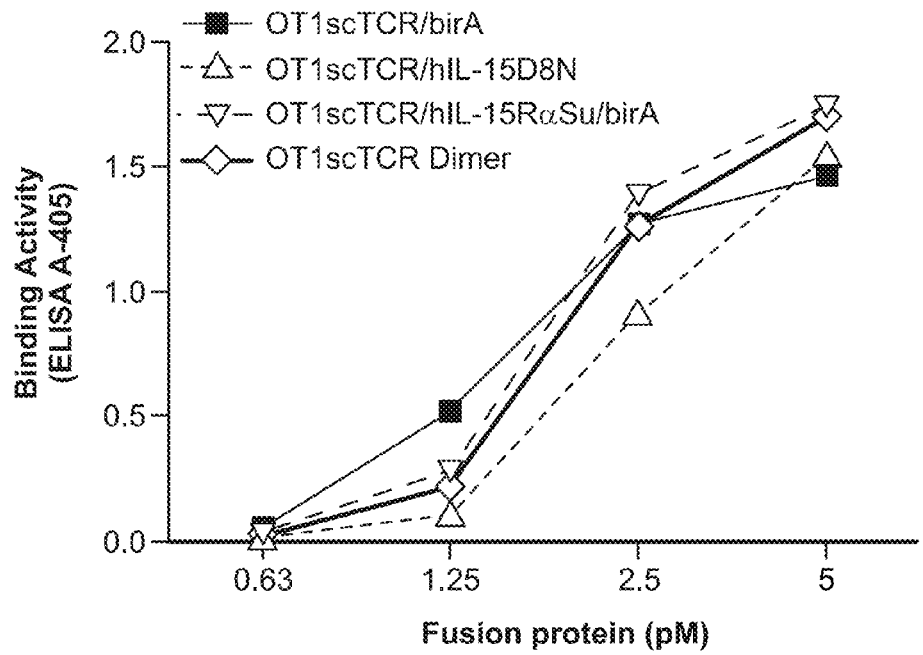
FIG. 42 shows OVA (aa257-264)/H-2K$^b$ binding activity of OT1scTCR/hIL-15D8N, OT1scTCR/hIL-15RαSu/birA and OT1scTCR dimer were determined by ELISA. Anti-mTCR H57-597 mAb was used as capturing antibody. Kb/OVA.257-264.HRP tetramer was used as a probe. The data represent the means±SD of triplicate determinations.

To demonstrate the broad utility of the hIL-15:hIL-15RαSu scaffold for protein dimerization, we created a second dimeric scTCR fusion complex by pairing two single-chain OT1 TCRs, one fused to the N-terminus of hIL-15 and another to the N-terminus of hIL-15RαSu/birA protein. OT1 is a well-characterized TCR recognizing an epitope of OVA protein spanning the amino acid residues 257 to 264 in the context of murine H-2Kb (34). OT1 single-chain TCR (OT1scTCR) gene was generated and fused to the hIL-15 and OT1scTCR/hIL-15RαSu/birA constructs for recombinant CHO cell expression. The affinity purified OT1scTCR fusion proteins were found to have pMHCI binding activity in ELISA using anti-mouse TCR Cβ H57 antibody as a capture reagent and HRP-labeled, OVA (aa257-264) peptide-loaded H-2Kb tetramer (FIG. 42). To distinguish the difference in binding activity between the OT1scTCR dimer and OT1scTCR/birA monomer, we conducted flow cytometry analysis similar to those described above for the c264scTCR dimers but with H-2Kb-positive EL4 cells loaded with OVA (aa257-264) peptide.

Figure 38:
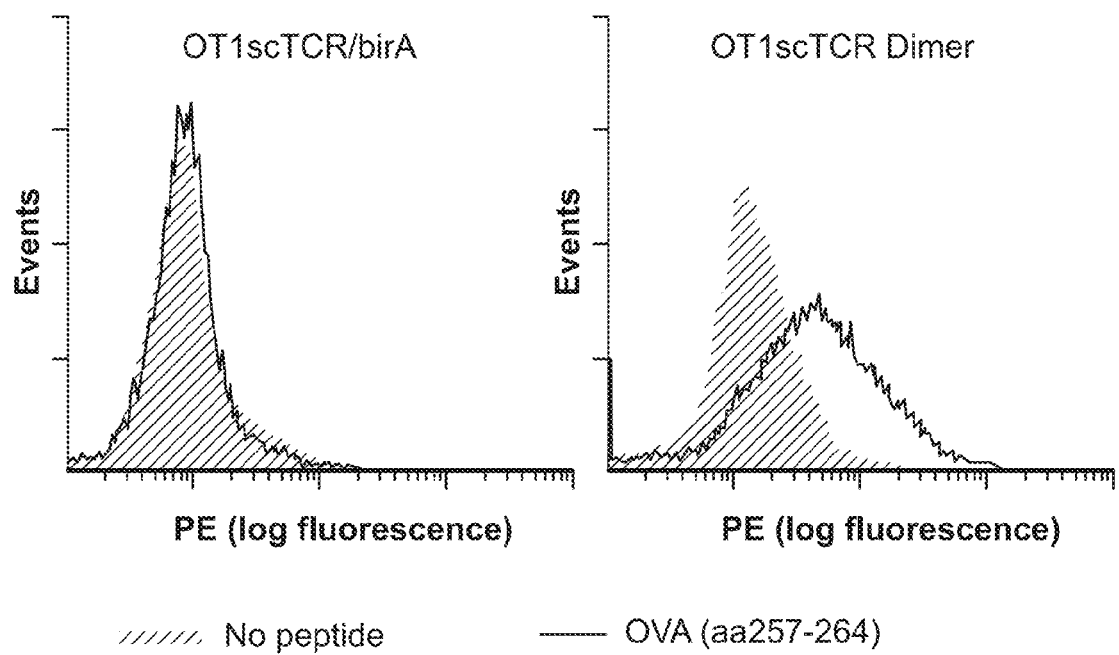
FIG. 38 shows the characterization of the binding activity of the OT1scTCR dimer comprising the OT1scTCR/hIL-15:OT1scTCR/hIL-15RαSu/birA complex. EL4 cells were loaded with OVA (aa257-264) peptide and stained with OT1scTCR/birA-SA-PE (top) and OT1scTCR dimer-SA-PE (bottom) at 200 nM.

As shown in FIG. 38, SA-PE tetramers comprising the OT1scTCR dimer indeed stained significantly better than those comprising monomeric OT1scTCR/birA fusions. We also performed surface plasmon resonance assays to assess the binding affinity of the OT1scTCR monomer and dimer against the biotinylated OVA (aa257-264) peptide-loaded H2-Kb/birA complexes immobilized on a streptavidin sensor chip. The apparent binding affinity (KD) of the OT1scTCR dimer to OVA peptide/H-2Kb complexes was estimated to be about 30 μM, whereas no binding was observed for the monomeric OT1scTCR/birA fusion protein (Table 1). These data confirm that dimerization through hIL-15:hIL-15Rαinteraction preserves the biological activity of the scTCRs and increases the effective affinity of the scTCR molecule to its cognate pMHCI complexes through increased avidity.

Creation of an OT1scTCR/scCD8 Heterodimer—

Since the CD8 molecule has been previously demonstrated to play a pivotal role in the interaction between OT1 TCR and its cognate OVA peptide/H2-Kb complex (35-37), the hIL-15:hIL-15RαSu scaffold provides an opportunity to assess whether CD8 molecule enhances OT1 TCR binding affinity to OVA peptide/H-2Kb expressed on the cell surface and under cell-free and adhesion molecule-free conditions. To achieve this, we first created a murine CD8 molecule in single-chain format (scCD8) by fusing the extracellular domains of the α and β chains of the murine CD8 using a flexible linker. This fusion gene was fused to the hIL-15RαSu/birA construct in a retroviral expression vector. Recombinant retrovirus was then used to infect a CHO cell line expressing the OT1scTCR/hIL-15 fusion protein. The heterodimeric fusion protein complex was purified from the supernatant of the cultured recombinant CHO cells using the anti-TCR antibody-based affinity chromatography as described above. This purified protein was subjected to ELISA using anti-TCR antibody as the capture reagent and either the biotinylated anti-mCD8α or anti-mCD8β3 mAbs as probes.

As shown in FIG. 39A, the anti-TCR Ab-immobilized fusion complex contains both the CD8α and CD8β and, thus, indicates formation of an OT1scTCR/scCD8 heterodimer. We used flow cytometry analysis to compare the binding activity of the OT1scTCR/scCD8 heterodimer with the OT1scTCR dimer to varying amounts of OVA peptide/H-2Kb complexes displayed on the cell surface. As shown in FIG. 39B, SA-PE staining reagents comprising the OT1scTCR/scCD8 heterodimer could readily detect OVA peptide/H-2Kb complexes on EL4 cells loaded with as little as 10 ng/ml OVA peptide, whereas little or no staining was observed at this peptide concentration when comparable reagents comprising the OT1scTCR dimer were used. Higher background OT1scTCR/scCD8 heterodimer staining was observed on EL4 cells that were not pulsed with peptide, suggesting peptide-independent interactions were occurring between the CD8 domain and MHC molecules on the cell surface. Similar effects have been reported for pMHCI tetramers binding to CD8 molecules expressed on T cells (38).

Figure 43:
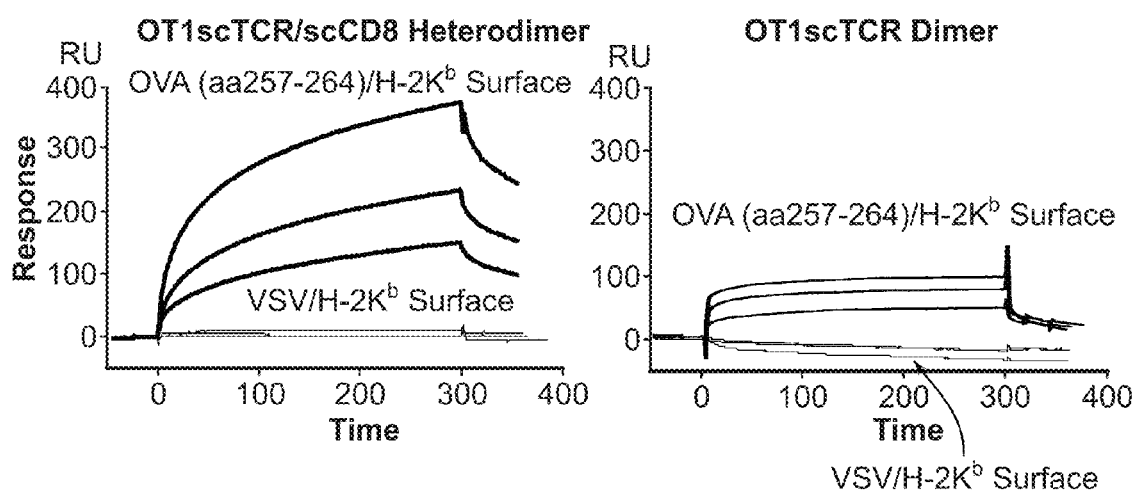
FIG. 43 shows OT1scTCR fusion protein binding curves to OVA (aa257-264)/H-2K$^b$ and control VSV/H-2K$^b$ complexes determined by SPR.

The results for peptide-specific interactions of the OT1scTCR/scCD8 heterodimer were further confirmed by surface plasmon resonance analysis. The binding affinity (KD) of the OT1scTCR/scCD8 heterodimer to OVA peptide/H-2Kb complexes was estimated to be 2.6 μM, which is significantly higher than the ~30 μM observed for the OT1scTCR dimer (Table 1, FIG. 43). Neither fusion protein showed any binding to control VSV peptide/H-2Kb complexes.

The difference in specific pMHCI binding activity is surprising given that the bivalent nature of the OT1scTCR dimer is expected to provide increased functional affinity in this assay format. Additionally, similar SPR binding studies conducted with soluble TCR, CD8 α/β and pMHCI proteins as independent components showed only weak interactions (KD 30-100 μM) between CD8 protein and peptide/H-2Kb complexes and no apparent cooperative effects of CD8 on TCR:peptide/H-2Kb interactions (39-41). Taken together, these data indicate that the addition of the CD8 α/β domain to the OT1scTCR fusion has a greater impact on pMHCI binding than creation of the bivalent OT1scTCR molecule. Our results further demonstrate that the hIL-15:hIL-15RαSu scaffold could be used to create functional bi-specific molecules with the flexibility to accommodate complex protein-protein interactions. In addition, we show for the first time that a functional CD8 molecule can be constructed as a soluble single-chain molecule and demonstrate that the scCD8 domain when complexed with OT1scTCR in a heterodimeric molecule enhances TCR:pMHCI interactions in cell-free conditions without the presence of other adhesion molecules.

Creation of Functional TCR α/β Heterodimers—

As indicated above, the N-termini of the hIL-15 and hIL-15Rα domains are at distal ends of the complex raising questions as to whether this scaffold is suitable for fusions to polypeptides of a multi-chain protein. To determine whether a soluble, biologically active, heterodimeric TCR α/β could be constructed using the hIL-15 and hIL-15RαSu scaffold, the C-terminal ends of the extracellular OT1 TCR Vα-Cα and Vβ-Cβ domains were linked to the N-termini of hIL-15 and hIL-15RαSu/birA chains, respectively. Based on the published α/β TCR crystal structures, the TCR Ca and Cβ C-terminal amino acids of the properly folded OT1 TCR α/β molecule are expected to be ~18 Å apart (42). The OT1 TCRα/hIL-15 and OT1 TCRβ/hIL-15RαSu/birA fusion genes were cloned into two separate expression vectors and co-transfected into CHO cells. The secreted fusion protein complex was purified using anti-TCR Cβ mAb affinity chromatography as described above. When analyzed by Coomassie-stained SDS-PAGE under reducing condition, the purified protein bands migrated at 50 kDa, consistent with the calculated monomeric MW (40 kDa) of each of the two fusion molecules (data not shown).

The purified protein was further characterized in the functional ELISA (anti-TCR Cβ mAb capture: OVA peptide/H2-Kb tetramer probe). As shown in FIG. 40A, the purified protein was found to have equivalent pMHCI binding activity as OT1 TCR in the single-chain format. Similar results were observed for hIL-15:hIL-15RαSu/birA fusions to the Vα-Cα and Vβ-Cβ chains of the p53-specific 264 TCR (FIG. 40B). Previous attempts to produce soluble α/β TCR heterodimers in mammalian cells have been largely unsuccessful (43,44). Thus, our results suggest that the TCR α and β chains were appropriately folded through the association of the hIL-15 and hIL-15RαSu/birA domains within the transfected cells. Intriguingly, the fusion to N-termini of the hIL-15:hIL-15RαSu scaffold is able to provide the spatial arrangement sufficient for functionally independent binding domains as observed with the c264scTCR/c149scTCR heterodimeric complex while retaining flexibility to permit folding of closely paired chains such as the α and β chains of OT1 TCR and 264 TCR.

Biological Activity of the hIL-15 Domain for the hIL-15:hIL-15RαSu Fusion Complexes—

The IL-15 receptor (IL-15RβγC) binding capability of the hIL-15:hIL-15Rα domain of the c264scTCR dimer was evaluated by flow cytometry analysis using 32Dβ cells which carries the hIL-15Rβ and the murine γC (mγC) chains. These studies were carried out using c264scTCR dimers containing the wild-type hIL-15 domain, as well as dimers with hIL-15 mutein domains previously shown to enhance (N72D) or reduce (D8N) binding to the hIL-15Rβ chain (25). Additionally we have demonstrated that these mutations do not affect formation of the hIL-15:hIL-15RαSu complex (25). Following incubation with the c264scTCR dimers, the 32Dβ cells were stained with anti-TCR mAb to detect cell-bound fusion protein dimers. As shown in FIG. 41A, the 32Dβ cells were stained positively by the c264scTCR dimers containing hIL-15 wild-type or hIL-15N72D domains but not with those containing the hIL-15D8N domain, indicating that the IL-15:hIL-15RαSu portion of the complex retains the expected IL-15RβγC binding activity.

The hIL-15 biological activity of the fusion protein dimers were also examined in cell proliferation assays using 32Dβ cells. As shown in FIG. 42B, the hIL-15 wild-type domain in the monomeric (scTCR/hIL-15 fusions) or dimeric (scTCR/hIL-15:scTCR/hIL-15RαSu) fusion formats were able to support the growth of 32Dβ cells in a concentration-dependent manner, exhibiting half-maximal stimulation ($EC_{50}$) at ~300 pM. The hIL-15N72D or D8N domains either increased or eliminated the biological activity of the fusion proteins, respectively, regardless whether they were present in the monomeric or dimeric fusions. These results are consistent with the functional activity observed for non-fusion IL-15 cytokine carrying the N72D or D8N mutations (25). Thus, formation of the fusion protein complex containing two independent TCR domains does not significantly change the biological activity of the IL-15 domain. In contrast, there was at least a 3 fold loss of IL-15 activity for the OT1 TCRα/β heterodimer complex (data not shown), suggesting formation of the heterodimeric TCR structure inhibits, to some extent, the ability of the hIL-15 domain to interact with hIL-15Rβ-mγC. Additionally, these results indicate that the hIL-15 domain can be readily manipulated to allow enhanced or reduced receptor binding and functional activity, thus providing additional flexibility for the use of the hIL-15:hIL-15RαSu scaffold in different applications.

Example 16

Toxicity Profile and Anti-Tumor Activity of T2 Molecules in Immunocompetent Mice To determine the further in vivo effects of the of the T2 molecules, T2M lacking the IgG1 CH1 domain (T2MΔCH1) and the non-targeted T2MΔTCRΔCH1 (Alt-803) protein complexes, we examined toxicity and antitumor activity in tumor-bearing immunocompetent C57BL mice. B16 ($5 \times 10^5$/mouse) or EG7 ($1 \times 10^6$/mouse) murine tumor cells were injected subcutaneously into C57BL/6NHsd mice on study day 0. Tumor-bearing mice were injected intravenously of study days 1, 4, 8 and 11 with 51 or 25.5 μg/dose T2 protein (composed of c264scTCR/huIL15N72D and c264scTCR/huIL15RαSushi/huIgG1 chains), 47.7 μg/dose T2MΔCH1 (composed of c264scTCR/huIL15N72D and c264scTCR/huIL15RαSushi/huIgG1 CH2-CH3 chains) (molar equivalent to 51 μg/dose T2 protein), 16.6 or 8.3 μg/dose T2MΔTCRΔCH1 (Alt-803) (composed of huIL15N72D and huIL15RαSushi/huIgG1 CH2-CH3 chains) (molar equivalent to 51 and 25.5m/dose T2 protein, respectively), or 1.2 μg/dose rhIL-15 (molar equivalent to 25.5m/dose T2 protein). During the study, animal weights and tumor volumes were measured and the results were plotted (FIGS. 44A-B and 45A-B).

Figure 44A:
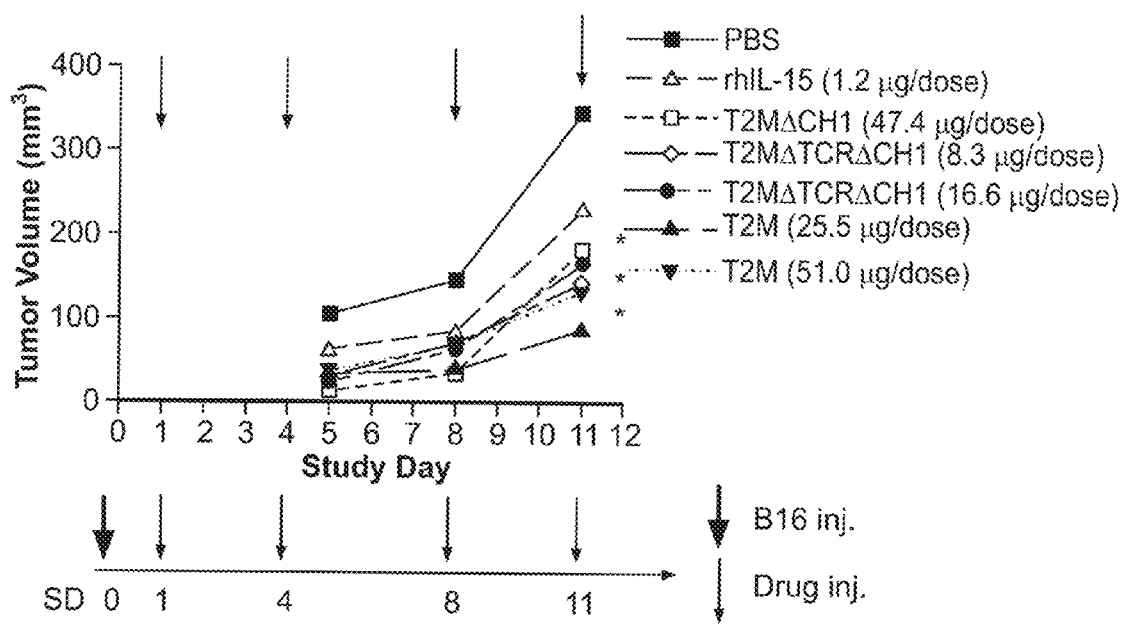
FIG. 44A and FIG. 44B shows results from a primary tumor growth model using murine B16 melanoma tumor cell line in immunocompetent mice. Tumor-bearing mice were injected intravenously with rhIL-15, T2M, T2MΔCH1 and T2MΔTCRΔCH1 (Alt-803) proteins or PBS (control). Tumor growth was measured and data are shown in FIG. 44A. Post treatment changes in animal body weight are shown in FIG. 44B. These results shown that Alt-803 is effective for treating melanoma.
Figure 44B:
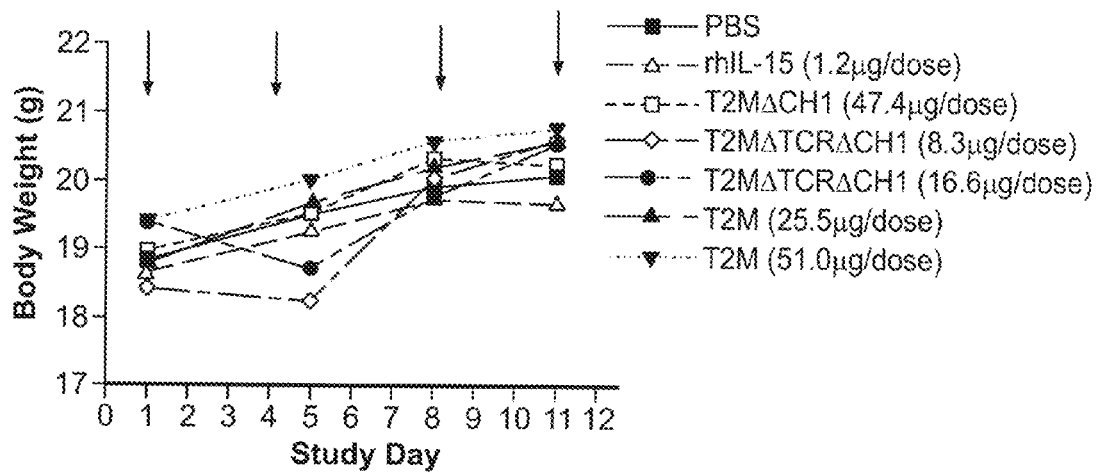
Figure 45A:
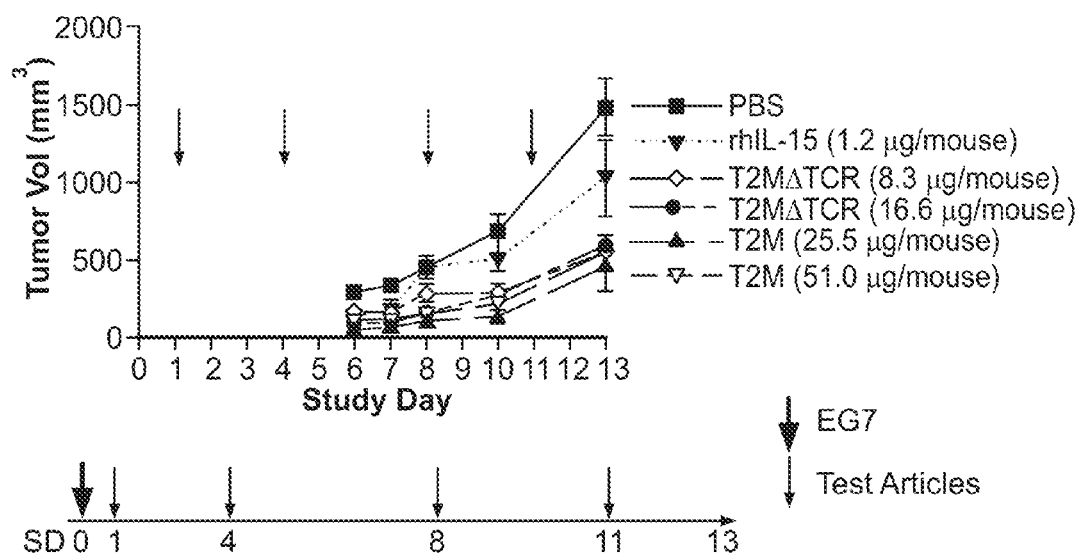
FIG. 45A and FIG. 45B show results from a primary tumor growth model using a murine EG7 thymoma/lymphoma tumor cell line in immunocompetent mice. Tumor-bearing mice were injected intravenously with rhIL-15, T2M and T2MΔTCRΔCH1 (Alt-803) proteins or PBS (control). Tumor growth was measured and data are shown in FIG. 45A. Post treatment changes in animal body weight are shown in FIG. 45B. These data demonstrate that Alt-803 is effective against thymoma/lymphoma.
Figure 45B:
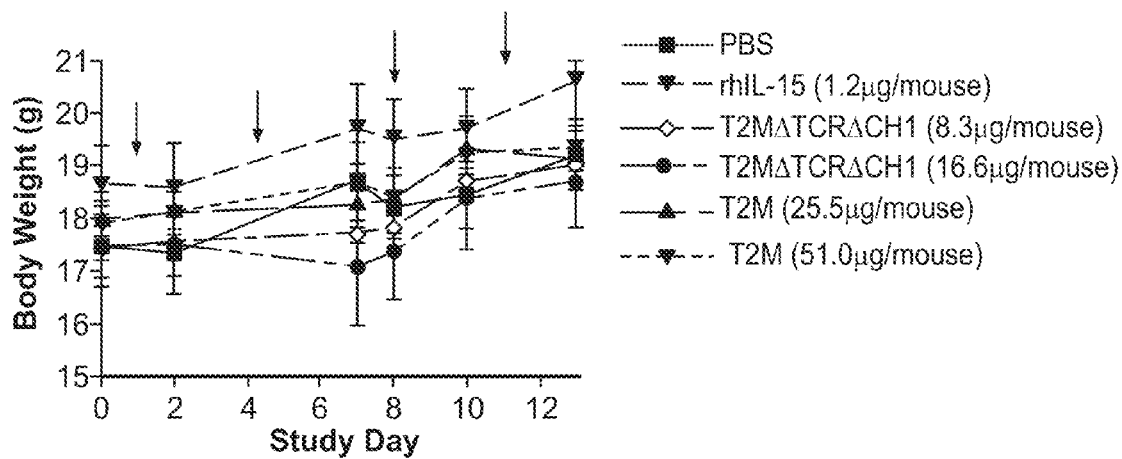

Treatment with the T2M, T2MΔCH1 and T2MΔTCRΔCH1 (Alt-803) proteins significantly inhibited B16 (FIG. 44A) and EG7 (FIG. 45A) tumor growth compared to that observed following PBS treatment and each of the fusion protein complexes was more efficacious than rhIL-15 administered at an equivalent molar level. Additionally, there was little of no toxicological effect of T2M, T2MΔCH1 and T2MΔTCRΔCH1 treatment as measured by changes in body weight of the tumor-bearing mice (FIGS. 44B and 45B). Without being bound by mechanism, these data are consistent with the in vivo immunostimulatory activity of these molecules in immunocompetent animals (Example 13).

Example 17

Further Characterization of the Immunostimulatory and Anti-Tumor Activity of T2M and Derivatives Thereof To further characterize similar targeted IL-15:IL-15Rα-Fc complexes, recombinant CHO cell lines were generated that co-express the c264scTCR/huIL-15 and c264scTCR/huIL15Rα/IgG1 Fc fusion proteins. In one case the human IgG1 domain contained the entire heavy chain constant (CH1-CH2-CH3) and in a second case the CH2-CH3 domain (i.e. ΔCH1) or Fc domain was used, as indicated above. The protein sequence of the human IgG1 CH2-CH3 domain or Fc domain is shown in FIG. 46. For simplicity, in this example, the resulting c264scTCR/huIL15N72D superagonist:c264scTCR/huIL15Rα/IgG1 CH1-CH2-CH3 complex is referred to as T2 molecules (T2M) and the c264scTCR/huIL15N72D superagonist:c264scTCR/huIL15Rα/IgG1 CH2-CH3 complex as T2M2 (also above as T2MΔCH1). The advantage of these complexes is that dimerization through the Fc domains and interactions between IL-15 and IL-15Rα domains yield tetrameric targeting molecules capable of binding to IL-15Rβγ-positive cells and Fc receptor (FcR)-positive cells. Additionally the activity of each of these domains can be analyzed by mutants that reduce interactions with the cognate receptors. Following soluble expression by recombinant CHO cells, these complexes were purified to homogeneity by affinity chromatography using anti-TCR Cβ mAb-Sepharose and Protein A Sepharose. Size exclusion chromatography indicated that the molecules migrated at the size expected for intact complexes.

Figure 47:
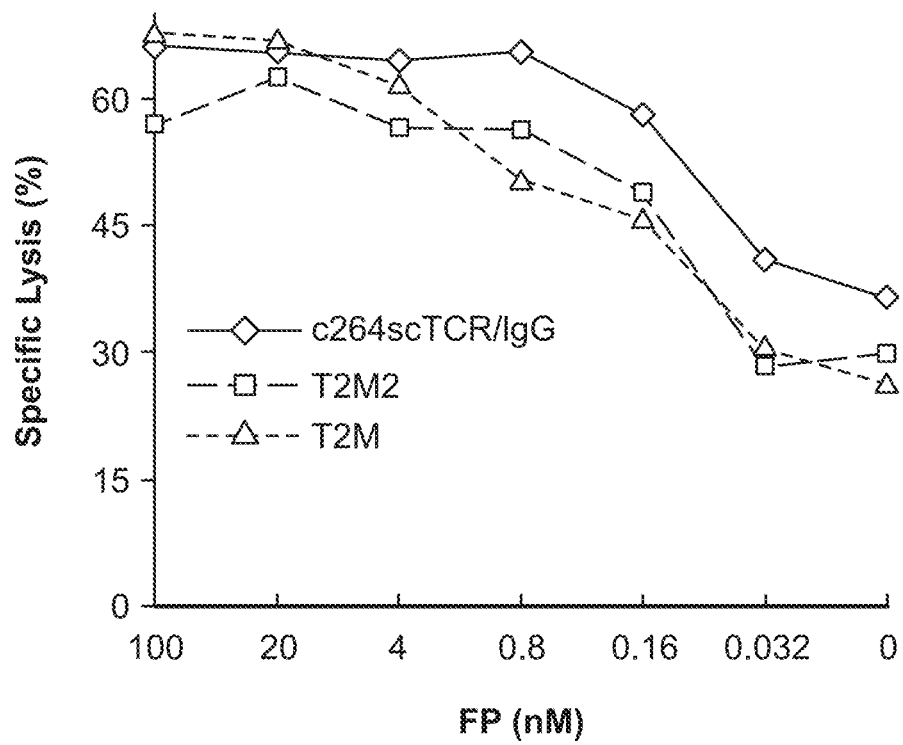
FIG. 47 shows results of an assay to determine the antibody dependent cellular cytotoxicity activity mediated by T2M and scTCR-huIgG1 proteins against cells expressing peptide MHC targets. Various amounts of fusion protein (T2M, T2M2 or c264scTCR-Ig) were mixed with fresh human PBMCs and p53 peptide-pulsed HLA-A2-positive T2 cells (Calcein labeled) (E:T ratio, 40:1). After 2 hr incubation, the culture medium was collected and analyzed quantitatively for Calcein released from lysed cells.
Figure 48A:
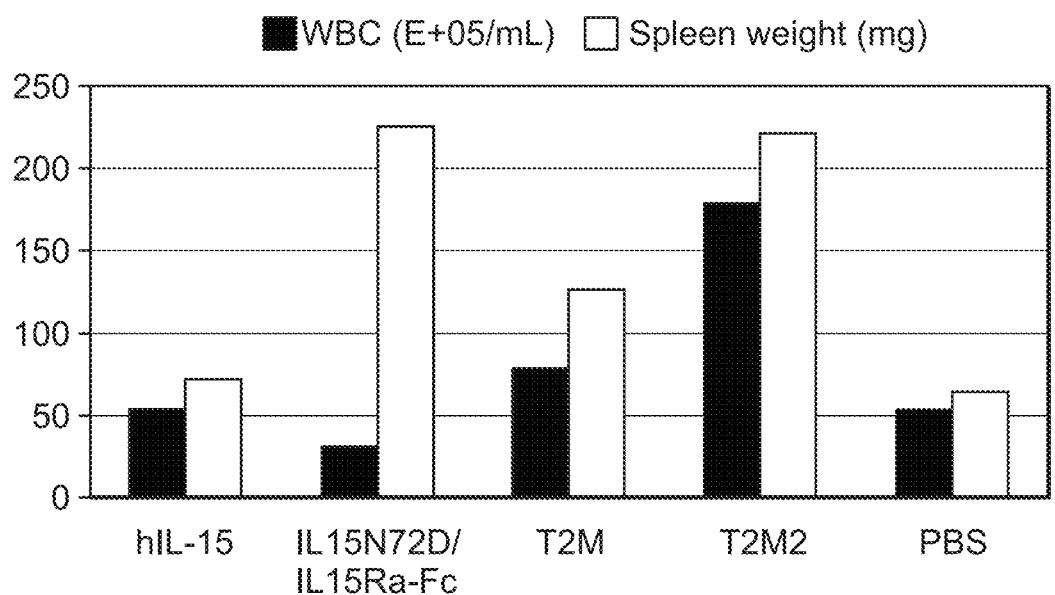
FIG. 48A-FIG. 48C shows results from in vivo assays to determine the immunostimulatory activity of various T2 molecules in mice. C57BL/6 mice were treated i.v. with equivalent molar IL-15 doses of hIL-15 (1 mg/kg), IL15N72D:IL15Rα-Fc (3.6 mg/kg), T2M (11 mg/kg), T2M2 (10 mg/kg) or an equivalent volume of PBS on study day 1. On study day 4, the mice were sacrificed and blood WBC counts and spleen weights were determined as shown in FIG. 48A. Changes in the percentage of peripheral blood mononuclear cells (PBMC) CD8+ and NKp46+ cells were assessed flow cytometry as shown in FIG. 48B. PBMCs were also used to assess NK cell activity based on lysis of NK-sensitive Yac-1 target cells in a calcein release assay as shown in FIG. 48C.
Figure 48B:
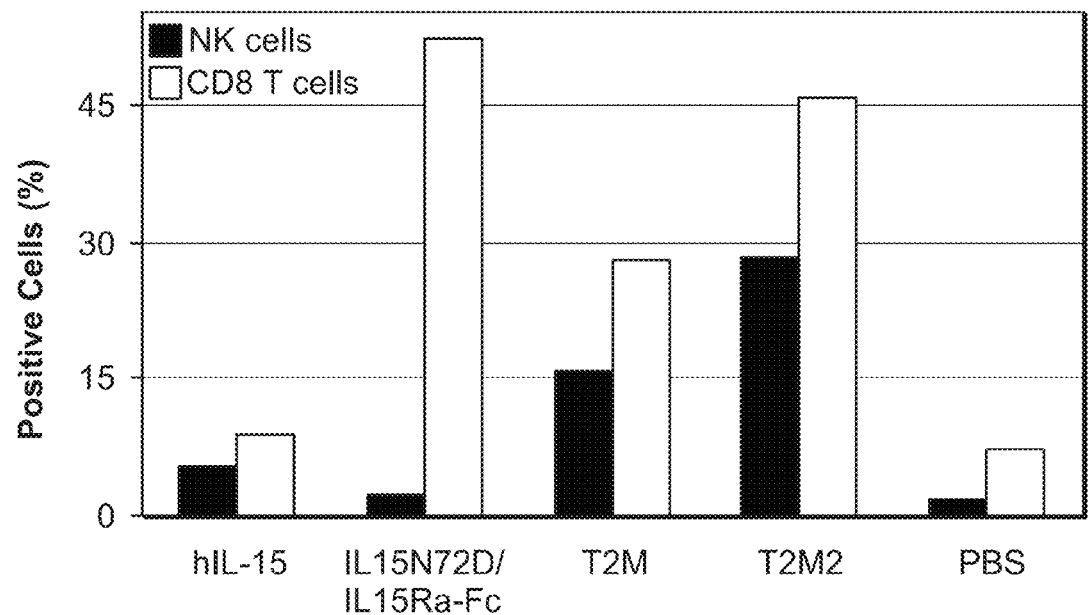
Figure 48C:
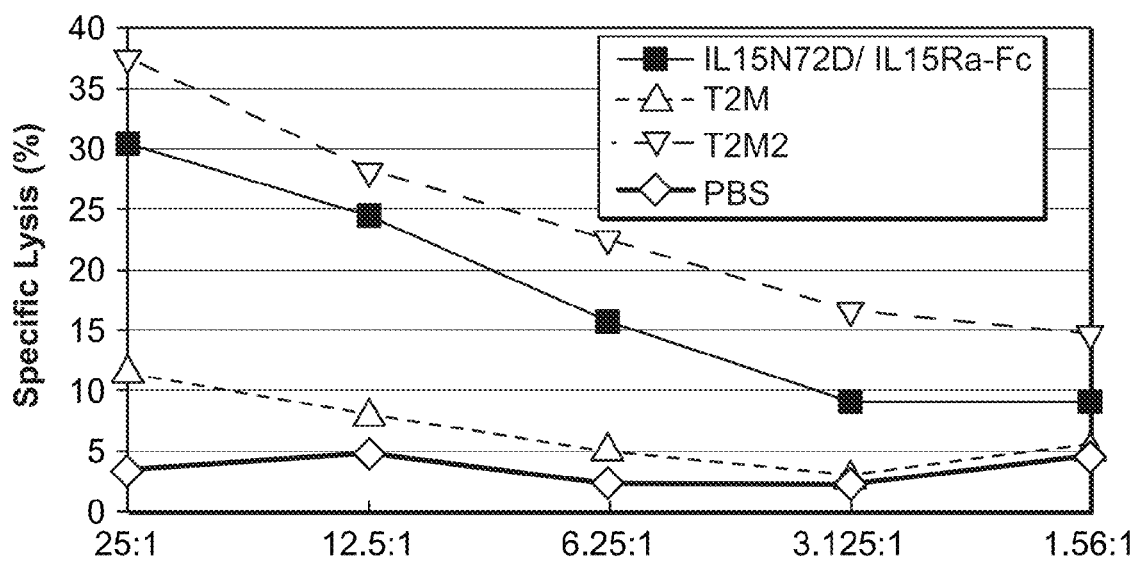
Figure 49A:
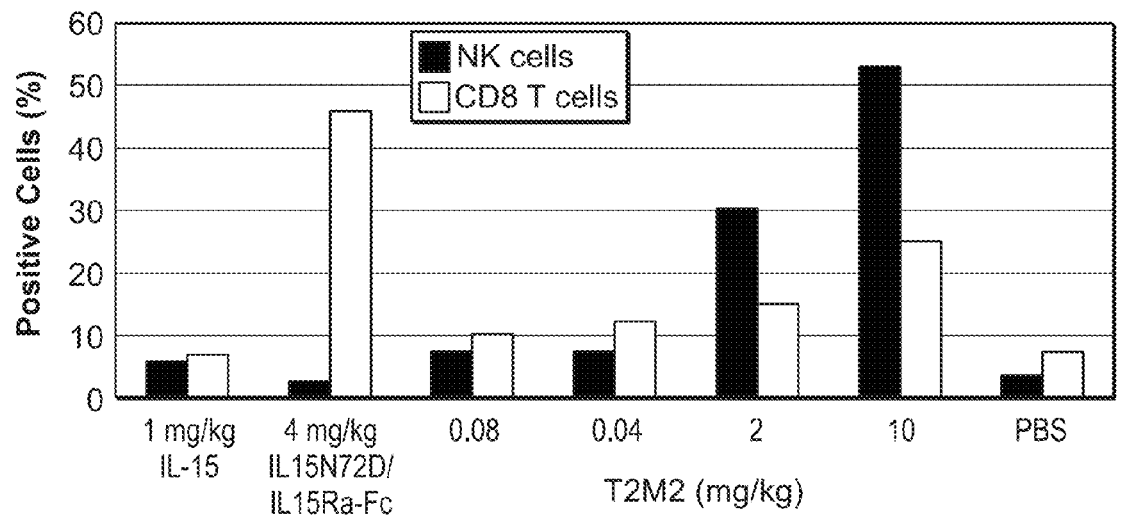
FIG. 49A-FIG. 49B shows results from in vivo assays to determine the dose and temporal responses of various T2 molecules on immune activity in mice. C57BL/6 mice were treated i.v. with equivalent molar IL-15 doses of hIL-15 (1 mg/kg), IL15N72D:IL15Rα-Fc (4 mg/kg), T2M2 (various doses) or an equivalent volume of PBS on study day 1. On study day 4, the percentage of PBMC CD8+ and NKp46+ cells were assessed by flow cytometry (FIG. 49A). Nude mice were treated i.v. with IL15N72D/IL15Rα-Fc (0.2 mg/kg) or T2M2 (2 mg/kg) of study day 1. On day 4 and 7 post treatment, the percentage of PBMC NKp46+ cells was assessed by flow cytometry (FIG. 49B).
Figure 49B:
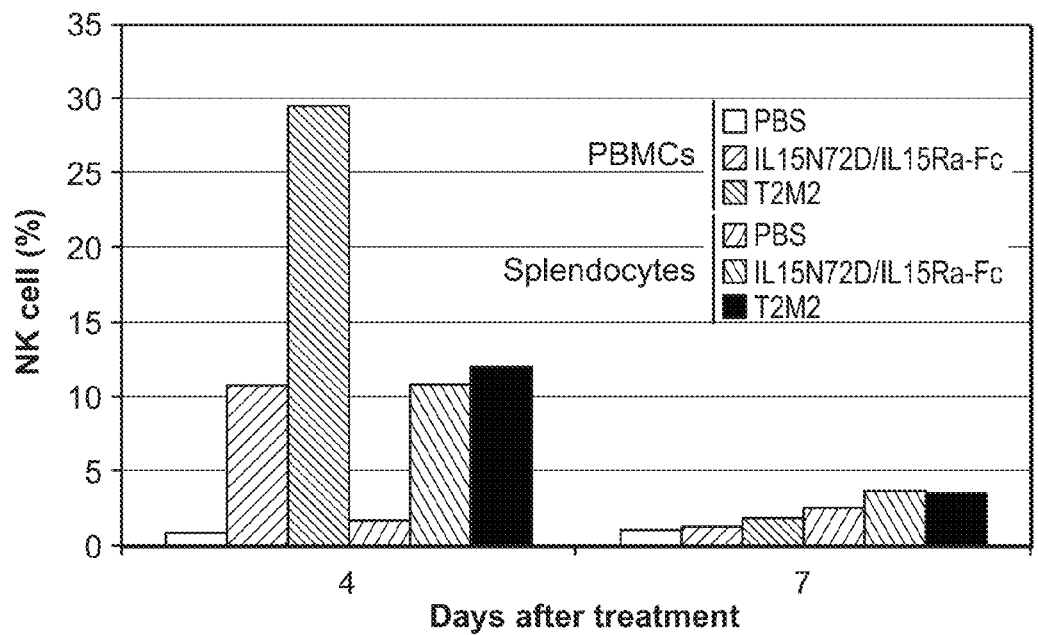

Similar to analysis described above, the ELISA-based methods have confirmed that the scTCR and IL-15 domains of T2M and T2M2 retain their respective binding activities. Additionally, the IgG1 domain of T2M and T2M2 retains the ability to bind Fc receptor (FcR) bearing cells, allowing specific detection with peptide/HLA tetramers with comparable activity to that of scTCR-IgG1 fusions. T2M and T2M2 were capable of mediating ADCC activity of human lymphocytes against target cells displaying the p53 (aa264-272)/HLA-A2 complex (FIG. 47). These results verify that T2M and T2M2 retain the antibody-like effector functions previously described for the scTCR-IgG fusions. Studies with complexes containing Fc mutations (LALA) that reduce FcR binding activity demonstrated that a functional Fc domain was required for ADCC activity. T2M and T2M2 also supported growth of the IL-15 dependent 32Dβ cell line, though T2M2 showed about ~3 fold less in vitro IL-15 activity than T2M. The ability of these molecules to stimulate immune responses in mice was also assessed. Treatment of C57BL/6 mice with IL-15 (1 mg/kg) had little or no effect on white blood cell (WBC) counts, spleen weight or the NK and CD8+ T cell populations in the blood whereas treatment with the IL-15N72D:IL-15Rα-IgG CH2-CH3 complex (Alt-803) (at a molar equivalent IL-15 dose) resulted in splenomegaly and elevated blood CD8+ T cell levels (FIGS. 48A & B), consistent with the results observed previously for similar IL-15:IL-15Rα-Fc complexes. Both the T2M and T2M2 complexes stimulated an increase in WBC levels, spleen weight and blood NK and CD8+ T cell populations, with the T2M2 complex showing the more potent immunostimulatory effect at an equivalent molar dose (despite exhibiting lower IL-15 activity on 32Dβ cells). Similar treatment dependent effects on NK and CD8+ T cell populations were observed in the spleen. Splenocytes isolated from T2M2 and IL-15N72D/IL-15Rα-IgG complex (Alt-803) treated mice showed cytolytic activity against NK-sensitive YAC cells (FIG. 48C). Dose response studies indicate that these effects are observed with a single dose level as low as 0.4 mg/kg (FIG. 49A). Treatment of nude mice with T2M2 and IL-15N72D/IL-15Rα-IgG show an increase in the percentage of NK cells in the blood and spleen 4 days post treatment that decreases to near baseline levels 7 days post treatment (FIG. 49B). Taken together, these results indicate that the T2M2 complex was capable stimulating CD8+ T cell and NK cell responses in mice with significantly higher activity than that of IL-15 and for NK cells than that of the IL-15N72D/IL-15Rα-IgG complex (Alt-803).

Figure 50A:
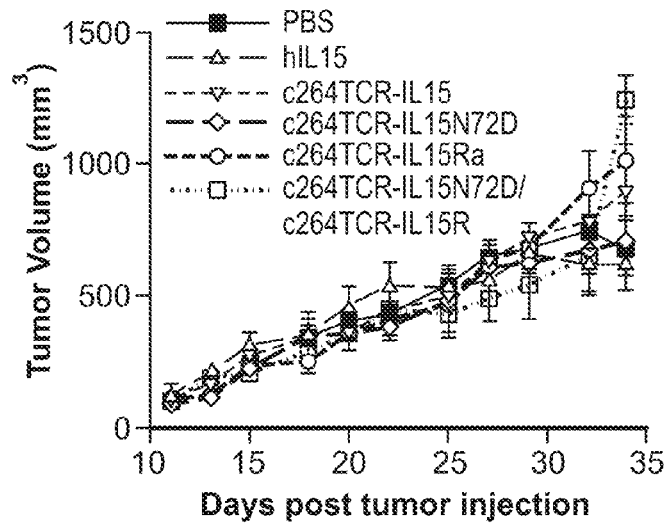
FIG. 50A-FIG. 50C shows results from a primary tumor growth model using a human p53+HLA-A2+A375 melanoma cell line in nude mice. A375 human melanoma tumor cells ($1 \times 10^6$) were injected s.c. into nude mice (5-6/group). Tumors were allowed to establish and mice were treated i.v. with equivalent molar doses of IL-15 (0.35 mg/kg), scTCR-IL15 fusions (1.6 mg/kg), scTCR-IL15/scTCR-IL15Rα complex (3.2 mg/kg), or PBS. The mice were treated three times a week for three weeks starting on study day 11 (FIG. 50A). A375-tumor bearing nude mice were also treated i.v. with 4 mg/kg T2M as in FIG. 50A (FIG. 50B). A375 tumor bearing nude mice were i.v. with equivalent molar doses of IL-15 (0.2 mg/kg), T2M2 (2 mg/kg) or PBS (FIG. 50C). Tumors were measured every other day and tumor volumes (mean±SEM) were plotted.
Figure 50B:
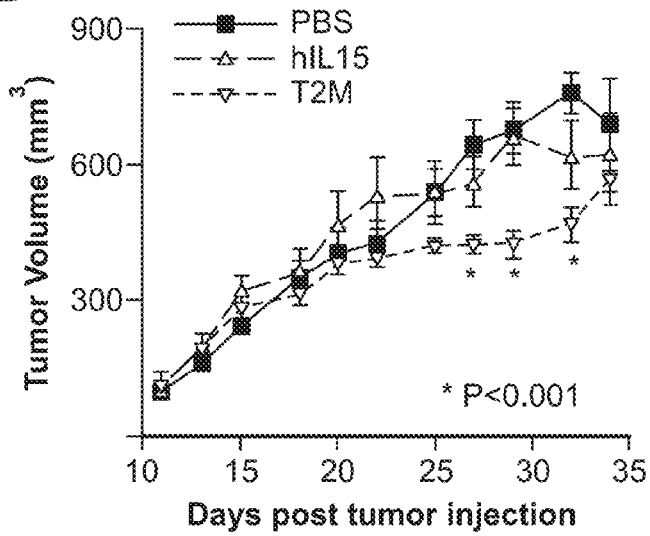
Figure 50C:
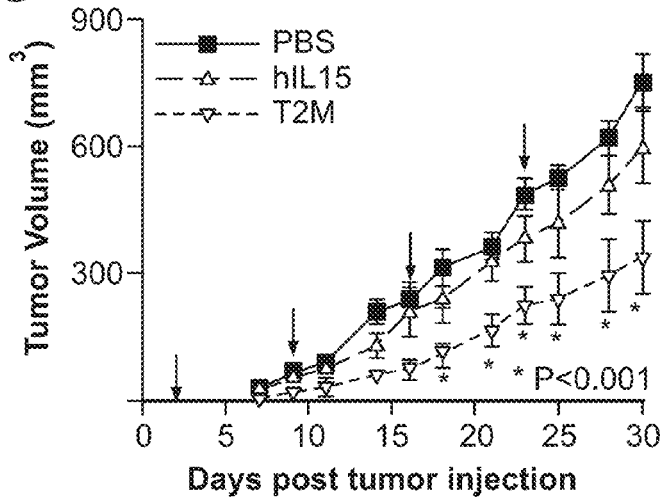

The antitumor activity of these complexes was further examined in the subcutaneous A375 xenograft model in nude mice. In initial studies, administration of recombinant human IL-15, the c264scTCR-IL15 and c264scTCR-IL15N72D fusion proteins or the c264scTCR-IL15N72D/c264scTCR-IL15Rα complex showed no effect on s.c. A375 tumor xenografts compared to PBS or c264scTCR-IL15Rα fusion protein treatment (FIG. 50A). The lack of an effect of the TCR-IL15 fusions in this model is likely due the inability of these proteins to stimulate NK cell responses in contrast to the reported results with the c264scTCR-IL2 fusion. As show above, when T2M complexes were tested in this model, they exhibited modest but statistically significant anti-tumor activity consistent with their ability to stimulate NK cell proliferation (FIG. 50B). However, in contrast to treatment with equivalent molar amounts of c264scTCR-IL15 fusion, the T2M dosing schedule (4 mg/kg every other day for 3 weeks) resulted in significant weight loss and two of 6 mice died after the last dose. Clinical observations included mouse inactivity, hunched posture, and ruddy skin. Concurrent studies of IL-15 protein complexes in other models confirmed that repeated every other day dosing was not well tolerated and that weekly dosing provided immune stimulation without excessive toxicity. A change of the dosing regimen from every other day to weekly schedule, T2M2 complex, at a dose level shown to be effective at inducing NK cell proliferation, exhibited significant more potent anti-tumor activity compared to IL-15 or PBS treatment (FIG. 50C). More importantly, this weekly dosing regimen was also well tolerated by the tumor-bearing nude mice and immunocompetent mice.

The toxicity profiles of the scTCR-IL15 fusions and T2M complexes were assessed concurrently with the in vivo activity studies described above. As indicated above, 3 weeks of every other day treatment with scTCR-IL15 fusions was well-tolerated by tumor bearing nude mice but T2M (4 mg/kg) treatment resulted in mortality in >30% of the animals. This was further evaluated in HLA-A*0201/Kb-transgenic mice administered 9, 18, or 36 mg/kg T2M or molar equivalent amounts of T2M2 complexes every other day for 1 week. At 1 week following initiation of treatment, dose and time dependent effects on body weight and clinical observations were seen. Mice receiving 36 mg/kg T2M exhibited a 20% loss in body weight compared to a 12% decrease observed in mice treated with equivalent amounts of T2M2. No change in body weight was observed in mice treated with ~9 mg/kg T2M or T2M2 over the 1 week period. Interestingly the higher toxicity observed with T2M did not correlate with increased immune cell activation as the mice treated with T2M2 showed higher levels of WBC counts and NK cell levels than T2M-treated mice. Minimal effects on mouse body weight, spleen weight and immune cells was observed following single dose i.v. administration of 0.4 mg/kg T2M2. Additionally preliminary studies in cynomolgus monkeys indicated that a single 0.5 mg/kg i.v. dose of T2M did not cause any observed toxicological effect but was capable of inducing CD8+ memory T cell and effector NK cell expansion. The results of these studies indicate that targeted IL-15 fusion complexes can be generated that have potent immunostimulatory and anticancer activity and favorable toxicity and pharmacokinetic profiles. Through these studies an optimized TCR-targeted T2M2 (also referred to as T2M.CH1 composed of c264scTCR/huIL15N72D and c264scTCR/huIL15RαSushi/huIgG1 CH2-CH3 chains) was defined and characterized. The nucleic acid and protein sequences of the c264scTCR/huIL15RαSushi/huIgG1 CH2-CH3 construct are shown in FIG. 51A, FIG. 51B, FIG. 51C, FIG. 51D and FIG. 52, respectively.

Example 18

Characterization of T2 Molecules Comprising Antibody Targeting Domains

To demonstrate the utility of the huIL-15:huIL-15RαSu scaffold to create additional disease targeted molecules, constructs were made linking the C-terminal end of an anti-human CD20 single chain antibody to the N-termini of huIL-15N72D and huIL-15RαSu/huIgG1 CH2-CH3 (Fc) chains. The anti-human CD20 single chain antibody (anti-CD20 scAb) sequence comprises the coding regions of the heavy and light chain V domains of the rituximab antibody linked via a flexible linker sequence. The nucleic acid and protein sequences of the anti-CD20 scAb/hIL-15N72D construct are shown in FIG. 53A and FIG. 53B and FIG. 54, respectively. The nucleic acid and protein sequences of the anti-CD20 scAb/huIL-15RαSu/huIgG1 Fc construct are shown in FIG. 55A, FIG. 55B, and FIGS. 55C and 56, respectively. These sequences were cloned into expression vectors as described above and the expression vectors transfected into CHO cells. Co-expression of the two constructs allowed formation and secretion of a soluble anti-CD20 scAb/huIL-15N72D:anti-CD20 scAb/huIL-15RαSu/huIgG1 Fc complex (referred to as anti-CD20 scAb T2M) which was purified from the CHO cell culture supernatant using Protein A affinity chromatography.

Figure 57:
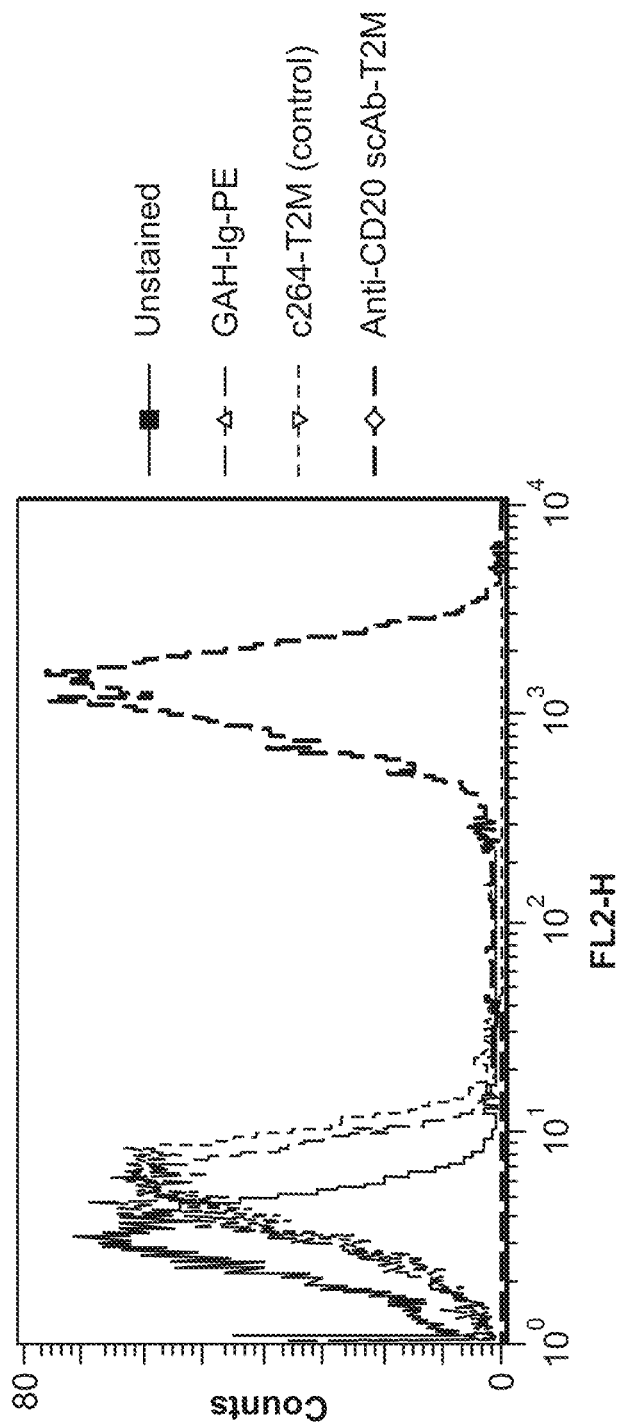
FIG. 57 show results from flow cytometry assays to test the CD20 antigen specific binding of anti-CD20 scAb T2M molecules to Daudi cells.

Similar to analysis described above, the ELISA-based methods have confirmed formation of the anti-CD20 scAb/huIL-15N72D:anti-CD20 scAb/huIL-15RαSu/huIgG1 Fc complex. Additionally, IL-15 receptor binding and cell proliferation assays using 32Dβ cells as described above indicated that the complex exhibited IL-15 binding and biologic activity. The anti-CD20 scAb T2M complex was then tested for antigen specific binding activity against the human CD20$^+$ Burkitt lymphoma Daudi cell line. Daudi cells were incubated with anti-CD20 scAb T2M, c264scTCR T2M or PBS. Following a wash step, cell bound fusion protein complexes were detected with PE-conjugated goat anti-human Ig antibody (GAH-Ig-PE) by flow cytometry (FIG. 57). The anti-CD20 scAb T2M complex showed significant binding to Daudi cells that was not observed with c264scTCR T2M or GAH-Ig-PE, indicating specific reactivity to these cells.

Figure 58:
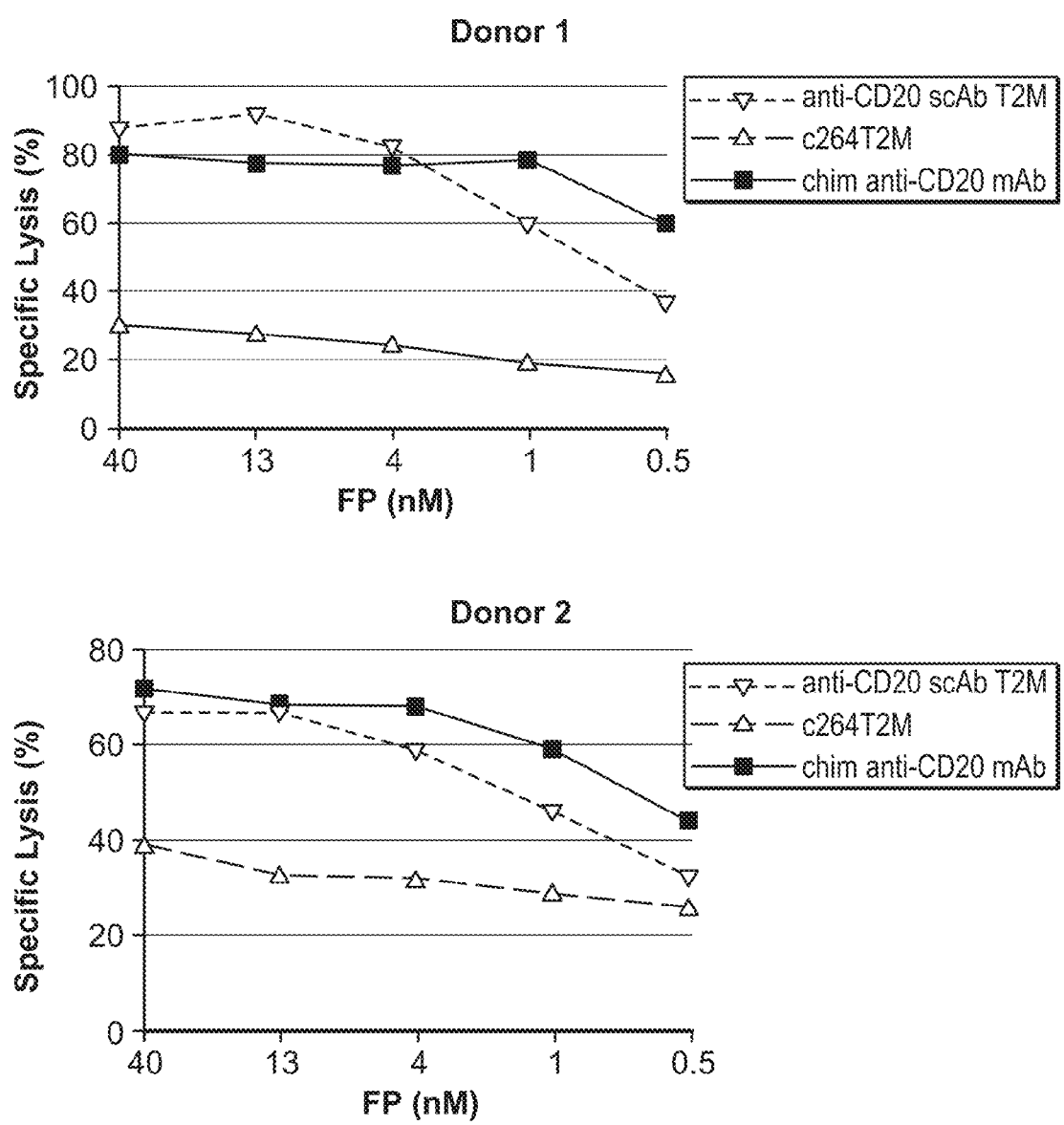
FIG. 58 shows results of an assay to determine the antibody dependent cellular cytotoxicity activity mediated by anti-CD20 scAb T2Ms against CD20+ human tumor cells. Various amounts of fusion protein (anti-CD20 scAb T2M, c264scTCR T2M (negative control) or chimeric anti-CD20 mAb (positive control)) were mixed with fresh human PBMCs (from 2 different donors) and Daudi cells (Calcein labeled) (E:T ratio, 100:1). After an incubation period, the culture medium was collected and analyzed quantitatively for Calcein released from lysed cells.
Figure 59:
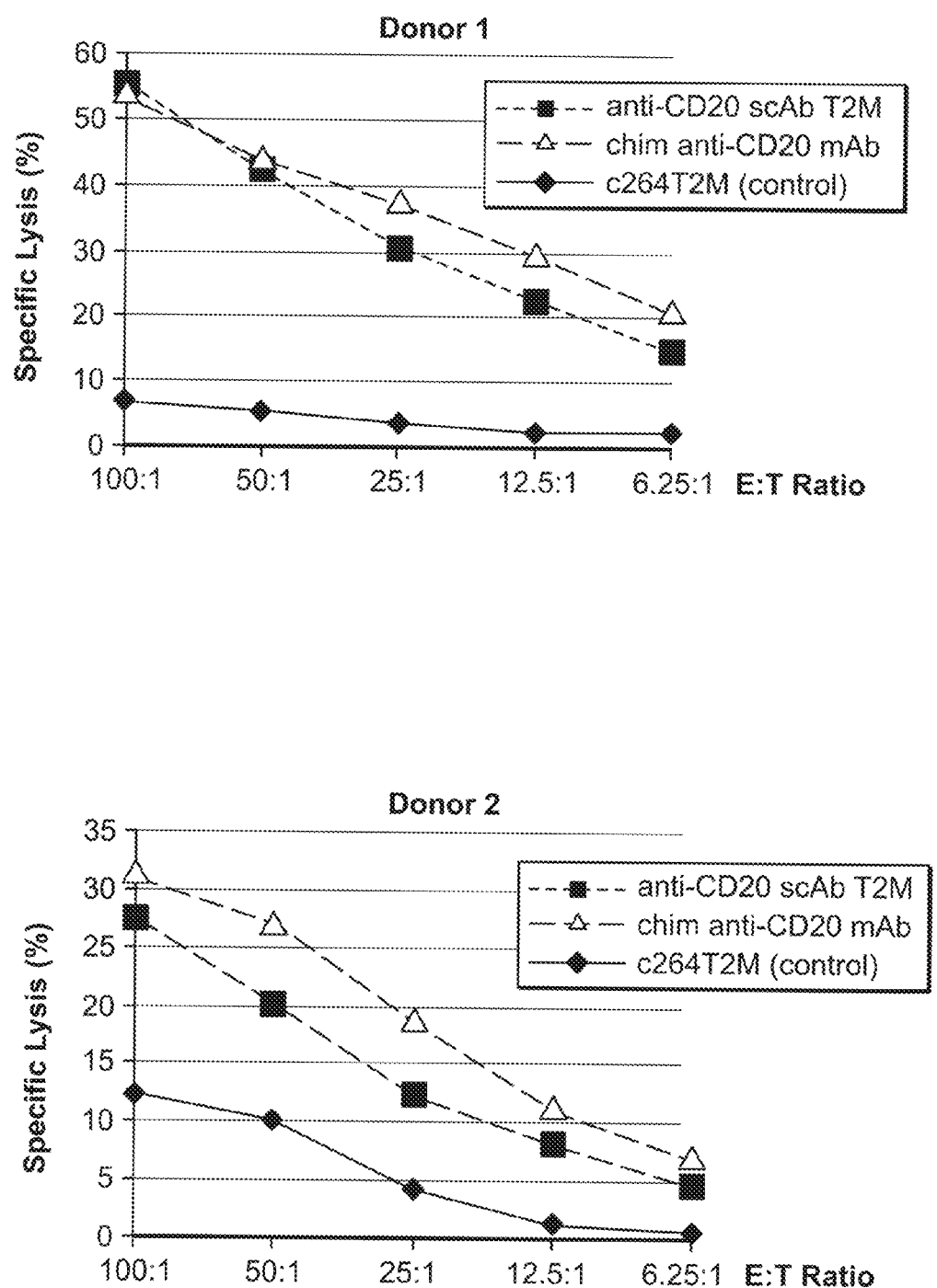
FIG. 59 shows results of an assay to determine the antibody dependent cellular cytotoxicity activity mediated by anti-CD20 scAb T2Ms against CD20+ human tumor cells. Fusion proteins (anti-CD20 scAb T2M, c264scTCR T2M (negative control) or chimeric anti-CD20 mAb (positive control)) were mixed with various rations of fresh human PBMCs (from 2 different donors) and Daudi cells (Calcein labeled). After an incubation period, the culture medium was collected and analyzed quantitatively for Calcein released from lysed cells.

Studies were also conducted to determine whether the anti-CD20 scAb T2M complexes were capable of killing CD20$^+$ tumor cells via an ADCC-based mechanism. Calcein-AM labeled Daudi target cells were mixed with human PMBCs (E:T-100:1) and various concentrations of anti-CD20 scAb T2M, c264scTCR T2M (negative control) or chimeric anti-CD20 mAb (positive control). After an incubation period, target cell lysis was evaluated as described above. As shown in FIG. 58, the anti-CD20 scAb T2M complex was highly effective at mediating ADCC activity against CD20$^+$ human lymphoma cells. This was verified by similar studies examining different effector to target cell ratios, where the anti-CD20 scAb T2M complex (at 2 nM) showed comparable activity as the chimeric anti-CD20 mAb (FIG. 59).

Based on these results, the anti-CD20 scAb T2M molecule is expected to exhibit antitumor activity against human lymphoma cells in standard xenograft tumor models (see for example, Rossi et al. Blood 2009; 114:3864; Gillis et al. Blood. 2005; 105:3972; and Xuan et al. Blood 2010; 115: 2864-2871).

Additionally T2M constructs comprising anti-CD20 light chains and heavy chain domains individually fused to the huIL-15N72D and huIL-15RαSu/huIgG1 CH2-CH3 (Fc) chains, respectively (or visa versa), could be generated and expressed as described herein. The nucleic acid and protein sequences of two such fusion constructs are shown in FIG. 60A and FIG. 60B, FIG. 61, FIG. 62A, FIG. 62B, and FIG. 62C and FIG. 63. Purified complexes comprising these fusion proteins are expected to exhibit Fc domain and IL-15 biologic activity, and CD20-specific binding activity, as described above. These complexes are expected to mediate ADCC activity against CD20$^+$ tumor cells and antitumor activity against CD20$^+$ tumor cells in vivo.

Similar T2M constructs comprising scAb or antibody recognition domains could be readily generated with antibody sequences specific to other CD antigens, cytokines or chemokine receptors or ligands, growth factor receptors or ligands, cell adhesion molecules, MHC/MHC-like molecules, Fc receptors, Toll-like receptors, NK receptors, TCRs, BCRs, positive/negative co-stimulatory receptors or ligands, death receptors or ligands, tumor associated antigens, virus-encoded and bacterial-encoded antigens, and bacterial-specific. Of particular interest are T2M with antibody domains specific to epitopes of CD3, CD4, CD19, CD21, CD22, CD23, CD25, CD30, CD33, CD38, CD40, CD44, CD51, CD52, CD70, CD74, CD80, CD152, CD147, CD221, EGFR, HER-2/neu, HER-1, HER-3, HER-4, CEA, OX40 ligand, cMet, tissue factor, Nectin-4, PSA, PSMA, EGFL7, FGFR, IL-6 receptor, IGF-1 receptor, GD2, CA-125, EpCam, death receptor 5 MUC1, VEGFR1, VEGFR2, PDGFR, Trail R2, folate receptor, angiopoietin-2, alphavbeta3 integrin receptor and HLA-DR antigens. Antibody domains against viral antigens from HIV, HCV, HBC, CMV, HTLV, HPV, EBV, RSV and other virus are also of interest, particularly those recognizing the HIV envelope spike and/or gp120 and gp41 epitopes. Such antibody domains can be generated from sequences known in the art or isolated de novo from a variety of sources (i.e., vertebrate hosts or cells, combinatorial libraries, random synthetic libraries, computational modeling, etc.) know in the art.

Additionally, as indicated above, it is useful to increase or decrease the activity of the IL-15 domain and the IgG Fc domains to optimize the therapeutic index and minimize toxicity of the antibody-targeted T2 complexes. Methods of modifying the activity of Fc domains are described above and are well characterized in the art. In such a case, complexes containing a mutation in the IL-15 domain that reduces its activity are expected to provide better therapeutic activity and lower toxicity. Antibody-targeted T2 molecules containing N65D or D8N substitutions in the IL-15 domain described above or other substitutions including I6S, DBA, D61A, N65A, N72R, V104P or Q108A, which has been found to reduce IL-15 activity, are of particular interest.

Example 19

Co-Expression of IL-15N72D and IL-15RαSu/Fc Fusion Gene in CHO Cells

Figure 64:
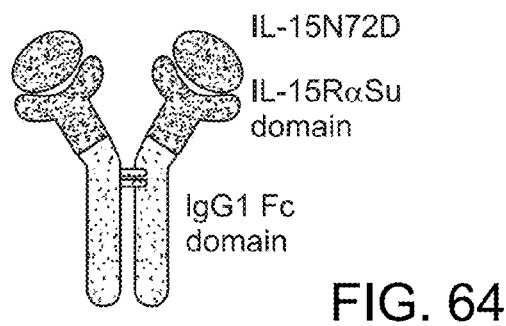
FIG. 64 is a schematic drawing of IL-15N72D:IL-15RαSu/Fc complex (also referred to as IL-15N72D:IL-15RαSu/huIgG1 CH2-CH3 complex, T2MΔTCRΔCH1 and ALT-803). Alt-803 includes IL-15N72D noncovalently associated with the dimeric IL-15RαSu/Fc fusion protein.

Previous studies have shown that recombinant IL-15 is poorly expressed by mammalian cells (A. Ward et al., Protein Expr Purif 68 (2009) 42-48). However, it has been reported that intracellular complex formation with IL-15Rα prevents IL-15 degradation in the ER (C. Bergamaschi et al., J Biol Chem 283 (2008) 4189-4199). Hence, it was postulated that IL-15 could be produced at a higher level if it is co-expressed with IL-15Rα. It is known that soluble IL-15Rα fragment, containing the so-called "sushi" domain (Su) at the N terminus, bears most of the structural elements responsible for cytokine binding. Soluble IL-15RαSu (without its transmembrane domain) and IL-15 are able to form very stable heterodimeric complexes in solution ($K_d$ of complex=100 pM (G. Bouchaud et al., J Mol Biol 382 (2008) 1-12)) and these complexes are capable of modulating (i.e. either stimulating or blocking) immune responses via the IL-15Rβγ$_c$ complex (E. Mortier et al., J Biol Chem 281 (2006) 1612-1619; M. P. Rubinstein et al., Proc Natl Acad Sci USA 103 (2006) 9166-9171; T. A. Stoklasek et al., J Immunol 177 (2006) 6072-6080; G. Bouchaud et al., J Mol Biol 382 (2008) 1-12). Thus, a complex consisting of IL-15N72D and an IL-15RαSu/Fc fusion protein was chosen for production (see FIG. 64). The IL-15RαSu domain was genetically fused to the human IgG1-Fc region to facilitate its purification and dimerization via interchain disulfide bonds. To co-express IL-15N72D and the IL-15RαSu/Fc, two individual retrovirus-based expression vectors, pMSGV-IL-15RαSu/Fc and pMSGV-IL-15N72D, were constructed and co-transfected into CHO cells. The recombinant CHO cells were selected based on the neomycin and puromycin resistance elements provided by the two expression vectors, and individual producing cell lines were then generated using limited dilution cloning. A clone that is capable of producing approximately 100 mg/L of IL-15N72D:IL-15RαSu/Fc complex (Alt-803), based on ELISA, in a serum-free, defined medium was identified. This result demonstrated that IL-15 could be expressed at high levels in mammalian cells if it is co-expressed with the IL-15RαSu domain.

Example 20

Purification and Characterization of the IL-15N72D:IL-15RαSu/Fc Complex (Alt-803)

When IL-15RαSu/Fc and IL-15N72D were co-expressed and assembled intracellularly in recombinant CHO cells, four different forms of proteins were expected in the cell culture supernatants: 1) dimeric IL-15RαSu/Fc molecule fully occupied with two IL-15N72D subunits, 2) dimeric IL-15RαSu/Fc molecule partially occupied with one IL-15N72D subunit, 3) a small amount of free homodimeric IL-15RαSu/Fc molecule with no IL-15 bound, and 4) free IL-15N72D. Since IL-15N72D lacks an Fc region, a rProtein A-based affinity purification step was used to separate the free IL-15N72D from all of the Fc-bearing fusion proteins in the culture supernatant.

Figure 65A:
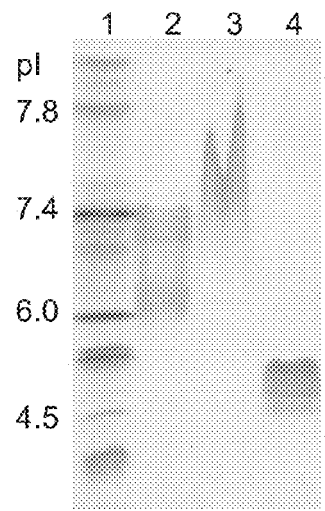
FIG. 65A to FIG. 65D are photographs of gel electrophoresis analysis profiles of IL-15N72D:IL-15RαSu/Fc (Alt-803) preparations.
Figure 65B:
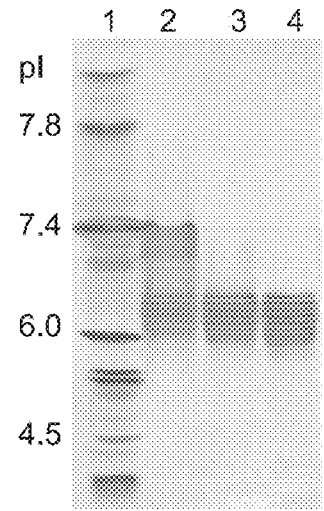

An ion exchange chromatography method was then developed to separate various forms of the IL-15RαSu/Fc complex. The calculated isoelectric point (pI) of the IL-15RαSu/Fc dimeric molecule is 8.5. As expected, this protein in 20 mM Tris-HCl, pH 8.0 solution was subsequently found to not bind to QSFF resin. Additionally, the calculated pI of IL-15N72D is 4.5. Therefore, it was predicted that the overall charge of the partially occupied IL-15N72D:IL-15RαSu/Fc (i.e. dimeric IL-15RαSu/Fc+one IL-15N72D molecule) and the fully occupied IL-15N72D:IL-15RαSu/Fc (dimeric IL-15RαSu/Fc+two IL-15N72D molecules) are different. This is consistent with IEF gel analysis of the Protein-A-purified preparations, which showed two major groups of complexes with pIs between 5.6-6.5 and 6.8-7.5 corresponding with the expected pIs of the fully occupied and partially occupied complexes, respectively (FIG. 65A). The heterogeneity among pI bands of each protein group is possibly due to the degree of glycosylation and C-terminal lysine variants in the IgG1 chain. Thus, buffers with different ionic strengths were employed to separately elute the partially occupied and fully occupied complexes from the QSFF. Using 130 mM NaCl, 20 mM Tris-HCl, pH 8.0, a single protein fraction (Q step 1) was eluted from QSSF and found to contain mainly the partially occupied complex based on ELISAs determining the fractional occupancy of the IL-15RαSu/Fc molecule. In the subsequent step using 300 mM NaCl, 20 mM Tris-HCl, pH 8.0, two protein fractions designated as Q1c and Q2c were further eluted from the QSFF. ELISA analyses performed on these preparations indicated that Q1c fraction contained a mixture of partially occupied (10% of total) and fully occupied (90%) complexes whereas Q2c fraction contained only the fully occupied complex (data not shown). These findings are consistent with IEF gel analysis of the purified protein preparations (FIG. 65B). Proteins eluted from Q step 1 have broad pIs ranging from 5.6 to 7.5; proteins of pIs 6.8 to 7.5 representing the partially occupied complex. Fraction Q1c of Q step 2 elution mainly contained protein with pIs ranging from 5.6 to 6.5 (i.e. fully occupied complex) but with small amounts of contaminant protein with pIs of 5.6 to 7.5. The Q2c fraction contained only proteins with pIs ranging from 5.6 to 6.5.

Figure 66:
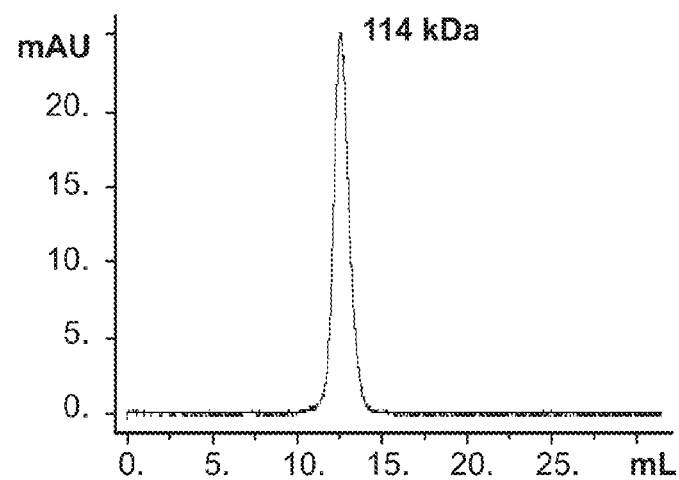
FIG. 66 is a graph of a SEC chromatogram using Superdex 200 HR 10/30 gel filtration column. The purified IL-15N72D:IL-15Rα/Fc complex was eluted as a single peak.

In SEC analysis, the purified IL-15N72D:IL-15RαSu/Fc (Alt-803) Q2c preparation was found to elute as a single molecule with high purity (FIG. 66). The estimated molecular weight of the homodimer was approximately 114 kDa, which was larger than the 92 kDa molecular weight calculated based on the deduced amino acid sequence of IL-15N72D and IL-15RαSu/Fc fusion proteins. This is likely due to the glycosylation of the proteins produced by mammalian cells.

Figure 65C:
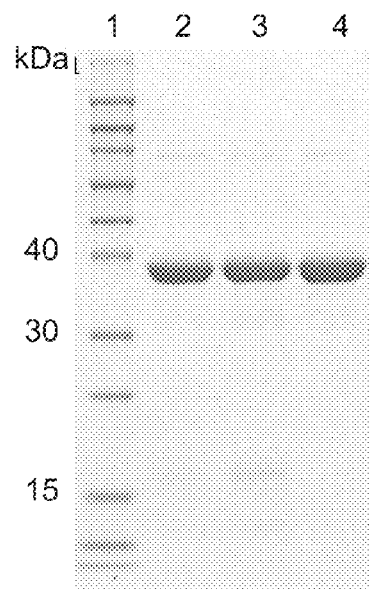
Figure 65D:
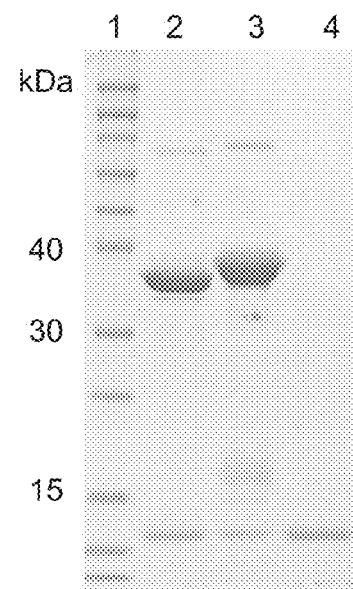

In reducing SDS-PAGE (FIG. 65C), the purified IL-15N72D:IL-15RαSu/Fc (Alt-803) preparation was found to contain three proteins with molecular weights of 40 kDa, 16 kDa and 13 kDa. However, after a digestion with N-Glycosidase F, only two proteins, with molecular weights of ~37 kDa and 13 kDa, were detected (FIG. 65D). These molecular weights closely match the calculated molecular weights of IL-15RαSu/Fc and IL-15 or IL-15N72D. This suggests that these two proteins were glycosylated during mammalian cell production and the IL-15N72D was produced in two major glycosylation forms with molecular weights of 13 kDa and 16 kDa. The relative abundance of these IL-15N72D species in the different purification fractions shown in FIG. 65C is consistent with levels of complex occupancy determined by ELISA and IEF gel analysis.

The IL-15N72D and IL-15RαSu/Fc were separated in reducing SDS-PAGE and the N-terminus amino acid sequences of these proteins were determined using the Edman degradation method. Approximately 15 N-terminal amino acid sequences were obtained for IL-15RαSu/Fc and IL15N72D, respectively. The determined N-terminal amino acid sequences of these proteins matched their amino acid sequences deduced from the coding regions of the two genes. The amino acid sequences for the two major bands that appeared on reduced SDS-PAGE at 13 and 16 kDa were confirmed to be IL-15N72D. This sequence confirmation again provided the evidence of glycosylation of IL-15N72D in mammalian cells.

Example 21

Pharmacokinetic Properties of the IL-15N72D:IL-15RαSu/Fc Complex (Alt-803)

It has previously been reported that IL-15 and in vitro assembled IL15:IL-15Rα/Fc complex (Alt-803) had a 1 h and 20 h serum half-life, respectively, in mice when these proteins were injected intraperitoneally (T. A. Stoklasek et al., J Immunol 177 (2006) 6072-6080). To assess whether IL-15 and the co-expressed, purified IL-15:IL-15αSu/Fc complex behaved similarly when administered intravenously, their pharmacokinetic parameters were determined in CD-1 mice. Intravenous administration was chosen because this is likely the route of drug delivery to be used for the IL-15:IL-15αSu-Fc complex in humans. Female mice were injected intravenously with 1.0 mg/kg IL-15:IL-15αSu/Fc or 0.28 mg/kg IL-15 (a molar equivalent dose) and blood was collected at various time points from 15 min to 8 h for IL-15 and 30 min to 72 h for IL-15N72D:IL-15αSu/Fc post injection. Serum concentrations of IL-15N72D:IL-15αSu/Fc were evaluated using two ELISA formats, one (anti-IL-15 Ab detection) which detects the intact complex and the other (anti-human IgG Fc Ab detection) which detects only the IL-15αSu/Fc fusion protein. Concentrations of IL-15 were evaluated with a standard IL-15-specific ELISA.

Figure 67:
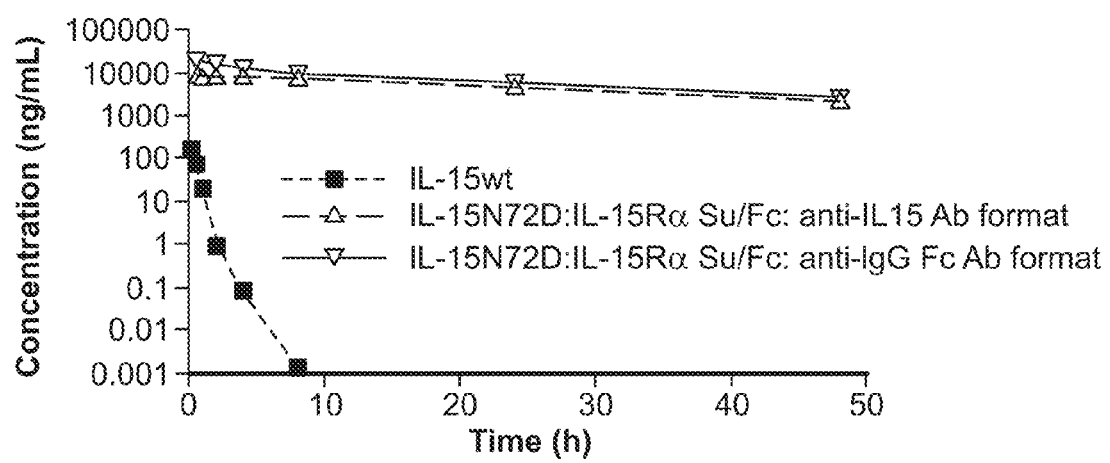
FIG. 67 is a graph showing a comparison of the pharmacokinetic profile of IL-15 wt and IL-15N72D:IL-15RαSu/Fc complex following intravenous administration in CD-1 mice. The anti-IL-15 Ab ELISA measures the concentration of IL-15 wt (■). The anti-IL-15 Ab ELISA measures the concentration of the intact IL-15N72D:IL-15RαSu/Fc molecule (Δ), whereas the anti-human IgG Fc Ab ELISA measures serum concentration of the IL-15RαSu/Fc fusion protein (▼). The observed concentrations are represented by symbols and the model-fitted curves are represented by lines.

The predicted fit and actual data for IL-15:IL-15αSu/Fc and IL-15 following the single intravenous bolus injections are shown in FIG. 67. The estimated half-life of IL-15:IL-15αSu/Fc using anti-IL-15 Ab-based or anti-human IgG Fc Ab-based ELISAs was about 25 or 18 h, respectively. These results indicate that the fusion protein was not cleaved and the IL-15 did not significantly disassociate from the IL-15RαSu/Fc molecule in vivo. The clearance (Cl) of IL-15:IL-15αSu/Fc ranged from 0.059 to 0.051 mL/h and the volume of distribution at steady state (Vss) ranged from 2.1 to 1.3 mL depending on the assay format. In comparison, IL-15 had an absorption half-life of 0.24 h and a terminal half-life of 0.64 h. The Cl of IL-15 was 49 mL/h, and the Vss was 18.4 mL. These results indicate that IL-15:IL-15αSu/Fc displays a >24 fold longer terminal half-life and is cleared >800 fold slower than IL-15.

Example 22

In Vitro and In Vivo Biological Activities of the IL-15N72D:IL-15RαSu/Fc Complex (Alt-803)

Figure 68:
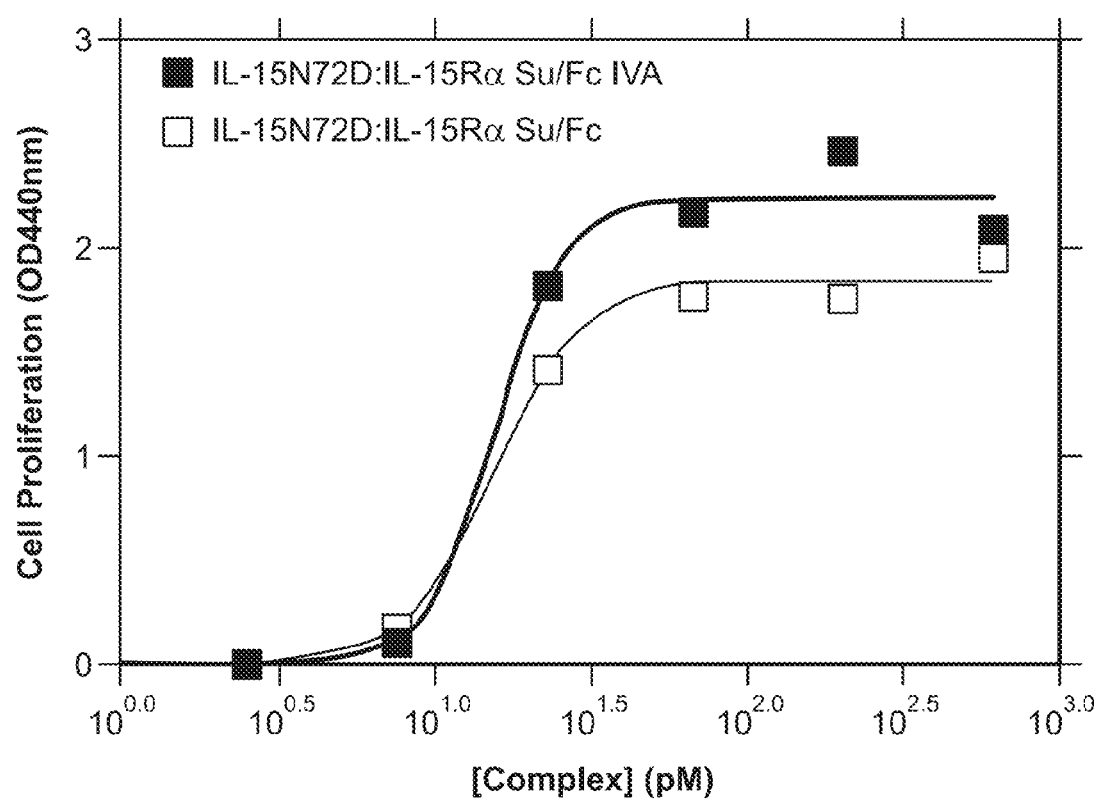
FIG. 68 is a graph showing a comparison of the biological activity of the in vitro assembled IL-15N72D:IL-15RαSu/Fc (IL-15N72D:IL-15RαSu/Fc IVA) with IL-15N72D:IL-15RαSu/Fc. 32Dβ cells were incubated with increasing concentrations of the in vitro assembled IL-15N72D:IL-15RαSu/Fc (■) or IL-15N72D:IL-15RαSu/Fc (□) for 72 h prior to addition of WST-1 for 4 h. Cell proliferation was quantitated by absorbance reading at 440 nm to assess formazan levels. The data points shown are means (±standard error) of triplicate samples and the lines represent sigmoidal dose-response curve fit for $EC_{50}$ determination. The results are representative of at least three experiments.

The biological activity of the co-expressed and purified IL-15N72D:IL-15RαSu/Fc complex (Alt-803) was evaluated using an IL-15 dependent 32Dβ cell proliferation assay. For this assay, an in vitro assembled (IVA) IL-15N72D:IL-15RαSu/Fc complex (IL-15N72D:IL-15RαSu/Fc IVA) (Alt-803) was also generated by mixing IL-15N72D and IL-15RαSu/Fc at a 1:1 ratio for 30 min at 4° C. As shown in FIG. 68, the IL-15N72D:IL-15RαSu/Fc complex (Alt-803) had equivalent biological activity as IL-15N72D:IL-15RαSu/Fc IVA (Alt-803) to support growth of 32Dβ cells. The IL-15N72D:IL-15RαSu/Fc complex (Alt-803) exhibited an $EC_{50}$ of 15.61 pM and the IL-15N72D:IL-15RαSu/Fc IVA (Alt-803) displayed an $EC_{50}$ of 15.83 pM. This demonstrates that the co-expressed IL-15N72D:IL-15RαSu/Fc complex (Alt-803) is appropriately processed intracellularly and retains full IL-15 activity after purification. Thus, the method presented herein represents a better approach for generating cGMP-grade clinical material than current strategies employing in vitro assembly individually produced and in some cases refolded proteins.

The IL-15N72D:IL-15RαSu/Fc complex (Alt-803) and IL-15 wt were also compared for their ability to induce the expansion of NK cells and CD8$^+$ T cells in C57BL/6 mice. As shown in FIG. 69, IL-15 wt has no significant effect on the expansion of NK and CD8$^+$ cells four days after a single intravenous dose of 0.28 mg/kg. In contrast, the IL-15N72D: IL-15RαSu/Fc complex (Alt-803) significantly promoted NK and CD8$^+$ T cell proliferation in the blood and spleen, which led to lymphocytosis in blood and splenomegaly (Figures. 69 and 70). These findings are consistent with previous reports that IL-15:IL-15Rα complexes significantly increased the biological activities of IL-15 in vivo (M. P. Rubinstein et al., Proc Natl Acad Sci USA 103 (2006) 9166-9171; T. A. Stoklasek et al., J Immunol 177 (2006) 6072-6080; S. Dubois et al., J Immunol 180 (2008) 2099-2106; M. Epardaud et al., Cancer Res 68 (2008) 2972-2983; A. Bessard et al., Mol Cancer Ther 8 (2009) 2736-2745). This enhanced activity of the IL-15N72D:IL-15RαSu/Fc complex is likely the result of a combination of the increased binding activity of the N72D mutein to the IL-15Rβγ$_c$ complex (X. Zhu et al., J Immunol 183 (2009) 3598-3607), optimized cytokine trans-presentation by the IL-15Rα chain in vivo (through the FcR receptors on dendritic cells and macrophage), the dimeric nature of the cytokine domain (increased avidity of binding to IL-15Rβγ$_c$) and its increased in vivo half-life compared to IL-15 (25 h vs. <40 min).

In sum, the results described herein demonstrate that the IL-15N72D and IL-15RαSu/Fc genes can be co-expressed in recombinant CHO cells and a fully occupied IL-15N72D:IL-15RαSu/Fc complex (Alt-803) can be highly purified from cell culture supernatants using a simple scalable purification method.

Example 23

Efficacy of ALT-803 in Murine Myeloma Models

Figure 71:
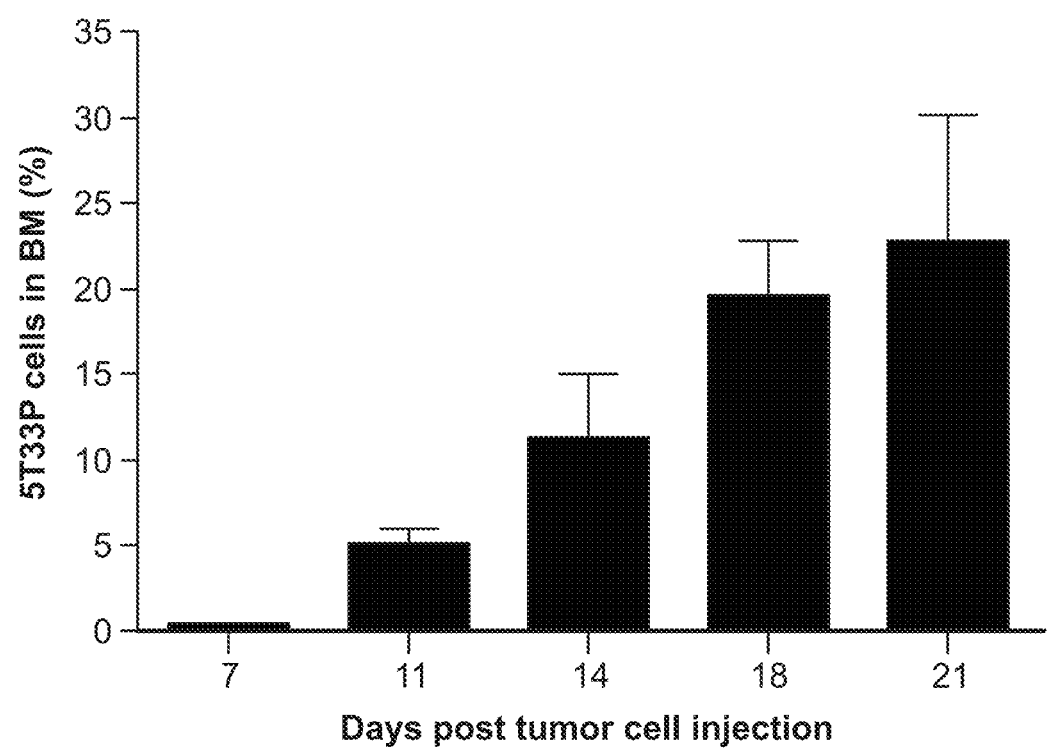
FIG. 71 is a histogram showing the growth pattern of 5T33P murine myeloma cells in the bone marrow (BM) of C57BL/6NHsd mice. Female C57BL/6NHsd mice (n=4–5/group) were injected intravenously (i.v.) with 5T33P myeloma cells ($1 \times 10^7$) on day 0. Bone marrow (BM) cells were collected on days 7, 11, 14, 18 and 21 after tumor cell inoculation. BM cells were then stained with phycoerythrin (PE)-conjugated rat anti-mouse IgG2b Ab and evaluated by flow cytometry to determine the percentage of 5T33P cells in BM. The plotted values represent the mean±SE.
Figure 72A:
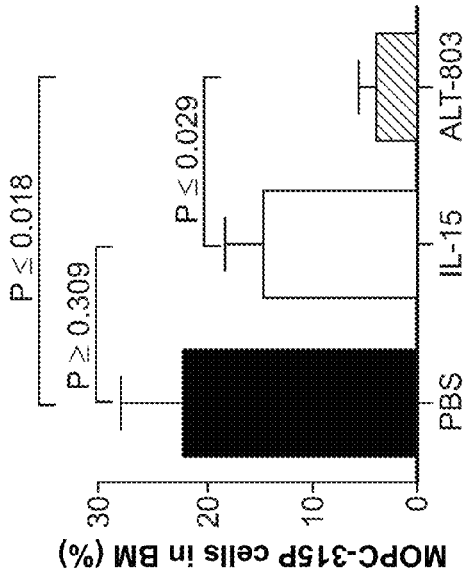
FIG. 72A-FIG. 72D are graphs showing the anti-tumor effects of ALT-803 in murine myeloma models.
Figure 72B:
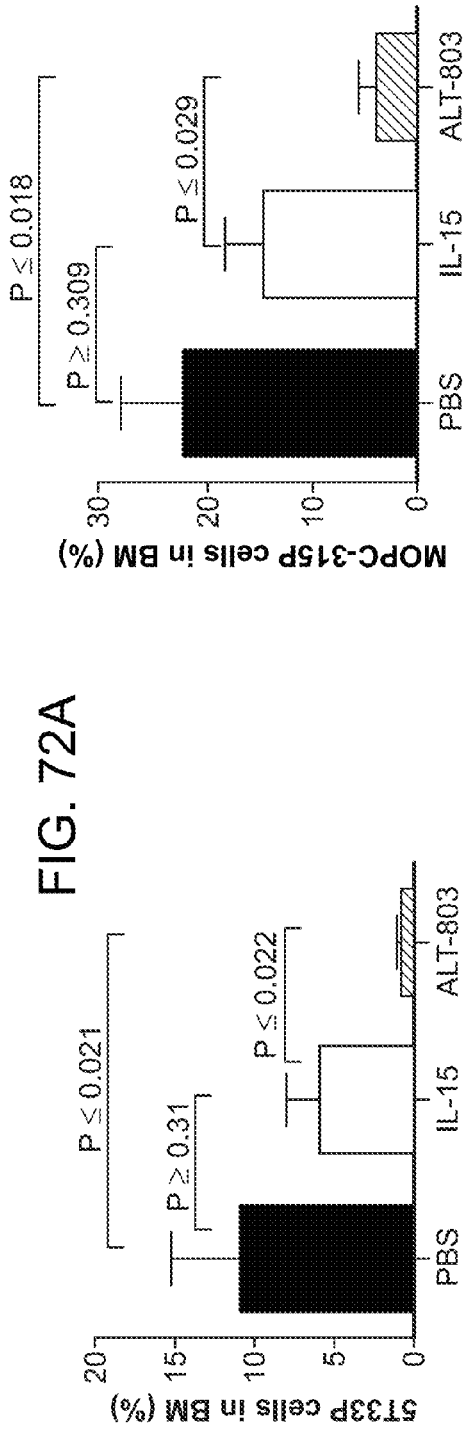
Figure 73A:
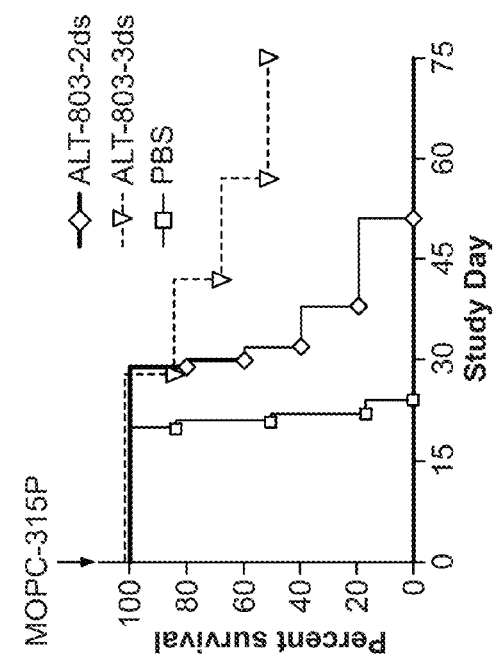
FIG. 73A and FIG. 73B are graphs showing ALT-803 activity in murine myeloma models.
Figure 73B:
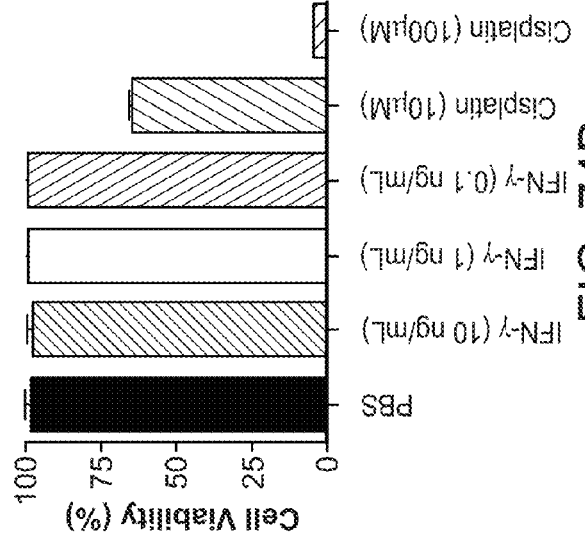

To conduct efficacy studies in hematologic tumor models, highly tumorigenic myeloma lines 5T33P and MOPC-315P were developed from the well-characterized 5T33 and MOPC-315 parental lines, respectively. These cells could populate the bone marrow (BM) and cause paralysis following i.v. inoculation of syngeneic mice. Tumor development in 5T33P-bearing C57BL/6NHsd mice and MOPC-315P-bearing BALB/c mice was assessed by staining myeloma cells in isolated BM cell preparations for intracellular 5T33P-specific IgG2b and MOPC-315P-specific IgA paraproteins. In C57BL/6NHsd mice, IgG2b paraprotein-positive myeloma cell levels increased to over 20% of the total BM cells by 21 days after 5T33P tumor cell inoculation (FIG. 71). A single i.v. treatment of ALT-803 (0.2 mg/kg) had a marked effect on 5T33P cells in the BM of mice with well-established tumors (14 days after tumor implantation), providing >90% reduction in BM IgG2b$^+$ myeloma cells four days after treatment compared to controls (0.8% versus 11.0%, P≤0.02) (FIG. 72A). However, a molar equivalent dose of IL-15 was much less effective and only reduced BM 5T33P cells by 53% compared to PBS-treated mice (P≥0.31). Dose response studies indicated that a single dose of ALT-803 as low as 0.05 mg/kg was capable of reducing 90% of the BM 5T33P myeloma cells (FIG. 73). Similar studies in BALB/c mice bearing well-established MOPC-315P tumors confirmed that treatment with ALT-803, but not IL-15, resulted in a significant decrease in BM myeloma cells compared to controls (P≤0.02, ALT-803 vs. PBS; P≥0.31, IL-15 vs. PBS) (FIG. 72B). No toxicity was observed following treatment, indicating that ALT-803 administration and its anti-tumor effects, which resulted in the rapid killing of a large number of myeloma cells over a short duration, were well tolerated by mice.

Figure 72C:
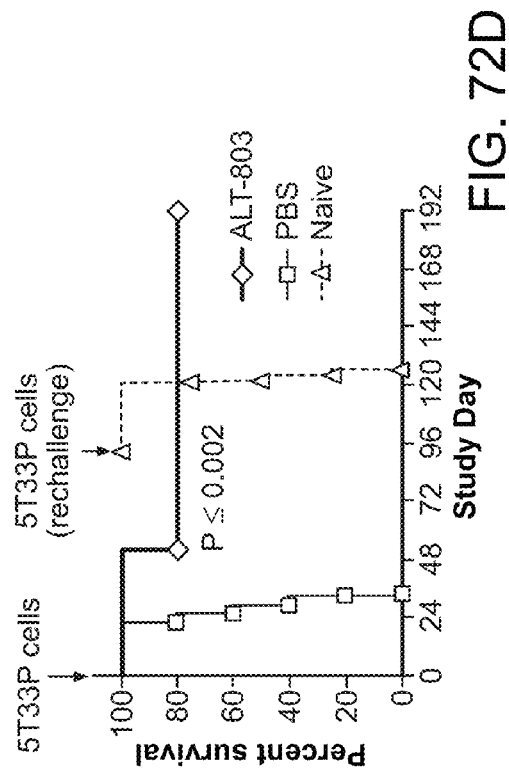

ALT-803 effects on mouse survival were also evaluated in these myeloma models. 5T33P-bearing C57BL/6NHsd mice treated with a single 0.2 mg/kg dose of ALT-803 showed significantly increased survival when compared to PBS-treated mice, which all exhibited hind leg paralysis (survival endpoint) between 21 to 35 days post tumor cell injection with a median survival time (MST) of 25 days (P≤0.006) (FIG. 72C). Two or three weekly doses of ALT-803 also provided a significant survival benefit in this model (P≤0.002, ALT-803 vs. PBS) (FIG. 72D) and in BALB/c mice bearing MOPC-315P tumors (FIG. 73).

Figure 72D:
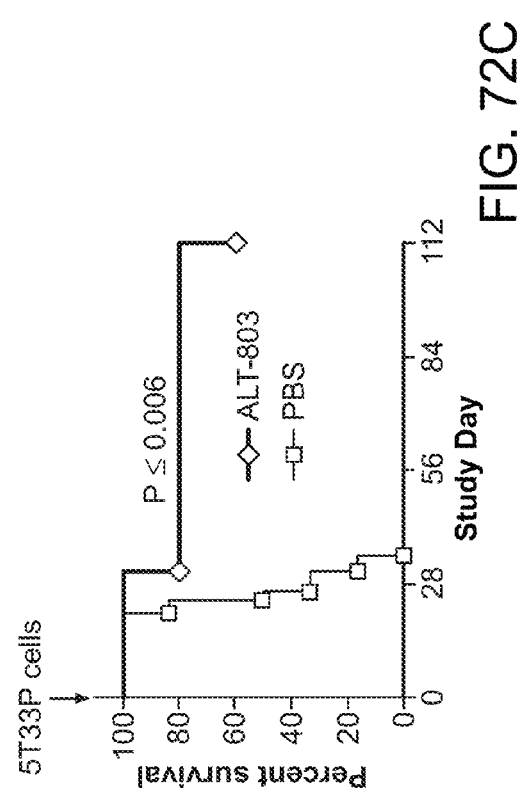

Since ALT-803 treatment was capable of essentially curing mice bearing 5T33P myeloma, these mice were evaluated to determine whether they retain immunological memory against the tumor cells. As shown in FIG. 72D, C57BL/6NHsd mice that survived initial 5T33P inoculation due to ALT-803 treatment were not affected by 5T33P cell upon rechallenge 3 months later, even in the absence of additional ALT-803 administration. These mice continued to survive over 190 days from the initial tumor cell inoculation. In contrast, all of the treatment-naïve mice administered 5T33P cells on the same study day subsequently exhibited paralysis with a MST of 29 days post tumor cell injection. Together, these results demonstrate that a short course of ALT-803 treatment has significantly greater anti-tumor activity against established BM myeloma cells than IL-15 treatment, resulting in prolonged survival of myeloma-tumor bearing mice. ALT-803 was also capable of inducing long-lasting protective immunologic memory against subsequent tumor cell rechallenge.

Example 24

CD8$^+$ T Cells Mediate Efficacy of ALT-803 Against Myeloma Cells

Figure 74A:
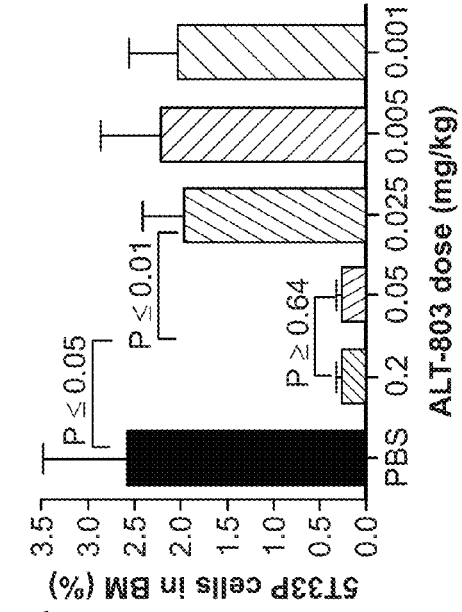
FIG. 74A and FIG. 74B are histograms showing that 5T33P cell apoptosis is not induced by culturing the cells with ALT-803 or IFNγ. 5T33P cells were incubated for 24 hours in the presence of media containing (FIG. 74A) PBS, ALT-803 (50 and 500 nM) or cisplatin (10 and 10 μM) (Sigma-Aldrich) and (FIG. 74B) PBS, IFN-γ (10, 1, and 0.1 ng/mL) or cisplatin (10 and 100 μM). After staining with FITC Annexin V and propidium iodine (PI) (BD Bioscience), the cells were analyzed by flow cytometry. Cell viability was assessed as negative staining with FITC Annexin V and PI. The plotted values represent the mean±SE.
Figure 74B:
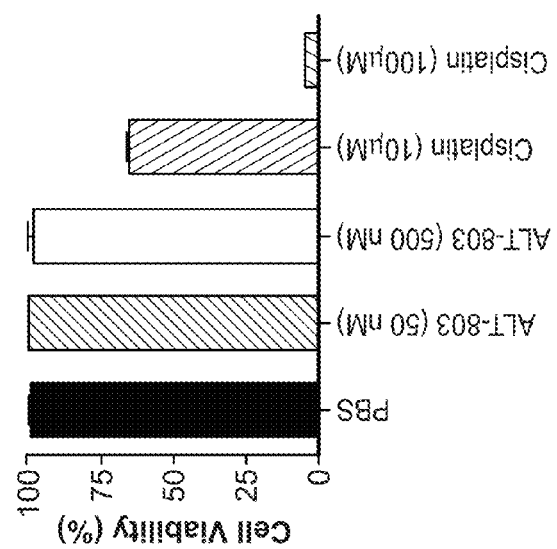

ALT-803 treatment effectively eliminated myeloma cells in vivo, it was tested whether ALT-803 had a direct effect on the viability and proliferation of 5T33P and MOPC-315P cells in vitro. Neither a decrease in cell numbers nor an increase in apoptotic cells was observed following incubation of tumor cells with ALT-803 even at high concentrations (FIG. 74). Thus, ALT-803 anti-myeloma activity in vivo is likely due to activation of immune responses rather than direct killing of tumor cells.

Figure 75A:
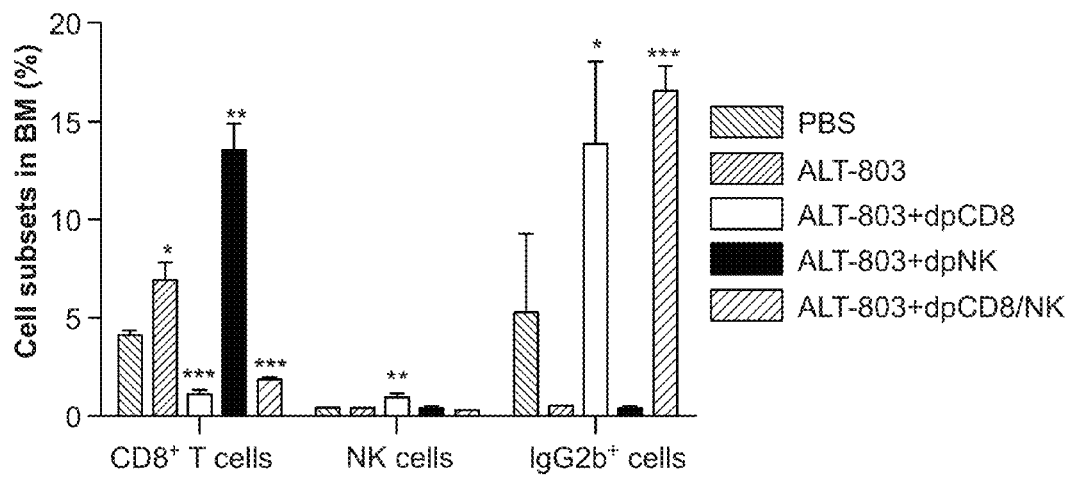
FIG. 75A and FIG. 75B are graphs showing immune cell effects on the anti-myeloma activity of ALT-803.
Figure 75B:
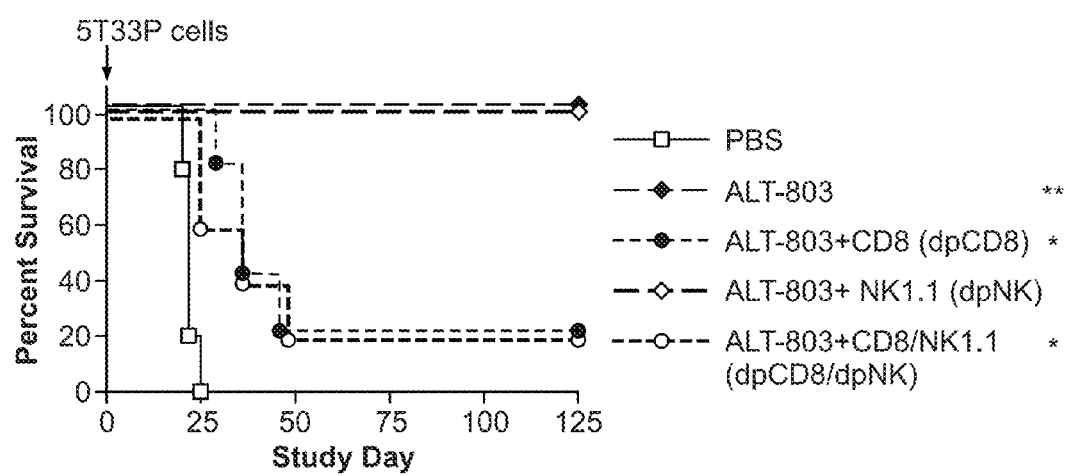

ALT-803 treatment is capable of significantly increasing the number of NK and T cells in vivo (Han et. al., Cytokine, 56: 804-810, 2011). To determine if these immune cells were responsible for ALT-803-mediated anti-myeloma efficacy, Ab-immunodepletion of CD8$^+$ T cells and NK1.1$^+$ cells was performed in tumor-bearing mice prior to ALT-803 treatment. Effective depletion of these immune cell subsets could be achieved by intraperitoneal (i.p) administration of anti-CD8 and/or anti-NK1.1 antibodies starting with injections 48 hours and 24 hours prior to tumor inoculation and weekly post-tumor inoculation. When ALT-803 efficacy was examined in 5T33P-bearing mice, it was found that CD8$^+$ T-cell depletion alone or in combination with NK1.1$^+$ cell depletion, but not NK1.1$^+$ cell depletion alone, eliminated the anti-tumor effects of ALT-803 on BM 5T33P myeloma cells (FIG. 75A). Consistent with these results, anti-tumor activity correlated with ALT-803-mediated increases in BM CD8$^+$ T-cell and not NK cell levels (FIG. 75A). We also conducted immune cell depletion studies in 5T33P-bearing C57BL/6NHsd mice treated with ALT-803 using survival as the efficacy endpoint. As described above, ALT-803 treatment effectively cured myeloma-bearing mice that otherwise developed paralysis within 28 days (FIG. 75B). Depletion of NK1.1$^+$ cells had no effect on the anti-tumor activity of ALT-803, whereas depletion of CD8$^+$ T cells or both CD8$^+$ T cells and NK1.1$^+$ cells significantly reduced the ALT-803-mediated survival benefit to 5T33P-bearing mice (P<0.013). These results support our conclusion that CD8$^+$ T cells, not NK1.1$^+$ cells, play a major role in ALT-803-mediated activity against 5T33P cells in C57BL/6NHsd mice.

Example 25

ALT-803 Induces CD8$^+$CD44$^{high}$ Memory T Cells to Expand, Up-Regulate Innate Receptors and Exhibit Non-Specific Cytotoxic Activity It was previously shown that a single dose of ALT-803 at 0.2 mg/kg dose level, but not IL-15, could significantly increase the CD8$^+$ T cells and NK cells in naïve mice (Han et. al., Cytokine, 56: 804-810, 2011). As shown in FIG. 76A, a single dose of ALT-803 (0.2 mg/kg) administered to either normal or 5T33P-bearing C57BL/6NHsd mice resulted in a similar 4-5 fold expansion of the CD8$^+$CD44$^{high}$ memory T cell population with little change in naïve T-cell levels. This is consistent with observations by others that certain cytokines, such as IL-12, IL-18, IFN-γ or IL-15, can promote proliferation of CD8$^+$CD44$^{high}$ T cells, but not the naïve CD8$^+$ T cells, in vivo (Zhang et al., Immunity, 8: 591-599, 1998; Tough et al., J Immunol, 166: 6007-6011, 2001; Sprent et al., Philos Trans R Soc Lond B Biol Sci, 355: 317-322, 2000).

Figure 76D:
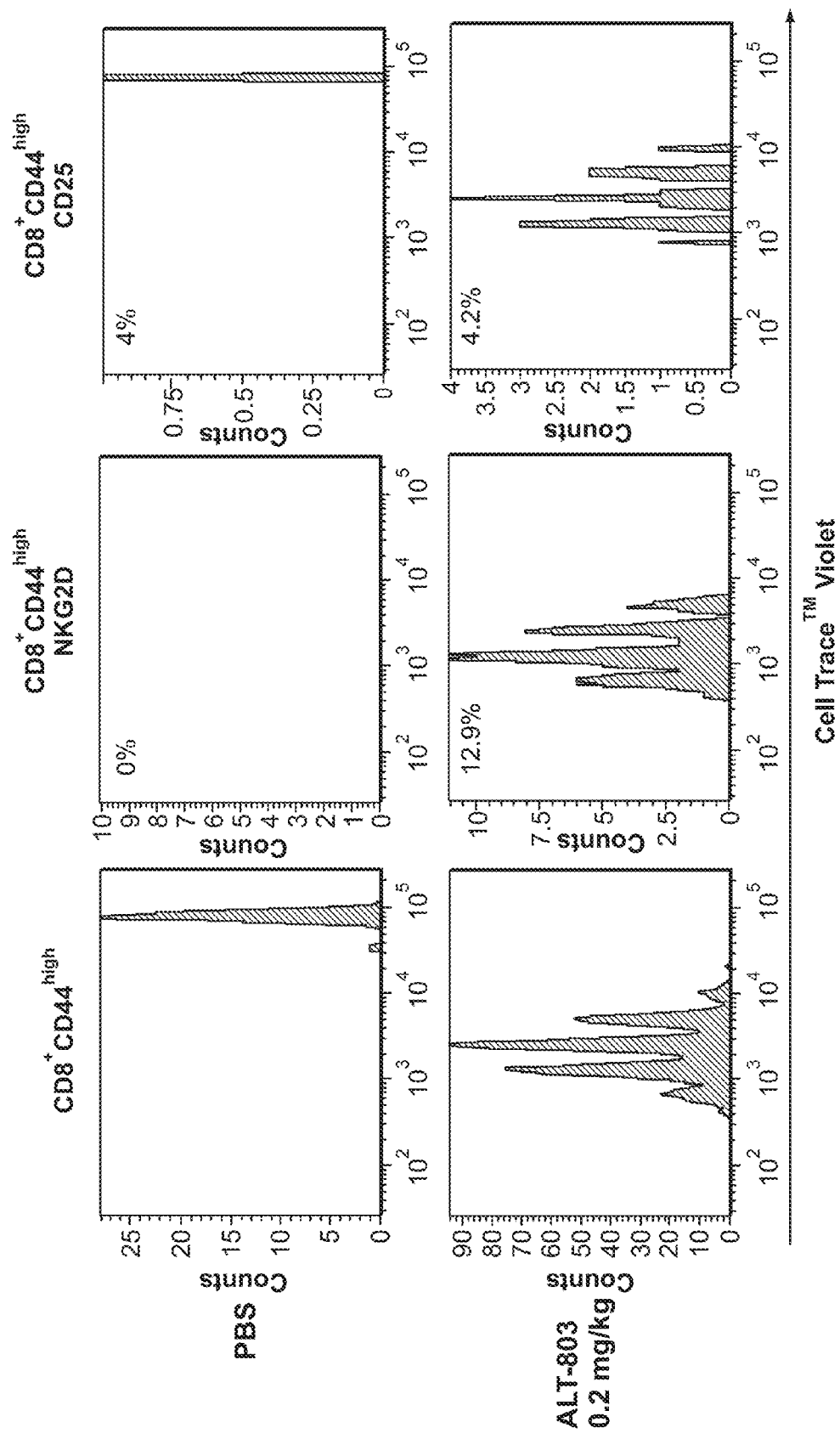
Figures 1, 77A:
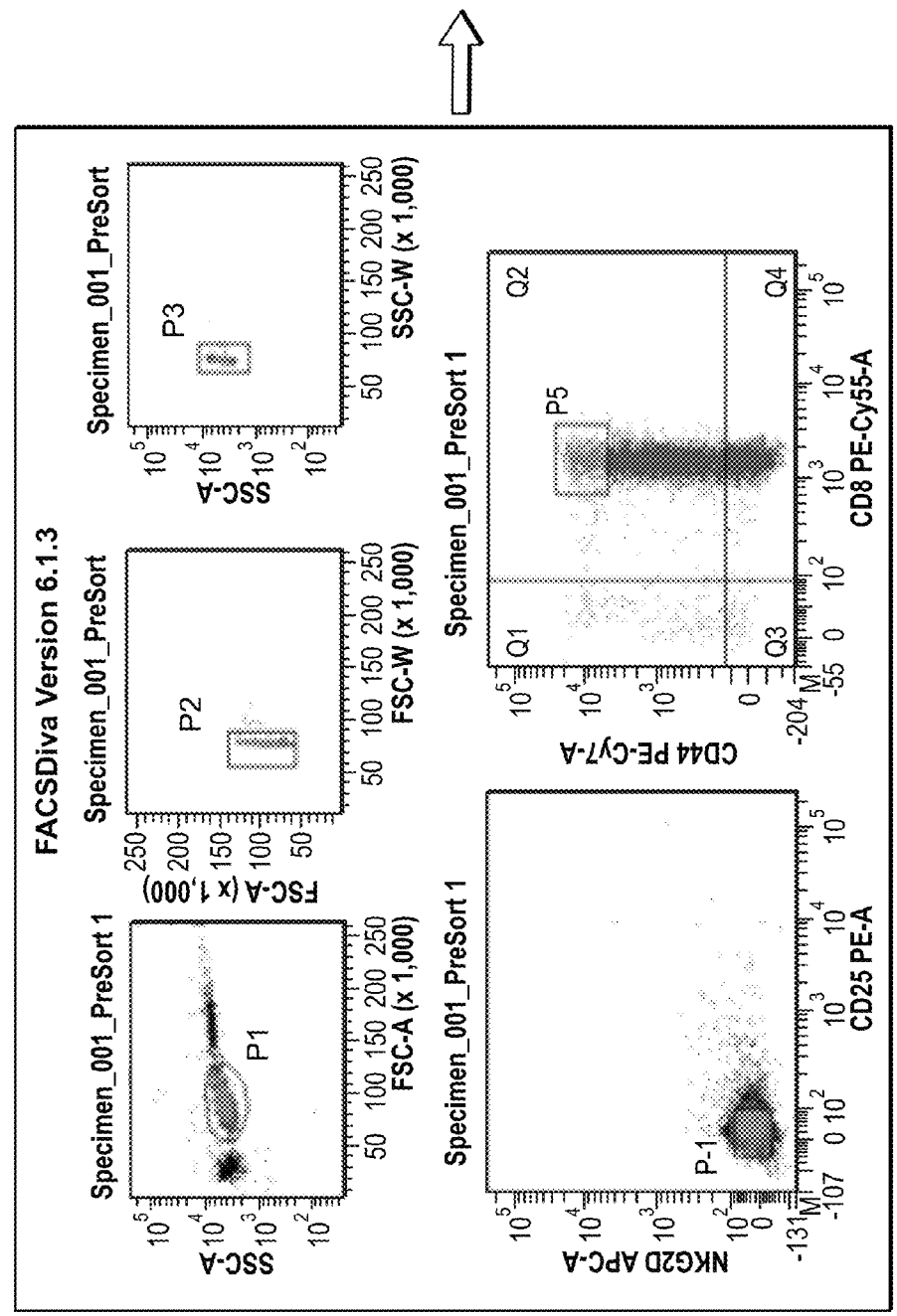
Figures 2, 77A:
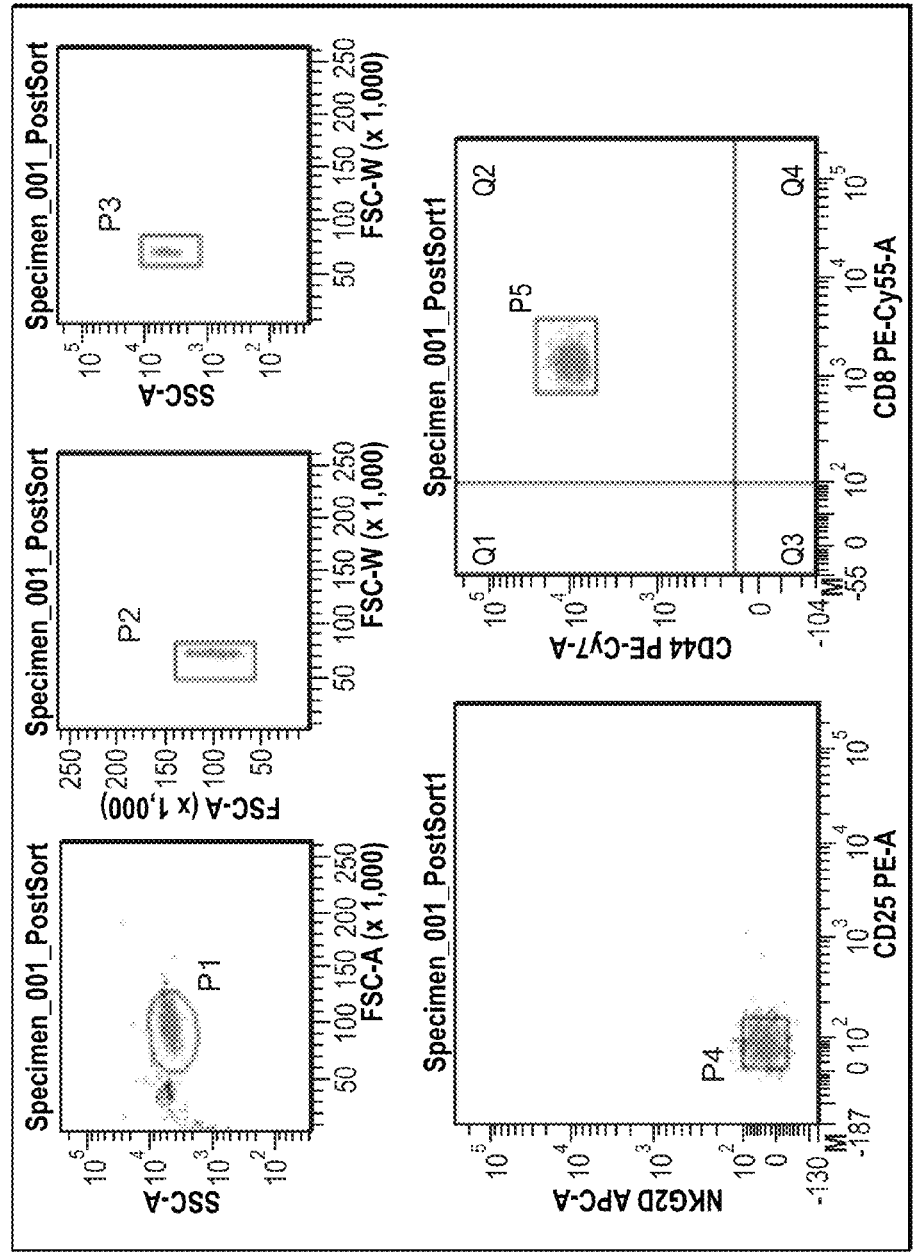
Figures 1, 77B:
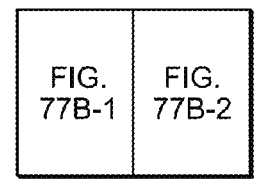
Figure 77B:
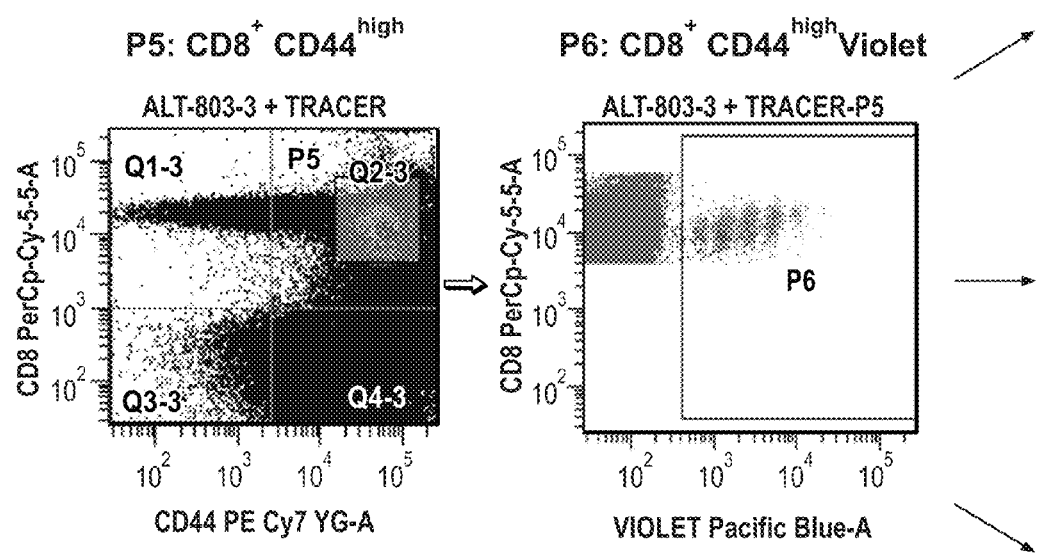

A recent study also showed that certain immunotherapies promote antigen-nonspecific expansion of memory CD8$^+$ T cells with innate-type cell receptors (Tietze et al., Blood, 119: 3073-3083, 2012). Unlike the memory CD8$^+$ T cells stimulated by antigen-dependent TCR signaling which up-regulate PD-1 and CD25 cell surface molecules, the immunotherapy-mediated expanded memory CD8$^+$ T cells express NKG2D, granzyme B, and possess broadly antigen-nonspecific lytic capability. Interestingly, it was found that the splenic memory CD8$^+$ T cells expanded in vivo by ALT-803 treatment also expressed NKG2D and not CD25 or PD-1 (FIG. 76B). To examine ALT-803-mediated changes in this cell population, CD3$^+$ enriched cells were isolated from spleens and lymph nodes of C57BL/6NHsd mice and labeled them with Celltrace™ Violet, and then adoptively transferred these cells into syngeneic recipients. Two days after transfer, the mice were treated with PBS or ALT-803 (0.02 mg/kg or 0.2 mg/kg) and the phenotype and proliferation of the adoptively transferred cells were examined 4 days later. As shown in FIG. 76C, ALT-803 treatment resulted in a significant, dose-dependent increase in proliferation of donor CD8$^+$CD44$^{high}$ T cells isolated from spleens of recipient mice, whereas donor memory CD8$^+$ T cells did not proliferate in PBS-treated mice. In the expanded memory CD8$^+$ T-cell population from 0.2 mg/kg ALT-803 treated mice, over 90% expressed NKG2D with increased positive staining in cells that underwent multiple rounds of proliferation. To rule out the possibility that this is due to an enormous expansion of a small population of NKG2D$^+$ cells following ALT-803 treatment, similar adoptive transfer studies with sorted NKG2D$^{neg}$CD25$^{neg}$CD8$^+$CD44$^{high}$ T cells labeled with Celltrace™ Violet were conducted. Treatment of recipient mice with 0.2 mg/kg ALT-803 caused an increase in NKG2D$^+$ memory CD8$^+$ T cells from 0% to 13% (FIG. 76D; see gating strategy in FIG. 77A-1, FIG. 77A-2, FIG. 77B-1, and FIG. 77B-2). Thus, ALT-803 treatment not only induced the proliferation of the memory CD8$^+$ T cells but also up-regulated the NKG2D receptor on their surface. Donor memory CD8$^+$ T cell expressing CD25 also proliferated following ALT-803 treatment but the percentage of these cells (~4%) was the same in ALT-803- and PBS-treated mice, consistent with the findings in 5T33P tumor-bearing mice.

Figure 78A:
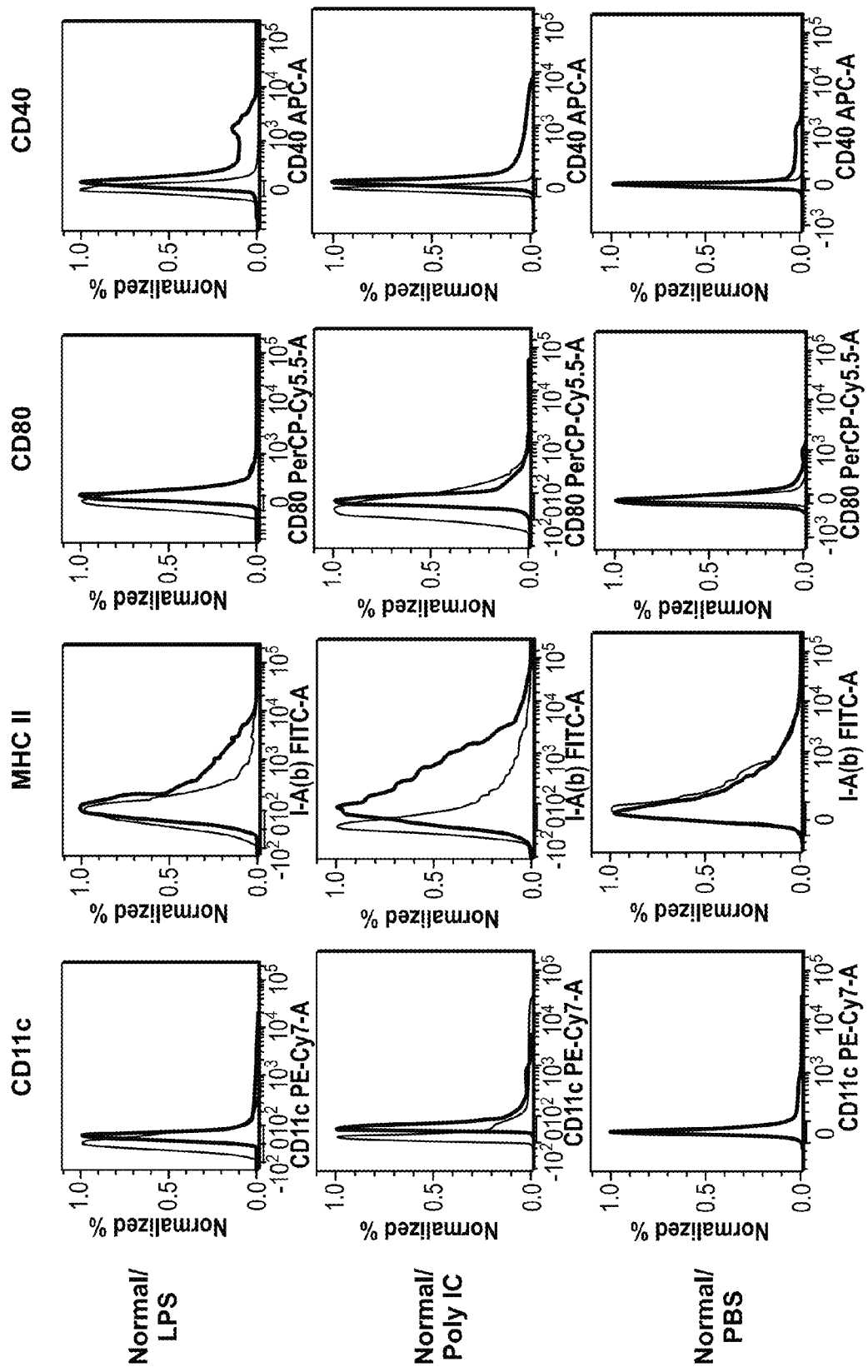
FIG. 78A and FIG. 78B shows that ALT-803 did not increase expression maturation markers on BM dendritic cells. Female C57BL/6NHsd mice (5-6 weeks-old, 3 mice/group) were untreated (normal) or injected i.v. with 5T33P myeloma cells (1×10$^7$/mouse) (5T33P-bearing) on day 0. ALT-803 (0.2 mg/kg) or PBS (dose volume equivalent) was administered i.v. on day 14. Four days after treatment, BM cells were isolated, pooled and stained with Abs specific to CD11c (PE-Cy7), MHC II [I-A(b)] (FITC), CD80 (PerCP-Cy5.5), and CD40 (APC), then analyzed by flow cytometry. Mice treated i.p. either with 12.5 µg of LPS (*E. coli* O55:B5, Sigma-Aldrich) and sacrificed 12 hrs later or with 10 µg of Poly IC (InvivoGene) and sacrificed 24 hrs later served as positive controls. Histograms show staining with positive Abs (black line) or isotype controls (gray line).
Figure 78B:
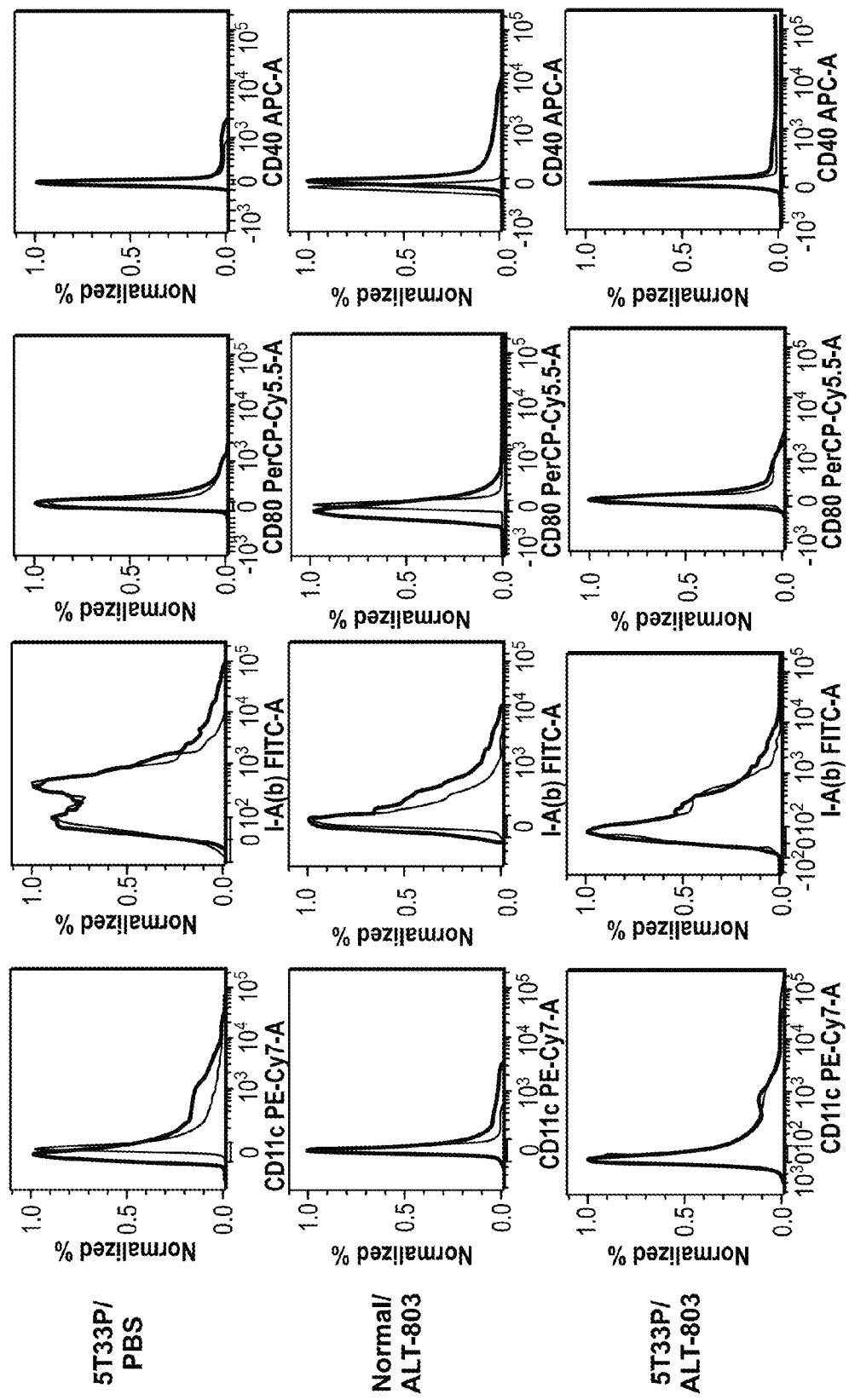

To assess whether the induced CD8$^+$ T cell responses were associated with changes in antigen presentation potential in vivo, ALT-803 (0.2 mg/kg), LPS (12.5 μg/mouse) or poly IC (10 μg/mouse) was administered to normal and 5T33P-bearing C57BL/6NHsd mice and examined the up-regulation of activation/maturation markers on BM dendritic cells (DCs). ALT-803, unlike poly IC or LPS, did not increase MHC II (I-A$^b$), CD80 or CD40 levels on BM DCs (FIG. 78A and FIG. 78B). Similar results were found for splenic DCs. Thus, the rapid expansion of CD8$^+$CD44$^{high}$ memory T-cell population stimulated by ALT-803 is unlikely a result of increased antigen-specific responses, consistent with the results of others demonstrating antigen-independent activation of innate-type memory T cells following immunotherapy or microbial or viral infection.

Figure 79A:
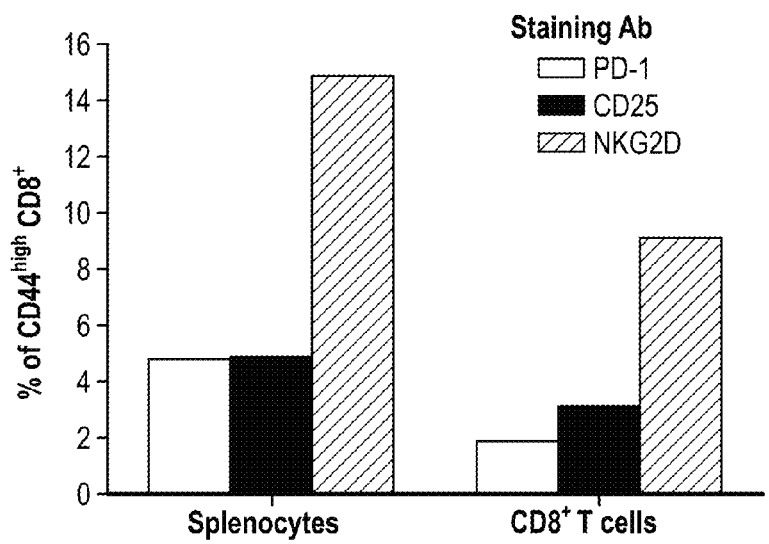
FIG. 79A-FIG. 79D are graphs showing the in vitro cytotoxic activity of ALT-803-treated immune cells.
Figure 79B:
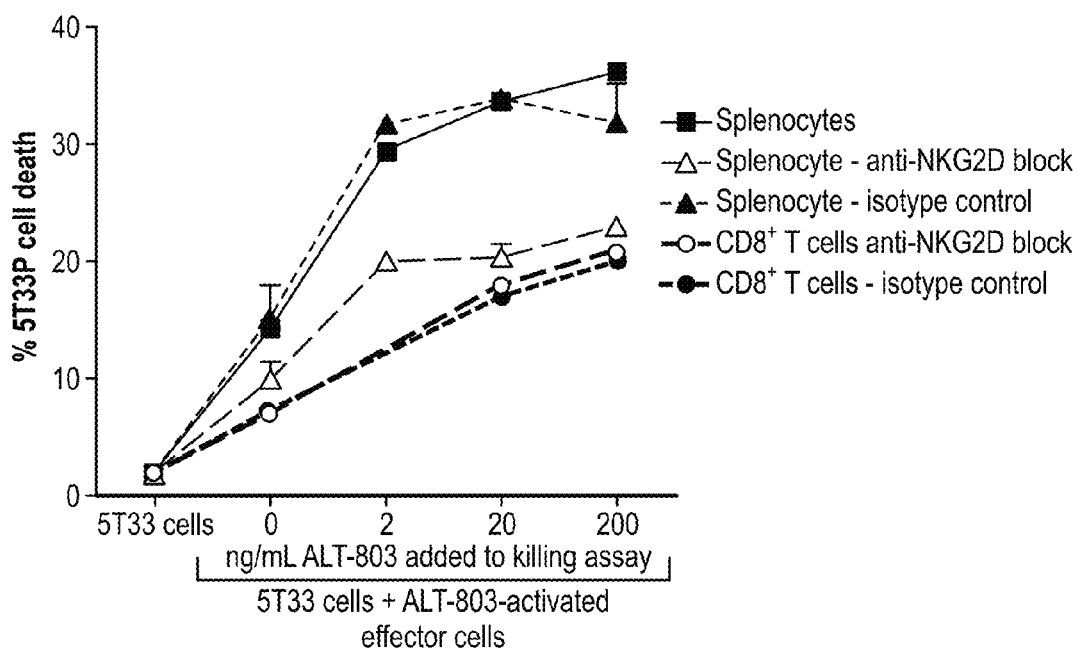
Figure 79C:
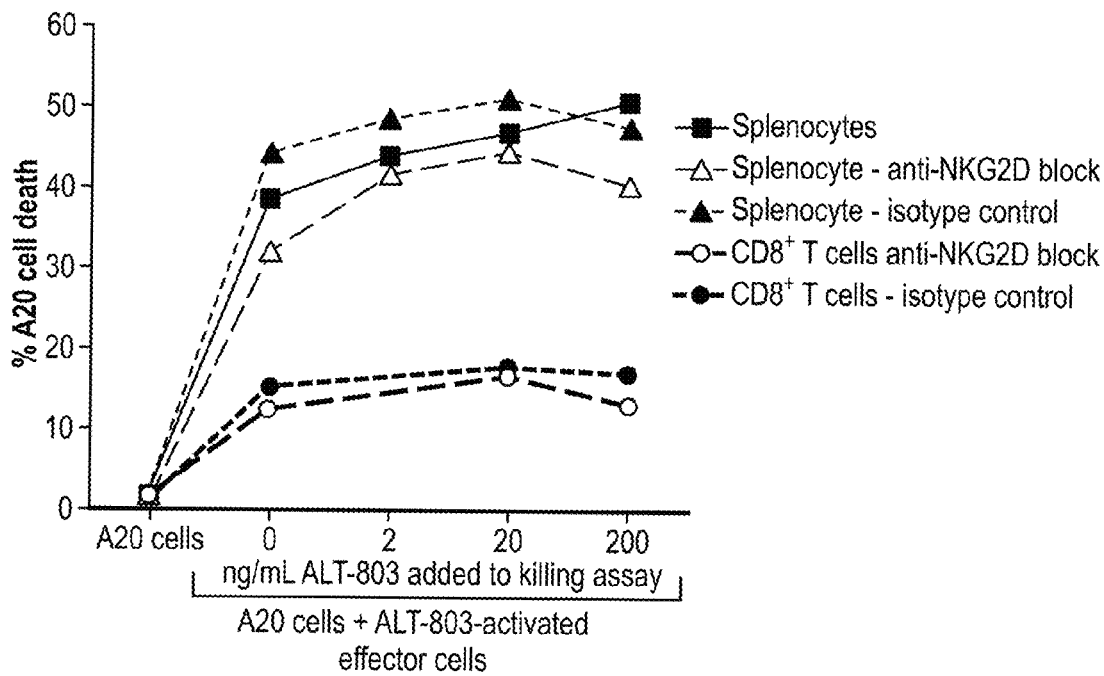
Figure 79D:
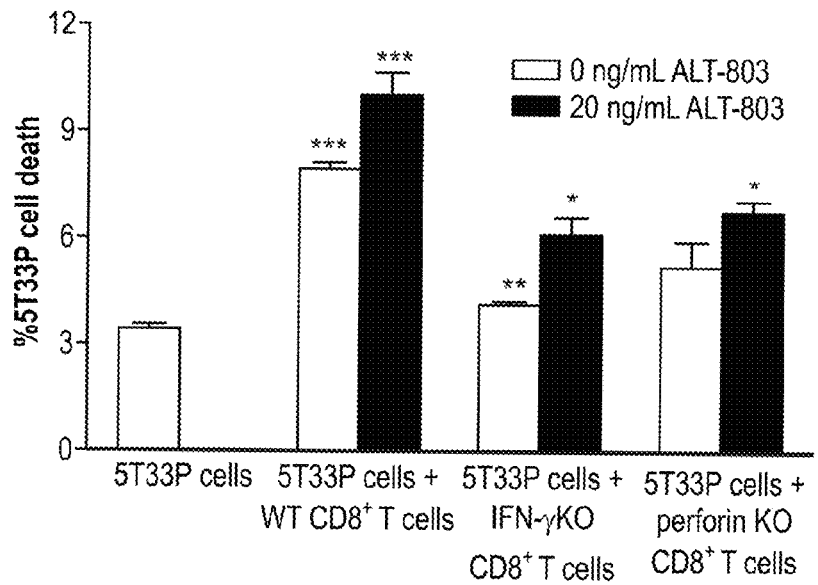

The cytotoxic activity of ALT-803-treated immune cells was also examined in vitro. CD8$^+$CD44$^{high}$ T cells increased 5-fold in splenocytes and 3-fold in CD8$^+$ enriched splenic T cells from normal C57BL/6NHsd mice following a 3-day incubation with 0.2 μg/mL ALT-803. Similar to the findings in vivo, up-regulation of NKG2D but not CD25 or PD-1 was observed on memory CD8$^+$ T cells following ALT-803 incubation (FIG. 79A). The ALT-803-stimulated splenocytes and CD8$^+$ enriched splenic T cells exhibited elevated cytolytic activity against 5T33P cells (FIG. 79B) as well as A20 lymphoma cell lines (FIG. 79C). Killing of 5T33P cells was further enhanced by inclusion of ALT-803 during the cytotoxicity assay, suggesting a continued activation of immune cell anti-tumor activity by ALT-803. Interestingly, 5T33P myeloma-targeted cytotoxicity of ALT-803-stimulated CD8$^+$ enriched splenocytes was not affected by inclusion of an NKG2D blocking antibody, whereas this antibody reduced 5T33P killing by whole splenocyte cultures (FIG. 79B). These results suggest that in vitro cytotoxicity of the NK cells in the whole splenocyte cultures are dependent on NKG2D whereas that of CD8$^+$ T cells does not require NKG2D, but may be mediated through other innate-like activating receptors induced by ALT-803. The cytotoxicity of CD8$^+$ T cells was partially dependent of perforin expression since CD8$^+$ T cells obtained from perforin knock-out mice showed reduced 5T33P cell killing in this assay (FIG. 79D).

Overall, these studies indicate that ALT-803 potently induces CD8$^+$CD44$^{high}$ T cells and up-regulates innate-cell receptor NKG2D without the requirement of antigen-specific stimulation. Also, this type of ALT-803-stimulated CD8$^+$ memory T cells exhibit cytotoxic activity against myeloma and other tumor cells.

Example 26

Figure 80A:
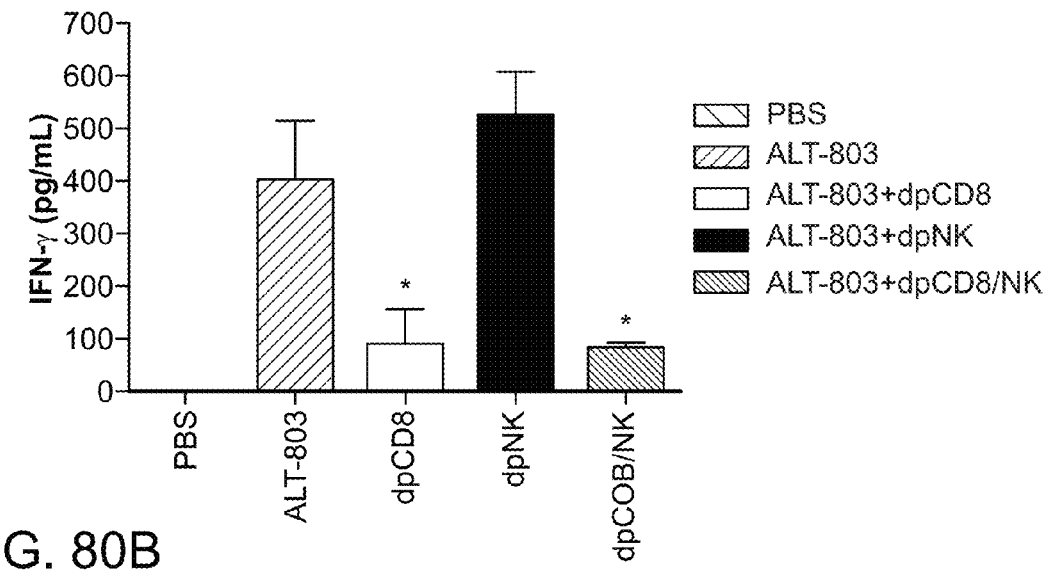
FIG. 80A-FIG. 80C show that CD8$^+$ T cell production of IFN-γ plays a role in ALT-803-mediated efficacy.
Figure 80B:
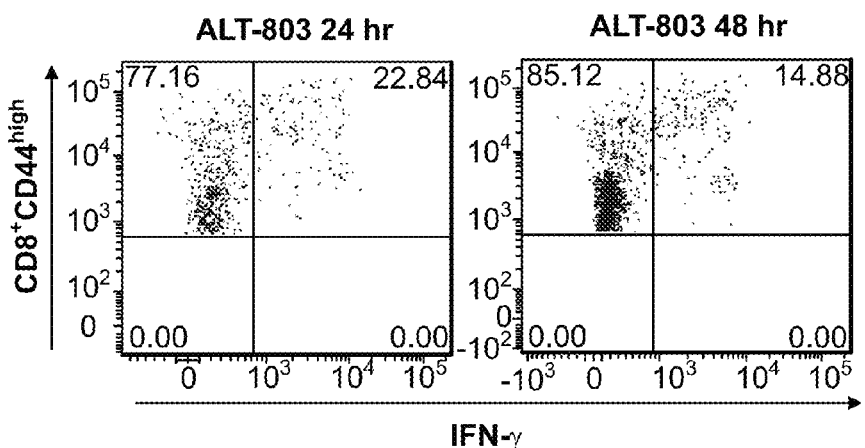

Serum IFN-γ is Elevated by ALT-803 Treatment in a CD8$^+$ T Cell-Dependent Manner and is Required for ALT-803-Mediated Efficacy In addition to stimulating immune cells, a single dose of ALT-803 to C57BL/6NHsd mice was found to significantly increase serum IFN-γ levels (FIG. 80A). Immune-depletion studies were then carried out to identify the immune cell type responsible for IFN-γ production after ALT-803 treatment. As shown in FIG. 80A, depletion of CD8$^+$ T cells, but not NK1.1$^+$ cells, eliminated most of the high-level expression of serum IFN-γ, indicating that CD8$^+$ T cells were the dominant source of ALT-803-induced IFN-γ. To further determine whether CD8$^+$CD44$^{high}$ memory or CD8$^+$CD44$^{low}$ naïve T cells were the primary producers of IFN-γ after ALT-803 treatment, IFN-γ production of splenic CD8$^+$ T cells from ALT-803-treated mice were analyzed. Intracellular IFN-γ was detectable as early as 12 hours after ALT-803 treatment in the CD8$^+$CD44$^{high}$ memory T-cell population and the percentage of IFN-γ producing memory T cells continued to remain elevated for at least 48 hrs after ALT-803 treatment (FIG. 80B). Significant ALT-803-mediated induction of intracellular IFN-γ was not observed in CD8$^+$CD44$^{low}$ naïve T cells. Thus, ALT-803 activates CD8$^+$CD44$^{high}$ memory T cells to proliferate and secrete IFN-γ via an antigen-independent pathway.

Figure 80C:
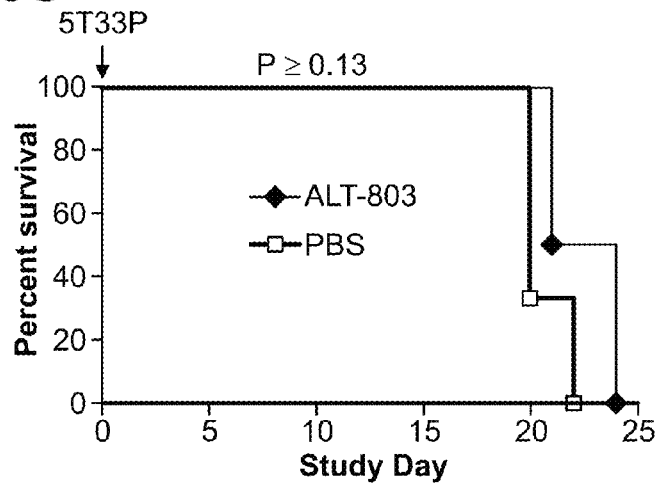

To determine whether induced IFN-γ plays a role in the anti-myeloma activity of ALT-803, treatment effects on survival were evaluated in IFN-γ KO B6 mice bearing 5T33P cells. Similar to the findings in myeloma-bearing C57BL/6NHsd mice following CD8$^+$ T cells depletion, ALT-803 treatment provided little or no protection from mortality to IFN-γ KO mice after 5T33P cell inoculation, indicating IFN-γ is required for ALT-803 efficacy (FIG. 80C). However, IFN-γ had no direct effect on 5T33P cell growth or apoptosis in vitro (FIG. 74), consistent with previous reports. These results support a mechanism where ALT-803 activates IFN-γ production and cytotoxic activity of CD8$^+$ memory T cells and together these responses promote rapid elimination of myeloma cells and prolonged survival of tumor bearing mice.

Figure 81A:
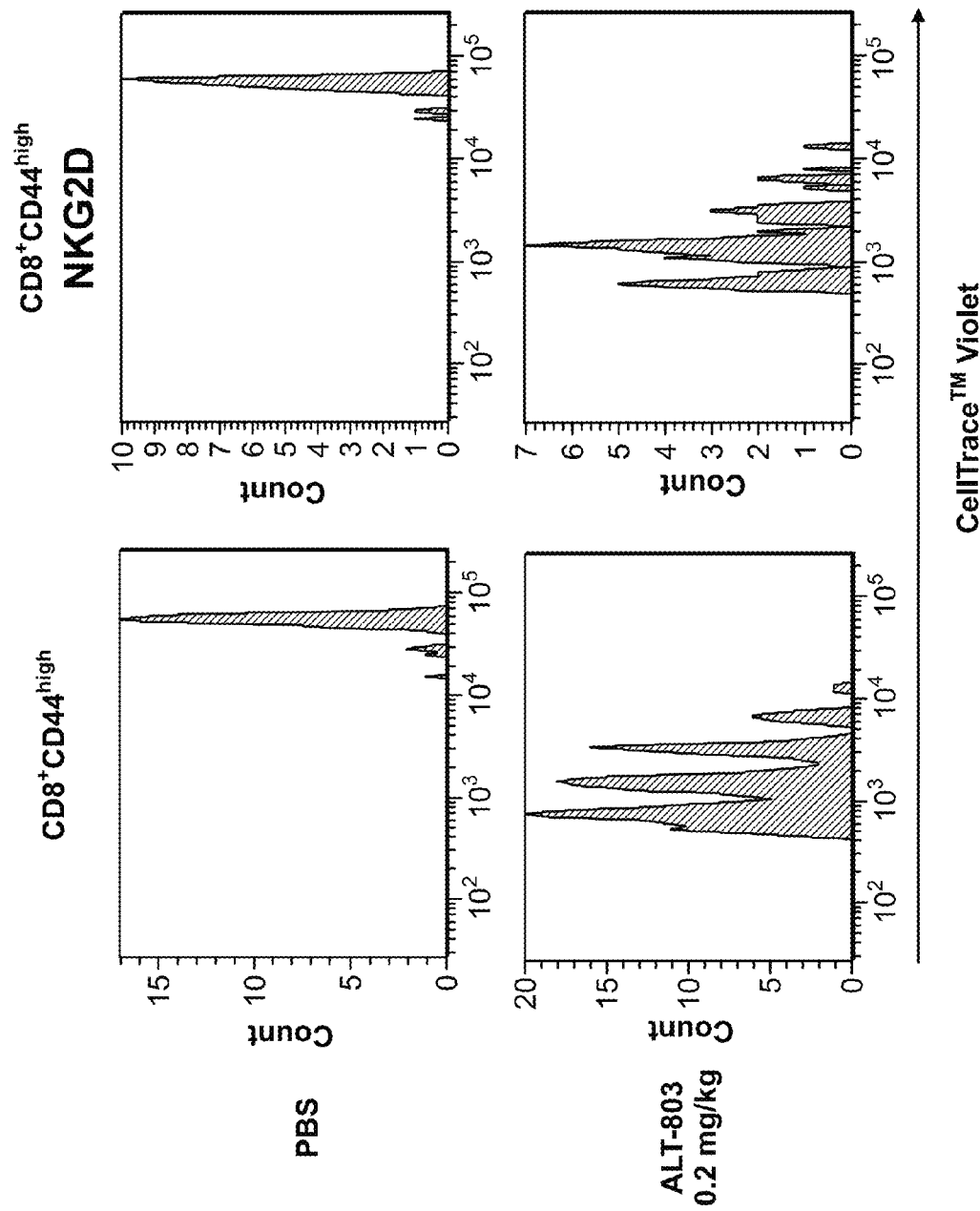
In FIG. 81A and FIG. 81B, ALT-803 induction of CD8$^+$ CD44$^{high}$ memory T cell responses was not dependent on IFN-γ.
Figure 81B:
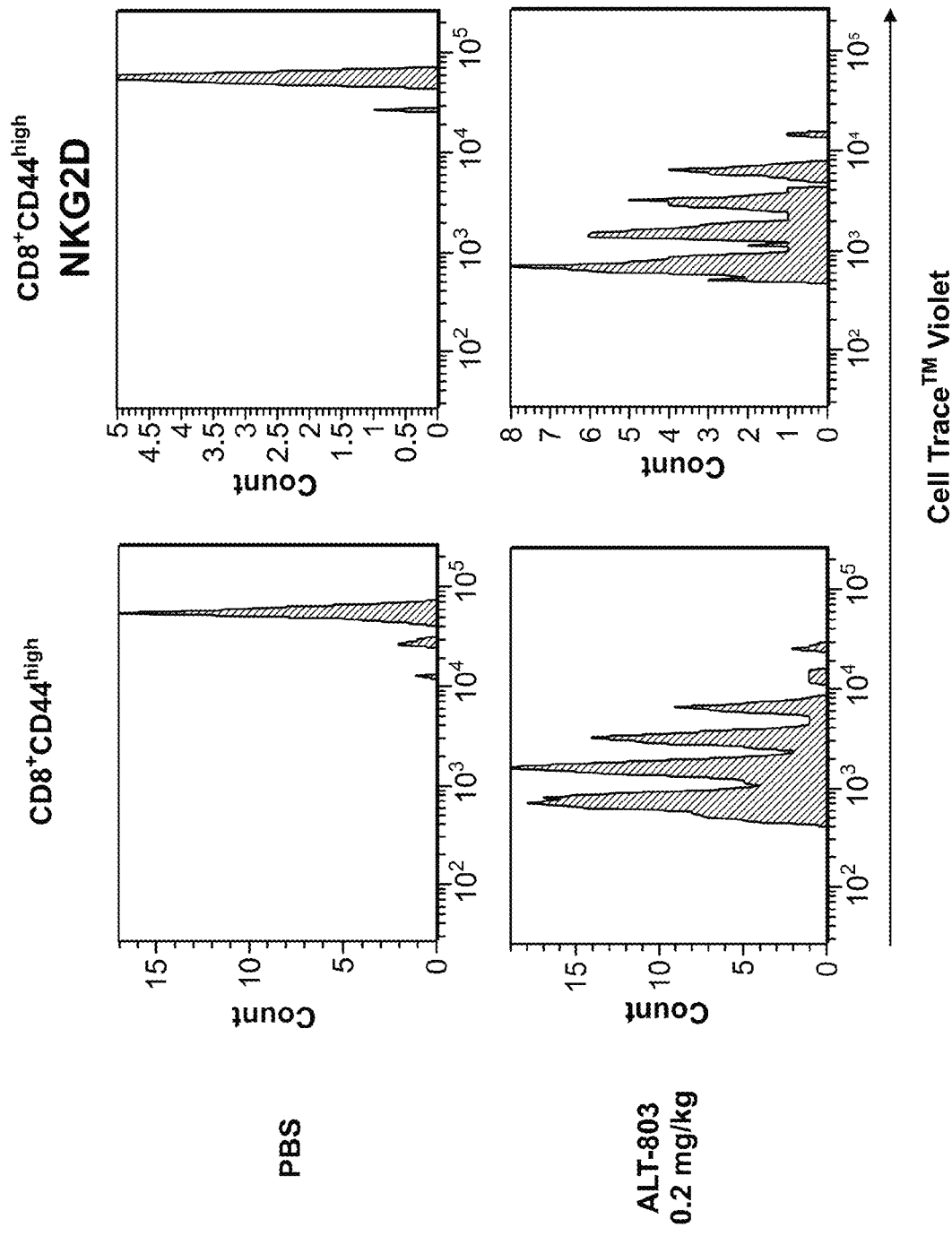

To assess whether IFN-γ is needed for ALT-803-mediated effects on CD8$^+$ memory T-cell responses, adoptive cell transfer studies were conducted using donor Celltrace™ Violet-labeled CD8$^+$ T cells from IFN-γ KO mice transferred into IFN-γ KO and wild-type recipient mice. As shown in FIG. 81, ALT-803 treatment of IFN-γ KO or wild-type recipients induced comparable CD8$^+$CD44$^{high}$ memory T-cell proliferation and up-regulation of NKG2D of the adoptively-transferred cells. This indicates that ALT-803-induced CD8$^+$CD44$^{high}$ memory T cell responses were IFN-γ independent. Interestingly, CD8$^+$ T cells isolated from IFN-γ KO mice exhibited less ALT-803-stimulated in vitro cytotoxic activity against 5T33P cells than was observed in CD8$^+$ T cells from normal C57BL/6NHsd mice. Without wishing to be bound by theory, together, these results suggest that while IFN-γ is not required for ALT-803-mediated activation and expansion of CD8$^+$ memory T cells, it still plays a role in augmenting the cytotoxicity of these cells against tumors via an as yet undetermined mechanism.

IL-15 and IL-15Rα are co-expressed and form a protein complex in antigen-presenting cells for trans-presentation to T and NK cells. Studies have shown that soluble IL-15:IL-15Rα complexes exhibit a 50 fold better immune stimulatory activity in vivo than IL-15 alone and potent efficacy against solid and metastatic tumors in various mouse models; however, its activity against hematologic tumors has not been reported. In this study, the anti-myeloma activity and mechanism-of-action of ALT-803, a protein complex consisting of an IL-15 super-agonist mutant associated with a dimeric IL-15Rα/Fc fusion protein, is described. As reported herein, a single dose of ALT-803 was much more effective than IL-15 at reducing the levels of well-established murine 5T33P and MOPC-315P myeloma cells in the BM of tumor-bearing immunocompetent mice. ALT-803 was also found to prolong survival of 5T33P and MOPC-315P tumor-bearing mice and effectively cured a majority of the mice of tumors. Moreover, 5T33P-bearing mice cured by prior ALT-803 treatment were protected against subsequent 5T33P rechallenge, indicating that ALT-803-mediated the induction of long lasting anti-myeloma immune memory responses. These results are consistent with the finding that ALT-803 exhibited significantly better activity compared to IL-15 in stimulating NK cell and CD8+ T-cell responses in vivo (Han et. al., Cytokine, 56: 804-810, 2011). This enhanced immunostimulatory activity is likely the result of a combination of the increased in vivo half-life of ALT-803 compared to IL-15 (25 h vs. <40 min) and the dimeric nature of the cytokine domain in the complex increasing its binding avidity to IL-15Rβγ$_c$ (Han et. al., Cytokine, 56: 804-810, 2011). Without wishing to be bound by theory, it is also possible that the Fc domain of the complex enables trans-presentation of the cytokine to IL-15Rβγ$_c$ receptor-bearing NK and T cells via binding to the Fc-γ receptors (FcγR) on the surface of dendritic cells, macrophages, NK cells and other cell types. An FcγR-binding deficient derivative of ALT-803 was recently generated to further evaluate the contribution of the Fc-γ domain to ALT-803-mediated immune stimulation.

Previous studies have shown that IL-15 and IL-15:IL-15Rα complexes can stimulate anti-tumor activity via either effector NK cells or T cells, demonstrating the remarkable capacity of IL-15 to induce different effector cell responses against diverse tumor types and tumor microenvironments. In the 5T33P myeloma model reported here, treatment with ALT-803 resulted in an increase in CD8+ T-cell levels in the BM of tumor-bearing mice that correlated with the complex's ability to reduce BM 5T33P-cell burden. However, systemic depletion of CD8+ T cells, but not NK1.1+ cells, was shown to largely eliminate the anti-tumor activity of ALT-803 on BM myeloma cells, the treatment-related survival benefit in 5T33P-bearing mice. This indicates that CD8+ T cells, but not NK1.1+ cells, play a pivotal role in ALT-803 anti-myeloma activity. This finding is perplexing since it was found that a single i.v. treatment of ALT-803 (0.2 mg/kg) had a marked effect on 5T33P cells in the BM of mice with well-established tumors, providing >90% reduction in BM IgG2b+ myeloma cells four days after treatment. Such a robust and rapid onset of immune responses is generally believed to only be associated with the innate immune system. Additionally, a single dose of ALT-803 was capable of inducing high serum levels of IFN-γ and promoting the proliferation of CD8+ cells in non-tumor bearing mice shortly after treatment. The source of serum IFN-γ was largely from CD8+CD44$^{high}$ T cells, not NK1.1+ cells, based on our immune-depletion analysis. Therefore, it was questioned whether the activation of CD8+ T cells and subsequent anti-tumor activity mediated by ALT-803 was antigen-dependent. To address this, ALT-803 induced dendritic cell activation/maturation was examined. ALT-803 treatment did not up-regulate CD86, CD80, MHC-II and CD40 in splenic DCs from either tumor- or non-tumor-bearing mice suggested that ALT-803 did not promote antigen presentation at the initial phase of the immune response. Thus, it appears unlikely that antigen-dependent clonal expansion of naïve CD8+ T cells immediately after ALT-803 treatment is responsible for the potent anti-myeloma activity observed in mice bearing established 5T33P and MOPC-315P tumors.

The proliferation of memory-phenotype (CD44$^{high}$) CD8+ T cells, but not naïve CD8+ T cells, can be induced in vivo by the cytokines IL-12, IL-18 and IFN-γ, most likely via production of IL-15, or directly by IL-15. A recent study also showed that cytokine-mediated stimulation could promote antigen-nonspecific expansion of memory CD8+ T cells with a unique phenotype. Unlike TCR signaling that up-regulates PD-1 and CD25 surface markers on memory CD8+ T cells, treatment with IL-2 in combination with anti-CD40 antibody resulted in expansion of memory CD8+ T cells that express NKG2D, granzyme B, and possess broad lytic capabilities. These cells have been suggested to be responsible for the dramatic anti-tumor effects of this therapy in animal models. Herein, using the adoptive-cell transfer approach, ALT-803 alone could also induce CD8+CD44$^{high}$ memory T cells, but not naïve T cells, to acquire innate cell receptors, such as NKG2D, without inducing PD-1, in vitro and in vivo. ALT-803 appears to act by both inducing CD8+ memory T cell proliferation and up-regulating NKG2D expression rather than preferentially expanding pre-existing CD8+CD44$^{high}$ memory T cells carrying this receptor. In vitro, the ALT-803-activated CD8+CD44$^{high}$ memory T cells exhibited antigen-nonspecific and potent anti-tumor activity against 5T33P myeloma. Due to the presence of the large numbers of the CD8+CD44$^{high}$ memory T cells after ALT-803 treatment with an innate-like phenotype and their high anti-tumor activity, it is conceivable that these cells represented the main effector cells responsible for mounting robust and rapid immune responses against myeloma in the initial phase after ALT-803 infusion.

A single dose of ALT-803 was capable of inducing high serum levels of IFN-γ in mice. This activity appeared to be different from that in previous studies in which monotherapy with IL-15 or single-chain IL-15:IL-15Rα complexes was shown to induce mouse immune cell proliferation, but not to affect serum IFN-γ levels. IL-15 has been reported to elevate IFN-γ levels in vivo when co-administered with IL-12, IL-18 or other immune-stimulatory molecules via a cytokine feedback cascade involving NK cells and macrophages. In contrast, the effect of ALT-803 on serum IFN-γ levels was largely dependent on CD8+CD44$^{high}$ memory T cells and not NK1.1+ cells. It has been found that treatment of mice with IL-15:IL-15Rα/Fc complexes similar to ALT-803 can cause naïve CD8+ T cells to expand and acquire an activated phenotype that includes the ability to secrete IFN-γ and mediate antigen-specific cytolytic function. These responses were dependent on MHC class I molecules, TCR avidity and were enhanced in the presence of peptide antigen, suggesting that IL-15:IL-15Rα/Fc complexes increase the sensitivity and responsiveness of naïve CD8+ T cells to endogenous antigen presentation. In contrast, ALT-803 has the unique feature of inducing high levels of serum IFN-γ by activating CD8+ memory T cells in an antigen-independent fashion in vivo. Although IFN-γ has no direct effects on growth or induction of apoptosis of 5T33P tumor cells in vitro as shown in this study, the loss of treatment-mediated anti-myeloma activity in the IFN-γ KO mice bearing 5T33 tumors demonstrates the pivotal role of IFN-γ in the therapeutic potency of ALT-803. The effect of IFN-γ on ALT-803 anti-tumor activity is apparently via an indirect mechanism since ALT-803 did not lose its ability to induce IFN-γ-deficient CD8+CD44$^{high}$ memory T cells in IFN-γ KO mice.

IFN-γ is a remarkable cytokine that orchestrates a diverse array of cellular programs through transcriptional regulation of immunologically relevant genes. IFN-γ skews the immune response toward a Th1 phenotype by inducing T-bet, a critical transcription factor of Th1 cells, which directly induces many Th1 cell-related genes, but indirectly suppresses the Th2 cell-related genes. IFN-γ also orchestrates the trafficking of specific immune cells to sites of inflammation (e.g., tumor sites) through up-regulating expression of adhesion molecules (e.g., ICAM-1, VCAM-1) and chemokines (e.g., IP-10, MCP-1, MIG-1α/β, RANTES) (35-42). Thus, the loss of IFN-γ could lead to the loss of the Th1 cell-type anti-tumor environment and the inability to up-regulate the necessary chemokine receptors and/or adhesion molecules on the ALT-803-activated CD8+CD44$^{high}$ T cells for trafficking to the tumor site. In addition, IFN-γ is a potent activator of macrophage which kill pathogens and tumor cells by producing reactive oxygen species and reactive nitrogen intermediates via induction of NADPH oxidase system and INOS. IFN-γ is also known to repolarize the stage M2 tumor-promoting tumor-associated macrophages (TAMs) to M1 tumor-destroying macrophages at the tumor sites, which in turn could mount an effective immune response against tumors (46, 47). Thus, IFN-γ secreted by ALT-803-activated memory T cells could significantly contribute to the anti-tumor potency of ALT-803 by directly activating macrophages to enhance their tumor-killing activities or to repolarize the TAMs for tumor destruction.

In summary, these results demonstrate the novel mechanism of action of ALT-803, an IL-15 super-agonist complex, against multiple myeloma that acts mainly through its stimulation of $CD8^+CD44^{high}$ memory T cells to expand, acquire an innate-type phenotype and secrete IFN-γ independent of antigen requirement resulting in enhancement of host survival. These findings suggest a novel therapeutic strategy of exploiting the innate-cell function of adoptive immune cells. Thus, the present invention not only provides for treatment of multiple myeloma, but also for the treatment of other cancers and infectious diseases.

Example 27

Alt-803 is Effective Against Lymphoma

ALT-803 is a fusion protein complex consisting of the IL-15N72D superagonist and a dimeric IL-15 receptor alpha (IL-15Rα) sushi domain/IgG1 Fc fusion protein. Previous studies have shown that interleukin-15:interleukin-15 receptor alpha complex exhibits potent activity against murine melanoma in immunocompetent mice. The study described herein below is designed to test the effect of ALT-803 on primary tumor growth of murine EG7-OVA lymphoma in immunocompetent C57BL/6 mice.

To evaluate the effect of ALT-803 when administered via intravenous (i.v.) injection in multi-dose regimen on primary subcutaneous tumor growth of murine EG7-OVA lymphoma in C57BL/6 mice the following studies were carried out. Four treatment groups, ALT-803 (0.415 and 0.83 mg/kg), recombinant human interleukine-15 (rhIL-15, 0.06 mg/kg) and PBS (control), were examined in the study (Table 1). Female C57BL/6 mice (8-10 weeks old) were injected subcutaneously (s.c.) with EG7-OVA (1×106 cells in 100 µl PBS) on study day (SD) 0. PBS (n=5), rhIL-15 (n=5) or ALT-803 (n=5) were administered i.v. on SD 1, 4, 8, and 11 post EG7-OVA tumor cell injection. Tumors (width and length) were measured over the course of study. Tumor volume was the primary end point of the study.

TABLE 1

Experiment design

| Grp | Test article | Dosing (mg/kg) | n = | EG7-OVA Inj on | ALT-803 i.v. Inj on |
|---|---|---|---|---|---|
| 1 | PBS | — | 5 | SD 0 | SD 1, SD 4, SD 8, SD 11 |
| 2 | ALT-803 | 0.415 | 5 | SD 0 | SD 1, SD 4, SD 8, SD 11 |
| 3 | | 0.830 | 5 | SD 0 | SD 1, SD 4, SD 8, SD 11 |
| 4 | rhIL15 | 0.060 | 5 | SD 0 | SD 1, SD 4, SD 8, SD 11 |

Female C57BL/6 mice were injected s.c. with EG7-OVA (1×10⁶ cells/mouse) on study day 0. Tumor bearing mice (n=5) were treated with ALT-803 at 0.415 mg/kg and 0.83 mg/kg, or rhIL-15 at 0.06 mg/kg via intravenous administration through the lateral tail vein for a total of 4 injections on SD 1, SD 4, SD 8 and SD 11. Mice received PBS served as a control. During the study, mouse body weight and tumor width and length were measured and recorded.

Four ALT-803 i.v. treatments at 0.415 mg/kg and 0.83 mg/kg significantly inhibited tumor growth when compared with PBS control (P<0.001 and P<0.001, respectively), with Tumor Growth Inhibition (TGI) of 63.5% and 68.3%, respectively, over PBS More importantly, ALT-803 treatment at both 0.415 mg/kg and 0.83 mg/kg showed significantly better anti-tumor effects than rhIL-15 treatment (P<0.001 and P<0.01, respectively) with TGIs of 47.1% (0.415 mg/kg ALT-803) and 54.1% (0.83 mg/kg ALT-803) compared to rhIL-15 treatment. ALT-803 treatment did not cause significant body weight reduction, suggesting that the treatment regimens are safe.

Figure 82:
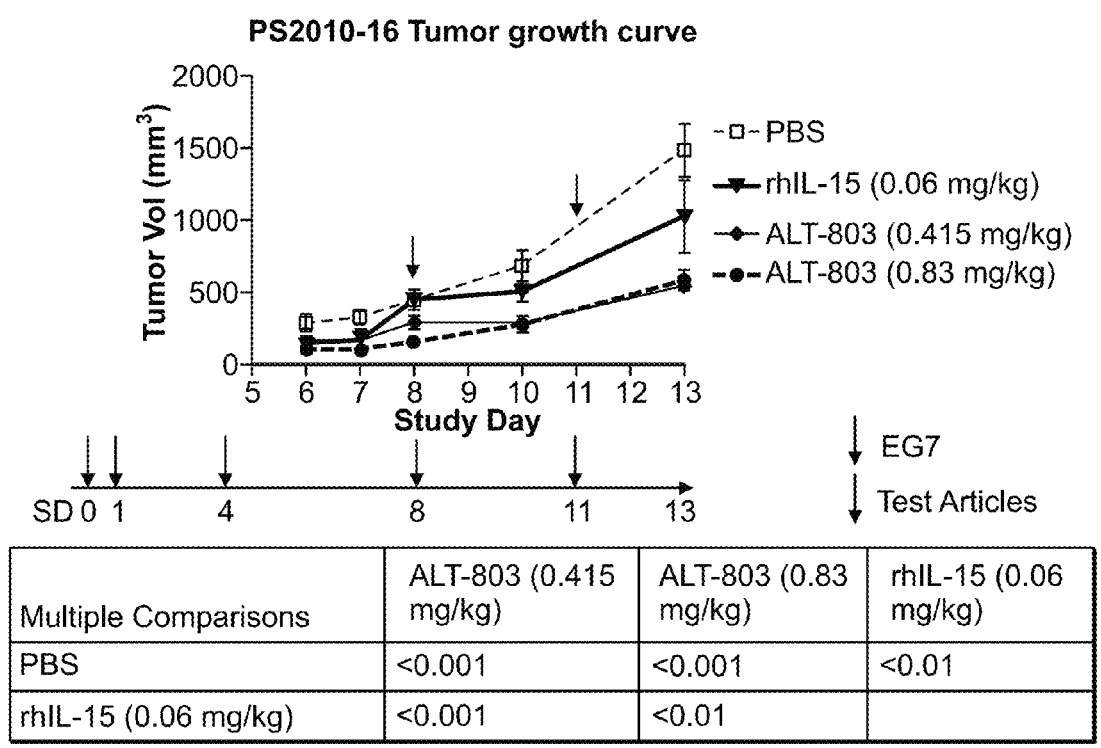
FIG. 82 shows a tumor growth curve. C57BL/6 mice (8-10 weeks old) (5 mice/group) were injected subcutaneously (s.c.) with EG7-OVA cells (1×106 cells/mouse) on study day 0. ALT-803 (0.415, or 0.83 mg/kg), rhIL-15 (0.06 mg/kg) or PBS was administered i.v. on 1, 4, 8, and 11 days post tumor cell injection. Tumor volumes were measured and the mean±SEM were plotted. Treatment with ALT-803 at the two dosing levels as well as rhIL-15 significantly inhibited EG7-OVA tumor growth. Two-way ANOVA data analyses are shown in the table beneath the graph.

The anti-tumor effect of ALT-803 intravenous treatment was evaluated in a mouse lymphoma model in immunocompetent C57BL/6 mice. C57BL/6 mice (8-10 weeks old) (n=5 mice/group) were injected s.c. with EG7-OVA cells (1×106 cells/mouse) on day 0. ALT-803 (0.415 or 0.83 mg/kg), rhIL-15 (0.06 mg/kg) or PBS (as a control) was administered i.v. on 1, 4, 8, and 11 days post tumor cell injection. Four i.v. administrations of ALT-803 significantly inhibited EG7-OVA primary tumor growth when compared with the PBS control (P<0.001) (FIG. 82). More importantly, ALT-803 treatment at either the 0.415 mg/kg and 0.83 mg/kg dose showed significant tumor growth inhibition when compared with rhIL-15 treatment (P<0.001, and P<0.01, respectively). In sum, Alt-803 significantly inhibited tumor growth (FIGS. 83A and 83B).

Example 28

ALT-803 Treatment Did not Significantly Affect Mouse Body Weight

Figure 84:
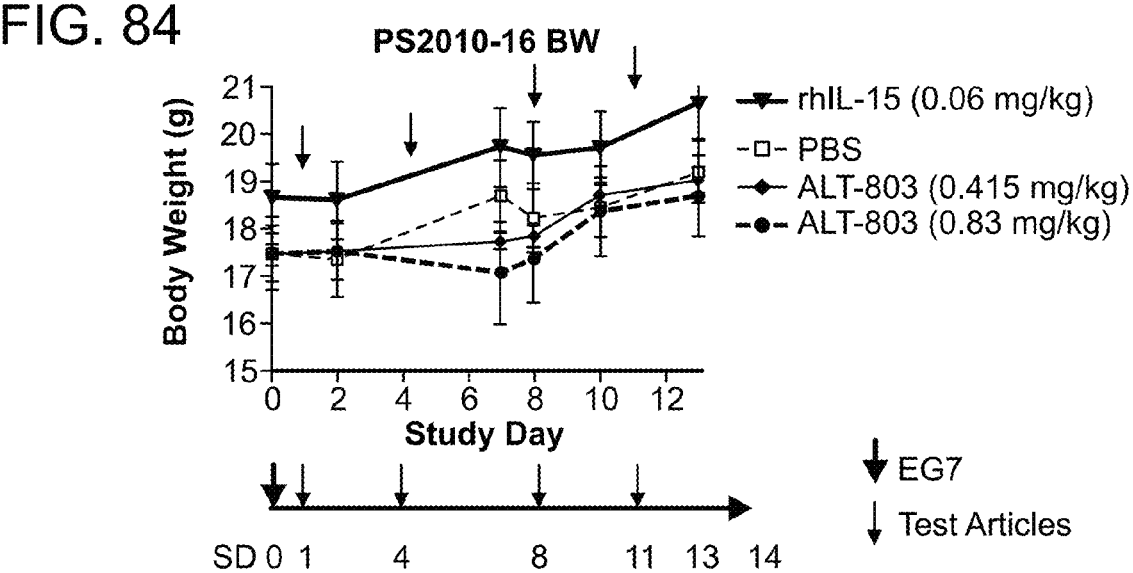
FIG. 84 is a graph showing that ALT-803 treatment did not cause mouse body weight reduction. EG7-OVA tumor bearing mice were treated with ALT-803 at 0.415 mg/kg or 0.83 mg/kg, or rhIL-15 at 0.06 mg/kg, along with PBS treatment as a control for 4 iv injections on 1, 4, 8, and 11 days post tumor cell injection.

ALT-803 treatment at the dose levels utilized did not cause significant mouse body weight reduction (FIG. 84), although ALT-803 at 0.83 mg/kg showed a transient body weight reduction after the 2nd injection. These data suggest that four ALT-803 i.v. treatments at 0.83 mg/kg were safe and efficacious in inhibiting murine EG7-OVA lymphoma primary tumor growth in C57BL/6 mice.

Example 29

Alt-803 Inhibited HIV Infection

Figure 85:
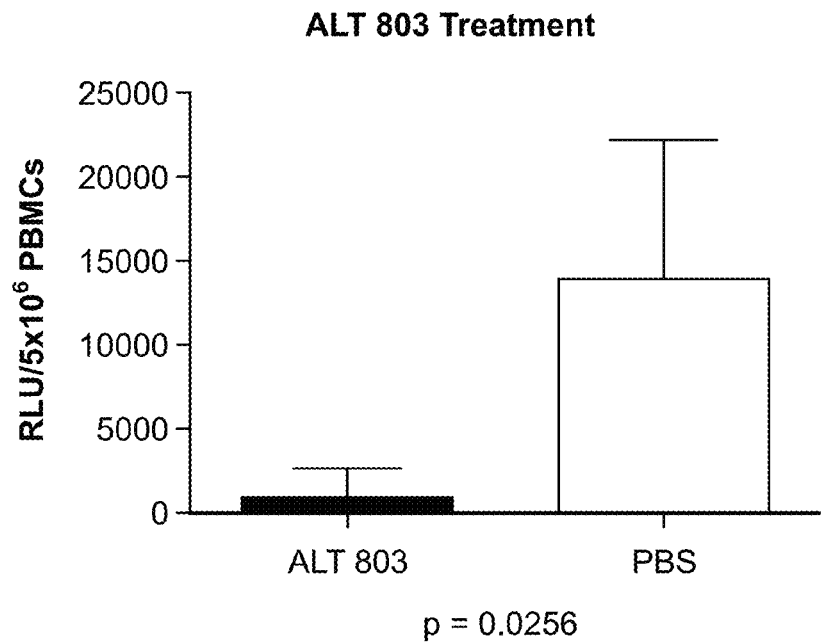
FIG. 85 shows that Alt-803 significantly inhibited HIV infection in an in vivo mouse model.

In the NSG mouse model, spleens were injected with human PBMC and replication competent HIV expressing luciferase. 16×10⁶ activated PBMCs were co-injected with replication-competent HIV that contains a luciferase reporter into NSG mouse spleens. 24 hours post injection, the mice were i.v. injected with either PBS (n=3) or 0.2 mg/kg of ALT-803 (n=4). One week later, the mice were sacrificed, the spleens were removed and splenic lysates were measured for luciferase activity. FIG. 85 shows that Alt-803 exhibited a high degree of inhibition of infection.

Example 30

Figure 87:
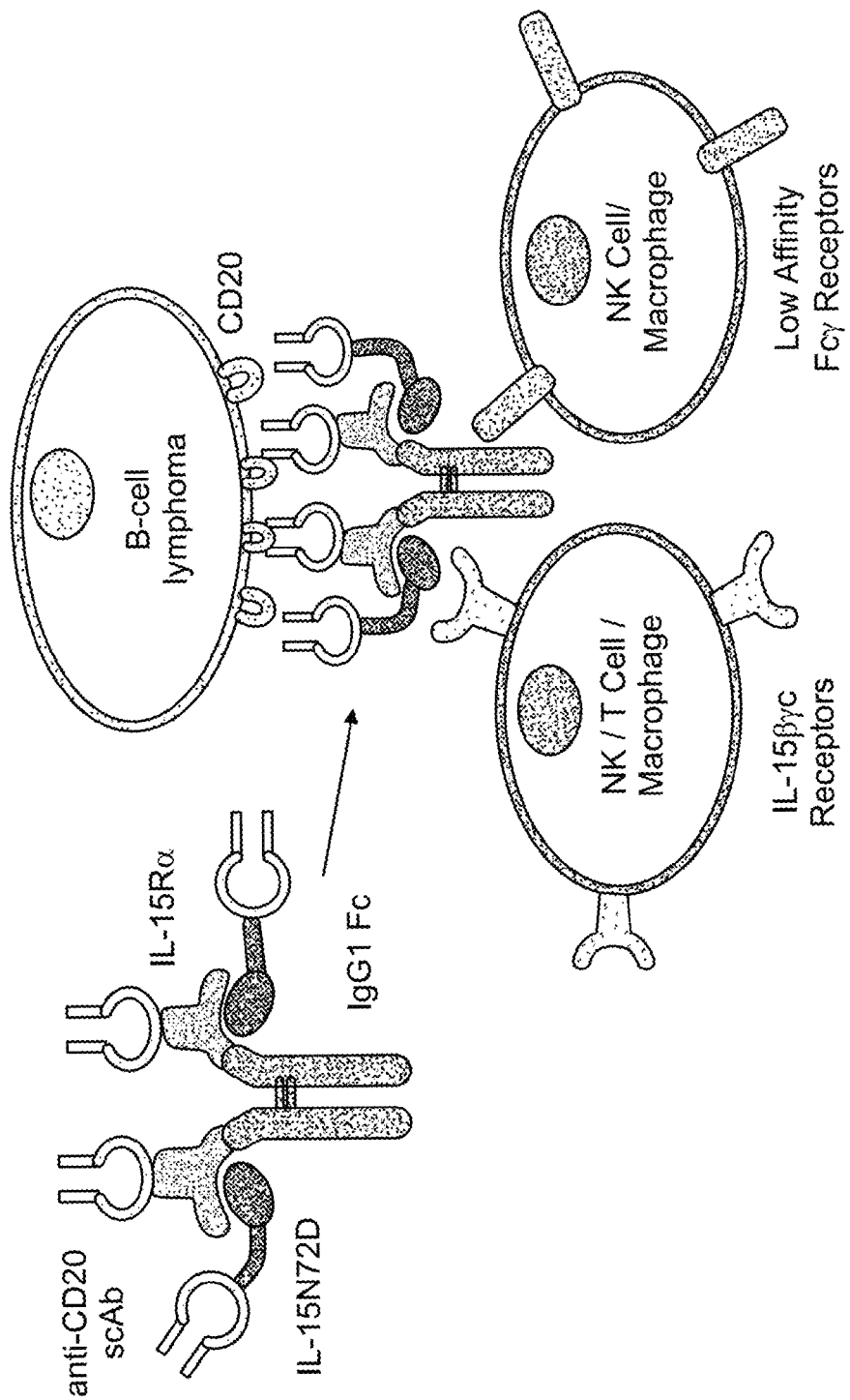
FIG. 87 depicts an anti-CD20 scFv/IL-15:anti-CD20 scFv/IL-15Rα/IgG Fc protein complex (2B8T2M) which comprises scFv anti-CD20 Ab domains linked to IL-15 and IL-15Rα/Fc domains. This complex mediates anti-B cell lymphoma activity through Fc-dependent ADCC and CDC and Fc-independent direct cell killing, and further enhances effector responses by IL-15 activation of IL-15Rβγc-bearing immune cells

CD20-Targeted IL-15N72D:IL-15Rα/Fc Fusion Protein Complexes (2B8T2M) have Anti-Lymphoma Activity As described herein, a scaffold comprising IL-15 and IL-15Rα/IgG Fc domains (Alt-803) was developed. Using this scaffold, novel cancer-targeted immunotherapeutic agents can be generated including those capable of binding CD20. Specifically, a fusion protein complex (2B8T2M) with a single-chain Ab (scFv) derived from the VL-VH domains of rituximab linked to both an IL-15 superagonist variant and an IL-15Rα/Fc fusion has been generated (FIG. 87). High affinity interactions between the IL-15 and IL-15 receptor α domains and disulfide bonding between the IgG domains resulted in a stable, soluble, four-chain polypeptide complex that retained functional binding activity of each of its components.

To create the CD20-targeted IL-15N72D:IL-15Rα/Fc fusion protein complex (2B8T2M), VL and VH gene fragments of rituximab (2B8 Ab) were cloned in an scFv format (2B8scFv), and this sequence was linked to the N-terminal coding region of the IL-15N72D and IL-15Rα/Fc gene constructs. Expression vectors carrying these constructs were co-transfected into CHO cells and stable cell lines with high-level production of the 2B8T2M complex (i.e., >50 mg/L) were selected. The 2B8T2M complex was produced and purified. To serve as Ab controls for testing, constructs were generated to produce the chimeric 2B8 mAb (C2B8) equivalent to rituximab in recombinant CHO cells.

Figure 88B:
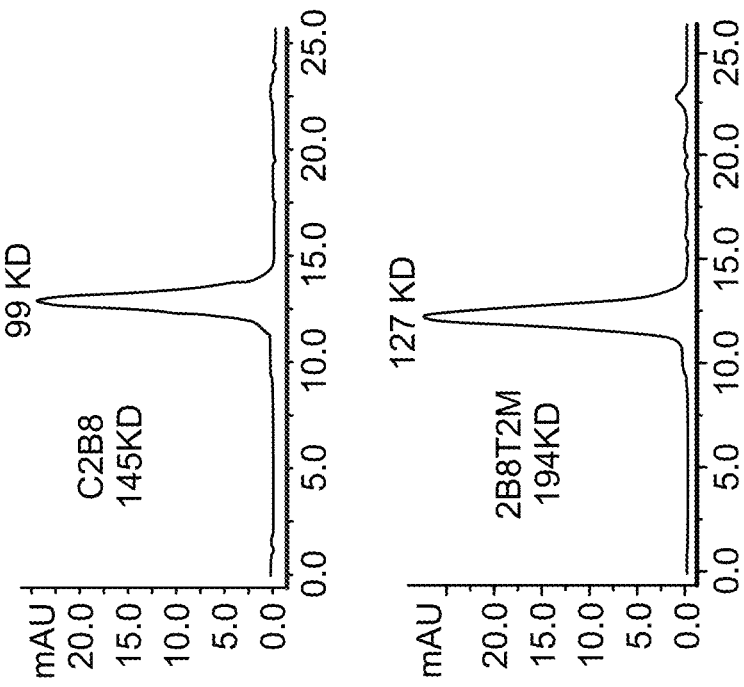
FIG. 88A and FIG. 88B show molecular weight analysis of the anti-CD20 scFv/IL-15:anti-CD20 scFv/IL-15Rα/IgG Fc protein complex (2B8T2M).
Figure 88A:
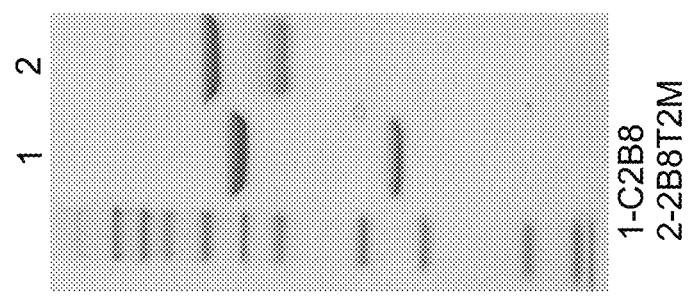

2B8T2M and C2B8 (rituximab) proteins were purified by Protein A affinity chromatography, and analyzed by SDS-PAGE and native size exclusion chromatography (SEC) (FIGS. 88A and 88B). Both purified 2B8T2M and C2B8 (rituximab) proteins exhibited two polypeptide bands at the appropriate MW on SDS-PAGE (i.e. 2B8T2M comprised of 2B8scFv/IL-15N72D and 2B8scFv/IL-15Rα/Fc) and eluted as a single peak for the tetrameric protein complex by SEC. The observed complex MW on SEC was less than the calculated MW for both proteins presumably due to their structural characteristics.

The 2B8T2M protein was also reactive in ELISAs with an anti-IgG Ab capture and anti-IL-15 Ab probe format. The results confirm formation of the stable 2B8T2M complex (FIG. 87). As a control for anti-CD20 targeting activity, an IL-15N72D:IL-15Rα/Fc complex comprising scTCR domains that bind p53 peptide/HLA-A2 complexes was used (Wong et al., Protein Eng Des Sel, 24: 373-383, 201). This protein (264T2M) does not bind the HLA-deficient Daudi lymphoma used in our studies. Finally, a CD20-targeted IL-15N72D:IL-15Rα/Fc complex (2B8T2MLA) containing Fc mutations that reduce FcR and complement binding activity was generated to define the role of the Fc domain in antitumor activity.

Figure 89:
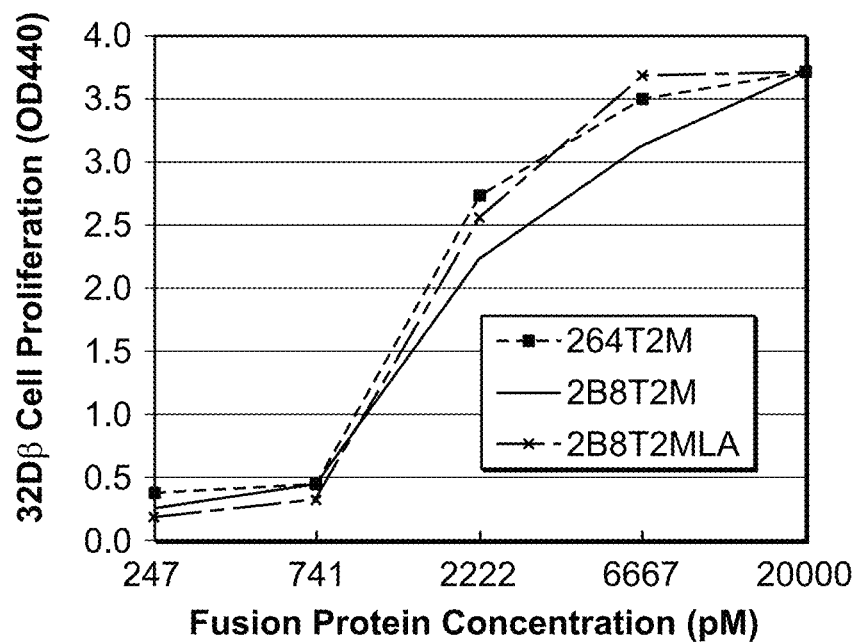
FIG. 89A and FIG. 89B show functional activity of IL-15 and anti-CD20 scFv domains of anti-CD20 scFv/IL-15:anti-CD20 scFv/IL-15Rα/IgG Fc protein complexes.
Figure 89:
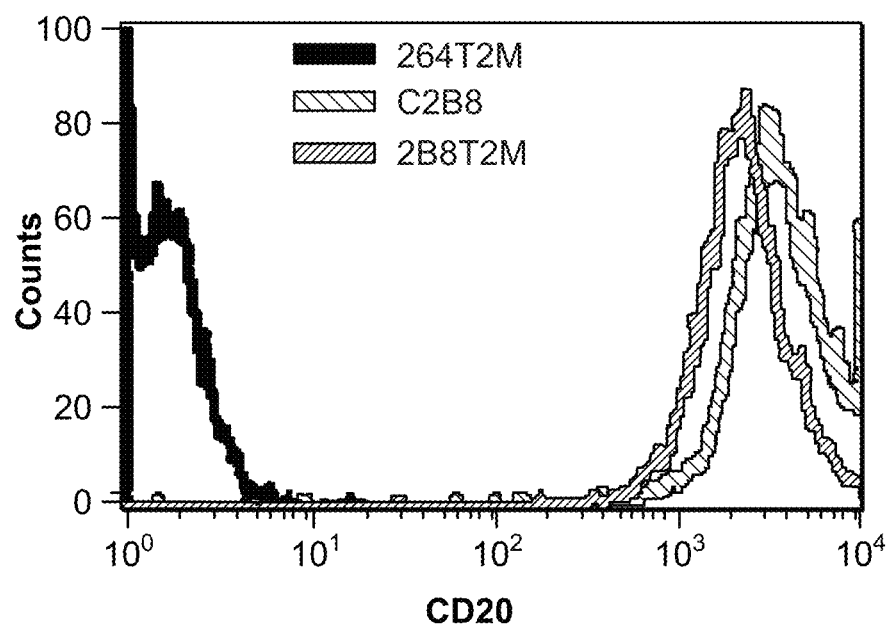

The IL-15 activity of the complexes was assessed based on proliferation of the IL-15-dependent 32Dβ cell line using the WST-1 reagent as described previously (Wong et al., Protein Eng Des Sel, 24: 373-383, 201). The 2B8T2M, 2B8T2MLA and 264T2M had similar IL-15 activity (FIG. 89A). Binding of the complexes to the CD20-positive human Daudi lymphoma cell line was assessed by flow cytometry. As expected, the 2B8T2M and C2B8 proteins showed CD20 binding with C2B8 binding slightly better than 2B8T2M (presumably due to reduced activity of the scFv format) whereas the control 264T2M complex does not bind Daudi cells (FIG. 89B). These results verify the functionally of the IL-15:IL-15Rα and anti-CD20 Ab domains of the 2B8T2M complex.

Figures 4, 4A:
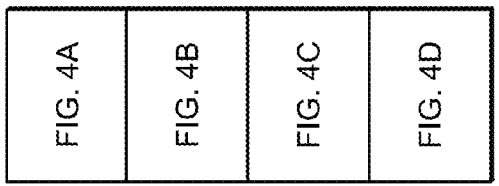
Figure 90:
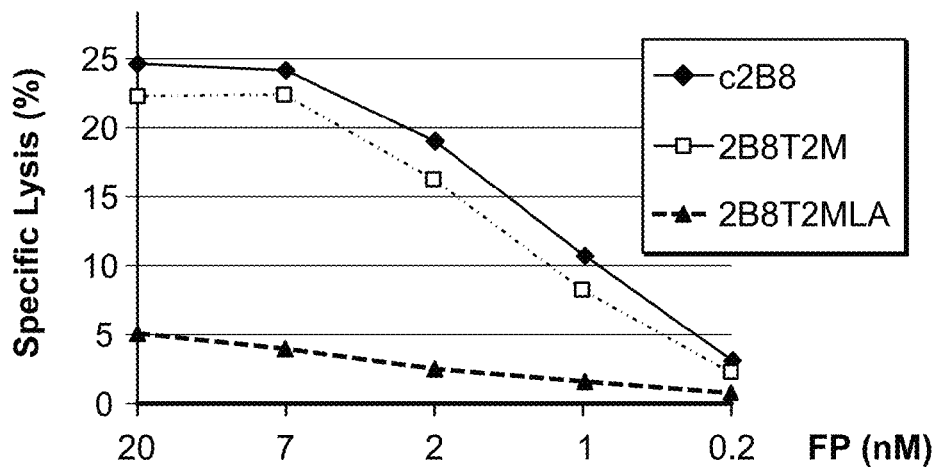
FIG. 90 is a graph depicting antibody-dependent cellular cytotoxicity (ADCC) activity of 2B8T2M complex. Purified fusion proteins were mixed with purified human T cells+NK cells and incubated 2 hrs with calcein labeled Daudi cells at a 20:1 E:T ratio. Cell lysis was determined by calcein release (Mosquera et al., J Immunol, 174: 4381-4388, 2005).
Figure 91:
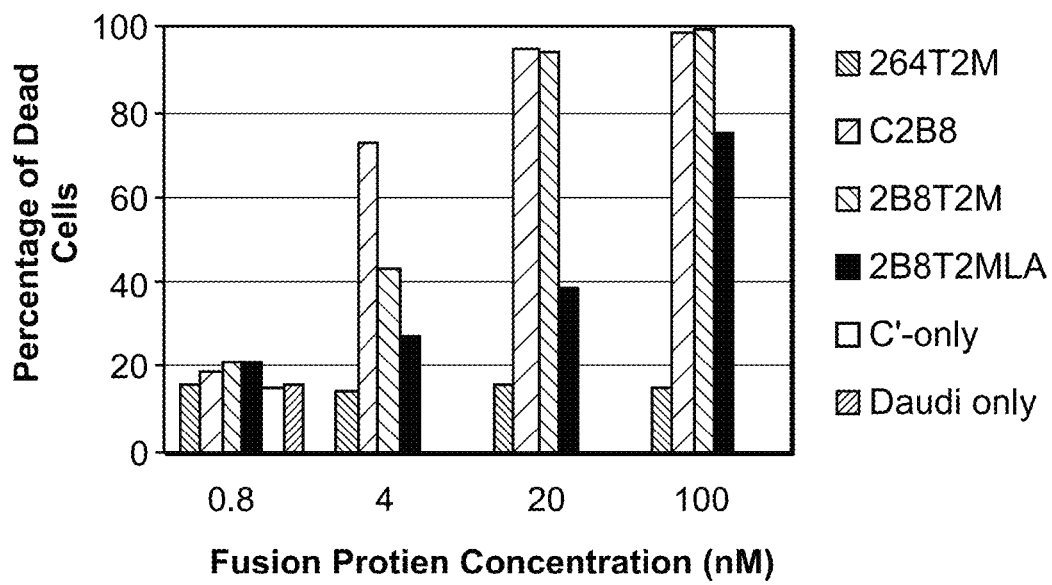
FIG. 91 is a graph depicting complement dependent cytotoxicity (CDC) activity of 2B8T2M complex. Purified proteins (concentrations, as indicated) were mixed with human serum and incubated 2 hrs with Daudi cells. Cell death was assessed by flow cytometry following staining with FITC-Annexin-V and propidium iodide (PI).
Figure 92:
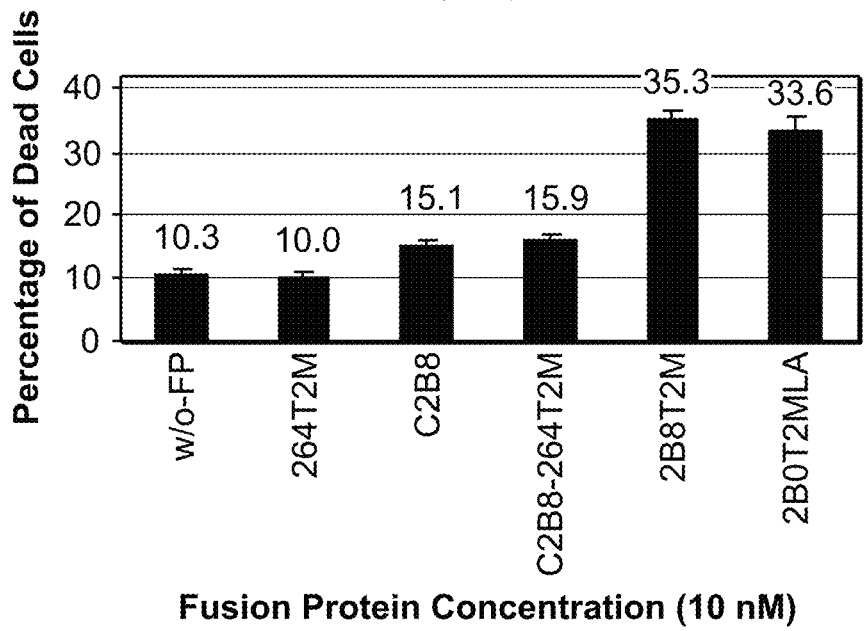
FIG. 92 is a graph depicting programmed cell death (PCD) activity of 2B8T2M complex. Purified proteins (10 nM) were incubated 2 days with Daudi cells. Cell death was assessed by flow cytometry as described in FIG. 5.

Anti-CD20 Abs mediate their activity against B-cell lymphomas in part through complement dependent cytotoxicity (CDC), antibody-dependent cellular cytotoxicity (ADCC), and direct programmed cell death (PCD). Additionally, due to different modes of binding, type I Abs such as rituximab primarily exhibit CDC and ADCC activity whereas type II Abs primarily exhibit PCD and ADCC. These activities were compared between the 2B8T2M complex and C2B8 (rituximab). 264T2M complex was used as a non-targeted IL-15 control, and 2B8T2MLA was used to assess the role of the Fc domain. Addition of the 2B8T2M complex and C2B8 Ab to human effector cells resulted in similar levels of ADCC against Daudi target cells as assessed in a calcein release assay (FIG. 90). Little or no activity was seen with the non-targeted 264T2M or the 2B8T2MLA Fc mutant complexes (FIG. 4). Both the 2B8T2M complex and C2B8 Ab were also capable of mediating comparable CDC activity of human serum against Daudi cells (FIG. 91). In contrast, 264T2M was inactive and the 2B8T2MLA Fc mutant showed reduced activity. The ability of the proteins to directly induce cell death of Daudi cells was evaluated (FIG. 92). As expected, C2B8 Ab showed minimal activity. However, surprisingly the 2B8T2M complex exhibited significant direct cell killing activity against Daudi cells consistent with the levels reported for type II Abs (Cragg et al., Blood, 103: 2738-2743, 2004). Daudi cell death was also mediated by the 2B8T2MLA Fc mutant, indicating independence of Fc function. However, CD20 binding is clearly required based on the lack of activity of the 264T2M control.

Figure 93:
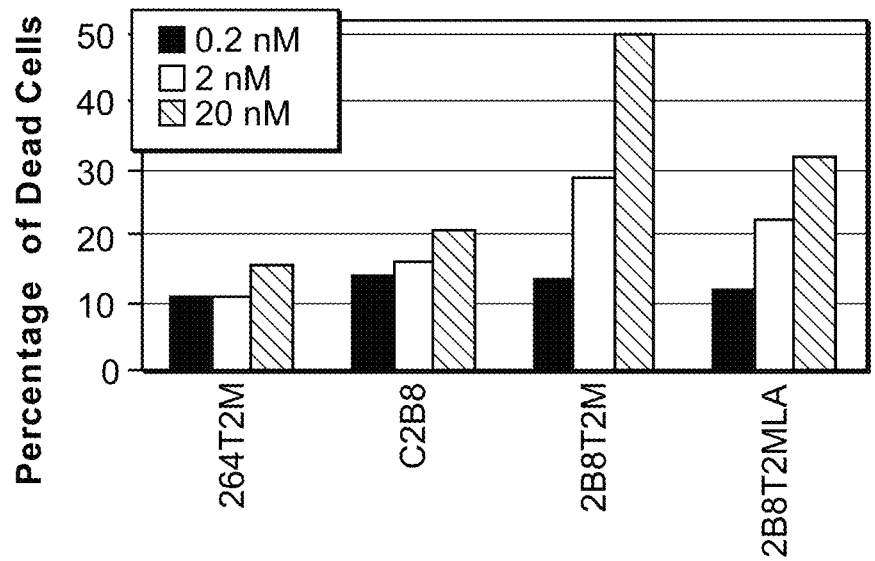
FIG. 93 is a graph depicting anti-lymphoma activity of 2B8T2M complex. Purified proteins (concentrations, as indicated) were mixed with purified human T cells+NK cells, and incubated 2 days with PKH67-labelled Daudi cells at a low 2:1 E:T ratio. Daudi cell death was determined by flow cytometry following staining with propidium iodide (PI).

Together, these studies demonstrate the 2B8T2M complex contains all of the properties seen in both type I and II anti-CD20 Abs, a novel characteristic. To evaluate the cumulative ADCC and PCD activity and immune stimulation by IL-15, purified human T cells+NK cells were incubated with PKH67-labelled Daudi cells (E:T 2:1) in media containing the fusion protein complexes for 2 days. Daudi cell death was then assessed by propidium iodide (PI) staining. All of the IL-15 complexes were capable of inducing LAK cell activity resulting in Daudi cell death (FIG. 93). Daudi cells incubated with 2B8T2M showed even higher levels of cell death presumably due to ADCC and PCD. This was further enhanced by CD20 targeting activity that was partially dependent on Fc activity. Overall, the antitumor activity of the 2B8T2M complex exceeded that of the C2B8 Ab, indicating that 2B8T2M is a superior therapeutic agent against CD20+ B-cell lymphomas.

In summary, the 2B8T2M complex was capable of directing ADCC and CDC against human lymphoma cells with comparable activity to that seen with rituximab (also referred to as C2B8 mAb). Importantly, higher levels of direct cell killing of human lymphomas were seen with 2B8T2M than with rituximab. Without being bound to a particular theory, this indicates the fusion protein complex, unlike rituximab, has both type I and type II anti-CD20 Ab characteristics. In addition, this also indicates that the IL-15 superagonist/IL-15Rα components of 2B8T2M provide potent antitumor immunostimulatory activity against human B-cell lymphomas.

Without being bound to a particular theory, the 2B8T2M complex could potentiate anti-CD20 Ab activity by: (1) providing a molecule with both type I and type II characteristics, and (2) expanding the population and activity of effector cells to augment the ADCC/phagocytic function. The IL-15 component of 2B8T2M may also provide potent immunostimulatory activity to IL-15βγ$_c$ receptor-bearing NK cells, macrophage and T cells for anti-CD20-independent tumor-killing activity (FIG. 87). The ability to target IL-15 to the tumor microenvironment increases IL-15 activity at the tumor site and reduces potential systemic toxicities.

Example 31

Figure 94:
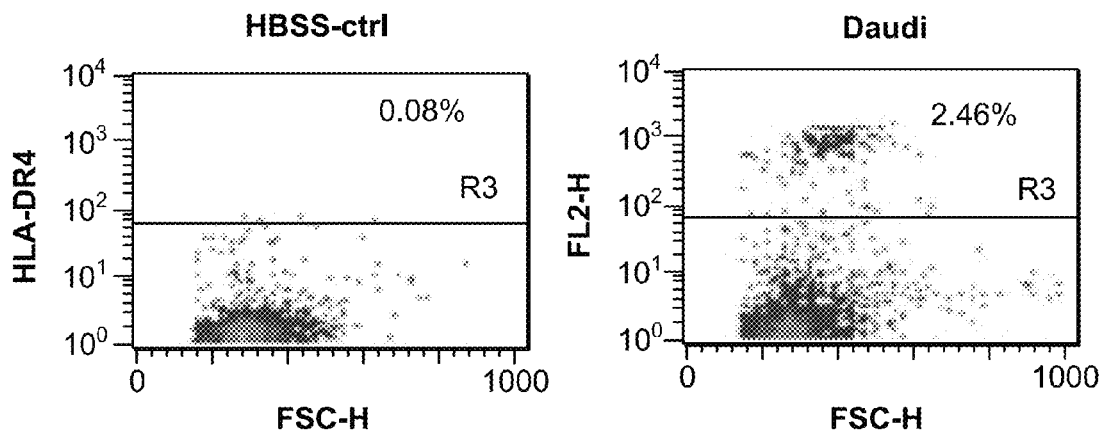
FIG. 94 depicts the detection of Daudi cells in bone marrow of tumor-bearing SCID mice. Female SCID mice (C.B-17/IcrHsd-Prkdc-scid) were injected i.v. with 107 Daudi cells or HBSS (control). After 2 weeks, animals were sacrificed and femoral bone marrow cells were collected. The cells were stained with PE-conjugated anti-HLA-DR mAb to detect Daudi cells in tumor-bearing mice.

CD20-Targeted IL-15N72D:IL-15Rα/Fc Fusion Protein Complexes (2B8T2M) Demonstrated Antitumor Efficacy in a Well-Established Human Lymphoma Xenograft Model As the Daudi-SCID mouse model has been used to assess the antitumor activity of various anti-CD20 antibodies including rituximab (Cragg et al., Blood, 103: 2738-2743, 2004), the Daudi-SCID mouse model was implemented to further characterize the anti-CD20 scFv/IL-15:anti-CD20 scFv/IL-15Rα/IgG Fc protein complex (2B8T2M) in vivo. SCID injected i.v. with $10^7$ Daudi cells developed lymphoma tumors in their bone marrow resulting in paralysis/mortality within 30 days. Daudi cells were also readily detectable 14 days after i.v. injection by staining with anti-HLA-DR Ab (FIG. 94).

Figure 95:
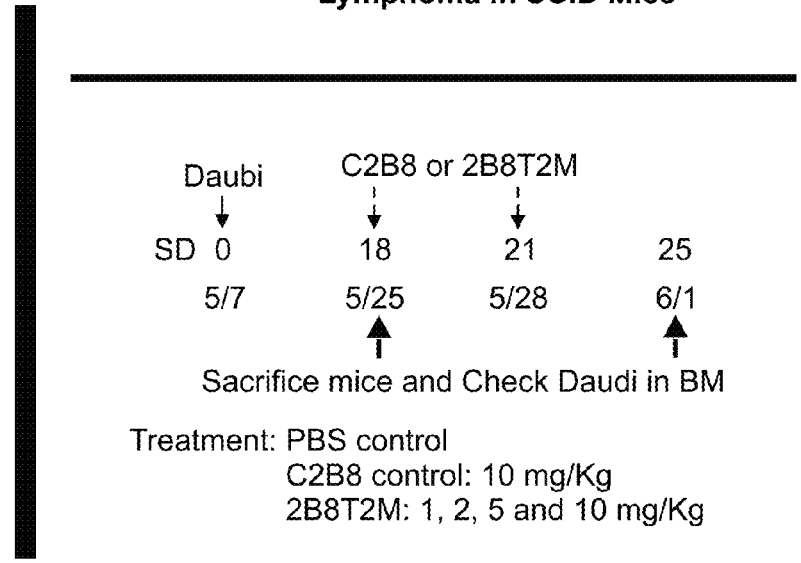
FIG. 95 depicts an efficacy study of 2B8T2M against Daudi B Lymphoma in SCID Mice.
Figure 96:
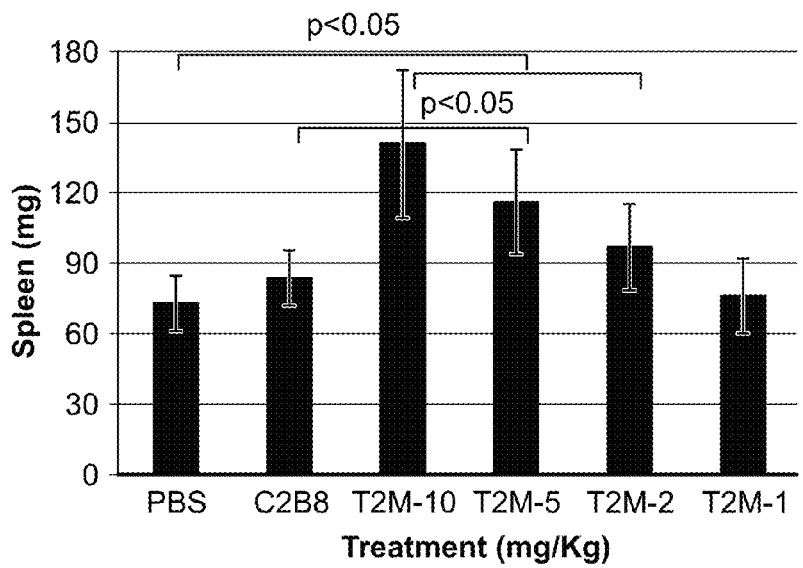
FIG. 96 is a graph showing that anti-Daudi Activity of 2B8T2M is more potent than C2B8 in SCID Mice.

An efficacy study of 2B8T2M against Daudi B Lymphoma in SCID Mice was performed (FIG. 95). Fox Chase SCID Female mice (6 per group) were injected (i.v.) with $10 \times 10^6$ human CD20+Burkitt lymphoma Daudi cells on study day (SD) 0. The tumor-bearing mice were intravenously treated on SD 18 and 21 with PBS, anti-CD20 antibody (C2B8) or anti-CD20 scAb T2M (2B8T2M) at various dose levels. There was a dose dependent increase in anti-CD20 scAb T2M (T2M) levels in the serum 4 days after treatment (FIG. 96). These results are consistent with the extended half life of the fusion protein complex. The mice were sacrificed on SD 25 and the levels of Daudi cell present in the bone marrow was determined based on positive staining with PE-conjugated anti-HLA-DR antibody. Comparison of survival may be analyzed using the log-rank test. Unpaired t tests with Welch's correction assuming unequal variances can be used to compare differences in continuous variables among the treatment groups. P<0.05 (two-tailed) is defined as statistically significant.

Figure 97:
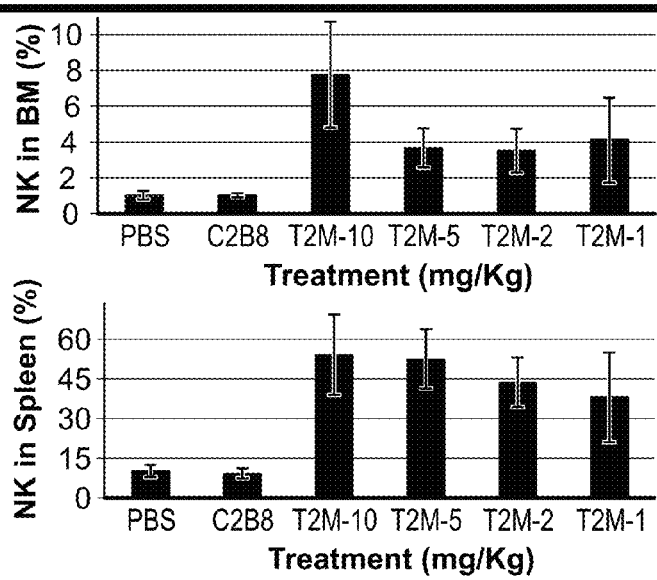
FIG. 97 is a graph showing immunostimulatory spleen enlargement induced by 2B8T2M in SCID Mice.
Figure 98:
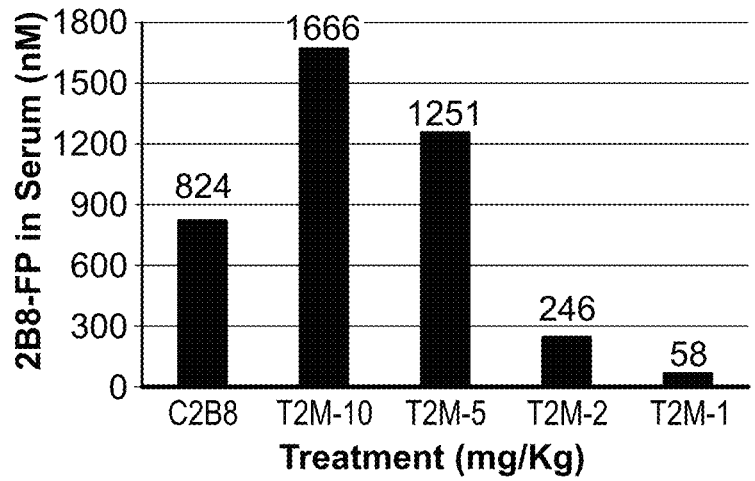
FIG. 98 is a graph showing induction of NK Cells by 2B8T2M in SCID Mice.
Figure 99:
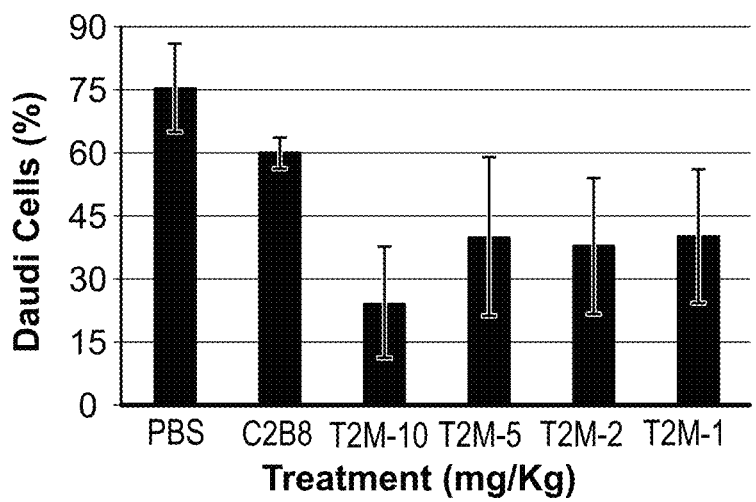
FIG. 99 is a graph showing extended half-life of 2B8T2M as determined by concentration in blood on day –4 after treatment.

At study day 25 post tumor cell injection, Daudi cells represented 75% of the cells of the bone marrow in mice treated with phosphate buffered saline (PBS) (FIG. 97). Treatment with 10 mg/kg anti-CD20 antibody (C2B8) resulted in a slight decrease in bone marrow Daudi cells whereas treatment with anti-CD20 scAb T2M (T2M) at 10 mg/kg further reduced the level of Daudi cells in the bone marrow to ~25%. Anti-CD20 scAb T2M (T2M) at as low as 1 mg/kg was also effective at reducing the Daudi cell levels in the bone marrow. Anti-CD20 scAb T2M (T2M) treatment also resulted in a dose dependent increase in spleen weights consistent with its immunostimulatory activity (FIG. 98). Additionally, anti-CD20 scAb T2M (T2M) treatment resulted in a dose dependent increase in NK cells in the bone marrow and spleen, consistent with its immunostimulatory activity (FIG. 99). NK cell percentages in the bone marrow and spleen were unchanged following treatment with anti-CD20 antibody (C2B8).

Thus, the combinations of activities exhibited by 2B8T2M have the potential to provide significant clinical benefit to treatment-naïve and refractory NHL and CLL patients beyond that seen with current anti-CD20 Ab-based approaches.

The above examples 1-22 were carried out using the following materials and methods.

Construction of Vectors for Protein Complex Expression

The IL-15RαSu/Fc fusion gene was constructed by overlap PCR amplification of DNA templates encoding the sushi domain of human IL-15Rα (aa1-66 of human IL-15Rα) and the human IgG1 Fc fragment. The signal peptide-IL-15RαSu coding region (R. L. Wong et al., Protein Eng Des Sel 24 (2011) 373-383) and human IgG1-Fc gene fragment (L. A. Mosquera et al., J Immunol 174 (2005) 4381-4388) were amplified using the primer pairs: BA494: 5'-GACTTCAAGCTTAATTAAGCCACCATGGACAGACTTAC-TTCTTC-3' (SEQ ID NO: 16); BA550R: 5'-GTGAGTTTTGTCACAAGATTTCGGCTCTCTAATGCAT-TTGAGACTGGGGGTTG-3' (SEQ ID NO: 27), and BA550F: 5'GAGCCGAAATCTTGTGACAAAACTCAC-3' (SEQ ID NO: 28); BA393R: 5'-GTAATATTCTAGACGCGT-TCATTATTTACCAGGAGACAGGGAGAGGCTCTTC-3' (SEQ ID NO: 15), respectively. The resulting IL-15RαSu/Fc fusion gene was ligated into a puromycin-resistant expression vector pMSGV-1 (M. S. Hughes et al., Hum Gene Ther 16 (2005) 457-472) to construct the expression vector pMSGV-IL-15RαSu/Fc.

The coding sequence of IL-15N72D (X. Zhu et al., J Immunol 183 (2009) 3598-3607) was cloned into a modified retrovirus expression vector pMSGV-1 (M. S. Hughes et al., Hum Gene Ther 16 (2005) 457-472) that carries the neomycin resistance gene after an IRES region to construct the expression vector pMSGV-IL-15N72D.

Co-Expression of IL-15N72D:IL-15RαSu/Fc Fusion Complex in CHO Cells

To co-express IL-15N72D and IL-15RαSu/Fc fusion proteins (see FIG. 64), pMSGV-IL-15RαSu/Fc and pMSGV-IL-15N72D were co-transfected into CHO cells followed by selection in medium containing 2 mg/mL G418 (Hyclone, Logan, Utah) and 10 µg/mL of puromycin (Hyclone, Logan, Utah). The IL-15RαSu/Fc fusion protein was also expressed individually in CHO cells for use in loading of recombinant human wild-type IL-15 (IL-15 wt) as a control. For production of the fusion proteins, the recombinant CHO cells were grown in serum free defined medium (SFM4CHO, Hyclone, Logan, Utah) at 37° C. When the viable cell density of the cultures reached a maximum, the incubation temperature was shifted down to 30° C. for accumulation of the soluble complex. Culture supernatants were then harvested when the viable cell density of the cultures reached approximately 10% viable cells.

Purification Procedure

The recombinant CHO cell culture medium was centrifuged and filtered to remove cells and debris before the supernatant was adjusted to pH 8.0 with 1 M Tris-HCl, pH 8.0. The soluble IL-15N72D:IL-15RαSu/Fc fusion protein complex (Alt-803) was purified using a two-step affinity and ion exchange chromatography-based process.

Since the IL-15N72D:IL-15RαSu/Fc complex (Alt-803) contains the IgG1-Fc domain, an rProtein A Sepharose Fast Flow (GE Healthcare) column was used as the first step in the purification process. Prior to sample loading, the column was washed with 5 column volumes (CV) of 20 mM Tris-HCl, pH 8.0, sanitized with 5 CV of 0.1 N NaOH for 1 h, and then equilibrated with 7 CV of 20 mM Tris-HCl, pH 8.0. The supernatant was loaded onto the 11 mL column at 2 mL/min, and the column was then washed with 8 CV of 20 mM Tris-HCl, pH8.0, followed by 7 CV of washing buffer (0.1 M Na-citrate, pH 5.0) to remove non-specifically bound proteins. The protein was then eluted with 0.2 M Na-citrate, pH 4.0 and the pH of collected peak fractions was immediately adjusted to pH 3.5 using 0.2 M citric acid; the eluted protein was held at this low pH for 30 minutes as a standard viral clearance step. After the low pH hold step, the pH of the eluted preparation was adjusted to pH 7.7 by using 2 M Tris-HCl, pH 8.0. The preparation was concentrated and buffer exchanged into 20 mM Tris-HCl, pH 8.0 by using an Amicon Ultra-15 centrifugal concentrator (30 kDa cut-off, Millipore, Billerica, Mass.) before sterile filtration using a 0.22 µm filter (Corning Life Sciences, Lowell, Mass.).

The protein preparation was then applied to a Q Sepharose Fast Flow (QSFF; GE Healthcare Bio-Sciences, Piscataway, N.J.) ion exchange column. A 5 mL column was washed with buffer A (20 mM Tris-HCl, pH 8.0), sanitized by 5 CV of 0.1

N NaOH for 1 h, and then equilibrated with buffer A. The protein concentration in the preparation was first adjusted to <1 mg/mL with 20 mM Tris-HCl, pH 8.0 and was then loaded onto the QSFF column at a rate of 1 mL/min. The protein was then eluted from the column using a three-step-gradient process as follows: 20 mM Tris-HCl, pH 8.0, 130 mM NaCl for four CV as the first step, 20 mM Tris-HCl, pH 8.0, 300 mM NaCl for four CV for the second step and 20 mM Tris-HCl, pH 8.0, 1 M NaCl for two CV as the last step. Protein peak fractions were collected, buffer exchanged into PBS (Hyclone, Logan, Utah), and filtered using a 0.22 µm filter. Protein concentration was determined by UV spectrophotometer at 280 nM using an extinction coefficient of 1 $A_{280nm}$=0.79 mg/mL. This extinction coefficient was calculated based on the deduced amino acid sequence of the IL-15N72D:IL-15RαSu/Fc complex (Alt-803).

Individually expressed IL-15RαSu/Fc was purified using rProtein A affinity chromatography as described above for assembling of complex in solution with IL-15N72D or IL-15 wt produced in E. coli and refolded (Zhu, 2009 #3315). These in vitro assembled complexes were used as standards for biological activity evaluation and estimation of degree of occupancy of the IL-15 binding sites in co-expressed complexes.

Gel Electrophoresis and Size Exclusion Chromatography (SEC) Analysis

Purified proteins were analyzed by different types of gel electrophoresis methods, which included NuPAGE 12% Bis-Tris gel (under reduced and non-reduced conditions), 4-20% Tris-glycine gel (native condition), and IEF pH3-10 gel (for pI determination). All supplies were from Invitrogen (Carlsbad, Calif.). Experimental methods were performed as described by the manufacturer. Superdex 200 HR 10/30 (GE Healthcare Bio-Sciences) chromatography with PBS (Hyclone, Logan, Utah) as the running buffer was used to examine purity and to estimate molecular mass of the proteins.

N-Terminal Amino Acid Sequence and Glycosylation Analysis

Protein bands of interest were separated on SDS-PAGE gels, blotted onto PVDF membrane and stained by Ponceau S solution. N-terminal amino acids sequencing was performed using the Edman degradation method (Molecular Structure Facility, UC Davis, Davis, Calif.).

To examine whether the fusion complex was glycosylated, 5014 of the highly purified protein after the ion exchange chromatography was digested with 2 µL of N-Glycosidase F (Calbiochem, La Jolla, Calif.) in a total volume of 50 µL in PBS at room temperature for 48 h and then was subjected to electrophoresis in NuPAGE 12% Bis-Tris gel under a reduced condition.

Determination of IL-15N72D Occupancy of the Purified IL-15N72D:IL-15RαSu/Fc Complex Purified IL-15RαSu/Fc was loaded with IL-15 wt (produced in E. coli and refolded, provided by J. Yovandich, NCI, Fredrick, Md.) at various ratios for 15 h at 4° C. After incubation, the IL-15 wt:IL-15RαSu/Fc complex was purified using rProtein A affinity chromatography as described above. This purified complex was evaluated using two ELISA formats, one (anti-human IgG Fc capture and anti-IL-15 detection) which detects the intact complex and the other (anti-human IgG Fc capture and anti-human IgG Fc detection) which detects only the IL-15αSu/Fc fusion protein. The ratio between the intact IL-15 wt: IL-15αSu/Fc complex and IL-15RαSu/Fc protein levels reflects the occupancy rate of the IL-15 binding sites of the complex. [Occupancy rate (%)=the intact complex (ng/mL)/IL-15RαSu/Fc (ng/mL)× 100%]. Fully occupied complex (pre-associated of IL-15RαSu/Fc and IL-15 wt at a 1:3 ratio) was then used as a standard to quantitate the occupancy rate of purified IL-15N72D:IL-15RαSu/Fc fusion protein complexes (Alt-803) after purification.

Determination of IL-15 Biological Activity

An in vitro cell proliferation assay using the IL-15-depended 32Dβ cell line was employed to assess the IL-15 biological activities of the purified complex and IL-15 wt proteins as previously described (X. Zhu et al., J Immunol 183 (2009) 3598-3607).

Pharmacokinetic Evaluation

The pharmacokinetic profile of IL-15N72D:IL-15RαSu/Fc complex (Alt-803) and IL-15 wt were evaluated in female CD-1 mice (4 mice/time point, Harlan, Indianapolis, Ind.) as previously described for IL-2 (H. J. Belmont et al., Clin Immunol 121 (2006) 29-39). Serum levels of the IL-15N72D:IL-15RαSu/Fc complex (Alt-803) were assessed with the two ELISA formats described above. IL-15 wt levels were assessed by ELISA using anti-IL-15 capture (MAB647; R&D Systems, Minneapolis, Minn.) and anti-IL-15 detection (BAM247; R&D Systems, Minneapolis, Minn.). IL-15N72D:IL-15RαSu/Fc (Alt-803) levels from each ELISA format were fit with a one-compartment model using PK Solution 2.0 (Summit Research Services, Montrose, Colo.). Data from mice treated with IL-15 wt were best modeled as a two-compartment model.

Lymphocyte Stimulation

C57BL/6 mice (male, 6 wks of age, Harlan, Indianapolis, Ind.) were injected intravenously with a single dose of IL-15N72D:IL-15RαSu/Fc fusion complex (Alt-803) at 1 mg/kg or human IL-15 wt at 0.28 mg/kg (molar equivalent dose), respectively, or PBS as a negative control. Four days after treatment, pooled blood (5 mice per group) and splenocytes were collected. PBMCs were isolated from the blood using histopaque (Sigma, St. Louis, Mo.). The PBMC and splenocytes were then stained with PE-labeled anti-CD19, PE-labeled anti-CD335 (NKp46), FITC-labeled anti-CD4 and FITC-labeled anti-CD8 antibodies (BioLegend, San Diego, Calif.). The stained cells were analyzed on a FACScan flow cytometer (BD Bioscience, San Jose, Calif.). All animal studies were performed following Altor's IACUC approved protocols.

The following peptides were used in the studies presented in the above Examples.

| Protein | Amino acids | Sequence | SEQ ID NO: |
| --- | --- | --- | --- |
| p53 | 149-157 | STPPPGTRV | 29 |
| p53 | 264-272 | LLGRNSFEV | 30 |
| OVA | 257-264 | SIINFEKL | 25 |
| VSV | 52-59 | RGYVYQGL | 31 |

The following protein domain linker sequences of the fusion proteins used in the Examples presented.

| Linker | Linker Sequences | Linker sequences disclosed as SEQ ID NO: | Fusion Protein |
|---|---|---|---|
| Single-chain TCR linker | TCR Vα-DTSGGGGSGGGGSGGGGSGGGGSSS-TCR Vβ | 32 | c264scTCR/hIL-15, c264scTCR/hIL-15RαSu/birA |
| | TCR Vα-TSGGGGSGGGGSPGGGGSGGGGSSS-TCR Vβ | 33 | c149scTCR/hIL15N72D |
| | TCR Vα-DTSGGGGSGGGASGGGGSGGGGSSS-TCR Vβ | 34 | OT1scTCR/birA |
| | TCR Vα-SGGGGSGGGASGGGGSGGGGS-TCR Vβ | 35 | OT1scTCR/hIL-15D8N, OT1scTCR/hIL-15RαSu/birA |
| Mutated human IgG1 hinge | TCR domain-VNEPKSSDKTHTSPPSPTR-hIL-15RαSu | 36 | c264scTCR/hIL-15RαSu/birA, OT1scTCR/hIL-15RαSu/birA, OT1TCRβ/hIL-15RαSu/birA, 264TCRβ/hIL-15RαSu/birA |
| | TCR domain-VNEPKSSDKTHTSPPSPTR-hIL-15 | 36 | 264TCRα/hIL-15D8N, OT1TCRα/hIL-15, OT1scTCR/hIL-15D8N |
| BirA linker | hIL-15RαSu-SGGGSGGGGSID-birA tag | 37 | c264scTCR/hIL-15RαSu/birA, OT1TCRβ/hIL-15RαSu/birA |
| Single-chain CD8 linker | CD8α-SGGGGSGGGGSGGGGSGGGGS-CD8β | 38 | scCD8αβ/hIL-15RαSu/birA |

Results presented in Examples 23-26 were carried out with the following materials and methods.

Mice and Tumor Cell Lines C57BL/6NHsd and BALB/c mice (5-6 week old females, Harlan Laboratories) and interferon-γ (IFN-γ) knockout (KO) [B6.129S7-Ifngtm1Ts/J] and perforin KO [C57BL/6-Prf1tm1Sdz/J] mice (5-6 week old females, The Jackson Laboratory) were housed in the animal facilities at Altor BioScience. All animal studies were performed according to NIH animal care guidelines under IACUC approved protocols.

The murine 5T33 multiple myeloma cell line (20) was kindly provided by Dr. Ulrich von Andrian, (Harvard Medical School, Boston, Mass.). The murine MOPC-315 myeloma cell line was purchased from American Type Culture Collection (ATCC). Tumor cell sublines, 5T33P and MOPC-315P, were developed by passage of the parental myeloma cells in C57BL/6NHsd and BALB/c mice, respectively. All cells were routinely cultured in I-10 media at 37° C. with 5% $CO_2$ and harvested for animal injection at 80-90% confluency.

Tumor Models

Following intravenous (i.v.) injection with $1\times10^7$ 5T33P cells/mouse, 100% of C57BL/6NHsd mice developed tumor-induced hind leg paralysis between 20-30 days. Similar tumor take rates were observed in BALB/c mice following i.v. injection of $1\times10^7$ MOPC-315P cells/mouse. Tumor-bearing mice were monitored daily for hind leg paralysis, signs of overt disease progression and mortality.

ALT-803 (IL-15N72D:IL-15RαSu/Fc) was generated as described previously (Han et. al., Cytokine, 56: 804-810, 2011). Recombinant human IL-15 (21) was kindly provided by Dr. Jason Yovandich (NCI, Fredrick, Md.). ALT-803 at 0.2 mg/kg/dose (or as indicated), IL-15 at 0.056 mg/kg/dose (IL-15 molar equivalent dose of 0.2 mg/kg ALT-803) or PBS as control was administered i.v. via the lateral tail vein to tumor-bearing mice. Levels of BM myeloma cells and hind leg paralysis or survival were assessed as study endpoints.

Flow Cytometry and ELISA Analysis.

To quantitate levels of murine lymphocyte subsets, BM, spleen, lymph node and blood were collected separately from each mouse, cells were prepared and stained with fluor-labeled antibodies (Abs) specific to CD4, CD8, CD11c, CD19, CD25, CD40, CD44, CD80, CD107a, I-A(b), IFN-γ, IgG2b, IgA, NK1.1, NKG2D, NKp46, and/or PD-1, and appropriate isotype controls (eBiosciences, BD Biosciences, and Biolegend) as indicated in figure legends. Cell staining was analyzed on a FACSverse (BD Biosciences). The sorting of $NKG2D^{neg}CD8^{neg}CD8^+CD44^{high}$ T cells was conducted with FACS Aria and analyzed with Diva software (BD Biosciences).

Levels of 5T33P and MOPC-316P cells in BM preparations, and IFN-γ in splenocytes were assessed by intracellular staining with Abs specific to IgG2b, IgA and IFN-γ, respectively.

IFN-γ levels in mouse serum were quantitated by ELISA using anti-IFN-γAb (AN-18) capture and biotinylated anti-IFN-γAb (R4-6A2) detection following the manufacturer's instruction (Biolegend).

In Vivo Depletion of Mouse $NK1.1^+$ Cells and $CD8^+$ T Cells.

For in vivo depletion of $NK1.1^+$ cells and $CD8^+$ T cells, mice were injected intraperitoneally (i.p.) with 200 μg/dose anti-NK1.1 (PK136, ATCC) and/or 500 μg/dose anti-CD8 (53-6.72, ATCC) Abs. Control mice received PBS (0.2 mL). In pilot studies, the efficiency of $NK1.1^+$ cell and $CD8^+$ T-cell depletion was monitored by flow cytometry following staining of PBMCs and BM cells with appropriate Abs.

T Cell Labeling and Adoptive Transfer.

$CD3^+$ enriched cells (prepared with Mouse $CD3^+$ T Cell Enrichment Column, R&D System), $CD8^+$ enriched T cells

[positive, CD8α (Ly-2) MicroBeads, mouse, Miltenyi Biotech] or sorted NKG2D$^{neg}$CD25$^{neg}$CD8$^+$CD44$^{high}$ memory T cells from spleens and lymph nodes of donor C57BL/6NHsd or IFN-γ KO B6 mice were labeled with Celltrace™ Violet (Invitrogen) at 1.5 μM/1×10$^6$ cells/ml, and then 1 to 1.5×10$^6$ violet labeled cells were adoptively transferred into syngeneic C57BL/6NHsd or IFN-γ KO B6 recipients on day 0 (SD0). On SD2, mice were treated (i.v.) with the following test articles 0.02 mg/kg ALT803, 0.2 mg/kg ALT-803 or PBS. On SD6, spleens were harvested and splenocytes were analyzed for proliferation of donor cells (violet label) or staining with antibodies specific to CD25, PD-1, CD44, CD8a, and NKG2D.

In Vitro Cytotoxicity Assay

Tumor target cells (i.e., 5T33P, A20) were labeled with PKH67 (Sigma-Aldrich) according to the manufacturer's instructions. CD8$^+$ T cell enriched spleen cells from normal, IFN-γ KO, and perforin KO B6 mice were isolated (untouched, CD8α$^±$ T Cell Isolation Kit II, mouse, Miltenyi Biotech). Effector populations were produced by culturing prepared cells (2×10$^7$) in RPMI-1640 complete media containing ALT-803 (200 ng/mL) for 72 hr. Resulting effector cells were harvested, washed twice, and re-plated into 24 well plates with PKH-labeled tumor target cells (E:T ratio; 10:1) in media containing varying doses of ALT-803. After incubation for 20-24 hrs at 37° C. with 5% $CO_2$, target cell killing was assessed by analysis of PI staining of PKH67-labeled tumor cells on a BD FACScan.

Data Analysis

Data are expressed as the mean±SE. Survival data was analyzed using the log-rank test and Kaplan-Meier method. Comparisons of continuous variables were done using Student's t tests or ANOVA (two-tailed) (GraphPad Prism Version 4.03). P values of less than or equal to 0.05 are considered significant.

Experiments described in Example 27 were carried out as follows.

Tumor Cells

Murine EG7-OVA tumor cell line, which was derived from mouse thymoma EL4 cells transfected with chicken albumin cDNA, was obtained from American Type Culture Collection, Manassas, Va., USA. EG7-OVA cells were cultured in RPMI 1640 medium with 1.0 mM sodium pyruvate and supplemented with 0.05 mM 2-mercaptoethanol and 10% fetal bovine serum in 5% CO2 and at 37° C.

Animals

Female C57BL/6 mice, 8-10 week-old, were purchased from Harlan Laboratories (Indianapolis, Ind., USA). Each mouse was identified by toe clipping. The animals were acclimated to the facility and released from quarantine by an animal caretaker one week after arrival. All experimental procedures and handling mice were performed according to NIH animal care guidelines under IACUC approved protocols.

Animals were housed 5-6 animals per cage in plastic cages with bedding. The cages were placed on stainless-steel racks and identified with a cage card bearing the animal identification numbers and equipped with a water bottle that provided autoclaved tap water. Autoclaved tap water and Harlan Teklad Global 18% Protein Rodent Diet (Harlan Teklad 2918S) were available ad libitum throughout the study. The feed was analyzed by the manufacturer for concentrations of specified heavy metals, aflatoxin, chlorinated hydrocarbons, organophosphates, and specific nutrients.

Environmental controls were set to maintain the following animal room conditions: temperature range between 68° F. and 79° F., relative humidity range between 30% and 70%, a minimum of 10 air changes per hour, and a controlled diurnal cycle (12-hour light/12-hour dark). Actual temperature and relative humidity in the animal room were monitored and recorded once daily.

Reagents

ALT-803, lot #: 051910, manufactured by Altor Bioscience Corporation.

Recombinant human interleukine-15, lot #L0801006, provided by Dr. J. Yovandich, NCI (4).

Dulbecco's phosphate buffered saline (PBS)-HyQ® DPBS, Ca++- and Mg++-free, Cat #SH30028FS, HyClone.

RPMI 1640 1x, Cat. #22400-089. lot #927164, GIBCO.

Fetal Bovine Serum, Cat. #SH30071.03, lot #AVB64134, Hyclone Laboratories, Inc.

GIBCO™ MEM Sodium Pyruvate Solution 100 mM (100×) liquid, Cat #11360070, GIBCO.

2-Mercaptoethanol, Cat #21985-023, GIBCO

Cell Culture

Mouse lymphoma tumor cells, EG7-OVA, were cultured in RPMI 1640 medium supplemented with 1.0 mM sodium pyruvate, 0.05 mM 2-mercaptoethanol and 10% fetal bovine serum at 37° C. with 5% CO2. The cells were washed twice with PBS and re-suspended in PBS at 10×106 cells/mL for s.c. injection.

Subcutaneous Injection of EG7-OVA Tumor Cells

C57BL/6 mice were shaved in the rear flank before injecting tumor cells. For each animal, EG7-OVA (1×106 cells in 100 μL of PBS) was injected s.c. on the rear flank.

Tumor Measurement

The length (mm) and width (mm) of the tumors were measured and recorded. The tumor volume was estimated using the following equation: Tumor volume=½(Length× Width2).

Experiment Design and Treatment Schedule

Mice injected with EG7-OVA cells were treated intravenously via the lateral vein on 1, 4, 8 and 11 days post-tumor implantation with either ALT-803 at 0.415 or 0.83 mg/kg in 100 μL PBS or rhIL-15 at 0.06 mg/kg or PBS (100 μL) as control (Table 1). The tumor-bearing mice were maintained to assess tumor growth rates among the treated groups.

Data Analysis

Data were analyzed by ANOVA using GraphPad Prism Version 4.03. P values of less than or equal to 0.05 are considered significant. Tumor growth inhibition (TGI) was calculated using the following equation: TGI (%)=(Vcontrol− Vtreated)/Vcontrol×100, where Vcontrol is the mean tumor volume of mice from the PBS or rhIL-15 treatment control, and Vtreated is the mean tumor volume of mice receiving test article treatment.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for treating neoplasia or human immunodeficiency virus (HIV) infection in a subject, the method comprising administering to said subject an effective amount of a pharmaceutical composition comprising interleukin-15 N72D: IL-15 receptor alpha Sushi/IgG1 CH2-CH3 (IL-15N72D:IL-15RαSu/Fc complex (Alt-803) comprising a dimeric IL-15RαSu/Fc and two IL-15N72D molecules, thereby treating the neoplasia or virus infection.

2. The method of claim 1, wherein the IL-15RaSu/Fc comprises the following sequences ("IL-15RaSu/Fc" (SEQ ID NO: 1): itcpppmsvehadiwvksyslysreryicnsgfkrkagtsslte-cvinkatnvahwttpslkcir [IL-15RαSu] (amino acids 1-65 of SEQ ID NO:1) and epkscdkthtcppcpapellggpsvflf-ppkpkdtlmisrtpevtcvvvdvshedpevkfnwyvdgvevhnaktkpreeq ynstyrvvsvltvlhqdwlngkeykckvsnkalpapiektiskakgqprep-qvytlppsrdeltknqvsltclvkgfypsdiav ewesngqpennykttppvlds-dgsfflyskltvdksrwqqgnvfscsvmhealhnhytqkslslspgk [IgG1 Ch2-CH3 (Fc domain)] (amino acids 66-297 of SEQ ID NO:1).

3. The method of claim 1, wherein the IL-15N72D molecule comprises the following sequence (SEQ ID NO: 2): nwvnvisdlkkiedliqsmhidat-lytesdvhpsckvtamkcfllelqvislesgdasihdtvenli ilandslssngn-vtesgckeceeleeknikeflqsfvhivqmfints [IL-15N72D].

4. The method of claim 1, wherein the neoplasia is selected from the group consisting of multiple myeloma, beta-cell lymphoma, urothelial/bladder carcinoma and melanoma.

5. The method of claim 1, wherein the effective amount is between about 1 and 20 μg/kg.

6. The method of claim 5, wherein the effective amount is about 1 μg/kg, 5 μg/kg, 10 μg/kg, 15 μg/kg, or 20 μg/kg.

7. The method of claim 6, wherein the effective amount is 10 μg/week.

8. The method of claim 1, wherein the effective amount is between about 20 μg and 100 μg/kg.

9. The method of claim 1, wherein the effective amount is 30 μg/kg, 50 μg/kg, 75 μg/kg, or 100 μg/kg.

10. The method of claim 1, wherein Alt-803 is administered once, twice, or three times per week.

11. The method of claim 1, wherein the pharmaceutical composition is administered systemically, intravenously, or by instillation.

12. The method of claim 1, wherein Alt-803
increases serum levels of IFN-γ;
increases the number of CD8$^+$CD44$^{high}$ memory T cells,
causes CD8$^+$CD44$^{high}$ memory T cells to acquire an innate-type phenotype and secrete IFN-γ independent of antigen requirement; and/or
induces a long lasting anti-myeloma immune memory response.

13. The method of claim 1, wherein the effective amount is between about 1 and 100 μg/kg.

14. A method of treating neoplasia in a subject, the method comprising administering to said subject an effective amount of a pharmaceutical composition comprising an anti-CD20 single chain antibody (scAb) T2 molecule (T2M) complex or a CD20-targeted IL-15N72D:IL-15Rα/Fc fusion protein complex (2B8T2M), thereby treating the neoplasia.

15. The method of claim 14, wherein anti-CD20 scAb T2M comprises a soluble anti-CD20 scAb/huIL-15N72D:anti-CD20 scAb/huIL-15RαSu/huIgG1 Fc complex, wherein anti-CD20 scAb/huIL-15RαSu/huIgG1 Fc has the sequence shown in SEQ ID NO: 51, and the anti-CD20 scAb/hIL-15N72D construct has the sequence shown in SEQ ID NO: 49.

16. The method of claim 14, wherein the neoplasia is beta-cell lymphoma or Burkitt's lymphoma.

\* \* \* \* \*

SEQUENCE LISTING

<160> NUMBER OF SEQ ID NOS: 57

<210> SEQ ID NO 1
<211> LENGTH: 297
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295
```

<210> SEQ ID NO 2
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
            20                  25                  30
Pro Ser Cys Lys Val Thr Ala Met Lys Cys Phe Leu Leu Glu Leu Gln
        35                  40                  45
Val Ile Ser Leu Glu Ser Gly Asp Ala Ser Ile His Asp Thr Val Glu
50                  55                  60
Asn Leu Ile Ile Leu Ala Asn Asp Ser Leu Ser Ser Asn Gly Asn Val
65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser
```

<210> SEQ ID NO 3
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Glu Thr Asp Thr Leu Leu Leu Trp Val Leu Leu Leu Trp Val Pro
1               5                   10                  15
Gly Ser Thr Gly Asn Trp Val Asn Val Ile Ser Asp Leu Lys Lys Ile
            20                  25                  30
Glu Asp Leu Ile Gln Ser Met His Ile Asp Ala Thr Leu Tyr Thr Glu
        35                  40                  45
Ser Asp Val His Pro Ser Cys Lys Val Thr Ala Met Lys Cys Phe Leu
50                  55                  60
Leu Glu Leu Gln Val Ile Ser Leu Glu Ser Gly Asp Ala Ser Ile His
65                  70                  75                  80
Asp Thr Val Glu Asn Leu Ile Ile Leu Ala Asn Asp Ser Leu Ser Ser
                85                  90                  95
Asn Gly Asn Val Thr Glu Ser Gly Cys Lys Glu Cys Glu Glu Leu Glu
            100                 105                 110
Glu Lys Asn Ile Lys Glu Phe Leu Gln Ser Phe Val His Ile Val Gln
        115                 120                 125
Met Phe Ile Asn Thr Ser
    130
```

<210> SEQ ID NO 4
<211> LENGTH: 316
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Asp Arg Leu Thr Ser Ser Phe Leu Leu Leu Ile Val Pro Ala Tyr
1               5                   10                  15
Val Leu Ser Ile Thr Cys Pro Pro Pro Met Ser Val Glu His Ala Asp
            20                  25                  30
```

```
Ile Trp Val Lys Ser Tyr Ser Leu Tyr Ser Arg Glu Arg Tyr Ile Cys
        35                  40                  45

Asn Ser Gly Phe Lys Arg Lys Ala Gly Thr Ser Ser Leu Thr Glu Cys
 50                  55                  60

Val Leu Asn Lys Ala Thr Asn Val Ala His Trp Thr Thr Pro Ser Leu
 65                  70                  75                  80

Lys Cys Ile Arg Glu Pro Lys Ser Cys Asp Lys Thr His Thr Cys Pro
                85                  90                  95

Pro Cys Pro Ala Pro Glu Leu Leu Gly Gly Pro Ser Val Phe Leu Phe
                100                 105                 110

Pro Pro Lys Pro Lys Asp Thr Leu Met Ile Ser Arg Thr Pro Glu Val
            115                 120                 125

Thr Cys Val Val Val Asp Val Ser His Glu Asp Pro Glu Val Lys Phe
        130                 135                 140

Asn Trp Tyr Val Asp Gly Val Glu Val His Asn Ala Lys Thr Lys Pro
145                 150                 155                 160

Arg Glu Glu Gln Tyr Asn Ser Thr Tyr Arg Val Val Ser Val Leu Thr
                165                 170                 175

Val Leu His Gln Asp Trp Leu Asn Gly Lys Glu Tyr Lys Cys Lys Val
            180                 185                 190

Ser Asn Lys Ala Leu Pro Ala Pro Ile Glu Lys Thr Ile Ser Lys Ala
        195                 200                 205

Lys Gly Gln Pro Arg Glu Pro Gln Val Tyr Thr Leu Pro Pro Ser Arg
    210                 215                 220

Asp Glu Leu Thr Lys Asn Gln Val Ser Leu Thr Cys Leu Val Lys Gly
225                 230                 235                 240

Phe Tyr Pro Ser Asp Ile Ala Val Glu Trp Glu Ser Asn Gly Gln Pro
                245                 250                 255

Glu Asn Asn Tyr Lys Thr Thr Pro Pro Val Leu Asp Ser Asp Gly Ser
            260                 265                 270

Phe Phe Leu Tyr Ser Lys Leu Thr Val Asp Lys Ser Arg Trp Gln Gln
        275                 280                 285

Gly Asn Val Phe Ser Cys Ser Val Met His Glu Ala Leu His Asn His
    290                 295                 300

Tyr Thr Gln Lys Ser Leu Ser Leu Ser Pro Gly Lys
305                 310                 315

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ser Gly Gly Gly Gly Ser Gly Gly Gly
 1               5                   10

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
```
tgttgggaat tcatcacgtg ccctc                                              25

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggtgtgaat tctctaatgc atttgagact gg                                      32

<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtacgactta attaactcga gccaccatgg agacagacac actcctgtta tgg               53

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cttcccgtta acccaccagc tcagctccac gtg                                     33

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctggtgggtt aacgggaagg aggtgcacag tggggtc                                 37

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagggcacgt gatgtctgct ctaccccagg cctc                                    34

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtagagcaga catcacgtgc cctccccca tg                                    32

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccttggtgct agctctaata catttgagac tgggggttgt cc                        42

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccagtctcaa atgtattaga gctagcacca agggcccatc ggtc                      44

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtaatattct agacgcgttc attatttacc aggagacagg gagaggctct tc             52

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gacttcaagc ttaattaagc caccatggac agacttactt cttc                      44

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctggtgggtt aacgggaagg aggtgcacag tggggtc                              37

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cacccagttg tctgctctac cccaggcctc                                      30

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctggggtaga gcagacaact gggtgaatgt aataagtgat ttg           43

<210> SEQ ID NO 20
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cctcatgcat tcgaatccgg atcattaaga agtgttgatg aacatttgg     49

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Glu Leu Leu Gly Gly
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Glu Ala Ala Gly Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Cys Lys Ser Leu
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Cys Ala Ser Leu
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Ile Ile Asn Phe Glu Lys Leu
1               5

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Gly Gly Ser Gly Gly Gly Gly Ser Gly Gly Gly Gly Ser Gly
1               5                   10                  15

Gly Gly Gly Ser
            20

<210> SEQ ID NO 27
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtgagttttg tcacaagatt tcggctctct aatgcatttg agactggggg ttg          53

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gagccgaaat cttgtgacaa aactcac                                       27

<210> SEQ ID NO 29
<211> LENGTH: 9
<212> TYPE: PRT
<213> ORGANISM: Homo sapiens

<400> SEQUENCE: 29

Ser Thr Pro Pro Pro Gly Thr Arg Val
1               5

<210> SEQ ID NO 30
<211> LENGTH: 9
<212> TYPE: PRT
<213> ORGANISM: Homo sapiens

<400> SEQUENCE: 30

```
Leu Leu Gly Arg Asn Ser Phe Glu Val
1               5

<210> SEQ ID NO 31
<211> LENGTH: 8
<212> TYPE: PRT
<213> ORGANISM: Vesicular stomatitis virus

<400> SEQUENCE: 31

Arg Gly Tyr Val Tyr Gln Gly Leu
1               5

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Thr Ser Gly Gly Gly Gly Ser Gly Gly Gly Gly Ser Gly Gly Gly
1               5                   10                  15

Gly Ser Gly Gly Gly Gly Ser Ser Ser
            20                  25

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Ser Gly Gly Gly Gly Ser Gly Gly Gly Gly Ser Pro Gly Gly Gly
1               5                   10                  15

Gly Ser Gly Gly Gly Gly Ser Ser Ser
            20                  25

<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Thr Ser Gly Gly Gly Gly Ser Gly Gly Gly Ala Ser Gly Gly Gly
1               5                   10                  15

Gly Ser Gly Gly Gly Gly Ser Ser Ser
            20                  25

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Gly Gly Gly Gly Ser Gly Gly Gly Ala Ser Gly Gly Gly Gly Ser
1               5                   10                  15
```

-continued

```
Gly Gly Gly Gly Ser
            20

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Asn Glu Pro Lys Ser Ser Asp Lys Thr His Thr Ser Pro Pro Ser
1               5                   10                  15

Pro Thr Arg

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Gly Gly Gly Ser Gly Gly Gly Gly Ser Ile Asp
1               5                   10

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 39
<211> LENGTH: 2397
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atggacagac ttacttcttc attcctgctc ctgattgtcc ctgcgtacgt cttgtcccag      60
tcagtgacgc agcccgatgc tcgcgtcact gtctctgaag agcctctctc gcagctgaga     120
tgcaagtatt cctactctgg acaccttat ctgttctggt atgtccagta cccgcggcag      180
gggctgcagc tgctcctcaa gtactattca ggagacccag tggttcaagg agtgaatggc     240
ttcgaggctg agttcagcaa gagtaactct tccttccacc tgcggaaagc ctctgtgcac     300
tggagcgact ctgctgtgta cttctgtgtt ttgagcgagg atagcaacta tcagttgatc     360
tggggctctg ggaccaagct aattataaag ccagacacta gtggtggcgg tggcagcggc     420
ggtggtggtt ccggtggcgg cggttctggc ggtggcggtt cctcgagcaa ttcaaaagtc     480
attcagactc caagatatct ggtgaaaggg caaggacaaa aagcaaagat gaggtgtatc     540
```

```
cctgaaaagg gacatccagt tgtattctgg tatcaacaaa ataagaacaa tgagtttaaa      600
tttttgatta actttcagaa tcaagaagtt cttcagcaaa tagacatgac tgaaaaacga      660
ttctctgctg agtgtccttc aaactcacct tgcagcctag aaattcagtc ctctgaggca      720
ggagactcag cactgtacct ctgtgccagc agtctgtcag ggggcggcac agaagttttc      780
tttggtaaag gaaccaggct cacagttgta gaggacctga acaaggtgtt cccacccgag      840
gtcgctgtgt ttgagccatc agaagcagag atctcccaca cccaaaaggc cacactggtg      900
tgcctggcca caggcttctt ccctgaccac gtggagctga gctggtgggt gaatgggaag      960
gaggtgcaca gtggggtcag cacggacccg cagcccctca aggagcagcc cgccctcaat     1020
gactccagat actgcctgag cagccgcctg agggtctcgg ccaccttctg gcagaacccc     1080
cgcaaccact tccgctgtca agtccagttc tacgggctct cggagaatga cgagtggacc     1140
caggataggg ccaaacccgt cacccagatc gtcagcgccg aggcctgggg tagagcagac     1200
gaattcatca cgtgccctcc ccccatgtcc gtggaacacg cagacatctg ggtcaagagc     1260
tacagcttgt actccaggga gcggtacatt tgtaactctg gtttcaagcg taaagccggc     1320
acgtccagcc tgacggagtg cgtgttgaac aaggccacga atgtcgccca ctggacaacc     1380
cccagtctca aatgcattag agaattcgcc tccaccaagg gcccatcggt cttccccctg     1440
gcacccctcc tcaagagcac ctctgggggc acagcggccc tgggctgcct ggtcaaggac     1500
tacttccccg aaccggtgac ggtgtcgtgg aactcaggcg ccctgaccag cggcgtgcac     1560
accttcccgg ctgtcctaca gtcctcagga ctctactccc tcagcagcgt ggtgaccgtg     1620
ccctccagca gcttgggcac ccagacctac atctgcaacg tgaatcacaa gcccagcaac     1680
accaaggtgg acaagaaagt tgagcccaaa tcttgtgaca aaactcacac atgcccaccg     1740
tgcccagcac ctgaactcct ggggggaccg tcagtcttcc tcttcccccc aaaacccaag     1800
gacaccctca tgatctcccg gacccctgag gtcacatgcg tggtggtgga cgtgagccac     1860
gaagaccctg aggtcaagtt caactggtac gtggacggcg tggaggtgca taatgccaag     1920
acaaagccgc gggaggagca gtacaacagc acgtaccgtg tggtcagcgt cctcaccgtc     1980
ctgcaccagg actggctgaa tggcaaggag tacaagtgca aggtctccaa caaagccctc     2040
ccagccccca tcgagaaaac catctccaaa gccaaagggc agccccgaga accacaggtg     2100
tacaccctgc cccatcccg ggatgagctg accaagaacc aggtcagcct gacctgcctg     2160
gtcaaaggct tctatcccag cgacatcgcc gtggagtggg agagcaatgg gcagccggag     2220
aacaactaca agaccacgcc tcccgtgctg gactccgacg gctccttctt cctctacagc     2280
aagctcaccg tggacaagag caggtggcag caggggaacg tcttctcatg ctccgtgatg     2340
catgaggctc tgcacaacca ctacacgcag aagagcctct ccctgtctcc gggtaaa         2397
```

<210> SEQ ID NO 40
<211> LENGTH: 799
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Met Asp Arg Leu Thr Ser Ser Phe Leu Leu Leu Ile Val Pro Ala Tyr
1               5                   10                  15

Val Leu Ser Gln Ser Val Thr Gln Pro Asp Ala Arg Val Thr Val Ser
                20                  25                  30
```

```
Glu Gly Ala Ser Leu Gln Leu Arg Cys Lys Tyr Ser Tyr Ser Gly Thr
         35                  40                  45
Pro Tyr Leu Phe Trp Tyr Val Gln Tyr Pro Arg Gln Gly Leu Gln Leu
     50                  55                  60
Leu Leu Lys Tyr Tyr Ser Gly Asp Pro Val Val Gln Gly Val Asn Gly
 65              70                  75                      80
Phe Glu Ala Glu Phe Ser Lys Ser Asn Ser Ser Phe His Leu Arg Lys
                 85                  90                  95
Ala Ser Val His Trp Ser Asp Ser Ala Val Tyr Phe Cys Val Leu Ser
                100                 105                 110
Glu Asp Ser Asn Tyr Gln Leu Ile Trp Gly Ser Gly Thr Lys Leu Ile
            115                 120                 125
Ile Lys Pro Asp Thr Ser Gly Gly Gly Ser Gly Gly Gly Gly Gly Ser
130                 135                 140
Gly Gly Gly Gly Ser Gly Gly Gly Ser Ser Asn Ser Lys Val
145                 150                 155                 160
Ile Gln Thr Pro Arg Tyr Leu Val Lys Gly Gln Gly Gln Lys Ala Lys
                165                 170                 175
Met Arg Cys Ile Pro Glu Lys Gly His Pro Val Val Phe Trp Tyr Gln
            180                 185                 190
Gln Asn Lys Asn Asn Glu Phe Lys Phe Leu Ile Asn Phe Gln Asn Gln
        195                 200                 205
Glu Val Leu Gln Gln Ile Asp Met Thr Glu Lys Arg Phe Ser Ala Glu
    210                 215                 220
Cys Pro Ser Asn Ser Pro Cys Ser Leu Glu Ile Gln Ser Ser Glu Ala
225                 230                 235                 240
Gly Asp Ser Ala Leu Tyr Leu Cys Ala Ser Ser Leu Ser Gly Gly Gly
                245                 250                 255
Thr Glu Val Phe Phe Gly Lys Gly Thr Arg Leu Thr Val Val Glu Asp
            260                 265                 270
Leu Asn Lys Val Phe Pro Pro Glu Val Ala Val Phe Glu Pro Ser Glu
        275                 280                 285
Ala Glu Ile Ser His Thr Gln Lys Ala Thr Leu Val Cys Leu Ala Thr
    290                 295                 300
Gly Phe Phe Pro Asp His Val Glu Leu Ser Trp Trp Val Asn Gly Lys
305                 310                 315                 320
Glu Val His Ser Gly Val Ser Thr Asp Pro Gln Pro Leu Lys Glu Gln
                325                 330                 335
Pro Ala Leu Asn Asp Ser Arg Tyr Cys Leu Ser Ser Arg Leu Arg Val
            340                 345                 350
Ser Ala Thr Phe Trp Gln Asn Pro Arg Asn His Phe Arg Cys Gln Val
        355                 360                 365
Gln Phe Tyr Gly Leu Ser Glu Asn Asp Glu Trp Thr Gln Asp Arg Ala
    370                 375                 380
Lys Pro Val Thr Gln Ile Val Ser Ala Glu Ala Trp Gly Arg Ala Asp
385                 390                 395                 400
Glu Phe Ile Thr Cys Pro Pro Met Ser Val Glu His Ala Asp Ile
                405                 410                 415
Trp Val Lys Ser Tyr Ser Leu Tyr Ser Arg Glu Arg Tyr Ile Cys Asn
            420                 425                 430
Ser Gly Phe Lys Arg Lys Ala Gly Thr Ser Ser Leu Thr Glu Cys Val
        435                 440                 445
```

| | | | | | | | | | | | | | | |
|---|---|---|---|---|---|---|---|---|---|---|---|---|---|---|
|Leu|Asn|Lys|Ala|Thr|Asn|Val|Ala|His|Trp|Thr|Thr|Pro|Ser|Leu|Lys|
|450| | | | |455| | | | |460| | | | |

| | | | | | | | | | | | | | | |
|---|---|---|---|---|---|---|---|---|---|---|---|---|---|---|
|Cys|Ile|Arg|Glu|Phe|Ala|Ser|Thr|Lys|Gly|Pro|Ser|Val|Phe|Pro|Leu|
|465| | | | |470| | | | |475| | | | |480|

| | | | | | | | | | | | | | | |
|---|---|---|---|---|---|---|---|---|---|---|---|---|---|---|
|Ala|Pro|Ser|Ser|Lys|Ser|Thr|Ser|Gly|Gly|Thr|Ala|Ala|Leu|Gly|Cys|
| | | | |485| | | | |490| | | | |495|

| | | | | | | | | | | | | | | |
|---|---|---|---|---|---|---|---|---|---|---|---|---|---|---|
|Leu|Val|Lys|Asp|Tyr|Phe|Pro|Glu|Pro|Val|Thr|Val|Ser|Trp|Asn|Ser|
| | | |500| | | | |505| | | | |510| | |

| | | | | | | | | | | | | | | |
|---|---|---|---|---|---|---|---|---|---|---|---|---|---|---|
|Gly|Ala|Leu|Thr|Ser|Gly|Val|His|Thr|Phe|Pro|Ala|Val|Leu|Gln|Ser|
| | |515| | | | |520| | | | |525| | | |

| | | | | | | | | | | | | | | |
|---|---|---|---|---|---|---|---|---|---|---|---|---|---|---|
|Ser|Gly|Leu|Tyr|Ser|Leu|Ser|Ser|Val|Val|Thr|Val|Pro|Ser|Ser|Ser|
|530| | | | |535| | | | |540| | | | | |

| | | | | | | | | | | | | | | |
|---|---|---|---|---|---|---|---|---|---|---|---|---|---|---|
|Leu|Gly|Thr|Gln|Thr|Tyr|Ile|Cys|Asn|Val|Asn|His|Lys|Pro|Ser|Asn|
|545| | | | |550| | | | |555| | | | |560|

| | | | | | | | | | | | | | | |
|---|---|---|---|---|---|---|---|---|---|---|---|---|---|---|
|Thr|Lys|Val|Asp|Lys|Lys|Val|Glu|Pro|Lys|Ser|Cys|Asp|Lys|Thr|His|
| | | |565| | | | |570| | | | |575| | |

| | | | | | | | | | | | | | | |
|---|---|---|---|---|---|---|---|---|---|---|---|---|---|---|
|Thr|Cys|Pro|Pro|Cys|Pro|Ala|Pro|Glu|Leu|Leu|Gly|Gly|Pro|Ser|Val|
| | |580| | | | |585| | | | |590| | | |

| | | | | | | | | | | | | | | |
|---|---|---|---|---|---|---|---|---|---|---|---|---|---|---|
|Phe|Leu|Phe|Pro|Pro|Lys|Pro|Lys|Asp|Thr|Leu|Met|Ile|Ser|Arg|Thr|
| |595| | | | |600| | | | |605| | | | |

| | | | | | | | | | | | | | | |
|---|---|---|---|---|---|---|---|---|---|---|---|---|---|---|
|Pro|Glu|Val|Thr|Cys|Val|Val|Val|Asp|Val|Ser|His|Glu|Asp|Pro|Glu|
|610| | | | |615| | | | |620| | | | | |

| | | | | | | | | | | | | | | |
|---|---|---|---|---|---|---|---|---|---|---|---|---|---|---|
|Val|Lys|Phe|Asn|Trp|Tyr|Val|Asp|Gly|Val|Glu|Val|His|Asn|Ala|Lys|
|625| | | | |630| | | | |635| | | | |640|

| | | | | | | | | | | | | | | |
|---|---|---|---|---|---|---|---|---|---|---|---|---|---|---|
|Thr|Lys|Pro|Arg|Glu|Glu|Gln|Tyr|Asn|Ser|Thr|Tyr|Arg|Val|Val|Ser|
| | | |645| | | | |650| | | | |655| | |

| | | | | | | | | | | | | | | |
|---|---|---|---|---|---|---|---|---|---|---|---|---|---|---|
|Val|Leu|Thr|Val|Leu|His|Gln|Asp|Trp|Leu|Asn|Gly|Lys|Glu|Tyr|Lys|
| | |660| | | | |665| | | | |670| | | |

| | | | | | | | | | | | | | | |
|---|---|---|---|---|---|---|---|---|---|---|---|---|---|---|
|Cys|Lys|Val|Ser|Asn|Lys|Ala|Leu|Pro|Ala|Pro|Ile|Glu|Lys|Thr|Ile|
| |675| | | | |680| | | | |685| | | | |

| | | | | | | | | | | | | | | |
|---|---|---|---|---|---|---|---|---|---|---|---|---|---|---|
|Ser|Lys|Ala|Lys|Gly|Gln|Pro|Arg|Glu|Pro|Gln|Val|Tyr|Thr|Leu|Pro|
| |690| | | | |695| | | | |700| | | | |

| | | | | | | | | | | | | | | |
|---|---|---|---|---|---|---|---|---|---|---|---|---|---|---|
|Pro|Ser|Arg|Asp|Glu|Leu|Thr|Lys|Asn|Gln|Val|Ser|Leu|Thr|Cys|Leu|
|705| | | | |710| | | | |715| | | | |720|

| | | | | | | | | | | | | | | |
|---|---|---|---|---|---|---|---|---|---|---|---|---|---|---|
|Val|Lys|Gly|Phe|Tyr|Pro|Ser|Asp|Ile|Ala|Val|Glu|Trp|Glu|Ser|Asn|
| | | |725| | | | |730| | | | |735| | |

| | | | | | | | | | | | | | | |
|---|---|---|---|---|---|---|---|---|---|---|---|---|---|---|
|Gly|Gln|Pro|Glu|Asn|Asn|Tyr|Lys|Thr|Thr|Pro|Pro|Val|Leu|Asp|Ser|
| | |740| | | | |745| | | | |750| | | |

| | | | | | | | | | | | | | | |
|---|---|---|---|---|---|---|---|---|---|---|---|---|---|---|
|Asp|Gly|Ser|Phe|Phe|Leu|Tyr|Ser|Lys|Leu|Thr|Val|Asp|Lys|Ser|Arg|
| | |755| | | | |760| | | | |765| | | |

| | | | | | | | | | | | | | | |
|---|---|---|---|---|---|---|---|---|---|---|---|---|---|---|
|Trp|Gln|Gln|Gly|Asn|Val|Phe|Ser|Cys|Ser|Val|Met|His|Glu|Ala|Leu|
|770| | | | |775| | | | |780| | | | | |

| | | | | | | | | | | | |
|---|---|---|---|---|---|---|---|---|---|---|---|
|His|Asn|His|Tyr|Thr|Gln|Lys|Ser|Leu|Ser|Leu|Ser|Pro|Gly|Lys|
|785| | | | |790| | | | |795| | | | |

<210> SEQ ID NO 41
<211> LENGTH: 2391
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
atggagacag acacactcct gttatgggta ctgctgctct gggttccagg ttccaccggt    60
```

```
cagtcagtga cgcagcccga tgctcgcgtc actgtctctg aaggagcctc tctgcagctg    120
agatgcaagt attcctactc tgggacacct tatctgttct ggtatgtcca gtacccgcgg    180
caggggctgc agctgctcct caagtactat tcaggagacc cagtggttca aggagtgaat    240
ggcttcgagg ctgagttcag caagagtaac tcttccttcc acctgcggaa agcctctgtg    300
cactggagcg actctgctgt gtacttctgt gttttgagcg aggatagcaa ctatcagttg    360
atctggggct ctgggaccaa gctaattata aagccagaca ctagtggtgg cggtggcagc    420
ggcggtggtg gttccggtgg cggcggttct ggcggtggcg gttcctcgag caattcaaaa    480
gtcattcaga ctccaagata tctggtgaaa gggcaaggac aaaaagcaaa gatgaggtgt    540
atccctgaaa agggacatcc agttgtattc tggtatcaac aaaataagaa caatgagttt    600
aaatttttga ttaactttca gaatcaagaa gttcttcagc aaatagacat gactgaaaaa    660
cgattctctg ctgagtgtcc ttcaaactca ccttgcagcc tagaaattca gtcctctgag    720
gcaggagact cagcactgta cctctgtgcc agcagtctgt caggggggcgg cacagaagtt    780
ttctttggta aaggaaccag gctcacagtt gtagaggacc tgaacaaggt gttcccaccc    840
gaggtcgctg tgtttgagcc atcagaagca gagatctccc acacccaaaa ggccacactg    900
gtgtgcctgg ccacaggctt cttccctgac cacgtggagc tgagctggtg gttaacggg    960
aaggaggtgc acagtggggt cagcacggac ccgcagcccc tcaaggagca gcccgccctc    1020
aatgactcca gatactgcct gagcagccgc ctgagggtct cggccacctt ctggcagaac    1080
ccccgcaacc acttccgctg tcaagtccag ttctacgggc tctcggagaa tgacgagtgg    1140
acccaggata gggccaaacc cgtcacccag atcgtcagcg ccgaggcctg ggtagagca    1200
gacatcacgt gcctcccccc catgtccgtg aacacgcag acatctgggt caagagctac    1260
agcttgtact ccagggagcg gtacatttgt aactctggtt tcaagcgtaa agccggcacg    1320
tccagcctga cggagtgcgt gttgaacaag gccacgaatg tcgcccactg acaaccccc    1380
agtctcaaat gtattagagc tagcaccaag ggcccatcgg tcttccccct ggcaccctcc    1440
tccaagagca cctctggggg cacagcggcc ctgggctgcc tggtcaagga ctacttcccc    1500
gaaccggtga cggtgtcgtg gaactcaggc gccctgacca gcggcgtgca caccttcccg    1560
gctgtcctac agtcctcagg actctactcc ctcagcagcg tggtgaccgt gccctccagc    1620
agcttgggca cccagaccta catctgcaac gtgaatcaca agcccagcaa caccaaggtg    1680
gacaagaaag ttgagcccaa atcttgtgac aaaactcaca catgcccacc gtgcccagca    1740
cctgaactcc tggggggacc gtcagtcttc ctcttccccc caaaacccaa ggacaccctc    1800
atgatctccc ggaccctga ggtcacatgc gtggtggtgg acgtgagcca cgaagaccct    1860
gaggtcaagt tcaactggta cgtggacggc gtggaggtgc ataatgccaa gacaaagccg    1920
cgggaggagc agtacaacag cacgtaccgt gtggtcagcg tcctcaccgt cctgcaccag    1980
gactggctga atggcaagga gtacaagtgc aaggtctcca acaaagccct cccagccccc    2040
atcgagaaaa ccatctccaa agccaaaggg cagccccgag aaccacaggt gtacaccctg    2100
cccccatccc gggatgagct gaccaagaac caggtcagcc tgacctgcct ggtcaaaggc    2160
ttctatccca gcgacatcgc cgtggagtgg gagagcaatg ggcagccgga gaacaactac    2220
aagaccacgc ctcccgtgct ggactccgac ggctccttct tcctctacag caagctcacc    2280
gtggacaaga gcaggtggca gcaggggaac gtcttctcat gctccgtgat gcatgaggct    2340
ctgcacaacc actacacgca gaagagcctc tccctgtctc cgggtaaata a            2391
```

```
<210> SEQ ID NO 42
<211> LENGTH: 796
<212> TYPE: PRT
<213> ORGANISM: Homo sapiens

<400> SEQUENCE: 42

Met Glu Thr Asp Thr Leu Leu Leu Trp Val Leu Leu Leu Trp Val Pro
1               5                   10                  15

Gly Ser Thr Gly Gln Ser Val Thr Gln Pro Asp Ala Arg Val Thr Val
            20                  25                  30

Ser Glu Gly Ala Ser Leu Gln Leu Arg Cys Lys Tyr Ser Tyr Ser Gly
        35                  40                  45

Thr Pro Tyr Leu Phe Trp Tyr Val Gln Tyr Pro Arg Gln Gly Leu Gln
    50                  55                  60

Leu Leu Leu Lys Tyr Tyr Ser Gly Asp Pro Val Val Gln Gly Val Asn
65                  70                  75                  80

Gly Phe Glu Ala Glu Phe Ser Lys Ser Asn Ser Ser Phe His Leu Arg
                85                  90                  95

Lys Ala Ser Val His Trp Ser Asp Ser Ala Val Tyr Phe Cys Val Leu
            100                 105                 110

Ser Glu Asp Ser Asn Tyr Gln Leu Ile Trp Gly Ser Gly Thr Lys Leu
        115                 120                 125

Ile Ile Lys Pro Asp Thr Ser Gly Gly Gly Ser Gly Gly Gly Gly
    130                 135                 140

Ser Gly Gly Gly Gly Ser Gly Gly Gly Ser Ser Asn Ser Lys
145                 150                 155                 160

Val Ile Gln Thr Pro Arg Tyr Leu Val Lys Gly Gln Gly Gln Lys Ala
                165                 170                 175

Lys Met Arg Cys Ile Pro Glu Lys Gly His Pro Val Val Phe Trp Tyr
            180                 185                 190

Gln Gln Asn Lys Asn Asn Glu Phe Lys Phe Leu Ile Asn Phe Gln Asn
        195                 200                 205

Gln Glu Val Leu Gln Gln Ile Asp Met Thr Glu Lys Arg Phe Ser Ala
    210                 215                 220

Glu Cys Pro Ser Asn Ser Pro Cys Ser Leu Glu Ile Gln Ser Ser Glu
225                 230                 235                 240

Ala Gly Asp Ser Ala Leu Tyr Leu Cys Ala Ser Ser Leu Ser Gly Gly
                245                 250                 255

Gly Thr Glu Val Phe Phe Gly Lys Gly Thr Arg Leu Thr Val Val Glu
            260                 265                 270

Asp Leu Asn Lys Val Phe Pro Pro Glu Val Ala Val Phe Glu Pro Ser
        275                 280                 285

Glu Ala Glu Ile Ser His Thr Gln Lys Ala Thr Leu Val Cys Leu Ala
    290                 295                 300

Thr Gly Phe Phe Pro Asp His Val Glu Leu Ser Trp Trp Val Asn Gly
305                 310                 315                 320

Lys Glu Val His Ser Gly Val Ser Thr Asp Pro Gln Pro Leu Lys Glu
                325                 330                 335

Gln Pro Ala Leu Asn Asp Ser Arg Tyr Cys Leu Ser Ser Arg Leu Arg
            340                 345                 350

Val Ser Ala Thr Phe Trp Gln Asn Pro Arg Asn His Phe Arg Cys Gln
        355                 360                 365

Val Gln Phe Tyr Gly Leu Ser Glu Asn Asp Glu Trp Thr Gln Asp Arg
    370                 375                 380
```

```
Ala Lys Pro Val Thr Gln Ile Val Ser Ala Glu Ala Trp Gly Arg Ala
385                 390                 395                 400

Asp Ile Thr Cys Pro Pro Met Ser Val Glu His Ala Asp Ile Trp
            405                 410                 415

Val Lys Ser Tyr Ser Leu Tyr Ser Arg Glu Arg Tyr Ile Cys Asn Ser
                420                 425                 430

Gly Phe Lys Arg Lys Ala Gly Thr Ser Ser Leu Thr Glu Cys Val Leu
            435                 440                 445

Asn Lys Ala Thr Asn Val Ala His Trp Thr Thr Pro Ser Leu Lys Cys
            450                 455                 460

Ile Arg Ala Ser Thr Lys Gly Pro Ser Val Phe Pro Leu Ala Pro Ser
465                 470                 475                 480

Ser Lys Ser Thr Ser Gly Gly Thr Ala Ala Leu Gly Cys Leu Val Lys
                485                 490                 495

Asp Tyr Phe Pro Glu Pro Val Thr Val Ser Trp Asn Ser Gly Ala Leu
            500                 505                 510

Thr Ser Gly Val His Thr Phe Pro Ala Val Leu Gln Ser Ser Gly Leu
            515                 520                 525

Tyr Ser Leu Ser Ser Val Val Thr Val Pro Ser Ser Ser Leu Gly Thr
530                 535                 540

Gln Thr Tyr Ile Cys Asn Val Asn His Lys Pro Ser Asn Thr Lys Val
545                 550                 555                 560

Asp Lys Lys Val Glu Pro Lys Ser Cys Asp Lys Thr His Thr Cys Pro
                565                 570                 575

Pro Cys Pro Ala Pro Glu Leu Leu Gly Gly Pro Ser Val Phe Leu Phe
            580                 585                 590

Pro Pro Lys Pro Lys Asp Thr Leu Met Ile Ser Arg Thr Pro Glu Val
            595                 600                 605

Thr Cys Val Val Val Asp Val Ser His Glu Asp Pro Glu Val Lys Phe
610                 615                 620

Asn Trp Tyr Val Asp Gly Val Glu Val His Asn Ala Lys Thr Lys Pro
625                 630                 635                 640

Arg Glu Glu Gln Tyr Asn Ser Thr Tyr Arg Val Val Ser Val Leu Thr
                645                 650                 655

Val Leu His Gln Asp Trp Leu Asn Gly Lys Glu Tyr Lys Cys Lys Val
            660                 665                 670

Ser Asn Lys Ala Leu Pro Ala Pro Ile Glu Lys Thr Ile Ser Lys Ala
            675                 680                 685

Lys Gly Gln Pro Arg Glu Pro Gln Val Tyr Thr Leu Pro Pro Ser Arg
690                 695                 700

Asp Glu Leu Thr Lys Asn Gln Val Ser Leu Thr Cys Leu Val Lys Gly
705                 710                 715                 720

Phe Tyr Pro Ser Asp Ile Ala Val Glu Trp Glu Ser Asn Gly Gln Pro
                725                 730                 735

Glu Asn Asn Tyr Lys Thr Thr Pro Pro Val Leu Asp Ser Asp Gly Ser
            740                 745                 750

Phe Phe Leu Tyr Ser Lys Leu Thr Val Asp Lys Ser Arg Trp Gln Gln
            755                 760                 765

Gly Asn Val Phe Ser Cys Ser Val Met His Glu Ala Leu His Asn His
            770                 775                 780

Tyr Thr Gln Lys Ser Leu Ser Leu Ser Pro Gly Lys
785                 790                 795
```

-continued

<210> SEQ ID NO 43
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
atggacagac ttacttcttc attcctgctc ctgattgtcc ctgcgtacgt cttggcccag     60
aaggtaacac agactcagac ttcaatttct gtgatggaga agacaacggt gacaatggac    120
tgtgtgtatg aaacccggga cagttcttac ttcttattct ggtacaagca aacagcaagt    180
ggggaaatag ttttccttat tcgtcaggac tcttacaaaa aggaaaatgc aacagaaggt    240
cattattctc tgaactttca gaagccaaaa agttccatcg gactcatcat cactgccaca    300
cagattgagg actcagcagt atatttctgt gctatgagag acacaaatgc ttacaaagtc    360
atctttggaa agggacacac tcttcatgtt ctgcctacta gtggtggcgg tggcagcggc    420
ggtggtggtt cccctggtgg cggcggttct ggcggtggcg gttcctcgag cgaggctgca    480
gtcacccaaa gtccaagaag caaggtggca gtaacaggag aaaggtgac attgagctgt    540
caccagacta ataaccatga ctatatgtac tggtatcggc aggacacggg gcatgggctg    600
aggctgatcc attactcata tgtcgctgac agcacggaga aggagatat ccctgatggg    660
tacaaggcct ccagaccaag ccaagagaat ttctctctca ttctggagtt ggcttccctt    720
tctcagacag ctgtatattt ctgtgccagc agcccccact cctatgaaca gtacttcggt    780
cccggcacca ggctcacggt tttagaggac ctgaacaagg tgttcccacc cgaggtcgct    840
gtgtttgagc catcagaagc agagatctcc cacacccaaa aggccacact ggtgtgcctg    900
gccacaggct tcttccctga ccacgtgag ctgagctggt gggttaacgg gaaggaggtg    960
cacagtgggg tcagcacgga cccgcagccc tcaaggagc agcccgccct caatgactcc   1020
agatactgcc tgagcagccg cctgagggtc tcggccacct tctggcagaa ccccgcaac   1080
cacttccgct gtcaagtcca gttctacggg ctctcggaga tgacgagtg gacccaggat   1140
agggccaaac tgtcaccca gatcgtcagc gccgaggcct ggggtagagc agacaactgg   1200
gtgaatgtaa taagtgattt gaaaaaaatt gaagatctta ttcaatctat gcatattgat   1260
gctactttat atacggaaag tgatgttcac cccagttgca aagtaacagc aatgaagtgc   1320
tttctcttgg agttacaagt tatttcactt gagtccggag atgcaagtat tcatgataca   1380
gtagaaaatc tgatcatcct agcaaacgac agtttgtctt ctaatgggaa tgtaacagaa   1440
tctggatgca aagaatgtga ggaactggag gaaaaaaata ttaaagaatt tttgcagagt   1500
tttgtacata ttgtccaaat gttcatcaac acttcttaa                         1539
```

<210> SEQ ID NO 44
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Met Asp Arg Leu Thr Ser Ser Phe Leu Leu Leu Ile Val Pro Ala Tyr
1               5                   10                  15

Val Leu Ala Gln Lys Val Thr Gln Thr Gln Thr Ser Ile Ser Val Met
            20                  25                  30
```

-continued

```
Glu Lys Thr Thr Val Thr Met Asp Cys Val Tyr Glu Thr Arg Asp Ser
         35                  40                  45

Ser Tyr Phe Leu Phe Trp Tyr Lys Gln Thr Ala Ser Gly Glu Ile Val
 50                  55                  60

Phe Leu Ile Arg Gln Asp Ser Tyr Lys Lys Glu Asn Ala Thr Glu Gly
 65                  70                  75                  80

His Tyr Ser Leu Asn Phe Gln Lys Pro Lys Ser Ser Ile Gly Leu Ile
             85                  90                  95

Ile Thr Ala Thr Gln Ile Glu Asp Ser Ala Val Tyr Phe Cys Ala Met
                100                 105                 110

Arg Asp Thr Asn Ala Tyr Lys Val Ile Phe Gly Lys Gly Thr His Leu
            115                 120                 125

His Val Leu Pro Thr Ser Gly Gly Gly Ser Gly Gly Gly Ser
        130                 135                 140

Pro Gly Gly Gly Ser Gly Gly Gly Ser Ser Ser Glu Ala Ala
145                 150                 155                 160

Val Thr Gln Ser Pro Arg Ser Lys Val Ala Val Thr Gly Gly Lys Val
            165                 170                 175

Thr Leu Ser Cys His Gln Thr Asn Asn His Asp Tyr Met Tyr Trp Tyr
        180                 185                 190

Arg Gln Asp Thr Gly His Gly Leu Arg Leu Ile His Tyr Ser Tyr Val
            195                 200                 205

Ala Asp Ser Thr Glu Lys Gly Asp Ile Pro Asp Gly Tyr Lys Ala Ser
    210                 215                 220

Arg Pro Ser Gln Glu Asn Phe Ser Leu Ile Leu Glu Leu Ala Ser Leu
225                 230                 235                 240

Ser Gln Thr Ala Val Tyr Phe Cys Ala Ser Ser Pro His Ser Tyr Glu
                245                 250                 255

Gln Tyr Phe Gly Pro Gly Thr Arg Leu Thr Val Leu Glu Asp Leu Asn
                260                 265                 270

Lys Val Phe Pro Pro Glu Val Ala Val Phe Glu Pro Ser Glu Ala Glu
            275                 280                 285

Ile Ser His Thr Gln Lys Ala Thr Leu Val Cys Leu Ala Thr Gly Phe
290                 295                 300

Phe Pro Asp His Val Glu Leu Ser Trp Trp Val Asn Gly Lys Glu Val
305                 310                 315                 320

His Ser Gly Val Ser Thr Asp Pro Gln Pro Leu Lys Glu Gln Pro Ala
                325                 330                 335

Leu Asn Asp Ser Arg Tyr Cys Leu Ser Ser Arg Leu Arg Val Ser Ala
            340                 345                 350

Thr Phe Trp Gln Asn Pro Arg Asn His Phe Arg Cys Gln Val Gln Phe
        355                 360                 365

Tyr Gly Leu Ser Glu Asn Asp Glu Trp Thr Gln Asp Arg Ala Lys Pro
    370                 375                 380

Val Thr Gln Ile Val Ser Ala Glu Ala Trp Gly Arg Ala Asp Asn Trp
385                 390                 395                 400

Val Asn Val Ile Ser Asp Leu Lys Lys Ile Glu Asp Leu Ile Gln Ser
                405                 410                 415

Met His Ile Asp Ala Thr Leu Tyr Thr Glu Ser Asp Val His Pro Ser
            420                 425                 430

Cys Lys Val Thr Ala Met Lys Cys Phe Leu Leu Glu Leu Gln Val Ile
        435                 440                 445

Ser Leu Glu Ser Gly Asp Ala Ser Ile His Asp Thr Val Glu Asn Leu
```

```
              450                 455                 460
Ile Ile Leu Ala Asn Asp Ser Leu Ser Ser Asn Gly Asn Val Thr Glu
465                 470                 475                 480

Ser Gly Cys Lys Glu Cys Glu Glu Leu Glu Glu Lys Asn Ile Lys Glu
                    485                 490                 495

Phe Leu Gln Ser Phe Val His Ile Val Gln Met Phe Ile Asn Thr Ser
                500                 505                 510

<210> SEQ ID NO 45
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 46
<211> LENGTH: 2097
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atggagacag acacactcct gttatgggta ctgctgctct gggttccagg ttccaccggt    60
```

```
cagtcagtga cgcagcccga tgctcgcgtc actgtctctg aaggagcctc tctgcagctg    120
agatgcaagt attcctactc tgggacacct tatctgttct ggtatgtcca gtacccgcgg    180
caggggctgc agctgctcct caagtactat tcaggagacc cagtggttca aggagtgaat    240
ggcttcgagg ctgagttcag caagagtaac tcttccttcc acctgcggaa agcctctgtg    300
cactggagcg actctgctgt gtacttctgt gttttgagcg aggatagcaa ctatcagttg    360 atctgggct ctgggaccaa gctaattata aagccagaca ctagtggtgg cggtggcagc     420
ggcggtggtg gttccggtgg cggcggttct ggcggtggcg gttcctcgag caattcaaaa    480
gtcattcaga ctccaagata tctggtgaaa gggcaaggac aaaaagcaaa gatgaggtgt    540
atccctgaaa agggacatcc agttgtattc tggtatcaac aaaataagaa caatgagttt    600 aaattttga ttaactttca gaatcaagaa gttcttcagc aaatagacat gactgaaaaa     660
cgattctctg ctgagtgtcc ttcaaactca ccttgcagcc tagaaattca gtcctctgag    720
gcaggagact cagcactgta cctctgtgcc agcagtctgt caggggcgg cacagaagtc     780 ttctttggta aaggaaccag gctcacagtt gtagaggacc tgaacaaggt gttcccaccc    840
gaggtcgctg tgtttgagcc atcagaagca gagatctccc acacccaaaa ggccacactg    900
gtgtgcctgg ccacaggctt cttccctgac cacgtggagc tgagctggtg ggttaacggg    960
aaggaggtgc acagtggggt cagcacggac ccgcagcccc tcaaggagca gcccgccctc    1020
aatgactcca gatactgcct gagcagccgc ctgagggtct cggccacctt ctggcagaac    1080
ccccgcaacc acttccgctg tcaagtccag ttctacgggc tctcggagaa tgacgagtgg    1140
acccaggata gggccaaacc cgtcacccag atcgtcagcg ccgaggcctg ggtagagca    1200 gacatcacgt gccctccccc catgtccgtg aacacgcag acatctgggt caagagctac    1260
agcttgtact ccagggagcg gtacatttgt aactctggtt tcaagcgtaa agccggcacg    1320
tccagcctga cggagtgcgt gttgaacaag gccacgaatg tcgcccactg gacaacccc    1380 agtctcaaat gcattagaga gccgaaatct tgtgacaaaa ctcacacatg cccaccgtgc    1440
ccagcacctg aactcctggg gggaccgtca gtcttcctct tccccccaaa acccaaggac    1500
accctcatga tctcccggac ccctgaggtc acatgcgtgg tggtggacgt gagccacgaa    1560
gaccctgagg tcaagttcaa ctggtacgtg gacggcgtgg aggtgcataa tgccaagaca    1620
aagccgcggg aggagcagta caacagcacg taccgtgtgg tcagcgtcct caccgtcctg    1680
caccaggact ggctgaatgg caaggagtac aagtgcaagg tctccaacaa agccctccca    1740
gcccccatcg agaaaaccat ctccaaagcc aaagggcagc ccgagaacc acaggtgtac     1800 accctgcccc catcccggga tgagctgacc aagaaccagg tcagcctgac ctgcctggtc    1860
aaaggcttct atcccagcga catcgccgtg gagtgggaga gcaatgggca gccggagaac    1920
aactacaaga ccacgcctcc cgtgctggac tccgacggct ccttcttcct ctacagcaag    1980
ctcaccgtgg acaagagcag gtggcagcag gggaacgtct tctcatgctc cgtgatgcat    2040
gaggctctgc acaaccacta cacgcagaag agcctctccc tgtctcctgg taaataa      2097
```

<210> SEQ ID NO 47
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Gln Ser Val Thr Gln Pro Asp Ala Arg Val Thr Val Ser Glu Gly Ala
1               5                   10                  15

Ser Leu Gln Leu Arg Cys Lys Tyr Ser Tyr Ser Gly Thr Pro Tyr Leu
            20                  25                  30

Phe Trp Tyr Val Gln Tyr Pro Arg Gln Gly Leu Gln Leu Leu Leu Lys
        35                  40                  45

Tyr Tyr Ser Gly Asp Pro Val Val Gln Gly Val Asn Gly Phe Glu Ala
    50                  55                  60

Glu Phe Ser Lys Ser Asn Ser Ser Phe His Leu Arg Lys Ala Ser Val
65                  70                  75                  80

His Trp Ser Asp Ser Ala Val Tyr Phe Cys Val Leu Ser Glu Asp Ser
                85                  90                  95

Asn Tyr Gln Leu Ile Trp Gly Ser Gly Thr Lys Leu Ile Ile Lys Pro
                100                 105                 110

Asp Thr Ser Gly Gly Gly Ser Gly Gly Gly Ser Gly Gly Gly
            115                 120                 125

Gly Ser Gly Gly Gly Ser Ser Asn Ser Lys Val Ile Gln Thr
    130                 135                 140

Pro Arg Tyr Leu Val Lys Gly Gln Gly Gln Lys Ala Lys Met Arg Cys
145                 150                 155                 160

Ile Pro Glu Lys Gly His Pro Val Val Phe Trp Tyr Gln Gln Asn Lys
                165                 170                 175

Asn Asn Glu Phe Lys Phe Leu Ile Asn Phe Gln Asn Gln Glu Val Leu
                180                 185                 190

Gln Gln Ile Asp Met Thr Glu Lys Arg Phe Ser Ala Glu Cys Pro Ser
            195                 200                 205

Asn Ser Pro Cys Ser Leu Glu Ile Gln Ser Ser Glu Ala Gly Asp Ser
210                 215                 220

Ala Leu Tyr Leu Cys Ala Ser Ser Leu Ser Gly Gly Thr Glu Val
225                 230                 235                 240

Phe Phe Gly Lys Gly Thr Arg Leu Thr Val Val Glu Asp Leu Asn Lys
                245                 250                 255

Val Phe Pro Pro Glu Val Ala Val Phe Glu Pro Ser Glu Ala Glu Ile
                260                 265                 270

Ser His Thr Gln Lys Ala Thr Leu Val Cys Leu Ala Thr Gly Phe Phe
    275                 280                 285

Pro Asp His Val Glu Leu Ser Trp Trp Val Asn Gly Lys Glu Val His
    290                 295                 300

Ser Gly Val Ser Thr Asp Pro Gln Pro Leu Lys Glu Gln Pro Ala Leu
305                 310                 315                 320

Asn Asp Ser Arg Tyr Cys Leu Ser Ser Arg Leu Arg Val Ser Ala Thr
                325                 330                 335

Phe Trp Gln Asn Pro Arg Asn His Phe Arg Cys Gln Val Gln Phe Tyr
            340                 345                 350

Gly Leu Ser Glu Asn Asp Glu Trp Thr Gln Asp Arg Ala Lys Pro Val
                355                 360                 365

Thr Gln Ile Val Ser Ala Glu Ala Trp Gly Arg Ala Asp Ile Thr Cys
    370                 375                 380

Pro Pro Pro Met Ser Val Glu His Ala Asp Ile Trp Val Lys Ser Tyr
385                 390                 395                 400

Ser Leu Tyr Ser Arg Glu Arg Tyr Ile Cys Asn Ser Gly Phe Lys Arg
                405                 410                 415
```

```
Lys Ala Gly Thr Ser Ser Leu Thr Glu Cys Val Leu Asn Lys Ala Thr
                420                 425                 430
Asn Val Ala His Trp Thr Thr Pro Ser Leu Lys Cys Ile Arg Glu Pro
            435                 440                 445
Lys Ser Cys Asp Lys Thr His Thr Cys Pro Pro Cys Pro Ala Pro Glu
        450                 455                 460
Leu Leu Gly Gly Pro Ser Val Phe Leu Phe Pro Pro Lys Pro Lys Asp
465                 470                 475                 480
Thr Leu Met Ile Ser Arg Thr Pro Glu Val Thr Cys Val Val Val Asp
                485                 490                 495
Val Ser His Glu Asp Pro Glu Val Lys Phe Asn Trp Tyr Val Asp Gly
            500                 505                 510
Val Glu Val His Asn Ala Lys Thr Lys Pro Arg Glu Glu Gln Tyr Asn
        515                 520                 525
Ser Thr Tyr Arg Val Val Ser Val Leu Thr Val Leu His Gln Asp Trp
530                 535                 540
Leu Asn Gly Lys Glu Tyr Lys Cys Lys Val Ser Asn Lys Ala Leu Pro
545                 550                 555                 560
Ala Pro Ile Glu Lys Thr Ile Ser Lys Ala Lys Gly Gln Pro Arg Glu
                565                 570                 575
Pro Gln Val Tyr Thr Leu Pro Pro Ser Arg Asp Glu Leu Thr Lys Asn
            580                 585                 590
Gln Val Ser Leu Thr Cys Leu Val Lys Gly Phe Tyr Pro Ser Asp Ile
        595                 600                 605
Ala Val Glu Trp Glu Ser Asn Gly Gln Pro Glu Asn Asn Tyr Lys Thr
610                 615                 620
Thr Pro Pro Val Leu Asp Ser Asp Gly Ser Phe Phe Leu Tyr Ser Lys
625                 630                 635                 640
Leu Thr Val Asp Lys Ser Arg Trp Gln Gln Gly Asn Val Phe Ser Cys
                645                 650                 655
Ser Val Met His Glu Ala Leu His Asn His Tyr Thr Gln Lys Ser Leu
            660                 665                 670
Ser Leu Ser Pro Gly Lys
        675

<210> SEQ ID NO 48
<211> LENGTH: 1140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
atggattttc aggtgcagat tatcagcttc ctgctaatca gtgcttcagt cataatgtcc      60
agaggacaaa ttgttctctc ccagtctcca gcaatcctgt ctgcatctcc aggggagaag     120
gtcacaatga cttgcagggc cagctcaagt gtaagttaca tccactggtt ccagcagaag     180
ccaggatcct cccccaaacc ctggatttat gccacatcca acctggcttc tggagtccct     240
gttcgcttca gtggcagtgg gtctgggact tcttactctc tcacaatcag cagagtggag     300
gctgaagatg ctgccactta ttactgccag cagtggacta gtaacccacc cacgttcgga     360
ggggggacca agctggaaat caaaagtgga ggtggcggat caggaggcgg aggttctggc     420
ggaggtggga gtcaggtaca actgcagcag cctgggggctg agctggtgaa gcctggggcc     480
tcagtgaaga tgtcctgcaa ggcttctggc tacacattta ccagttacaa tatgcactgg     540
```

-continued

```
gtaaaacaga cacctggtcg gggcctggaa tggattggag ctatttatcc cggaaatggt     600
gatacttcct acaatcagaa gttcaaaggc aaggccacat tgactgcaga caaatcctcc     660
agcacagcct acatgcagct cagcagcctg acatctgagg actctgcggt ctattactgt     720
gcaagatcga cttactacgg cggtgactgg tacttcaatg tctggggcgc agggaccacg     780
gtcaccgtct ctgcaaactg ggtgaatgta ataagtgatt tgaaaaaaat tgaagatctt     840
attcaatcta tgcatattga tgctacttta tatacgaaaa gtgatgttca ccccagttgc     900
aaagtaacag caatgaagtg ctttctcttg gagttacaag ttatttcact tgagtccgga     960
gatgcaagta ttcatgatac agtagaaaat ctgatcatcc tagcaaacga cagtttgtct    1020
tctaatggga atgtaacaga atctggatgc aaagaatgtg aggaactgga ggaaaaaaat    1080
attaaagaat ttttgcagag ttttgtacat attgtccaaa tgttcatcaa cacttcttaa    1140
```

<210> SEQ ID NO 49
<211> LENGTH: 357
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ser Gly Gly Gly Gly Ser
            100                 105                 110

Gly Gly Gly Gly Ser Gly Gly Gly Ser Gln Val Gln Leu Gln Gln
        115                 120                 125

Pro Gly Ala Glu Leu Val Lys Pro Gly Ala Ser Val Lys Met Ser Cys
    130                 135                 140

Lys Ala Ser Gly Tyr Thr Phe Thr Ser Tyr Asn Met His Trp Val Lys
145                 150                 155                 160

Gln Thr Pro Gly Arg Gly Leu Glu Trp Ile Gly Ala Ile Tyr Pro Gly
                165                 170                 175

Asn Gly Asp Thr Ser Tyr Asn Gln Lys Phe Lys Gly Lys Ala Thr Leu
            180                 185                 190

Thr Ala Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Ser Thr Tyr Tyr
    210                 215                 220

Gly Gly Asp Trp Tyr Phe Asp Val Trp Gly Ala Gly Thr Thr Val Thr
225                 230                 235                 240

Val Ser Ala Asn Trp Val Asn Val Ile Ser Asp Leu Lys Lys Ile Glu
                245                 250                 255
```

-continued

Asp Leu Ile Gln Ser Met His Ile Asp Ala Thr Leu Tyr Thr Glu Ser
            260                 265                 270

Asp Val His Pro Ser Cys Lys Val Thr Ala Met Lys Cys Phe Leu Leu
        275                 280                 285

Glu Leu Gln Val Ile Ser Leu Glu Ser Gly Asp Ala Ser Ile His Asp
    290                 295                 300

Thr Val Glu Asn Leu Ile Ile Leu Ala Asn Asp Ser Leu Ser Ser Asn
305                 310                 315                 320

Gly Asn Val Thr Glu Ser Gly Cys Lys Glu Cys Glu Glu Leu Glu Glu
                325                 330                 335

Lys Asn Ile Lys Glu Phe Leu Gln Ser Phe Val His Ile Val Gln Met
            340                 345                 350

Phe Ile Asn Thr Ser
        355

<210> SEQ ID NO 50
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
atggattttc aggtgcagat tatcagcttc ctgctaatca gtgcttcagt cataatgtcc      60
agaggacaaa ttgttctctc ccagtctcca gcaatcctgt ctgcatctcc aggggagaag     120
gtcacaatga cttgcagggc cagctcaagt gtaagttaca tccactggtt ccagcagaag     180
ccaggatcct cccccaaacc ctggatttat gccacatcca acctggcttc tggagtccct     240
gttcgcttca gtggcagtgg gtctgggact tcttactctc tcacaatcag cagagtggag     300
gctgaagatg ctgccactta ttactgccag cagtggacta gtaacccacc cacgttcgga     360
gggggaacca agctggaaat caaaagtgga ggtggcggat ccggaggtgg aggttctggt     420
ggaggtggga gtcaggtaca actgcagcag cctggggctg agctggtgaa gcctggggcc     480
tcagtgaaga tgtcctgcaa ggcttctggc tacacattta ccagttacaa tatgcactgg     540
gtaaaacaga cacctggtcg gggcctggaa tggattggag ctatttatcc cggaaatggt     600
gatacttcct acaatcagaa gttcaaaggc aaggccacat tgactgcaga caaatcctcc     660
agcacagcct acatgcagct cagcagcctg acatctgagg actctgcggt ctattactgt     720
gcaagatcga cttactacgg cggtgactgg tacttcgatg tctggggcgc agggaccacg     780
gtcacmgtct ctgcaatcac gtgccctccc cccatgtccg tggaacacgc agacatctgg     840
gtcaagagct acagcttgta ctccagggag cggtacattt gtaactctgg tttcaagcgt     900
aaagccggca cgtccagcct gacggagtgc gtgttgaaca aggccacgaa tgtcgcccac     960
tggacaaccc ccagtctcaa atgcattaga gagccgaaat cttgtgacaa aactcacaca    1020
tgcccaccgt gcccagcacc tgaactcctg ggggaccgtc agtcttcctc ttccccccca    1080
aaacccaagg acaccctcat gatctcccgg acccctgagg tcacatgcgt ggtggtggac    1140
gtgagccacg aagaccctga ggtcaagttc aactggtacg tggacggcgt ggaggtgcat    1200
aatgccaaga caaagccgcg ggaggagcag tacaacagca cgtaccgtgt ggtcagcgtc    1260
ctcaccgtcc tgcaccagga ctggctgaat ggcaaggagt acaagtgcaa ggtctccaac    1320
aaagccctcc cagcccccat cgagaaaacc atctccaaag ccaaagggca gccccgagaa    1380

-continued

```
ccacaggtgt acaccctgcc cccatcccgg gatgagctga ccaagaacca ggtcagcctg   1440
acctgcctgg tcaaaggctt ctatcccagc gacatcgccg tggagtggga gagcaatggg   1500
cagccggaga caactacaa gaccacgcct cccgtgctgg actccgacgg ctccttcttc    1560
ctctacagca agctcaccgt ggacaagagc aggtggcagc aggggaacgt cttctcatgc   1620
tccgtgatgc atgaggctct gcacaaccac tacacgcaga gagcctctc cctgtctcct    1680 ggtaaataa                                                            1689
```

<210> SEQ ID NO 51
<211> LENGTH: 540
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ser Gly Gly Gly Gly Ser
            100                 105                 110

Gly Gly Gly Gly Ser Gly Gly Gly Ser Gln Val Gln Leu Gln Gln
        115                 120                 125

Pro Gly Ala Glu Leu Val Lys Pro Gly Ala Ser Val Lys Met Ser Cys
    130                 135                 140

Lys Ala Ser Gly Tyr Thr Phe Thr Ser Tyr Asn Met His Trp Val Lys
145                 150                 155                 160

Gln Thr Pro Gly Arg Gly Leu Glu Trp Ile Gly Ala Ile Tyr Pro Gly
                165                 170                 175

Asn Gly Asp Thr Ser Tyr Asn Gln Lys Phe Lys Gly Lys Ala Thr Leu
            180                 185                 190

Thr Ala Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Ser Thr Tyr Tyr
    210                 215                 220

Gly Gly Asp Trp Tyr Phe Asn Val Trp Gly Ala Gly Thr Thr Val Thr
225                 230                 235                 240

Val Ser Ala Ile Thr Cys Pro Pro Pro Met Ser Val Glu His Ala Asp
                245                 250                 255

Ile Trp Val Lys Ser Tyr Ser Leu Tyr Ser Arg Glu Arg Tyr Ile Cys
            260                 265                 270

Asn Ser Gly Phe Lys Arg Lys Ala Gly Thr Ser Ser Leu Thr Glu Cys
        275                 280                 285

Val Leu Asn Lys Ala Thr Asn Val Ala His Trp Thr Thr Pro Ser Leu
    290                 295                 300
```

```
Lys Cys Ile Arg Glu Pro Lys Ser Cys Asp Lys Thr His Thr Cys Pro
305                 310                 315                 320

Pro Cys Pro Ala Pro Glu Leu Leu Gly Gly Pro Ser Val Phe Leu Phe
            325                 330                 335

Pro Pro Lys Pro Lys Asp Thr Leu Met Ile Ser Arg Thr Pro Glu Val
            340                 345                 350

Thr Cys Val Val Val Asp Val Ser His Glu Asp Pro Glu Val Lys Phe
            355                 360                 365

Asn Trp Tyr Val Asp Gly Val Glu Val His Asn Ala Lys Thr Lys Pro
            370                 375                 380

Arg Glu Glu Gln Tyr Asn Ser Thr Tyr Arg Val Val Ser Val Leu Thr
385                 390                 395                 400

Val Leu His Gln Asp Trp Leu Asn Gly Lys Glu Tyr Lys Cys Lys Val
            405                 410                 415

Ser Asn Lys Ala Leu Pro Ala Pro Ile Glu Lys Thr Ile Ser Lys Ala
            420                 425                 430

Lys Gly Gln Pro Arg Glu Pro Gln Val Tyr Thr Leu Pro Pro Ser Arg
            435                 440                 445

Asp Glu Leu Thr Lys Asn Gln Val Ser Leu Thr Cys Leu Val Lys Gly
            450                 455                 460

Phe Tyr Pro Ser Asp Ile Ala Val Glu Trp Glu Ser Asn Gly Gln Pro
465                 470                 475                 480

Glu Asn Asn Tyr Lys Thr Thr Pro Pro Val Leu Asp Ser Asp Gly Ser
            485                 490                 495

Phe Phe Leu Tyr Ser Lys Leu Thr Val Asp Lys Ser Arg Trp Gln Gln
            500                 505                 510

Gly Asn Val Phe Ser Cys Ser Val Met His Glu Ala Leu His Asn His
            515                 520                 525

Tyr Thr Gln Lys Ser Leu Ser Leu Ser Pro Gly Lys
            530                 535                 540
```

<210> SEQ ID NO 52
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
atggattttc aggtgcagat tatcagcttc ctgctaatca gtgcttcagt cataatgtcc      60
agaggacaaa ttgttctctc ccagtctcca gcaatcctgt ctgcatctcc aggggagaag    120
gtcacaatga cttgcagggc cagctcaagt gtaagttaca tccactggtt ccagcagaag    180
ccaggatcct cccccaaacc ctggatttat gccacatcca acctggcttc tggagtccct    240
gttcgcttca gtggcagtgg gtctgggact tcttactctc tcacaatcag cagagtggag    300
gctgaagatg ctgccactta ttactgccag cagtggacta gtaacccacc cacgttcgga    360
ggggggacca agctggaaat caaacgtacg gttgctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
```

```
ggcctgagct cgcccgtcac aaagagcttc aacaggggag agtgtaactg ggtgaatgta    720
ataagtgatt tgaaaaaaat tgaagatctt attcaatcta tgcatattga tgctacttta    780
tatacggaaa gtgatgttca ccccagttgc aaagtaacag caatgaagtg ctttctcttg    840
gagttacaag ttatttcact tgagtccgga gatgcaagta ttcatgatac agtagaaaat    900
ctgatcatcc tagcaaacga cagtttgtct tctaatggga atgtaacaga atctggatgc    960
aaagaatgtg aggaactgga ggaaaaaaat attaaagaat ttttgcagag ttttgtacat   1020
attgtccaaa tgttcatcaa cacttcttaa                                    1050
```

<210> SEQ ID NO 53
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Asn Trp Val Asn Val Ile Ser Asp Leu Lys Lys
    210                 215                 220

Ile Glu Asp Leu Ile Gln Ser Met His Ile Asp Ala Thr Leu Tyr Thr
225                 230                 235                 240

Glu Ser Asp Val His Pro Ser Cys Lys Val Thr Ala Met Lys Cys Phe
                245                 250                 255

Leu Leu Glu Leu Gln Val Ile Ser Leu Glu Ser Gly Asp Ala Ser Ile
            260                 265                 270

His Asp Thr Val Glu Asn Leu Ile Ile Leu Ala Asn Asp Ser Leu Ser
        275                 280                 285
```

Ser Asn Gly Asn Val Thr Glu Ser Gly Cys Lys Glu Cys Glu Glu Leu
        290                 295                 300

Glu Glu Lys Asn Ile Lys Glu Phe Leu Gln Ser Phe Val His Ile Val
305                 310                 315                 320

Gln Met Phe Ile Asn Thr Ser
                325

<210> SEQ ID NO 54
<211> LENGTH: 1608
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
atgggttgga gtctcatctt gctcttcctt gtcgctgttg ctacacgtgt cctgtcccag      60
gtacaactgc agcagcctgg ggctgagctg gtgaagcctg ggcctcagt gaagatgtcc     120
tgcaaggctt ctggctacac atttaccagt tacaatatgc actgggtaaa acagacacct     180
ggtcggggcc tggaatggat tggagctatt tatcccggaa atggtgatac ttcctacaat     240
cagaagttca aggcaaggc cacattgact gcagacaaat cctccagcac agcctacatg     300
cagctcagca gcctgacatc tgaggactct gcggtctatt actgtgcaag atcgacttac     360
tacggcggtg actggtactt cgatgtctgg ggcgcaggga ccacggtcac cgtctctgca     420
gctagcacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagaa agttatcacg     720
tgccctcccc ccatgtccgt ggaacacgca gacatctggg tcaagagcta cagcttgtac     780
tccagggagc ggtacatttg taactctggt ttcaagcgta aagccggcac gtccagcctg     840
acggagtgcg tgttgaacaa ggccacgaat gtcgcccact ggacaacccc cagtctcaaa     900
tgcattagag agcccaaatc ttgtgacaaa actcacacat gcccaccgtg cccagcacct     960
gaactcctgg gggaccgtc agtcttcctc ttccccccaa aacccaagga caccctcatg    1020
atctcccgga cccctgaggt cacatgcgtg gtggtggacg tgagccacga agaccctgag    1080
gtcaagttca actggtacgt ggacggcgtg gaggtgcata atgccaagac aaagccgcgg    1140
gaggagcagt acaacagcac gtaccgtgtg gtcagcgtcc tcaccgtcct gcaccaggac    1200
tggctgaatg gcaaggagta caagtgcaag gtctccaaca aagccctccc agcccccatc    1260
gagaaaacca tctccaaagc caagggcag ccccgagaac acaggtgta cccctgccc    1320
ccatcccggg atgagctgac caagaaccag gtcagcctga cctgcctggt caaaggcttc    1380
tatcccagcg acatcgccgt ggagtgggag agcaatgggc agccggagaa caactacaag    1440
accacgcctc ccgtgctgga ctccgacggc tccttcttcc tctacagcaa gctcaccgtg    1500
gacaagagca ggtggcagca ggggaacgtc ttctcatgct ccgtgatgca tgaggctctg    1560
cacaaccact acacgcagaa gagcctctcc ctgtctcctg gtaaataa              1608
```

<210> SEQ ID NO 55
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asp Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Ile Thr Cys Pro Pro
    210                 215                 220

Pro Met Ser Val Glu His Ala Asp Ile Trp Val Lys Ser Tyr Ser Leu
225                 230                 235                 240

Tyr Ser Arg Glu Arg Tyr Ile Cys Asn Ser Gly Phe Lys Arg Lys Ala
                245                 250                 255

Gly Thr Ser Ser Leu Thr Glu Cys Val Leu Asn Lys Ala Thr Asn Val
            260                 265                 270

Ala His Trp Thr Thr Pro Ser Leu Lys Cys Ile Arg Glu Pro Lys Ser
        275                 280                 285

Cys Asp Lys Thr His Thr Cys Pro Pro Cys Pro Ala Pro Glu Leu Leu
    290                 295                 300

Gly Gly Pro Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
                325                 330                 335

His Glu Asp Pro Glu Val Lys Phe Asn Trp Tyr Val Asp Gly Val Glu
            340                 345                 350

Val His Asn Ala Lys Thr Lys Pro Arg Glu Glu Gln Tyr Asn Ser Thr
        355                 360                 365

Tyr Arg Val Val Ser Val Leu Thr Val Leu His Gln Asp Trp Leu Asn
    370                 375                 380

Gly Lys Glu Tyr Lys Cys Lys Val Ser Asn Lys Ala Leu Pro Ala Pro
```

Ile Glu Lys Thr Ile Ser Lys Ala Lys Gly Gln Pro Arg Glu Pro Gln
385                 390                 395                 400
                405                 410                 415

Val Tyr Thr Leu Pro Pro Ser Arg Asp Glu Leu Thr Lys Asn Gln Val
                420                 425                 430

Ser Leu Thr Cys Leu Val Lys Gly Phe Tyr Pro Ser Asp Ile Ala Val
            435                 440                 445

Glu Trp Glu Ser Asn Gly Gln Pro Glu Asn Asn Tyr Lys Thr Thr Pro
        450                 455                 460

Pro Val Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Met His Glu Ala Leu His Asn His Tyr Thr Gln Lys Ser Leu Ser Leu
            500                 505                 510

Ser Pro Gly Lys
        515

<210> SEQ ID NO 56
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atggagacag acacactcct gttatgggta ctgctgctct gggttccagg ttccaccggt        60
aactgggtga atgtaataag tgatttgaaa aaaattgaag atcttattca atctatgcat       120
attgatgcta ctttatatac ggaaagtgat gttcacccca gttgcaaagt aacagcaatg       180
aagtgctttc tcttggagtt acaagttatt tcacttgagt ccggagatgc aagtattcat       240
gatacagtag aaaatctgat catcctagca acgacagtt tgtcttctaa tgggaatgta       300
acagaatctg gatgcaaaga atgtgaggaa ctggaggaaa aaaatattaa gaattttttg       360
cagagttttg tacatattgt ccaaatgttc atcaacactt cttaa                      405

<210> SEQ ID NO 57
<211> LENGTH: 951
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atggacagac ttacttcttc attcctgctc ctgattgtcc ctgcgtacgt cttgtccatc        60
acgtgccctc cccccatgtc cgtggaacac gcagacatct gggtcaagag ctacagcttg       120
tactccaggg agcggtacat tgtaactct ggtttcaagc gtaaagccgg cacgtccagc       180
ctgacggagt gcgtgttgaa caaggccacg aatgtcgccc actggacaac ccccagtctc       240
aaatgtatta gagagcccaa atcttgtgac aaaactcaca catgcccacc gtgcccagca       300
cctgaactcc tggggggacc gtcagtcttc ctcttccccc caaaacccaa ggacaccctc       360
atgatctccc ggacccctga ggtcacatgc gtggtggtgg acgtgagcca cgaagaccct       420
gaggtcaagt tcaactggta cgtggacggc gtggaggtgc ataatgccaa gacaaagccg       480
cgggaggagc agtacaacag cacgtaccgt gtggtcagcg tcctcaccgt cctgcaccag       540

-continued

```
gactggctga atggcaagga gtacaagtgc aaggtctcca acaaagccct cccagccccc      600
atcgagaaaa ccatctccaa agccaaaggg cagccccgag aaccacaggt gtacaccctg      660
cccccatccc gggatgagct gaccaagaac caggtcagcc tgacctgcct ggtcaaaggc      720
ttctatccca gcgacatcgc cgtggagtgg gagagcaatg ggcagccgga gaacaactac      780
aagaccacgc ctcccgtgct ggactccgac ggctccttct tcctctacag caagctcacc      840
gtggacaaga gcaggtggca gcaggggaac gtcttctcat gctccgtgat gcatgaggct      900
ctgcacaacc actacacgca gaagagcctc tccctgtctc cgggtaaata a               951
```